(12) United States Patent
Holt et al.

(10) Patent No.: US 8,921,528 B2
(45) Date of Patent: Dec. 30, 2014

(54) BISPECIFIC FUSION ANTIBODIES WITH ENHANCED SERUM HALF-LIFE

(75) Inventors: Lucy J. Holt, Cambridge (GB); Ian M. Tomlinson, Cambridge (GB)

(73) Assignee: Domantis Limited (GB)

(*) Notice: Subject to any disclaimer, the term of this patent is extended or adjusted under 35 U.S.C. 154(b) by 1545 days.

(21) Appl. No.: 11/628,149

(22) PCT Filed: May 31, 2005

(86) PCT No.: PCT/GB2005/002163
§ 371 (c)(1),
(2), (4) Date: Feb. 2, 2007

(87) PCT Pub. No.: WO2005/118642
PCT Pub. Date: Dec. 15, 2005

(65) Prior Publication Data
US 2008/0260757 A1   Oct. 23, 2008

Related U.S. Application Data

(60) Provisional application No. 60/576,271, filed on Jun. 1, 2004, provisional application No. 60/632,361, filed on Dec. 2, 2004.

(51) Int. Cl.
  *C07K 16/18*   (2006.01)
  *C07K 19/00*   (2006.01)
  *C07K 16/44*   (2006.01)
  *C07K 14/765*  (2006.01)
  *A61K 47/48*   (2006.01)
  *A61K 39/00*   (2006.01)

(52) U.S. Cl.
  CPC ............ *C07K 16/18* (2013.01); *C07K 2319/00* (2013.01); *C07K 2317/21* (2013.01); *A61K 2039/505* (2013.01); *A61K 47/48415* (2013.01); *A61K 47/48538* (2013.01); *C07K 2317/569* (2013.01); *C07K 2317/565* (2013.01)
  USPC ................ 530/389.3; 530/391.9; 530/391.7; 424/134.1; 424/145.1; 424/178.1

(58) Field of Classification Search
  None
  See application file for complete search history.

(56) References Cited

U.S. PATENT DOCUMENTS

| | | | |
|---|---|---|---|
| 5,609,869 A * | 3/1997 | Quertermous et al. | .... 424/133.1 |
| 5,624,821 A | 4/1997 | Winter et al. | |
| 5,648,260 A | 7/1997 | Winter et al. | |
| 5,702,892 A | 12/1997 | Mulligan-Kehoe | |
| 5,733,743 A | 3/1998 | Johnson et al. | |
| 5,831,012 A | 11/1998 | Nilsson et al. | |
| 5,834,597 A | 11/1998 | Tso et al. | |
| 5,969,108 A | 10/1999 | McCafferty et al. | |
| 6,267,964 B1 | 7/2001 | Nygren et al. | |
| 6,555,313 B1 | 4/2003 | Griffiths et al. | |
| 2003/0108992 A1 | 6/2003 | Lenardo et al. | |
| 2003/0166524 A1 | 9/2003 | Ford et al. | |
| 2004/0077022 A1 | 4/2004 | Feige et al. | |
| 2007/0178082 A1* | 8/2007 | Silence et al. | ............ 424/131.1 |
| 2013/0202527 A1* | 8/2013 | Tse et al. | ..................... 424/1.49 |

FOREIGN PATENT DOCUMENTS

| | | |
|---|---|---|
| EP | 0 453 082 A1 | 10/1991 |
| EP | 0 368 684 B2 | 3/1994 |
| EP | 0 585 939 B1 | 3/1994 |
| EP | 0 486 525 B1 | 6/1994 |
| EP | 0 739 984 A1 | 10/1996 |
| EP | 1 026 239 A2 | 8/2000 |
| EP | 0 672 142 B1 | 2/2001 |
| EP | 0 666 868 B2 | 4/2002 |
| EP | 1 325 932 B9 | 7/2003 |
| EP | 1 378 520 A1 | 1/2004 |
| EP | 1 454 917 A2 | 9/2004 |
| WO | WO 89/07142 A1 | 8/1989 |
| WO | WO 90/05144 A1 | 5/1990 |
| WO | WO 90/14430 A1 | 11/1990 |
| WO | WO 91/01743 A1 | 2/1991 |
| WO | WO 92/01047 A1 | 1/1992 |
| WO | WO 92/20791 A1 | 11/1992 |
| WO | WO 93/11236 A1 | 6/1993 |
| WO | WO 94/13804 A1 | 6/1994 |
| WO | WO 95/10302 A1 | 4/1995 |
| WO | WO 00/29004 A1 | 5/2000 |
| WO | WO 01/45746 A2 | 6/2001 |
| WO | WO 01/58953 A3 | 8/2001 |
| WO | WO 01/77342 A1 | 10/2001 |
| WO | WO 01/90192 A2 | 11/2001 |
| WO | WO 02/02773 A2 | 1/2002 |
| WO | WO 02/076489 A1 | 10/2002 |
| WO | WO 02/096948 A2 | 12/2002 |
| WO | WO 03/002609 A2 | 1/2003 |
| WO | WO 03/030835 A2 | 4/2003 |

(Continued)

OTHER PUBLICATIONS

Franz et al, Int J Rad Appl Instrum B 14(5): 479-84, 1987, abstract only.*
Shen et al, Proc Natl Acad Sci 81: 1445-1447, Mar. 1984.*
Dennis et al, J Biol Chemistry 277(38): 35035-35043, Sep. 2002.*
Kobrin et al, J Immunology 146: 2017-2020, 1991.*
Barrios et al, J Molecular Recognition 17: 332-338, 2004.*
Wu et al., J Mol Biol 294: 151-162, 1999.*
Rudikoff et al., Proc. Natl. Acad. Sci. USA vol. 79 p. 1979-1983, 1982.*

(Continued)

*Primary Examiner* — Phuong Huynh
(74) *Attorney, Agent, or Firm* — Jason C. Fedon; William T. Han

(57) ABSTRACT

Drug compositions, fusions and conjugates are provided. The drug fusions and conjugates contain a therapeutic or diagnostic agent that is fused or conjugated to an antigen-binding fragment of an antibody that binds serum albumin. The drug compositions, fusions and conjugates have a longer in vivo half-life in comparison with the unconjugated or unfused therapeutic or diagnostic agent.

38 Claims, 36 Drawing Sheets

(56) References Cited

FOREIGN PATENT DOCUMENTS

| | | |
|---|---|---|
| WO | WO 03/066824 A2 | 8/2003 |
| WO | WO 03/106487 A1 | 12/2003 |
| WO | WO 04/001064 A2 | 12/2003 |
| WO | WO 2004/003019 A2 | 1/2004 |
| WO | WO 2004/032961 A1 | 4/2004 |
| WO | WO 2004/041862 A2 | 5/2004 |
| WO | WO 2004/041867 A2 | 5/2004 |
| WO | WO 2004/058821 A2 | 7/2004 |
| WO | WO 2004/081026 A2 | 9/2004 |
| WO | WO 2005/004809 A2 | 1/2005 |
| WO | WO 2005/014618 A2 | 2/2005 |
| WO | WO 2005/027978 A2 | 3/2005 |
| WO | WO 2005/035572 A2 | 4/2005 |
| WO | WO 2005/097202 A2 | 10/2005 |
| WO | WO 2005/118642 A2 | 12/2005 |
| WO | WO 2006/051288 | 5/2006 |

OTHER PUBLICATIONS

Dennis, M., et al., "Albumin Binding as a General Strategy for Improving the Pharmacokinetics of Proteins," *J. of Biol. Chem.*, 227(38)35035-35043 (2002).

Harmsen, M.M., et al., "Prolonged in vivo Residence Times of Llama Single-domain Antibody Fragments in Pigs by Binding to Porcine Immunoglobulins," *Vaccine*, 23(41):4926-4934 (2005).

Smith, B. J., et al., "Prolonged in vivo Residence Times of Antibody Fragments Associated with Albumin," *Bioconjugate Chem.* 12(5):750-756 (2001).

Holt, L.J., et al., "Domain Antibodies: Proteins for Therapy," *Trends in Biotechnol.*, 21(11):484-490 (2003).

Cortez-Retamozo, V. et al., "Efficient Cancer Therapy with a Nanobody-Based Conjugate," *Cancer Research*, 64(8)2853-2857, (2004).

Holliger, P., et al., "Retargeting Serum Immunoglobulin with Bispecific Diabodies," *Nature Biotechnol.*, 15(7):632-636, (1997).

Gouze, J-N., et al., "A Comparative Study of the Inhibitory Effects of Interleukin-1 Receptor Antagonist Following Administration as a Recombinant Protein or by Gene Transfer," *Arthritis Res. Ther.*, 5(5):301-309, (2003).

Eisenberg, S. P., et al., "Primary Structure and Functional Expression from Complementary DNA of a Human Interleukin-1 Receptor Antagonist," *Nature*, 343:341-346 (1990).

Hannum, C. H., et al., "Interleukin-1 Receptor Antagonist Activity of a Human Interleukin-1 Inhibitor," *Nature*, 343:336-340 (1990).

Barthelemy, I., et al., "The Expression of Saporin, a Ribosome-inactivating Protein from the Plant *Saponaria officinalis*, in *Escherichia coli*," *J. Biol. Chem.*, 268(9)6541-6548 (1993).

Bagga, S., et al., "The Cytotoxic Activity of Ribosome-inactivating Protein Saporin-6 is Attributed to Its rRNA N-Glycosidase and Internucleosomal DNA Fragmentation Activities," *J. Biol. Chem.*, 278(7)4813-4820 (2003).

Stirpe, F., et al., "Ribosome-inactivating Proteins from the Seeds of *Saponaria officinalis* L. (soapwort), of *Agrostemma githago* L. (corn cockle) and of *Asparagus officinalis* L. (asparagus), and from the Latex of *Hura crepitans* L. (sandbox tree)," *Biochem. J.*, 216:617-625 (1983).

Janin, Y.L., "Peptides with Anticancer Use or Potential," *Amino Acids*, 25:1-40 (2003).

Sehgal, A., "Peptide Products" In Peptide Therapeutics Applications in the Treatment of Human Disease, (MA: D&MD Publications), pp. 6-1-6-15(2004).

Poznansky, M. J., "Enzyme-Albumin Polymers: New Approaches to the Use of Enzymes in Medicine" In Applied Biochemistry and Biotechnology, Weetal, H. H., et al. eds .(The Humana Press), pp. 41-56 (1984).

Remy, M. H. and M. J. Poznansky, "Immunogenicity and Antigenicity of Soluble Cross-Linked Enzyme/Albumin Polymers: Advantages for Enzyme Therapy," *The Lancet*, 2(8080): 68-70 (1978).

Deng, Guo-Min, et al., "Amelioration of Inflammatory Arthritis by Targeting the Pre-ligand Assembly Domain of Tumor Necrosis Factor Receptors," *Nature Medicine*,11(10):1066-1072 (2005).

Deng, Guo-Min, et al, "A Potential Therapeutic Molecule for Inflammatory Arthritis Targeting Pre-ligand Assembly Domain (PLAD) of TNF Receptors," *FASEB Journal*, 19(4):A915 (2005).

Golstein P., "Signal Transduction: FasL Binds Preassembled Fas," *Science*, 288(5475):2328-2329 (2000).

Chan, F.K-M., et al., "A Domain in TNF Receptors that Mediates Ligand-independent Receptor Assembly and Signaling," *Science*, 222(5475):2351-2354 (2000).

Siegel, R.M., et al., "Fas Preassociation Required for Apoptosis Signaling and Dominant Inhibition by Pathogenic Mutations," *Science*, 288(5475):2354-2357 (2000).

Carter, P., et al., "Toward the Production of Bispecific Antibody Fragments for Clinical Applications," *J. Hematother.*, 4: 463-470.

Wörn, A., et al., "Mutual Stabilization of $V_L$ and $V_H$ in Single-chain Antibody Fragments, Investigated With Mutants Engineered for Stability," *Biochemistry*, 37: 13120-13127 (1998).

Alfthan, K, et al., "Properties of a Single-chain Antibody Containing Different Linker Peptides," *Prot. Eng.*, 8(7): 725-731 (1995).

Atwell, J., et al., "Design and Expression of a Stable Bispecific scFv Dimer With Affinity for Both Glycophorin and N9 Neuraminidase." *Mol. Immunol.*, 33(17/18): 1301-1312 (1996).

Carter, P., et al., "Toward the Production of Bispecific Antibody Fragments for Clinical Applications," *J. Hematother.*, 4: 463-470, (1995).

Chapman, A., "PEGylated Antibodies and Antibody Fragments for Improved Therapy: A Review," *Advanced Drug Delivery Reviews*, 54(4): 531-545 (2002).

Conrath, K., et al., "Camel Single-domain Antibodies as Modular Building Units in Bispecific and Bivalent Antibody Constructs," *J. Biol. Chem.*, 276(10): 7346-7350 (2001).

Cunningham-Rundles, C., et al., "Biological Activities of Polyethylene-glycol Immunoglobulin Conjugates. Resistance to Enzymatic Degradation," *Journal of Immunological Methods*, 152: 177-190 (1992).

Winter, G., et al., "Man-made Antibodies," *Nature*, 349: 293-299 (1991).

Holliger, P., et al., "Diabodies: Small Bispecific Antibody Fragments," *Cancer Immunol. Immunother.*, 45(3-4): 128-130 (1997).

Merchant, A., et al., "An Efficient Route to Human Bispecific IgG," *Nature Biotechnology*, 16(7): 677-681 (1998).

Pluckthun, A., et al., "New Protein Engineering Approaches to Multivalent and Bispecific Antibody Fragments," *Immunotechnology*, 3: 83-105 (1997).

Nissim, A., et al., "Antibody Fragments From a 'Single Pot' Phage Display Library as Immunochemical Reagents," *The Embo J.*, 13(3): 692-698 (1994).

Tang, Y., et al., "Selection of Linkers for a Catalytic Single-chain Antibody Using Phage Display Technology," *J. Biol. Chem.*, 271(26): 15682-15686 (1996).

Wörn, A., et al., "Mutual Stabilization of $V_L$, and $V_H$ in Single-chain Antibody Fragments, Investigated With Mutants Engineered for Stability," *Biochemistry*, 37: 13120-13127 (1998).

\* cited by examiner

FIG. 1A

VKs selected vs MSA

| Kabat_Numbering | 5 | 10 | 15 | 20 | 25 | 30 | 35 |
|---|---|---|---|---|---|---|---|
| MSA16 | DIQMT | QSPSS | LSAS | VGDRVT | ITCR A | SQSI I | KHLK W |
| MSA 12 | DIQMT | QSPSS | LSAS | VGDRVT | ITCR A | SQSI F | RHLK W |
| MSA 26 | DIQMT | QSPSS | LSAS | VGDRVT | ITCR A | SQSI Y | YHLK W |

| Kabat_Numbering | 40 | 45 | 50 | 55 | 60 | 65 | 70 |
|---|---|---|---|---|---|---|---|
| MSA16 | YQQK P | GKAP K | LLIY G | ASRL Q | SGVP S | RFSG S | GSGT D |
| MSA 12 | YQQK P | GKAP K | LLIY A | ASRL Q | SGVP S | RFSG S | GSGT D |
| MSA 26 | YQQK P | GKAP K | LLIY K | ASTL Q | SGVP S | RFSG S | GSGT D |

| Kabat_Numbering | 75 | 80 | 85 | 90 | 95 | 100 | 105 |
|---|---|---|---|---|---|---|---|
| MSA16 | FTLT I | SSLQ P | EDFA T | YYCQ Q | GARW P | QTFG Q | GTKV E |
| MSA 12 | FTLT I | SSLQ P | EDFA T | YYCQ Q | VALY P | KTFG Q | GTKV E |
| MSA 26 | FTLT I | SSLQ P | EDFA T | YYCQ Q | VRKV P | RTFG Q | GTKV E |

| Kabat_Numbering | |
|---|---|
| MSA16 | IKR |
| MSA 12 | IKR |
| MSA 26 | IKR |

FIG. 1B

VKs selected vs RSA

| Kabat_Numbering | 5 | 10 | 15 | 20 | 25 | 30 | 35 |
|---|---|---|---|---|---|---|---|
| DOM7r-1 | DIQT | TQSPS | SLSAS | VGDRV | TITCR | ASQYI | GRYLR W |
| DOM7r-3 | DIQM | TQSPS | SLSAS | VGDRV | TITCR | ASQYI | GRYLR W |
| DOM7r-4 | DIQM | TQSPS | SLSAS | VGDRV | TITCR | ASQWI | GRYLR W |
| DOM7r-5 | DIQM | TQSPS | SLSAS | VGDRV | TITCR | ASQYI | SRQLR W |
| DOM7r-7 | DIQM | TQSPS | SLSAS | VGDRV | TITCR | ASQYI | GRYLR W |
| DOM7r-8 | DIQM | TQSPS | SLSAS | VGDRV | TITCR | ASQWI | HRQLK W |

| Kabat_Numbering | 40 | 45 | 50 | 55 | 60 | 65 | 70 |
|---|---|---|---|---|---|---|---|
| DOM7r-1 | YQQK | PGKAP | KLLIY D | SSVL Q | SGVP | SRFSG | S GSGT D |
| DOM7r-3 | YQQK | PGKAP | KLLIY D | SSVL Q | SGVP | SRFSG | S GSGT D |
| DOM7r-4 | YQQK | PGKAP | KLLIY N | GSQL Q | SGVP | SRFSG | S GSGT D |
| DOM7r-5 | YQQK | PGKAP | RLLIY G | ASVL Q | SGIP | SRFSG | S GSGT D |
| DOM7r-7 | YQQK | PGKAP | KLLIY D | SSVL Q | SGVP | SRFSG | S GSGT D |
| DOM7r-8 | YQQK | PGKAP | KLLIY Y | ASIL Q | SGVP | SRFSG | S GSGT D |

| Kabat_Numbering | 75 | 80 | 85 | 90 | 95 | 100 | 105 |
|---|---|---|---|---|---|---|---|
| DOM7r-1 | FTLT | ISSLQ | PEDFA | TYYCQ Q | RYRM P | YTFG | Q GTRV E |
| DOM7r-3 | FTLT | ISSLQ | PEDFA | TYYCQ Q | RYMQ P | FTFG | Q GTKV E |
| DOM7r-4 | FTLT | ISSLQ | PEDFA | TYYCQ Q | RYLQ P | YTFG | Q GTKV E |
| DOM7r-5 | FTLT | ISSLQ | PEDFA | TYYCQ Q | RYIT P | YTFG | Q GTKV E |
| DOM7r-7 | FTLT | ISSLQ | PEDFA | TYYCQ Q | RYSS P | YTFG | Q GTKV E |
| DOM7r-8 | FTLT | ISSLQ | PEDFA | TYYCQ Q | TFSK P | STFG | Q GTKV E |

| Kabat_Numbering | |
|---|---|
| DOM7r-1 | IKR |
| DOM7r-3 | IKR |
| DOM7r-4 | IKR |
| DOM7r-5 | VKR |
| DOM7r-7 | IKR |
| DOM7r-8 | IKR |

FIG. 1C

VKs selected vs HSA

| Kabat_Numbering | 5 | 10 | 15 | 20 | 25 | 30 | 35 |
|---|---|---|---|---|---|---|---|
| DOM7h-2 | DIQM T QSPS S LSAS V GDRV T ITCR A SQKI A TYLN W |
| DOM7h-3 | DIQM T QSPS S LSAS V GDRV T ITCR A SQWI D TGLA W |
| DOM7h-4 | DIQM T QSPS S LSAS V GDRV T ITCR A SQEI Y SWLA W |
| DOM7h-6 | DIQM T QSPS S LSAS V GDRV T ITCR A SQSI S SYLN W |
| DOM7h-1 | DIQM T QSPS S LSAS V GDRV T ITCR A SQSI S SYLN W |
| DOM7h-7 | DIQM T QSPS S LSAS V GDRV T ITCR A SQSI S SYLN W |

| Kabat_Numbering | 40 | 45 | 50 | 55 | 60 | 65 | 70 |
|---|---|---|---|---|---|---|---|
| DOM7h-2 | YQQK P GKAP K LLIY R SSSL Q SAVP S RFSG S GSGT V |
| DOM7h-3 | YQQK P GKAP R LLIY N VSRL Q SGVP S RFSG S GSGT D |
| DOM7h-4 | YQQR P GKAP K LLIY N ASHL Q SGVP S RFSG S GSGT D |
| DOM7h-6 | YQQK P GKAP T LLIY R LSVL Q SGVP S RFSG S GSGT D |
| DOM7h-1 | YQQK P GKAP K LLIY R NSFL Q SGVP S RFSG S GSGT D |
| DOM7h-7 | YQQK P GKAP K LLIY R NSQL Q SGVP S RFSG S GSGT D |

| Kabat_Numbering | 75 | 80 | 85 | 90 | 95 | 100 | 105 |
|---|---|---|---|---|---|---|---|
| DOM7h-2 | FTLT I SSLQ P EDFA T YYCQ Q TYAV P PTFG Q GTKV E |
| DOM7h-3 | FTLT I SSLQ P EDFA T YYCQ Q YWGS P TTFG Q GTKV E |
| DOM7h-4 | FTLT I SSLQ P EDFA T YYCQ Q VIGD P VTFG Q GTKV E |
| DOM7h-6 | FTLT I SSLQ P EDFA T YYCQ Q TYNV P PTFG Q GTKV E |
| DOM7h-1 | FTLT I SSLQ P EDFA T YYCQ Q TYTV P PTFG Q GTKV E |
| DOM7h-7 | FTLT I SSLQ P EDFA T YYCQ Q TFAV P PTFG Q GTKV E |

| Kabat_Numbering | |
|---|---|
| DOM7h-2 | IKR |
| DOM7h-3 | IKR |
| DOM7h-4 | IKR |
| DOM7h-6 | IKR |
| DOM7h-1 | IKQ |
| DOM7h-7 | IKR |

FIG. 1D

VHs selected vs HSA

| Kabat_Numbering | | 5 | | 10 | | 15 | | 20 | | 25 | | 30 | | 35 |
|---|---|---|---|---|---|---|---|---|---|---|---|---|---|---|
| DOM7h-22 | EVQL | L | ESGG | G | LVQP | G | GSLR | L | SCAA | S | GFTF | S | KYWM | S |
| DOM7h-23 | EVQL | L | ESGG | G | LVQP | G | GSLR | L | SCAA | S | GFTF | Y | DYNM | S |
| DOM7h-24 | EVQL | L | ESGG | G | LVQP | G | GSLR | L | SCAA | S | GFTF | H | RYSM | S |
| DOM7h-25 | EVQL | L | ESGG | G | LVQP | G | GSLR | L | SCAA | S | GFTF | W | KYNM | A |
| DOM7h-26 | EVQL | L | ESGG | G | LVQP | G | GSLR | L | SCTA | S | GFTF | D | EYNM | S |
| DOM7h-21 | EVQL | L | ESGG | G | LVQP | G | GSLR | L | SCAA | S | GFTF | D | LYDM | S |
| DOM7h-27 | EVQL | L | ESGG | G | LVQP | G | GSLR | L | SCAA | S | GFTF | S | DYRM | S |
| Consensus | EVQL | L | ESGG | G | LVQP | G | GSLR | L | SCAA | S | GFTF | X | XYNM | S |

| Kabat_Numbering | | 40 | | 45 | | 50 | | 54 | | 59 | | 64 | | 69 |
|---|---|---|---|---|---|---|---|---|---|---|---|---|---|---|
| DOM7h-22 | WVRQ | A | PGKG | L | EWVS | S | IDFM | G | PHTY | Y | ADSV | K | GRFT | I |
| DOM7h-23 | WVRQ | A | PGKG | L | EWVS | T | ITHT | G | GVTY | Y | ADSV | K | GRFT | I |
| DOM7h-24 | WVRQ | A | PGKG | L | EWVS | T | ILPG | G | DVTY | Y | ADSV | K | GRFT | I |
| DOM7h-25 | WVRQ | A | PGKG | L | EWVS | T | ILGE | G | NNTY | Y | ADSV | K | GRFT | I |
| DOM7h-26 | WVRQ | A | PGKG | L | EWVS | T | ILPH | G | DRTY | Y | ADSV | K | GRFT | I |
| DOM7h-21 | WVRQ | A | PGKG | L | EWVS | S | IVNS | G | VRTY | Y | ADSV | K | GRFT | I |
| DOM7h-27 | WVRQ | A | PGKG | L | EWVS | T | IISN | G | KFTY | Y | ADSV | K | GRFT | I |

| Kabat_Numbering | | 74 | | 79 | | 82b | | 86 | | 91 | | 96 | | 100a |
|---|---|---|---|---|---|---|---|---|---|---|---|---|---|---|
| DOM7h-22 | SRDN | S | KNTL | Y | LQMN | S | LRAE | D | TAVY | Y | CAKG | R | TSML | P |
| DOM7h-23 | SRDN | S | KNTL | Y | LQMN | S | LRAE | D | TAVY | Y | CAKQ | N | PSYQ | - |
| DOM7h-24 | SRDN | S | KNTL | Y | LQMN | S | LRAE | D | TAVY | Y | CAKQ | T | PDYM | - |
| DOM7h-25 | SRDN | S | KNTL | Y | LQMN | S | LRAE | D | TAVY | Y | CAKT | M | DYK- | - |
| DOM7h-26 | SRDN | S | KNTL | Y | LQMN | S | LRAE | D | TAVY | Y | CAKQ | D | PLYR | - |
| DOM7h-21 | SRDN | S | KNTL | Y | LQMN | S | LRAE | D | TAVY | Y | CAKL | N | QSYH | W |
| DOM7h-27 | SRDN | S | KNTL | Y | LQMN | S | LRAE | D | TAVY | Y | CAKQ | D | WMYM | - |

| Kabat_Numbering | | 100o | | 105 | | 110 |
|---|---|---|---|---|---|---|
| DOM7h-22 | MKGK | F | DYWG | Q | GTLV | T | VSS |
| DOM7h-23 | ---- | F | DYWG | Q | GTLV | T | VSS |
| DOM7h-24 | ---- | F | DYWG | Q | GTLV | T | VSS |
| DOM7h-25 | ---- | F | DYWG | Q | GTLV | T | VSS |
| DOM7h-26 | ---- | F | DYWG | Q | GTLV | T | VSS |
| DOM7h-21 | D--- | F | DYWG | Q | GTLV | T | VSS |
| DOM7h-27 | ---- | F | DYWG | Q | GTLV | T | VSS |

FIG. 1E

VKs selected vs HSA and RSA

| Kabat_Numbering | 5 | 10 | 15 | 20 | 25 | 30 | 35 |
|---|---|---|---|---|---|---|---|
| DOM7h-8 | D I Q M T | Q S P S S | L S A S V | G D R V T | I T C R A | S Q S I | S S Y L N W |
| DOM7r-13 | D I Q M T | Q S P S S | L S A S V | G D R V T | I T C R A | S Q H I | H R E L R W |
| DOM7r-14 | D I Q M T | Q S P S S | L S A S V | G D R V T | I T C R A | S Q H I | H R E L R W |

| Kabat_Numbering | 40 | 45 | 50 | 55 | 60 | 65 | 70 |
|---|---|---|---|---|---|---|---|
| DOM7h-8 | Y Q Q K P | G K A P K | L L I Y R | N S P L Q | S G V P | S R F S G | S G S G T D |
| DOM7r-13 | Y Q Q K P | G K A P K | L L I Y Q | A S R L Q | S G V P | S R F S G | S G S G T D |
| DOM7r-14 | Y Q Q K P | G K A P K | L L I Y Q | A S R L Q | S G V P | S R F S G | S G S G T D |

| Kabat_Numbering | 75 | 80 | 85 | 90 | 95 | 100 | 105 |
|---|---|---|---|---|---|---|---|
| DOM7h-8 | F T L T I | S S L Q P | E D F A T | Y Y C Q Q | T Y R V P | P T F G | Q G T K V E |
| DOM7r-13 | F T L T I | S S L Q P | E D F A T | Y Y C Q Q | K Y L P P | Y T F G | Q G T K V E |
| DOM7r-14 | F T L T I | S S L Q P | E D F A T | Y Y C Q Q | R Y R V P | Y T F G | Q G T K V E |

| Kabat_Numbering | |
|---|---|
| DOM7h-8 | I K R |
| DOM7r-13 | I K R |
| DOM7r-14 | I K R |

(i) vector diagrams

FIG. 2C (ii) amino acid and nucleic acid sequence of human IL-1ra, dAb fusions IL-1raMSA16

```
  1   R   P   S   G   R   K   S   S   K   M   Q   A   F   R   I   W   D   V   N   Q
  1   AGGCCTTCTGGGAGAAAATCCAGCAAGATGCAAGCCTTCAGAATCTGGGATGTTAACCAG

21   K   T   F   Y   L   R   N   N   Q   L   V   A   G   Y   L   Q   G   P   N   V
 61   AAGACCTTCTATCTGAGGAACAACCAACTAGTTGCCGGATACTTGCAAGGACCAAATGTC

41   N   L   E   E   K   I   D   V   V   P   I   E   P   H   A   L   F   L   G   I
121   AATTTAGAAGAAAAGATAGATGTGGTACCCATTGAGCCTCATGCTCTGTTCTTGGGAATC

61   H   G   G   K   M   C   L   S   C   V   K   S   G   D   E   T   R   L   Q   L
181   CATGGAGGGAAGATGTGCCTGTCCTGTGTCAAGTCTGGTGATGAGACCAGACTCCAGCTG

81   E   A   V   N   I   T   D   L   S   E   N   R   K   Q   D   K   R   F   A   F
241   GAGGCAGTTAACATCACTGACCTGAGCGAGAACAGAAAGCAGGACAAGCGCTTCGCCTTC

101   I   R   S   D   S   G   P   T   T   S   F   E   S   A   A   C   P   G   W   F
301   ATCCGCTCAGACAGTGGCCCCACCACCAGTTTTGAGTCTGCCGCCTGCCCCGGTTGGTTC

121   L   C   T   A   M   E   A   D   Q   P   V   S   L   T   N   M   P   D   E   G
361   CTCTGCACAGCGATGGAAGCTGACCAGCCCGTCAGCCTCACCAATATGCCTGACGAAGGC

141   V   M   V   T   K   F   Y   F   Q   E   D   E   S   S   G   G   G   G   S   G
421   GTCATGGTCACCAAATTCTACTTCCAGGAGGACGAGAGCTCAGGTGGAGGCGGTTCAGGC

161   G   G   S   G   G   G   S   G   G   G   S   G   G   G   S   T
481   GGAGGTGGCAGCGGCGGTGGCGGGTCAGGTGGTGGCGGAAGCGGCGGTGGCGGGTCGACG

181   D   I   Q   M   T   Q   S   P   S   S   L   S   A   S   V   G   D   R   V   T
541   GACATCCAGATGACCCAGTCTCCATCCTCCCTGTCTGCATCTGTAGGAGACCGTGTCACC

201   I   T   C   R   A   S   Q   S   I   I   K   H   L   K   W   Y   Q   Q   K   P
601   ATCACTTGCCGGGCAAGTCAGAGCATTATTAAGCATTTAAAGTGGTACCAGCAGAAACCA

221   G   K   A   P   K   L   L   I   Y   G   A   S   R   L   Q   S   G   V   P   S
661   GGGAAAGCCCCTAAGCTCCTGATCTATGGTGCATCCCGGTTGCAAAGTGGGGTCCCATCA

241   R   F   S   G   S   G   S   G   T   D   F   T   L   T   I   S   S   L   Q   P
721   CGTTTCAGTGGCAGTGGATCTGGGACAGATTTCACTCTCACCATCAGCAGTCTGCAACCT
```

FIG. 2D

```
261  E  D  F  A  T  Y  Y  C  Q  Q  G  A  R  W  P  Q  T  F  G  Q
781  GAAGATTTTGCTACGTACTACTGTCAACAGGGGGCTCGGTGGCCTCAGACGTTCGGCCAA

281  G  T  K  V  E  I  K  R  A  A  A  -  -
841  GGGACCAAGGTGGAAATCAAACGGGCGGCCGCATAATAA
```

MSA16IL-1ra        FIG. 2E

```
  1    S   T   D   I   Q   M   T   Q   S   P   S   S   L   S   A   S   V   G   D   R
  1    TCGACGGACATCCAGATGACCCAGTCTCCATCCTCCCTGTCTGCATCTGTAGGAGACCGT

21    V   T   I   T   C   R   A   S   Q   S   I   I   K   H   L   K   W   Y   Q   Q
 61    GTCACCATCACTTGCCGGGCAAGTCAGAGCATTATTAAGCATTTAAAGTGGTACCAGCAG

41    K   P   G   K   A   P   K   L   L   I   Y   G   A   S   R   L   Q   S   G   V
121    AAACCAGGGAAAGCCCCTAAGCTCCTGATCTATGGTGCATCCCGGTTGCAAAGTGGGGTC

61    P   S   R   F   S   G   S   G   S   G   T   D   F   T   L   T   I   S   S   L
181    CCATCACGTTTCAGTGGCAGTGGATCTGGGACAGATTTCACTCTCACCATCAGCAGTCTG

81    Q   P   E   D   F   A   T   Y   Y   C   Q   Q   G   A   R   W   P   Q   T   F
241    CAACCTGAAGATTTTGCTACGTACTACTGTCAACAGGGGGCTCGGTGGCCTCAGACGTTC

101    G   Q   G   T   K   V   E   I   K   R   A   A   A   S   G   G   G   G   S   G
301    GGCCAAGGGACCAAGGTGGAAATCAAACGGGCGGCCGCAAGCGGTGGAGGCGGTTCAGGC

121    G   G   S   G   G   G   G   S   G   G   G   S   G   G   G   S   R
361    GGAGGTGGCAGCGGCGGTGGCGGGTCAGGTGGTGGCGGAAGCGGCGGTGGCGGCTCGAGG

141    P   S   G   R   K   S   S   K   M   Q   A   F   R   I   W   D   V   N   Q   K
421    CCCTCTGGGAGAAAATCCAGCAAGATGCAAGCCTTCAGAATCTGGGATGTTAACCAGAAG

161    T   F   Y   L   R   N   N   Q   L   V   A   G   Y   L   Q   G   P   N   V   N
481    ACCTTCTATCTGAGGAACAACCAACTAGTTGCCGGATACTTGCAAGGACCAAATGTCAAT

181    L   E   E   K   I   D   V   V   P   I   E   P   H   A   L   F   L   G   I   H
541    TTAGAAGAAAAGATAGATGTGGTACCCATTGAGCCTCATGCTCTGTTCTTGGGAATCCAT

201    G   G   K   M   C   L   S   C   V   K   S   G   D   E   T   R   L   Q   L   E
601    GGAGGGAAGATGTGCCTGTCCTGTGTCAAGTCTGGTGATGAGACCAGACTCCAGCTGGAG

221    A   V   N   I   T   D   L   S   E   N   R   K   Q   D   K   R   F   A   F   I
661    GCAGTTAACATCACTGACCTGAGCGAGAACAGAAAGCAGGACAAGCGCTTCGCCTTCATC

241    R   S   D   S   G   P   T   T   S   F   E   S   A   A   C   P   G   W   F   L
721    CGCTCAGACAGTGGCCCCACCACCAGTTTTGAGTCTGCCGCCTGCCCCGGTTGGTTCCTC
```

FIG. 2F

```
261  C  T  A  M  E  A  D  Q  P  V  S  L  T  N  M  P  D  E  G  V
781  TGCACAGCGATGGAAGCTGACCAGCCCGTCAGCCTCACCAATATGCCTGACGAAGGCGTC

281  M  V  T  K  F  Y  F  Q  E  D  E  -  -
841  ATGGTCACCAAATTCTACTTCCAGGAGGACGAGTAATAA
```

DummyIL-1ra  FIG. 2G

```
  1    S   T   D   I   Q   M   T   Q   S   P   S   S   L   S   A   S   V   G   D   R
  1    TCGACGGACATCCAGATGACCCAGTCTCCATCCTCCCTGTCTGCATCTGTAGGAGACCGT

21    V   T   I   T   C   R   A   S   Q   S   I   S   S   Y   L   N   W   Y   Q   Q
 61    GTCACCATCACTTGCCGGGCAAGTCAGAGCATTAGCAGCTATTTAAATTGGTACCAGCAG

41    K   P   G   K   A   P   K   L   L   I   Y   A   A   S   S   L   Q   S   G   V
121    AAACCAGGGAAAGCCCCTAAGCTCCTGATCTATGCTGCATCCAGTTTGCAAAGTGGGGTC

61    P   S   R   F   S   G   S   G   S   G   T   D   F   T   L   T   I   S   S   L
181    CCATCACGTTTCAGTGGCAGTGGATCTGGGACAGATTTCACTCTCACCATCAGCAGTCTG

81    Q   P   E   D   F   A   T   Y   Y   C   Q   Q   S   Y   S   T   P   N   T   F
241    CAACCTGAAGATTTTGCTACGTACTACTGTCAACAGAGTTACAGTACCCCTAATACGTTC

101    G   Q   G   T   K   V   E   I   K   R   A   A   A   S   G   G   G   G   S   G
301    GGCCAAGGGACCAAGGTGGAAATCAAACGGGCGGCCGCAAGCGGTGGAGGCGGTTCAGGC

121    G   G   G   S   G   G   G   G   S   G   G   G   G   S   G   G   G   G   S   R
361    GGAGGTGGCAGCGGCGGTGGCGGGTCAGGTGGTGGCGGAAGCGGCGGTGGCGGCTCGAGG

141    P   S   G   R   K   S   S   K   M   Q   A   F   R   I   W   D   V   N   Q   K
421    CCCTCTGGGAGAAAATCCAGCAAGATGCAAGCCTTCAGAATCTGGGATGTTAACCAGAAG

161    T   F   Y   L   R   N   N   Q   L   V   A   G   Y   L   Q   G   P   N   V   N
481    ACCTTCTATCTGAGGAACAACCAACTAGTTGCCGGATACTTGCAAGGACCAAATGTCAAT

181    L   E   E   K   I   D   V   V   P   I   E   P   H   A   L   F   L   G   I   H
541    TTAGAAGAAAAGATAGATGTGGTACCCATTGAGCCTCATGCTCTGTTCTTGGGAATCCAT

201    G   G   K   M   C   L   S   C   V   K   S   G   D   E   T   R   L   Q   L   E
601    GGAGGGAAGATGTGCCTGTCCTGTGTCAAGTCTGGTGATGAGACCAGACTCCAGCTGGAG

221    A   V   N   I   T   D   L   S   E   N   R   K   Q   D   K   R   F   A   F   I
661    GCAGTTAACATCACTGACCTGAGCGAGAACAGAAAGCAGGACAAGCGCTTCGCCTTCATC

241    R   S   D   S   G   P   T   T   S   F   E   S   A   A   C   P   G   W   F   L
721    CGCTCAGACAGTGGCCCCACCACCAGTTTTGAGTCTGCCGCCTGCCCCGGTTGGTTCCTC
```

FIG. 2H

```
261   C  T  A  M  E  A  D  Q  P  V  S  L  T  N  M  P  D  E  G  V
781   TGCACAGCGATGGAAGCTGACCAGCCCGTCAGCCTCACCAATATGCCTGACGAAGGCGTC

281   M  V  T  K  F  Y  F  Q  E  D  -  -
841   ATGGTCACCAAATTCTACTTCCAGGAGGACGAGTAATAA
```

*(i) HeLa IL-8 assay*

*(ii) HeLa IL-8 bioassay results for MSAIL-1ra orientations*

Example biacore data for clone DOM7h-1

FIG. 6A (contd.)

Report

|  | ka (1/Ms) | kd (1/s) | Rmax (RU) | RI (RU) | Conc of analyte |
|---|---|---|---|---|---|
| 12.05.04 offrate, onrat Fc=2-3 | 5.63e4 | 0.0539 | 12.7 | 160 | 2000n |
| 12.05.04 offrate, onrat Fc=2-4 | 1.49e5 | 0.0523 | 39.3 | 117 | 1000n |
| 12.05.04 offrate, onrat Fc=2-5 | 1.12e5 | 0.0481 | 80.1 | 58 | 500n |
| 12.05.04 offrate, onrat Fc=2-6 | 5.01e4 | 0.0486 | 136 | 40.6 | 250n |

|  | KA (1/M) | KD (M) | Req (RU) | kobs (1/s) | Chi2 |
|---|---|---|---|---|---|
|  |  |  |  |  | 0.12 |
| 12.05.04 offrate,onrat Fc=2-3 | 1.05e6 | 9.57e-7 | 8.59 | 0.167 |  |
| 12.05.04 offrate,onrat Fc=2-4 | 2.85e6 | 3.51e-7 | 29.1 | 0.201 |  |
| 12.05.04 offrate,onrat Fc=2-5 | 2.33e6 | 4.29e-7 | 43.1 | 0.104 |  |
| 12.05.04 offrate,onrat Fc=2-6 | 1.03e6 | 9.7e-7 | 27.8 | 0.0611 |  |

Parameters

|  | ka | T(ka) | Rmax | T(Rmax) | Conc | t0 | kd |
|---|---|---|---|---|---|---|---|
| 12.05.04 offrate, onrat Fc=2-3 | 5.63E+04 | 10.7 | 12.7 | 28.9 | 2000n | 91.5 | 0.0539 |
| 12.05.04 offrate, onrat Fc=2-4 | 1.49E+05 | 40.3 | 39.3 | 114 | 1000n | 91.5 | 0.0523 |
| 12.05.04 offrate, onrat Fc=2-5 | 1.12E+05 | 35.1 | 80.1 | 68.1 | 500n | 91.5 | 0.0481 |
| 12.05.04 offrate, onrat Fc=2-6 | 5.01E+04 | 5.32 | 136 | 6.21 | 250n | 91.5 | 0.0486 |

|  | RI | T(RI) |
|---|---|---|
| 12.05.04 offrate, onrat Fc=2-3 | 160 | 632 |
| 12.05.04 offrate, onrat Fc=2-4 | 117 | 442 |
| 12.05.04 offrate, onrat Fc=2-5 | 58 | 257 |
| 12.05.04 offrate, onrat Fc=2-6 | 40.6 | 198 |

Example biacore data for clone DOM7h-7
7h7 on HSA

FIG. 6B (contd.)

Report

|  | ka (1/Ms) | kd (1/s) | Rmax (RU) | RI (RU) | Conc of analyte |
|---|---|---|---|---|---|
| 12.05.04 offrate, onra Fc=2- 41 | 11 | 0.107 | 6.32e3 | 196 | 5000n |
| 12.05.04 offrate, onra Fc=2- 42 | 2.35e3 | 0.106 | 60.9 | 185 | 3000n |
| 12.05.04 offrate, onra Fc=2- 43 | 2.51e5 | 0.108 | 39 | 140 | 2000n |
| 12.05.04 offrate, onra Fc=2- 44 | 6.23e5 | 0.105 | 46.2 | 132 | 1000n |
| 12.05.04 offrate, onra Fc=2- 45 | 3.02e5 | 0.103 | 106 | 57.8 | 500n |
| 12.05.04 offrate, onra Fc=2- 46 | 2.83e5 | 0.0998 | 122 | 44 | 250n |
| 12.05.04 offrate, onra Fc=2- 47 | 1.43e5 | 0.0946 | 181 | 29 | 125n |
| 12.05.04 offrate, onra Fc=2- 48 | 5.01e5 | 0.1 | 62.8 | 26 | 62.5n |

|  | KA (1/M) | KD (M) | Req (RU) | kobs (1/s) | Chi2 |
|---|---|---|---|---|---|
|  |  |  |  |  | 0.542 |
| 12.05.04 offrate, onrat Fc=2- 41 | 103 | 9.71e-3 | 3.25 | 0.107 |  |
| 12.05.04 offrate, onrat Fc=2- 42 | 2.21e4 | 4.51e-5 | 3.79 | 0.113 |  |
| 12.05.04 offrate, onrat Fc=2- 43 | 2.33e6 | 4.3e-7 | 32.1 | 0.61 |  |
| 12.05.04 offrate, onrat Fc=2- 44 | 5.93e6 | 1.69e-7 | 39.6 | 0.728 |  |
| 12.05.04 offrate, onrat Fc=2- 45 | 2.93e6 | 3.41e-7 | 63 | 0.254 |  |
| 12.05.04 offrate, onrat Fc=2- 46 | 2.83e6 | 3.53e-7 | 50.7 | 0.171 |  |
| 12.05.04 offrate, onrat Fc=2- 47 | 1.51e6 | 6.62e-7 | 28.8 | 0.112 |  |
| 12.05.04 offrate, onrat Fc=2- 48 | 5.01e6 | 2e-7 | 15 | 0.131 |  |

Example biacore data for clone DOM7r-1

FIG. 6C (contd.)

Report

|  | ka (1/Ms) | kd (1/s) | Rmax (RU) | RI (RU) | Conc of analyte |
|---|---|---|---|---|---|
|  |  |  |  |  |  |
| 7r1, 7r3, 7r8, 7r13, 7 Fc=3-1 | 3.23e6 | 0.0345 | 40.8 | 53 | 25n |
| 7r1, 7r3, 7r8, 7r13, 7 Fc=3-2 | 2.89e6 | 0.0344 | 45.1 | 39.9 | 20n |
| 7r1, 7r3, 7r8, 7r13, 7 Fc=3-3 | 2.52e6 | 0.0331 | 52.8 | 34.8 | 15n |
| 7r1, 7r3, 7r8, 7r13, 7 Fc=3-4 | 2.87e6 | 0.0316 | 53.5 | 30.5 | 10n |
| 7r1, 7r3, 7r8, 7r13, 7 Fc=3-5 | 1.93e6 | 0.0316 | 79.8 | 27.1 | 5n |

|  | KA (1/M) | KD (M) | Req (RU) | kobs (1/s) | Chi2 |
|---|---|---|---|---|---|
|  |  |  |  |  | 0.0252 |
| 7r1, 7r3, 7r8, 7r13, 7 Fc=3-1 | 9.35e7 | 1.07e-8 | 28.5 | 0.115 |  |
| 7r1, 7r3, 7r8, 7r13, 7 Fc=3-2 | 8.41e7 | 1.19e-8 | 28.3 | 0.0923 |  |
| 7r1, 7r3, 7r8, 7r13, 7 Fc=3-3 | 7.62e7 | 1.31e-8 | 28.2 | 0.071 |  |
| 7r1, 7r3, 7r8, 7r13, 7 Fc=3-4 | 9.07e7 | 1.1e-8 | 25.5 | 0.0603 |  |
| 7r1, 7r3, 7r8, 7r13, 7 Fc=3-5 | 6.12e7 | 1.63e-8 | 18.7 | 0.0413 |  |

Parameters

|  | ka | T(ka) | Rmax | T(Rmax) | Conc | t0 | kd |
|---|---|---|---|---|---|---|---|
|  |  |  |  |  |  |  |  |
| 7r1, 7r3, 7r8, 7r13, 7 Fc=3-1 | 3.23E+06 | 58.2 | 40.8 | 138 | 25n | 87.5 | 0.0345 |
| 7r1, 7r3, 7r8, 7r13, 7 Fc=3-2 | 2.89E+06 | 42.9 | 45.1 | 82.9 | 20n | 87.5 | 0.0344 |
| 7r1, 7r3, 7r8, 7r13, 7 Fc=3-3 | 2.52E+06 | 27.6 | 52.8 | 43 | 15n | 87.5 | 0.0331 |
| 7r1, 7r3, 7r8, 7r13, 7 Fc=3-4 | 2.87E+06 | 18.3 | 53.5 | 25.6 | 10n | 87.5 | 0.0316 |
| 7r1, 7r3, 7r8, 7r13, 7 Fc=3-5 | 1.93E+06 | 3.91 | 79.8 | 4.38 | 5n | 87.5 | 0.0316 |

|  | RI | T(RI) |
|---|---|---|
|  |  |  |
| 7r1, 7r3, 7r8, 7r13, 7 Fc=3-1 | 53 | 488 |
| 7r1, 7r3, 7r8, 7r13, 7 Fc=3-2 | 39.9 | 383 |
| 7r1, 7r3, 7r8, 7r13, 7 Fc=3-3 | 34.8 | 348 |
| 7r1, 7r3, 7r8, 7r13, 7 Fc=3-4 | 30.5 | 312 |

FIG. 7

AFFINITIES OF ANTI-SA dAbs

| dAB | Scaffold | Affinity (KD) | | |
|---|---|---|---|---|
| | | Mouse serum albumin | Rat serum albumin | Human serum albumin |
| DOM7h-1 | Vκ | + | + | 800 nM |
| DOM7h-2 | Vκ | + | + | 70 nM |
| DOM7h-7 | Vκ | + | + | 400 nM |
| DOM7r-3 | Vκ | + | 12 nM | - |
| DOM7h-8 | Vκ | 200 nM | 120 nM | 70 nM |
| DOM7r-16 | Vκ | 1 μM | 1 μM | - |
| DOM7m-16 | Vκ | 50 nM | ND | + |
| DOM7m-26 | Vκ | 60 nM | ND | + |
| DOM7r-1 | Vκ | - | 15 nM | - |
| DOM7r-8 | Vκ | 40 nM | 20 nM | - |
| DOM7r-13 | Vκ | - | 80 nM | - |
| DOM7r-14 | Vκ | - | 50 nM | - |
| DOM7r-27 | $V_H$ | 250 nM | 250 nM | - |
| DOM7r-31 | $V_H$ | 1 μM | 5 μM | + (10 μM estimate) |
| DOM7h-22 | $V_H$ | - | - | 60 nM |
| DOM7h-23 | $V_H$ | - | - | 900 nM |
| DOM7h-26 | $V_H$ | - | - | 300 nM |

- No detectable binding
+ detectable binding but weak (estimated KD > 5 μM)
ND not determined

FIG. 8A

```
   1 atttctttat aaaccacaac tctgggcccg caatggcagt ccactgcctt gctgcagtca
  61 cagaatggaa atctgcagag gcctccgcag tcacctaatc actctcctcc tcttcctgtt
 121 ccattcagag acgatctgcc gaccctctgg gagaaaatcc agcaagatgc aagccttcag
 181 aatctgggat gttaaccaga agaccttcta tctgaggaac aaccaactag ttgctggata
 241 cttgcaagga ccaaatgtca atttagaaga aagatagat gtggtaccca ttgagcctca
 301 tgctctgttc ttgggaatcc atggagggaa gatgtgcctg tcctgtgtca agtctggtga
 361 tgagaccaga ctccagctgg aggcagttaa catcactgac ctgagcgaga acagaaagca
 421 ggacaagcgc ttcgccttca tccgctcaga cagcggcccc accaccagtt ttgagtctgc
 481 cgcctgcccc ggttggttcc tctgcacagc gatggaagct gaccagcccg tcagcctcac
 541 caatatgcct gacgaaggcg tcatggtcac caaattctac ttccaggagg acgagtagta
 601 ctgcccaggc ctgcctgttc ccattcttgc atggcaagga ctgcagggac tgccagtccc
 661 cctgccccag ggctcccggc tatgggggca ctgaggacca gccattgagg ggtggaccct
 721 cagaaggcgt cacaagaacc tggtcacagg actctgcctc ctcttcaact gaccagcctc
 781 catgctgcct ccagaatggt ctttctaatg tgtgaatcag agcacagcag ccctgcaca
 841 aagcccttcc atgtcgcctc tgcattcagg atcaaacccc gaccacctgc ccaacctgct
 901 ctcctcttgc cactgcctct tcctccctca ttccaccttc ccatgccctg gatccatcag
 961 gccacttgat gaccccaac caagtggctc ccacaccctg ttttacaaaa aagaaaagac
1021 cagtccatga gggaggtttt taagggtttg tggaaaatga aaattaggat ttcatgattt
1081 tttttttttca gtccccgtga aggagagccc ttcatttgga gattatgttc tttcggggag
1141 aggctgagga cttaaaatat tcctgcattt gtgaaatgat ggtgaaagta agtggtagct
1201 tttcccttct tttcttctt tttttgtgat gtcccaactt gtaaaaatta aaagttatgg
1261 tactatgtta gccccataat ttttttttc cttttaaaac acttccataa tctggactcc
1321 tctgtccagg cactgctgcc cagcctccaa gctccatctc cactccagat tttttacagc
1381 tgcctgcagt actttaccctc ctatcagaag tttctcagct cccaaggctc tgagcaaatg
1441 tggctcctgg gggttctttc ttcctctgct gaaggaataa attgctcctt gacattgtag
1501 agcttctggc acttggagac ttgtatgaaa gatggctgtg cctctgcctg tctccccac
1561 cgggctggga gctctgcaga gcaggaaaca tgactcgtat atgtctcagg tccctgcagg
1621 gccaagcacc tagcctcgct cttggcaggt actcagcgaa tgaatgctgt atatgttggg
1681 tgcaaagttc cctacttcct gtgacttcag ctctgtttta caataaaatc ttgaaaatgc
1741 ctaaaaaaaa aaaaaaaaa
```

FIG. 8B

MEICRGLRSH LITLLLFLFH SETICRPSGR KSSKMQAFRI WDVNQKTFYL
RNNQLVAGYL QGPNVNLEEK IDVVPIEPHA LFLGIHGGKM CLSCVKSGDE
TRLQLEAVNI TDLSENRKQD KRFAFIRSDS GPTTSFESAA CPGWFLCTAM
EADQPVSLTN MPDEGVMVTK FYFQEDE

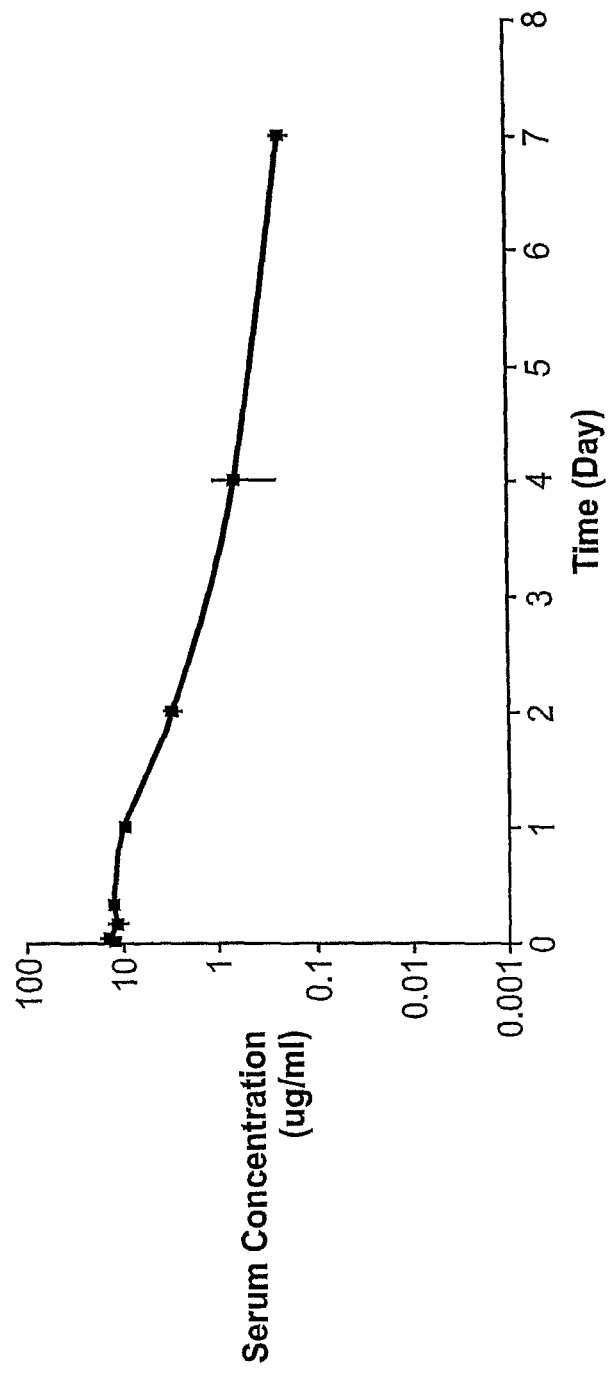

FIG. 10

| Kabat_Numbering | 5 | 10 | 15 | 20 | 25 | 30 | 35 |
|---|---|---|---|---|---|---|---|
| DOM7r-15 | DIQM | TQSPS | SLSAS | VGDRV | TITCR | ASQSI | GRRLK W |
| DOM7r-16 | DIQM | TQSPS | SLSAS | VGDRV | TITCR | ASQKI | YKNLR W |
| DOM7r-17 | DIQM | TQSPS | SLSAS | VGDRV | TITCR | ASQKI | YNNLR W |
| DOM7r-18 | DIQM | TQSPS | SLSAS | VGDRV | TITCR | ASQWI | YKSLG W |
| DOM7r-19 | DIQM | TQSPS | SLSAS | VGDRV | TITCR | ASQWI | YRHLR W |

| Kabat_Numbering | 40 | 45 | 50 | 55 | 60 | 65 | 70 |
|---|---|---|---|---|---|---|---|
| DOM7r-15 | YQQK | PGAAP | RLLIY | RTSWL | QSGVP | SRFSG | SGSGT D |
| DOM7r-16 | YQQK | PGKAP | KLLIY | NSSIL | QSGVP | SRFSG | SGSGT D |
| DOM7r-17 | YQQK | PGKAP | KLLIY | NTSIL | QSGVP | SRFSG | SGSGT D |
| DOM7r-18 | YQQK | PGKAP | KLLIY | QSSLL | QSGVP | SRFSG | SGSGT D |
| DOM7r-19 | YQQK | PGKAP | KLLIY | DASRL | QSGVP | TRFSG | SGSGT D |

| Kabat_Numbering | 75 | 80 | 85 | 90 | 95 | 100 | 105 |
|---|---|---|---|---|---|---|---|
| DOM7r-15 | FTLT | ISSLQ | PEDFA | TYYCQ | QTSQW | PHTFG | QGTKV E |
| DOM7r-16 | FTLT | ISSLQ | PEDFA | TYYCQ | QRYLS | PYTFG | QGTKV E |
| DOM7r-17 | FTLT | ISSLQ | PEDFA | TYYCQ | QRWRA | PYTFG | QGTKV E |
| DOM7r-18 | FTLT | ISSLQ | PEDFA | TYYCQ | QYHQM | PRTFG | QGTKV E |
| DOM7r-19 | FTLT | ISSLQ | PEDFA | TYYCQ | QTHNP | PKTFG | QGTKV E |

| Kabat_Numbering | |
|---|---|
| DOM7r-15 | IKR |
| DOM7r-16 | IKR |
| DOM7r-17 | IKR |
| DOM7r-18 | IKR |
| DOM7r-19 | IKR |

FIG. 11A

| Kabat_Numbering | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 |
|---|---|---|---|---|---|---|---|---|---|---|---|---|---|---|---|---|---|---|---|---|---|---|---|---|---|---|---|---|---|---|---|---|---|---|---|
| DOM7r-20 | E | V | Q | L | L | E | S | G | G | G | L | V | Q | P | G | G | S | L | R | L | S | C | A | A | S | G | F | T | F | W | P | Y | T | M | S |
| DOM7r-21 | E | V | Q | L | L | E | S | G | G | G | L | V | Q | P | G | G | S | L | R | L | S | C | A | A | S | G | F | T | F | W | P | Y | T | M | S |
| DOM7r-22 | E | V | Q | L | L | E | S | G | G | G | L | V | Q | P | G | G | S | L | R | L | S | C | A | A | S | G | F | T | F | W | P | Y | T | M | S |
| DOM7r-23 | E | V | Q | L | L | E | S | G | G | G | L | V | Q | P | G | G | S | L | R | L | S | C | A | A | S | G | F | T | F | W | P | Y | T | M | S |
| DOM7r-24 | E | V | Q | L | L | E | S | G | G | G | L | V | Q | P | G | G | S | L | R | L | S | C | A | A | S | G | F | T | F | W | P | Y | T | M | S |
| DOM7r-25 | E | V | Q | L | L | E | S | G | G | G | L | V | Q | P | G | G | S | L | R | L | S | C | A | A | S | G | F | T | F | W | P | Y | T | M | S |
| DOM7r-26 | E | V | Q | L | L | E | S | G | G | G | L | V | Q | P | G | G | S | L | R | L | S | C | A | A | S | G | F | T | F | W | P | Y | T | M | S |
| DOM7r-27 | E | V | Q | L | L | E | S | G | G | G | L | V | Q | P | G | G | S | L | R | L | S | C | A | A | S | G | F | T | F | M | A | Y | Q | M | A |
| DOM7r-28 | E | V | Q | L | L | E | S | G | G | G | L | V | Q | P | G | G | S | L | R | L | S | C | A | A | S | G | F | T | F | K | D | Y | D | M | T |
| DOM7r-29 | E | V | Q | L | L | E | S | G | G | G | L | V | Q | P | G | G | S | L | R | L | S | C | A | A | S | G | F | T | F | H | D | Y | V | M | G |
| DOM7r-30 | E | V | Q | L | L | E | S | G | G | G | L | V | Q | P | G | G | S | L | R | L | S | C | A | T | S | G | F | T | F | R | R | Y | R | M | G |
| DOM7r-31 | E | V | Q | L | L | E | S | G | G | G | L | V | Q | P | G | G | S | L | R | L | S | C | A | A | S | G | F | T | F | M | W | D | K | M | G |
| DOM7r-32 | E | V | Q | L | L | E | S | G | G | G | L | V | Q | P | G | G | S | L | R | L | S | C | A | A | S | G | F | T | F | W | A | Y | P | M | S |

FIG. 11A(contd.)

| Kabat_Numbering | | | | 40 | | | | 45 | | | | | 50 | | | | 54 | | | | 59 | | | | 64 | | | | 69 |
|---|---|---|---|---|---|---|---|---|---|---|---|---|---|---|---|---|---|---|---|---|---|---|---|---|---|---|---|---|---|
| DOM7r-20 | W | V | R | Q | A | P | G | K | G | L | E | W | V | S | T | I | S | P | F | G | S | T | Y | Y | A | D | S | V | K | G | R | F | T | I |
| DOM7r-21 | W | V | R | Q | A | P | G | K | G | L | E | W | V | S | T | I | S | P | F | G | S | T | Y | Y | A | D | S | V | K | G | R | F | T | I |
| DOM7r-22 | W | V | R | Q | A | P | G | K | G | L | E | W | V | S | T | I | S | P | F | G | S | T | Y | Y | A | D | S | V | K | G | R | F | T | I |
| DOM7r-23 | W | V | R | Q | A | P | G | K | G | L | E | W | V | S | T | I | S | P | F | G | S | T | Y | Y | A | D | S | V | K | G | R | F | T | I |
| DOM7r-24 | W | V | R | Q | A | P | G | K | G | L | E | W | V | S | T | I | S | P | F | G | S | T | Y | Y | A | D | S | V | K | G | R | F | T | I |
| DOM7r-25 | W | V | R | Q | A | P | G | K | G | L | E | W | V | S | T | I | S | P | F | G | S | T | Y | Y | A | D | S | V | K | G | R | F | T | I |
| DOM7r-26 | W | V | R | Q | A | P | G | K | G | L | E | W | V | S | T | I | S | P | F | G | S | T | Y | Y | A | D | S | V | K | G | R | F | T | I |
| DOM7r-27 | W | V | R | Q | A | P | G | K | G | L | E | W | V | S | T | I | S | P | F | T | F | S | L | W | Y | A | D | S | V | K | G | R | F | T | I |
| DOM7r-28 | W | V | R | Q | A | P | G | K | G | L | E | W | V | S | M | I | S | S | S | G | L | W | T | Y | A | D | S | V | K | G | R | F | T | I |
| DOM7r-29 | W | V | R | Q | A | P | G | K | G | L | E | W | V | S | L | I | K | P | N | G | S | P | T | Y | A | D | S | V | K | G | R | F | T | I |
| DOM7r-30 | W | A | R | Q | A | P | G | K | G | L | E | W | V | S | W | I | R | P | D | G | T | F | Y | Y | A | D | S | V | K | G | R | F | T | I |
| DOM7r-31 | W | V | R | Q | A | P | G | K | G | L | E | W | V | S | F | I | G | R | E | G | Y | G | F | Y | A | D | S | V | K | G | R | F | T | I |
| DOM7r-32 | W | V | R | Q | A | P | G | K | G | L | E | W | V | S | S | I | S | S | W | G | T | G | F | Y | A | D | S | V | K | G | R | F | T | I |
| DOM7r-33 | W | V | R | Q | A | P | G | K | G | L | E | W | V | S | S | I | S | S | W | G | T | G | F | Y | A | D | S | V | K | G | R | F | T | I |

FIG. 11A(contd.)

| Kabat_Numbering | 74 | | | | | 79 | | | | | 82 | | | | 86 | | | | | 91 | | | | | 96 | | | | | | | | 10 |
|---|---|---|---|---|---|---|---|---|---|---|---|---|---|---|---|---|---|---|---|---|---|---|---|---|---|---|---|---|---|---|---|---|---|
| DOM7r-20 | S | R | D | N | S | K | N | T | L | Y | L | Q | M | N | S | L | R | A | E | D | T | A | V | Y | Y | C | A | K | G | G | K | D | F | - | - | - | F |
| DOM7r-21 | S | R | D | N | S | K | N | T | L | Y | L | Q | M | N | S | L | R | A | E | D | T | A | V | Y | Y | C | A | K | G | N | L | E | P | F | - | - | F |
| DOM7r-22 | S | R | D | N | S | K | N | T | L | Y | L | Q | M | N | S | L | R | A | E | D | T | A | V | Y | Y | C | A | K | K | L | S | N | G | F | - | - | F |
| DOM7r-23 | S | R | D | N | S | K | N | T | L | Y | L | Q | M | N | S | L | R | A | E | D | T | A | V | Y | Y | C | A | K | V | V | K | D | N | T | F | - | F |
| DOM7r-24 | S | R | D | N | S | K | N | T | L | Y | L | Q | M | N | S | L | R | A | E | D | T | A | V | Y | Y | C | A | K | N | T | G | G | K | Q | F | - | F |
| DOM7r-25 | S | R | D | N | S | K | N | T | L | Y | L | Q | M | N | S | L | R | A | E | D | T | A | V | Y | Y | C | A | K | K | T | G | P | S | S | F | - | F |
| DOM7r-26 | S | R | D | N | S | K | N | T | L | Y | L | Q | M | N | S | L | R | A | E | D | T | A | V | Y | Y | C | A | K | R | T | E | N | R | G | V | - | F |
| DOM7r-27 | S | R | D | N | S | K | N | T | L | Y | L | Q | M | N | S | L | R | A | E | D | T | A | V | Y | Y | C | A | K | S | D | V | L | K | T | G | - | F |
| DOM7r-28 | S | R | D | N | S | K | N | T | L | Y | L | Q | M | N | S | L | R | A | E | D | T | A | V | Y | Y | C | A | K | V | R | S | M | R | P | Y | - | F |
| DOM7r-29 | S | R | D | N | S | K | N | T | L | Y | L | Q | M | N | S | L | R | A | E | D | T | A | V | Y | Y | C | A | K | G | F | R | L | F | P | R | - | F |
| DOM7r-30 | S | R | D | N | S | K | N | T | L | Y | L | Q | M | N | S | L | R | A | E | D | T | A | V | Y | Y | C | A | K | G | R | G | R | F | N | V | - | F |
| DOM7r-31 | S | R | D | N | S | K | N | T | L | Y | L | Q | M | N | S | L | R | A | E | D | T | A | V | Y | Y | C | A | K | S | Y | M | G | D | R | F | - | F |
| DOM7r-32 | S | R | D | N | S | K | N | T | L | Y | L | Q | M | N | S | L | R | A | E | D | T | A | V | Y | Y | C | A | K | S | V | A | S | F | - | - | - | F |
| DOM7r-33 | S | R | D | N | S | K | N | T | L | Y | L | Q | M | N | S | L | R | A | E | D | T | A | V | Y | Y | C | A | K | G | G | Q | G | S | F | - | - | F |

FIG. 11B

| Kabat_Numbering | | | | | | | | 10 | | | | 10 | | | | 11 | | |
|---|---|---|---|---|---|---|---|---|---|---|---|---|---|---|---|---|---|---|
| DOM7r-20 | - | - | - | - | D | Y | W | G | Q | G | T | L | V | T | V | S | S |
| DOM7r-21 | - | - | - | - | D | Y | W | G | Q | G | T | L | V | T | V | S | S |
| DOM7r-22 | - | - | - | - | D | Y | W | G | Q | G | T | L | V | T | V | S | S |
| DOM7r-23 | - | - | - | - | D | Y | W | G | Q | G | T | L | V | T | V | S | S |
| DOM7r-24 | - | - | - | - | D | Y | W | G | Q | G | T | L | V | T | V | S | S |
| DOM7r-25 | - | - | - | - | D | Y | W | G | Q | G | T | L | V | T | V | S | S |
| DOM7r-26 | S | F | - | - | D | Y | W | G | Q | G | T | L | V | T | V | S | S |
| DOM7r-27 | L | D | G | F | D | Y | W | G | Q | G | T | L | V | T | V | S | S |
| DOM7r-28 | K | F | - | - | D | Y | W | G | Q | G | T | L | V | T | V | S | S |
| DOM7r-29 | T | F | - | - | D | Y | W | G | Q | G | T | L | V | T | V | S | S |
| DOM7r-30 | L | Q | F | - | D | Y | W | G | Q | G | T | L | V | T | V | S | S |
| DOM7r-31 | - | - | - | - | D | Y | W | G | Q | G | T | L | V | T | V | S | S |
| DOM7r-32 | - | - | - | - | D | Y | W | G | Q | G | T | L | V | T | V | S | S |
| DOM7r-33 | - | - | - | - | D | Y | W | G | Q | G | T | L | V | T | V | S | S |

FIG. 14A

1 MKIYVVATIA WILLQFSAWT TTDAVTSITL DLVNPTAGQY SSFVDKIRNN VKDPNLKYGG

61 TDIAVIGPPS KDKFLRINFQ SSRGTVSLGL KRDNLYVVAY LAMDNTNVNR AYYFKSEITS

121 AELTALFPEA TTANQKALEY TEDYQSIEKN AQITQGDKSR KELGLGIDLL LTFMEAVNKK

181 ARVVKNEARF LLIAIQMTAE VARFRYIQNL VTKNFPNKFD SDNKVIQFEV SWRKISTAIY

241 GDAKNGVFNK DYDFGFGKVR QVKDLQMGLL MYLGKPKSSN EANSTAYATT VL

FIG. 14B

1 DPNLKYGGTD IAVIGPPSRD KFLRLNFQSS RGTVSLGLKR ENLYVVAYLA MDNANVNRAY

61 YFGTEITSAE LTTLLPEATV ANQKALEYTE DYQSIEKNAK ITEGDKTRKE LGLGINLLST

121 LMDAVNKKAR VVKNEARFLL IAIQMTAEAA RFRYIQNLVT KNFPNKFNSE DKVIQFQVNW

181 SKISKAIYGD AKNGVFNKDY DFGFGKVRQV KDLQMGLLMY LGTTPNNAAD RYRAEL

FIG. 14C

1 MKIYVVATIA WILLQFSAWT TTDAVTSITL DLVNPTAGQY SSFVDKIRNN VKDPNLKYGG

61 TDIAVIGPPS KGKFLRINFQ SSRGTVSLGL KRDNLYVVAY LAMDNTNVNR AYYFRSEITS

121 AELTALFPEA TTANQKALEY TEDYQSIEKN AQITQED

FIG. 14D

1 VTSITLDLVN PTAGQYSSFV DKIRNNVKDP NLKYGGTDIA VIGPPSKEKF LRINFQSSRG

61 TVSLGLKRDN LYVVAYLAMD NTNVNRAYYF RSEITSAELT ALFPEATTAN QKALEYTEDY

121 QSIEKNAQIT QGDKSRKELG LGIDLLLTSM EAVNKKARVV KNEARFLLIA IQMTAEVARF

181 RYIQNLVTKN FPNKFDSDNK VIQFEVSWRK ISTAIYGDAK NGVFNKDYDF GFGKVRQVKD

241 LQMGLLMYLG KPK

FIG. 14E

1 MKIYVVATIA WILLQFSAWT TTDAVTSITL DLVNPTAGQY SSFVDKIRNN VKDPNLKYGG

61 TDIAVIGPPS KEKFLRINFQ SSRGTVSLGL KRDNLYVVAY LAMDNTNVNR AYYFRSEITS

121 AESTALFPEA TTANQKALEY TEDYQSIEKN AQITQGDQSR KELGLGIDLL STSMEAVNKK

181 ARVVKDEARF LLIAIQMTAE AARFRYIQNL VIKNFPNKFN SENKVIQFEV NWKKISTAIY

241 GDAKNGVFNK DYDFGFGKVR QVKDLQMGLL MYLGKPKSSN EANSTVRHYG PLKPTLLIT

FIG. 14F

1 VTSITLDLVN PTAGQYSSFV DKIRNNVKDP NLKYGGTDIA VIGPPSKEKF LRINFQSSRG

61 TVSLGLKRDN LYVVAYLAMD NTNVNRAYYF RSEITSAELT ALFPEATTAN QKALEYTEDY

121 QSIEKNAQIT QGDKSRKELG LGIDLLLTSM EAVNKKARVV KNEARFLLIA IQMTAEAARF

181 RYIQNLVIKN FPNKFNSENK VIQFEVNWKK ISTAIYGDAK NGVFNKDYDF GFGKVRQVKD

241 LQMGLLMYLG KPK

FIG. 14G

VTSITLDLVN PTAGQYSSFV DKIRNNVKDP NLKYGGTDIA VIGPPSK(E/D)KF LRINFQSSRG

TVSLGLKRDN LYVVAYLAMD NTNVNRAYYF (R/K)SEITSAE(S/L)T ALFPEATTAN

QKALEYTEDY QSIEKNAQIT QGD(Q/K)SRKELG LGIDLL(S/L)T(S/F)M EAVNKKARVV

K(D/N)EARFLLIA IQMTAE(A/V)ARF RYIQNLV(I/T)KN FPNKF(N/D)S(E/D)NK

VIQFEV(N/S)W(K/R)K ISTAIYGDAK NGVFNKDYDF GFGKVRQVKD LQMGLLMYLG

KPKSSNEANS TVRHYGPLKP TLLIT

FIG. 15

| | Sequence |
|---|---|
| | Anti-mouse serum albumin |
| A | QVQLQESGGGLVQPGGSLRLSCEASGFTFSRFGMTWVRQAPGKGVEWV SGISSLGDSTLYADSVKGRFTISRDNAKNTLYLQMNSLKPEDTAVYYC TIGGSLNPGGQGTQVTVSS |
| B | QVQLQESGGGLVQPGNSLRLSCAASGFTFRNFGMSWVRQAPGKEPEWV SSISGSGSNTIYADSVKDRFTISRDNAKSTLYLQMNSLKPEDTAVYYC TIGGSLSRSSQGTQVTVSS |
| C | QVQLQESGGGLVQPGGSLRLTCTASGFTFSSFGMSWVRQAPGKGLEWV SAISSDSGTKNYADSVKGRFTISRDNAKKMLFLQMNSLRPEDTAVYYC VIGRGSPSSQGTQVTVSS |
| D | QVQLQESGGGLVQPGGSLRLTCTASGFTFRSFGMSWVRQAPGKGLEWV SAISADGSDKRYADSVKGRFTISRDNGKKMLTLDMNSLKPEDTAVYYC VIGRGSPASQGTQVTVSS |
| E | AVQLVESGGGLVQAGDSLRLSCVVSGTTFSSAAMGWFRQAPGKEREFV GAIKWSGTSTYYTDSVKGRFTISRDNVKNTVYLQMNNLKPEDTGVYTC AADRDRYRDRMGPMTTTDFRFWGQGTQVTVSS |
| F | QVKLEESGGGLVQTGGSLRLSCAASGRTFSSFAMGWFRQAPGREREFV ASIGSSGITTNYADSVKGRFTISRDNAKNTVYLQMNSLKPEDTGLCYC AVNRYGIPYRSGTQYQNWGQGTQVTVSS |
| G | EVQLEESGGGLVQPGGSLRLSCAASGLTFNDYAMGWYRQAPGKERDMV ATISIGGRTYYADSVKGRFTISRDNAKNTVYLQMNSLKPEDTAIYYCV AHRQTVVRGPYLLWGQGTQVTVSS |
| H | QVQLVESGGKLVQAGGSLRLSCAASGRTFSNYAMGWFRQAPGKEREFV AGSGRSNSYNYYSDSVKGRFTISRDNAKNTVYLQMNSLKPEDTAVYYC AASTNLWPRDRNLYAYWGQGTQVTVSS |
| I | EVQLVESGGGLVQAGDSLRLSCAASGRSLGIYRMGWFRQVPGKEREFV AAISWSGGTTRYLDSVKGRFTISRDSTKNAVYLQMNSLKPEDTAVYYC AVDSSGRLYWTLSTSYDYWGQGTQVTVSS |
| J | QVQLVEFGGGLVQAGDSLRLSCAASGRSLGIYKMAWFRQVPGKEREFV AAISWSGGTTRYIDSVKGRFTLSRDNTKNMVYLQMNSLKPDDTAVYYC AVDSSGRLYWTLSTSYDYWGQGTQVTVSS |
| K | EVQLVESGGGLVQAGGSLSLSCAASGRTFSPYTMGWFRQAPGKEREFL AGVTWSGSSTFYGDSVKGRFTASRDSAKNTVTLEMNSLNPEDTAVYYC AAAYGGGLYRDPRSYDYWGRGTQVTVSS |
| L | AVQLVESGGGLVQAGGSLRLSCAASGFTLDAWPIAWFRQAPGKEREGV SCIRDGTTYYADSVKGRFTISSDNANNTVYLQTNSLKPEDTAVYYCAA PSGPATGSSHTFGIYWNLRDDYDNWGQGTQVTVSS |
| M | EVQLVESGGGLVQAGGSLRLSCAASGFTFDHYTIGWFRQVPGKEREGV SCISSSDGSTYYADSVKGRFTISSDNAKNTVYLQMNTLEPDDTAVYYC AAGGLLLRVEELQASDYDWGQGIQVTVSS |
| N | AVQLVDSGGGLVQPGGSLRLSCTASGFTLDYYAIGWFRQAPGKEREGV ACISNSDGSTYYGDSVKGRFTISRDNAKTTVYLQMNSLKPEDTAVYYC ATADRHYSASHHPFADFAENSWGQGTQVTVSS |
| O | EVQLVESGGGLVQAGGSLRLSCAAYGLTFWRAAMAWFRRAPGKERELV VARNWGDGSTRYADSVKGRFTISRDNAKNTVYLQMNSLKPEDTAVYYC AAVRTYGSATYDIWGQGTQVTVSS |
| P | EVQLVESGGGLVQDGGSLRLSCIFSGRTFANYAMGWFRQAPGKEREFV AAINRNGGTTNYADALKGRFTISRDNTKNTAFLQMNSLKPDDTAVYYC AAREWPFSTIPSGWRYWGQGTQVTVSS |
| Q | DVQLVESGGGWVQPGGSLRLSCAASGPTASSHAIGWFRQAPGKEREFV VGINRGGVTRDYADSVKGRFAVSRDNVKNTVYLQMNRLKPEDSAIYIC AARPEYSFTAMSKGDMDYWGKGTLVIVSS |

BISPECIFIC FUSION ANTIBODIES WITH ENHANCED SERUM HALF-LIFE

RELATED APPLICATIONS

This application is the U.S. National stage of International Application No. PCT/GB2005/002163, filed on May 31, 2005, published in English, which claims the benefit of U.S. Provisional Patent Application No. 60/632,361, filed on Dec. 2, 2004 and the benefit of U.S. Provisional Patent Application No. 60/576,271, filed on Jun. 1, 2004. The entire teachings of the above applications are incorporated herein by reference.

BACKGROUND OF THE INVENTION

Many drugs that possess activities that could be useful for therapeutic and/or diagnostic purposes have limited value because they are rapidly eliminated from the body when administered. For example, many polypeptides that have therapeutically useful activities are rapidly cleared from the circulation via the kidney. Accordingly, a large dose must be administered in order to achieve a desired therapeutic effect. A need exists for improved therapeutic and diagnostic agents that have improved pharmacokinetic properties. Polypeptides that bind serum albumin are known in the art. (See, e.g., EP 0486525 B1 (Cemu Bioteknik AB); U.S. Pat. No. 6,267,964 B1 (Nygren et al.); WO 04/001064 A2 (Dyax, Corp.); WO 02/076489 A1 (Dyax, Corp.); WO 01/45746 (Genentech, Inc.).)

SUMMARY OF THE INVENTION

The invention relates to drug compositions (e.g., drug conjugates, noncovalent drug conjugates, drug fusions) that have improved serum half-lives. In one aspect, the invention is a drug fusion, wherein the drug fusion is a continuous polypeptide chain having the formula:

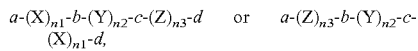

wherein

X is a polypeptide drug that has binding specificity for a first target;

Y is an immunoglobulin heavy chain variable domain ($V_H$) that has binding specificity for serum albumin, or an immunoglobulin light chain variable domain ($V_L$) that has binding specificity for serum albumin;

Z is a polypeptide drug that has binding specificity for a second target;

a, b, c and d are each independently absent or one to about 100 amino acid residues;

n1 is one to about 10;

n2 is one to about 10; and n3 is zero to about 10, with the proviso that when n1 and n2 are both one and n3 is zero, X does not comprise an antibody chain or a fragment of an antibody chain.

In some embodiments, Y comprises an amino acid sequence selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25 and SEQ ID NO:26, or an amino acid sequence selected from the group consisting of SEQ ID NO:16, SEQ ID NO:17, SEQ ID NO:18, SEQ ID NO:19, SEQ ID NO:20, SEQ ID NO:21, SEQ ID NO:22 and SEQ ID NO:23. In particular embodiments, X is IL-1ra or a functional variant of IL-1ra.

In another aspect, the drug fusion comprises a continuous polypeptide chain, said chain comprising moieties X' and Y', wherein X' is a polypeptide drug, with the proviso that X' does not comprise an antibody chain or a fragment of an antibody chain; and Y' is an immunoglobulin heavy chain variable domain ($V_H$) that has binding specificity for serum albumin, or an immunoglobulin light chain variable domain ($V_L$) that has binding specificity for serum albumin. In some embodiments, Y' comprises an amino acid sequence selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25 and SEQ ID NO:26, or an amino acid sequence selected from the group consisting of SEQ ID NO:16, SEQ ID NO:17, SEQ ID NO:18, SEQ ID NO:19, SEQ ID NO:20, SEQ ID NO:21, SEQ ID NO:22 and SEQ ID NO:23. In particular embodiments, X' is IL-1ra or a functional variant of IL-1ra.

In another aspect, the invention is a drug conjugate comprising an immunoglobulin heavy chain variable domain ($V_H$) that has binding specificity for serum albumin, or an immunoglobulin light chain variable domain ($V_L$) that has binding specificity for serum albumin, and a drug that is covalently bonded to said $V_H$ or $V_L$. In some embodiments, the immunoglobulin heavy chain variable domain comprises an amino acid sequence selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25 and SEQ ID NO:26, or an amino acid sequence selected from the group consisting of SEQ ID NO:16, SEQ ID NO:17, SEQ ID NO:18, SEQ ID NO:19, SEQ ID NO:20, SEQ ID NO:21, SEQ ID NO:22 and SEQ ID NO:23. In particular embodiments, the drug is IL-1ra or a functional variant of IL-1ra.

In another aspect, the invention is a noncovalent drug conjugate comprising an immunoglobulin heavy chain variable domain ($V_H$) that has binding specificity for serum albumin, or an immunoglobulin light chain variable domain ($V_L$) that has binding specificity for serum albumin, and a drug that is noncovalently bonded to said $V_H$ or $V_L$. In some embodiments, the immunoglobulin heavy chain variable domain comprises an amino acid sequence selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25 and SEQ ID NO:26, or an amino acid sequence selected from the group consisting of SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

The invention also provides recombinant nucleic acids and constructs that encode the drug fusions described herein, and host cells that comprise the recombinant nucleic acids and/or constructs. The invention further provides a method for producing a drug fusion comprising maintaining a host cell that comprises a recombinant nucleic acid and/or construct that encodes a drug fusion described herein under conditions suitable for expression of said recombinant nucleic acid, whereby a drug fusion is produced.

The invention also provides compositions (e.g., pharmaceutical compositions) comprising a drug composition (e.g., drug conjugate, noncovalent drug conjugate, drug fusion) of the invention. The invention also provides a method for treating an individual having a disease or disorder, such as those described herein, comprising administering to said individual a therapeutically effective amount of a drug composition (e.g., drug conjugate, noncovalent drug conjugate, drug fusion) of the invention. In some embodiments, the disease or disorder is an inflammatory disease, such as arthritis (e.g., rheumatoid arthritis). The invention also provides for use of a drug composition (e.g., drug conjugate, noncovalent drug conjugate, drug fusion) of the invention for the manufacture of a medicament for treatment of a disease or disorder, such as an inflammatory disease (e.g., arthritis (e.g., rheumatoid arthritis)). The invention also relates to a drug composition (e.g., drug conjugate, noncovalent drug conjugate, drug fusion) as described herein for use in therapy, diagnosis or prophylaxis.

BRIEF DESCRIPTION OF THE DRAWINGS

FIG. 1A is an alignment of the amino acid sequences of three $V_{KS}$ selected by binding to mouse serum albumin (MSA). The aligned amino acid sequences are from $V_{KS}$ designated MSA16, which is also referred to as DOM7m-16 (SEQ ID NO:1), MSA 12, which is also referred to as DOM7m-12 (SEQ ID NO:2), and MSA 26, which is also referred to as DOM7m-26 (SEQ ID NO:3).

FIG. 1B is an alignment of the amino acid sequences of six $V_{KS}$ selected by binding to rat serum albumin (RSA). The aligned amino acid sequences are from $V_{KS}$ designated DOM7r-1 (SEQ ID NO:4), DOM7r-3 (SEQ ID NO:5), DOM7r-4 (SEQ ID NO:6), DOM7r-5 (SEQ ID NO:7), DOM7r-7 (SEQ ID NO:8), and DOM7r-8 (SEQ ID NO:9).

FIG. 1C is an alignment of the amino acid sequences of six $V_{KS}$ selected by binding to human serum albumin (HSA). The aligned amino acid sequences are from $V_{KS}$ designated DOM7h-2 (SEQ ID NO:10), DOM7h-3 (SEQ ID NO:11), DOM7h-4 (SEQ ID NO:12), DOM7h-6 (SEQ ID NO:13), DOM7h-1 (SEQ ID NO:14), and DOM7h-7 (SEQ ID NO:15).

FIG. 1D is an alignment of the amino acid sequences of seven $V_H$s selected by binding to human serum albumin and a consensus sequence (SEQ ID NO:23). The aligned sequences are from $V_H$s designated DOM7h-22 (SEQ ID NO:16), DOM7h-23 (SEQ ID NO:17), DOM7h-24 (SEQ ID NO:18), DOM7h-25 (SEQ ID NO:19), DOM7h-26 (SEQ ID NO:20), DOM7h-21 (SEQ ID NO:21), and DOM7h-27 (SEQ ID NO:22).

FIG. 1E is an alignment of the amino acid sequences of three $V_{KS}$ selected by binding to human serum albumin and rat serum albumin. The aligned amino acid sequences are from $V_{KS}$ designated DOM7h-8 (SEQ ID NO:24), DOM7r-13 (SEQ ID NO:25), and DOM7r-14 (SEQ ID NO:26).

FIG. 2C-2D is an illustration of the nucleotide sequence (SEQ ID NO:27) encoding the IL-1raMSA16 fusion (also referred to as IL-1ra/DOM7m-16) and of the amino acid sequence (SEQ ID NO:28) of the fusion.

FIG. 2E-2F is an illustration of the nucleotide sequence (SEQ ID NO:29) encoding the MSA16IL-1ra fusion (also referred to as DOM7m-16/IL-1ra) and of the amino acid sequence (SEQ ID NO:30) of the fusion.

FIG. 2G-2H is an illustration of the nucleotide sequence (SEQ ID NO:31) encoding the DummyIL-1ra fusion that did not bind serum albumin, and of the amino acid sequence (SEQ ID NO:32) of the fusion.

FIG. 7 is a table showing the affinities of DOM7h-1, DOM7r-1, DOM7h-2, DOM7r-3, DOM7h-7, DOM7h-8, DOM7r-8, DOM7r-13, DOM7r-14, DOM7m-16, DOM7h-22, DOM7h-23, DOM7h-26, DOM7r-16, DOM7m-26, DOM7r-27 and DOM7R-31 for the serum albumins that they bind. DOM7h-8 also binds porcine serum albumin with and affinity (KD) of 60 nM.

FIG. 8A is an illustration of the nucleotide sequence (SEQ ID NO:33) of a nucleic acid encoding human interleukin 1 receptor antagonist (IL-1ra) deposited in GenBank under accession number NM_173842. The nucleic acid has an open reading frame starting at position 65.

FIG. 8B is an illustration of the amino acid sequence of human IL-1ra (SEQ ID NO:34) encoded by the nucleic acid shown in FIG. 8A (SEQ ID NO:33). The mature protein consists of 152 amino acid residues (amino acid residues 26-177 of SEQ ID NO:34).

FIG. 9 is a graph showing the concentration (µg/mL) of MSA binding dAb/HA epitope tag fusion protein in mouse serum following a single intravenous (i.v.) injection (dose was about 1.5 mg/kg) into CD1 strain male animals over time (days). Serum concentration was determined by ELISA using goat anti-HA (Abcam, UK) capture and protein L-HRP (Invitrogen, USA) detection reagents. Standard curves of known concentrations of MSA binding dAb/HA fusion were set up in the presence of 1× mouse serum to ensure comparability with the test samples. Modelling with a 1 compartment model (WinNonlin Software, Pharsight Corp., USA) showed the MSA binding dAb/HA epitope tag fusion protein had a terminal phase t½ of 29.1 hours and an area under the curve of 559 hr·µg/mL.

FIG. 10 is an illustration of the amino acid sequences of $V_{KS}$ selected by binding to rat serum albumin (RSA). The illustrated sequences are from $V_{KS}$ designated DOM7r-15 (SEQ ID NO:37), DOM7r-16 (SEQ ID NO:38), DOM7r-17 (SEQ ID NO:39), DOM7r-18 (SEQ ID NO:40), DOM7r-19 (SEQ ID NO:41).

FIG. 11A-11B is an illustration of the amino acid sequences of the amino acid sequences of $V_H$s that bind rat serum albumin (RSA). The illustrated sequences are from $V_H$s designated DOM7r-20 (SEQ ID NO:42), DOM7r-21 (SEQ ID NO:43), DOM7r-22 (SEQ ID NO:44), DOM7r-23 (SEQ ID NO:45), DOM7r-24 (SEQ ID NO:46), DOM7r-25 (SEQ ID NO:47), DOM7r-26 (SEQ ID NO:48), DOM7r-27 (SEQ ID NO:49), DOM7r-28 (SEQ ID NO:50), DOM7r-29

(SEQ ID NO:51), DOM7r-30 (SEQ ID NO:52), DOM7r-31 (SEQ ID NO:53), DOM7r-32 (SEQ ID NO:54), and DOM7r-33 (SEQ ID NO:55).

Figure 12:
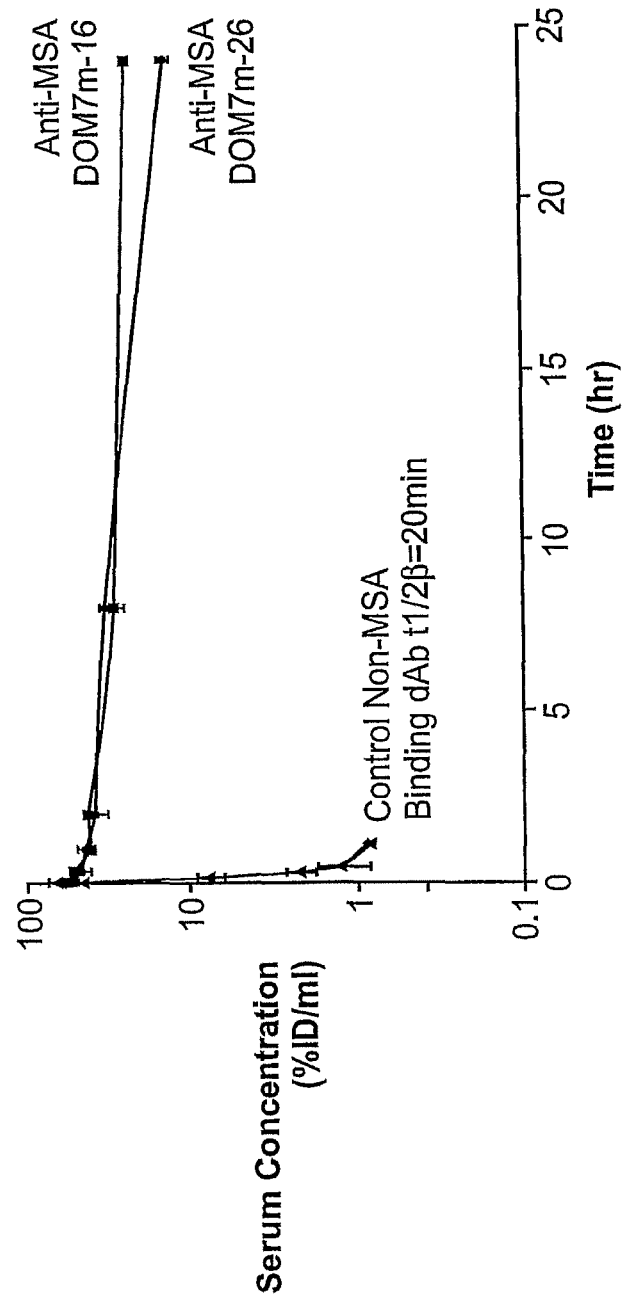

FIG. 12 is a graph showing the concentration (% initial dose) of DOM7m-16, DOM7m-26 or a control dAb that does not bind MSA, each of which contained an HA epitope tag, in mouse serum following a single intravenous (i.v.) injection (dose was about 1.5 mg/kg) into CD1 strain male animals over time. Serum concentration was determined by ELISA using goat anti-HA (Abcam, UK) capture and protein L-HRP (Invitrogen, USA) detection reagents. Standard curves of known concentrations of MSA binding dAb/HA fusion were set up in the presence of 1× mouse serum to ensure comparability with the test samples. Modelling with a 1 compartment model (WinNonlin Software, Pharsight Corp., USA) showed control dAb had a terminal phase t½β of 20 minutes, while DOM7m-16, DOM7m-26 persisted in serum significantly longer.

Figure 13:
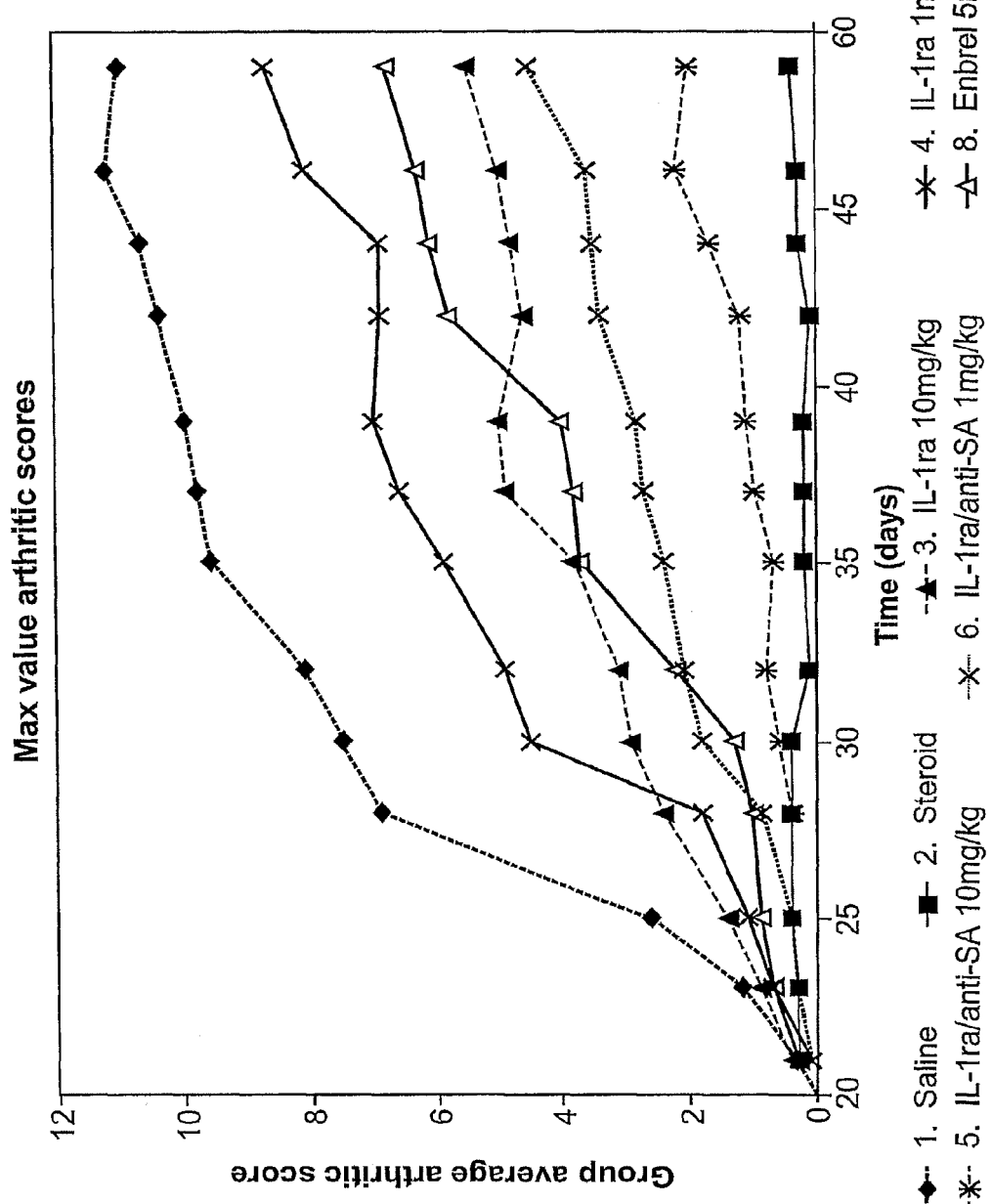

FIG. 13 is a graph showing that DOM7m-16/IL-1ra was more effective than IL-1ra or ENBREL® (entarecept; Immunex Corporation) in treating arthritis in a mouse collagen-induced arthritis (CIA) model. Arthritis was induced and, beginning on day 21, mice were treated with Dexamethasone at 0.4 mg/Kg (Steroid), DOM7m-16/IL-1ra at 1 mg/Kg (IL-1ra/anti-SA 1 mg/kg) or 10 mg/Kg (IL-1ra/anti-SA 10 mg/kg), IL-1ra at 1 mg/Kg or 10 mg/Kg, ENBREL® (entarecept; Immunex Corporation) at 5 mg/Kg, or saline. The results show that DOM7m-16/IL-1ra was more effective than IL-1ra or ENBREL® (entarecept; Immunex Corporation) in this study. The response to IL-1ra was dose dependent, as expected, and that the response to DOM7m-16/IL-1ra was also dose dependent. The average scores for treatment with DOM7m-16/IL-1ra at 1 mg/Kg were consistently lower than the average scores obtained by treatment with IL-1ra at 10 mg/kg. The results indicate that treatment with DOM7m-16/IL-1ra was 10 times more effective than IL-1ra in this study.

FIGS. 14A-14G illustrate the amino acid sequences of saporin polypeptides. FIG. 14A illustrates the amino acid sequence of saporin-2 precursor deposited as Swissprot Accession Number P27559 (SEQ ID NO:60). The signal peptide is amino acids 1-24 of SEQ ID NO:60. FIG. 14B illustrates the amino acid sequence of saporin-3 deposited as Swissprot Accession Number P27560 (SEQ ID NO:61). FIG. 14C illustrates the amino acid sequence of saporin-4 precursor deposited as Swissprot Accession Number P27561 (SEQ ID NO:62). The signal peptide is amino acids 1-24 of SEQ ID NO:62. FIG. 14D illustrates the amino acid sequence of saporin-5 deposited as Swissprot Accession Number Q41389 (SEQ ID NO:63). FIG. 14E illustrates the amino acid sequence of saporin-6 precursor deposited as Swissprot Accession Number P20656 (SEQ ID NO:64). The signal peptide is amino acids 1-24 of SEQ ID NO:64, and a potential propeptide is amino acids 278-299 of SEQ ID NO:64. The mature polypeptide is amino acids 25-277 of SEQ ID NO:64 (SEQ ID NO:65). FIG. 14F illustrates the amino acid sequence of saporin-7 deposited as Swissprot Accession Number Q41391 (SEQ ID NO:66). FIG. 14G illustrates a consensus amino acid sequence encompassing several variants and isoforms of saporin-6 (SEQ ID NO:67).

FIG. 15 illustrates the amino acid sequences of several Camelid $V_{HH}$s that bind mouse serum albumin that are disclosed in WO 2004/041862. Sequence A (SEQ ID NO:72), Sequence B (SEQ ID NO:73), Sequence C (SEQ ID NO:74), Sequence D (SEQ ID NO:75), Sequence E (SEQ ID NO:76), Sequence F (SEQ ID NO:78), Sequence G (SEQ ID NO:78), Sequence H (SEQ ID NO:79), Sequence I (SEQ ID NO:80), Sequence J (SEQ ID NO:81), Sequence K (SEQ ID NO:82), Sequence L (SEQ ID NO:83), Sequence M (SEQ ID NO:84), Sequence N (SEQ ID NO:85), Sequence 0 (SEQ ID NO:86), Sequence P (SEQ ID NO:87), Sequence Q (SEQ ID NO:88).

DETAILED DESCRIPTION OF THE INVENTION

Within this specification embodiments have been described in a way which enables a clear and concise specification to be written, but it is intended and will be appreciated that embodiments may be variously combined or separated without parting from the invention.

Known compositions of matter having a structural formula identical to any one of the embodiments of the invention are explicitly disclaimed per se. In contrast, novel compositions of matter, novel combinations of the known compositions, novel uses of the known compositions or novel methods involving the known compositions are not disclaimed.

As used herein, "drug" refers to any compound (e.g., small organic molecule, nucleic acid, polypeptide) that can be administered to an individual to produce a beneficial therapeutic or diagnostic effect though binding to and/or altering the function of a biological target molecule in the individual. The target molecule can be an endogenous target molecule encoded by the individual's genome (e.g., an enzyme, receptor, growth factor, cytokine encoded by the individual's genome) or an exogenous target molecule encoded by the genome of a pathogen (e.g., an enzyme encoded by the genome of a virus, bacterium, fungus, nematode or other pathogen).

As used herein, "drug composition" refers to a composition comprising a drug that is covalently or noncovalently bonded to a polypeptide binding moiety, wherein the polypeptide binding moiety contains a binding site (e.g., an antigen-binding site) that has binding specificity for a polypeptide that enhances serum half-life in vivo. The drug composition can be a conjugate wherein the drug is covalently or noncovalently bonded to the polypeptide binding moiety. The drug can be covalently or noncovalently bonded to the polypeptide binding moiety directly or indirectly (e.g., through a suitable linker and/or noncovalent binding of complementary binding partners (e.g., biotin and avidin)). When complementary binding partners are employed, one of the binding partners can be covalently bonded to the drug directly or through a suitable linker moiety, and the complementary binding partner can be covalently bonded to the polypeptide binding moiety directly or through a suitable linker moiety. When the drug is a polypeptide or peptide, the drug composition can be a fusion protein, wherein the polypeptide or peptide drug and the polypeptide binding moiety are discrete parts (moieties) of a continuous polypeptide chain.

As used herein "conjugate" refers to a composition comprising an antigen-binding fragment of an antibody that binds serum albumin that is bonded to a drug. Such conjugates include "drug conjugates," which comprise an antigen-binding fragment of an antibody that binds serum albumin to which a drug is covalently bonded, and "noncovlaent drug conjugates," which comprise an antigen-binding fragment of an antibody that binds serum albumin to which a drug is noncovalently bonded.

As used herein, "drug conjugate" refers to a composition comprising an antigen-binding fragment of an antibody that binds serum albumin to which a drug is covalently bonded. The drug can be covalently bonded to the antigen-binding fragment directly or indirectly through a suitable linker moiety. The drug can be bonded to the antigen-binding fragment at any suitable position, such as the amino-terminus, the carboxyl-terminus or through suitable amino acid side chains (e.g., the ε amino group of lysine).

As used herein, "noncovalent drug conjugate" refers to a composition comprising an antigen-binding fragment of an antibody that binds serum albumin to which a drug is noncovalently bonded. The drug can be noncovalently bonded to the antigen-binding fragment directly (e.g., electrostatic interaction, hydrophobic interaction) or indirectly (e.g., through noncovalent binding of complementary binding partners (e.g., biotin and avidin), wherein one partner is covalently bonded to drug and the complementary binding partner is covalently bonded to the antigen-binding fragment). When complementary binding partners are employed, one of the binding partners can be covalently bonded to the drug directly or through a suitable linker moiety, and the complementary binding partner can be covalently bonded to the antigen-binding fragment of an antibody that binds serum albumin directly or through a suitable linker moiety.

As used herein, "drug fusion" refers to a fusion protein that comprises an antigen-binding fragment of an antibody that binds serum albumin and a polypeptide drug. The antigen-binding fragment of an antibody that binds serum albumin and the polypeptide drug are present as discrete parts (moieties) of a single continuous polypeptide chain.

As used herein the term "drug basis" refers to activities of drug compositions and drugs that are normalized based on the amount of drug (or drug moiety) used to assess, measure or determine activity. Generally, the drug compositions of the invention (e.g., drug conjugate, noncovalent drug conjugate, drug fusion) have a larger molecular weight than the drug they contain. Thus, equivalent amounts of drug composition and drug, by weight, will contain different amounts of drug on a molecular or molar basis. For example, if a drug composition of the invention has a molecular weight that is twice the molecular weight of the drug it comprises, activities can be determined on a "drug basis" using 2 μg of drug composition and 1 μg of drug, because these quantities would contain the same amount of drug (as free drug or as part of the drug composition). Activities can be normalized and expressed on a "drug basis" using appropriate calculations, for example, by expressing activity on a per target binding site basis or, for enzyme drugs, on a per active site basis.

As used herein "interleukin 1 receptor antagonist" (IL-1ra) refers to naturally occurring or endogenous mammalian IL-1ra proteins and to proteins having an amino acid sequence which is the same as that of a naturally occurring or endogenous corresponding mammalian IL-1ra protein (e.g., recombinant proteins, synthetic proteins (i.e., produced using the methods of synthetic organic chemistry)). Accordingly, as defined herein, the term includes mature protein, polymorphic or allelic variants, and other isoforms of a IL-1ra (e.g., produced by alternative splicing or other cellular processes), and modified or unmodified forms of the foregoing (e.g., lipidated, glycosylated, PEGylated). Naturally occurring or endogenous IL-1ra include wild type proteins such as mature IL-1ra, polymorphic or allelic variants and other isoforms which occur naturally in mammals (e.g., humans, non-human primates). Such proteins can be recovered or isolated from a source which naturally produces IL-1ra, for example. These proteins and IL-1ra proteins having the same amino acid sequence as a naturally occurring or endogenous corresponding IL-1ra, are referred to by the name of the corresponding mammal. For example, where the corresponding mammal is a human, the protein is designated as a human IL-1ra.

"Functional variants" of IL-1ra include functional fragments, functional mutant proteins, and/or functional fusion proteins which can be produce using suitable methods (e.g., mutagenesis (e.g., chemical mutagenesis, radiation mutagenesis), recombinant DNA techniques). A "functional variant" antagonizes interleukin-1 type 1 receptor. Generally, fragments or portions of IL-1ra include those having a deletion and/or addition (i.e., one or more amino acid deletions and/or additions) of an amino acid (i.e., one or more amino acids) relative to the mature IL-1ra (such as N-terminal, C-terminal or internal deletions). Fragments or portions in which only contiguous amino acids have been deleted or in which non-contiguous amino acids have been deleted relative to mature IL-1ra are also envisioned.

A functional variant of human IL-1ra can have at least about 80%, or at least about 85%, or at least about 90%, or at least about 95%, or at least about 96%, or at least about 97%, or at least about 98%, or at least about 99% amino acid sequence identity with the mature 152 amino acid form of human IL-1ra and antagonize human Interleukin-1 type 1 receptor. (See, Eisenberg et al., *Nature* 343:341-346 (1990).) The variant can comprise one or more additional amino acids (e.g., comprise 153 or 154 or more amino acids). For example, the variant IL-1ra can have an amino acid sequence that consists of an amino-terminal methionine residue followed by residues 26 to 177 of SEQ ID NO:33. (KINERET® (anakinra), Amgen Inc.).

As used herein "saporin" refers to a family of single-chain ribosome-inactivating polypeptides produced by the plant *Saponaria officinalis*. (Stirpe, F., et al., *Biochem. J.* 216:617-625 (1983), Bagga, S. et al., *J. Biol. Chem.* 278:4813-4820 (2003).) Saporin polypeptides exist is several forms that differ in length and/or amino acid sequence. (See, e.g., Id. and Barthelemy, I. et al., *J. Biol. Chem.* 268:6541-6548 (1993).) Saporin-6 is the most active form of saporin. (Bagga, S. et al., *J. Biol. Chem.* 278:4813-4820 (2003).) At least four naturally occurring isoforms of saporin-6 in which the amino acid at position 48 of the mature polypeptide (SEQ ID NO:65) is Asp or Glu, and the amino acid a position 91 of the mature polypeptide (SEQ ID NO:65) is Arg or Lys have been described. (Barthelemy, I. et al., *J. Biol. Chem.* 268:6541-6548 (1993).) Additional forms of saporin-6 include polypeptides in which the amino acid at position 99 of the mature polypeptide (SEQ ID NO:65) is Ser or Leu; the amino acid at position 134 of the mature polypeptide (SEQ ID NO:65) is Gln or Lys; the amino acid at position 147 of the mature polypeptide (SEQ ID NO:65) is Ser or Leu; the amino acid at position 149 of the mature polypeptide (SEQ ID NO:65) is Ser or Phe; the amino acid at position 162 of the mature polypeptide (SEQ ID NO:65) is Asp or Asn; the amino acid at position 177 of the mature polypeptide (SEQ ID NO:65) is Ala or Val; the amino acid at position 188 of the mature polypeptide (SEQ ID NO:65) is Ile or Thr; the amino acid at position 196 of the mature polypeptide (SEQ ID NO:65) is Asn or Asp; the amino acid at position 198 of the mature polypeptide (SEQ ID NO:65) is Glu or Asp; the amino acid at position 231 of the mature polypeptide (SEQ ID NO:65) is Asn or Ser; and polypeptides in which the amino acid at position 233 of the mature polypeptide (SEQ ID NO:65) is Lys or Arg. (Id.) A consensus sequence encompassing these isoforms and variants is presented in FIG. 14G (SEQ ID NO:67).

Accordingly, the term "saporin" includes precursor protein, mature polypeptide, native protein, polymorphic or allelic variants, and other isoforms (e.g., produced by alternative splicing or other cellular processes), and modified or unmodified forms of the foregoing (e.g., lipidated, glycosylated, PEGylated) including naturally occurring, synthetic or recombinantly produced polypeptides. Naturally occurring or endogenous saporin include wild type proteins such as mature saporin (e.g., mature saporin-6), polymorphic or allelic variants and other isoforms which occur naturally in *Saponaria officinalis*. Such proteins can be recovered or isolated from *Saponaria officinalis* using any suitable methods. "Functional variants" of saporin include functional fragments, functional mutant proteins, and/or functional fusion proteins which can be produced using suitable methods (e.g., mutagenesis (e.g., chemical mutagenesis, radiation mutagenesis), recombinant DNA techniques). Generally, fragments or portions of saporin (e.g., saporin-6) include those having a deletion and/or addition (i.e., one or more amino acid deletions and/or additions) of an amino acid (i.e., one or more amino acids) relative to mature saporin (such as N-terminal, C-terminal or internal deletions). Fragments or portions in which only contiguous amino acids have been deleted or in which non-contiguous amino acids have been deleted relative to mature saporin are also envisioned. A variety of functional variants of saporin can be prepared. For example, fusion proteins of saporin-6 that contain amino-terminal extensions have been prepared and shown to retain full ribosome-inhibiting activity in rabbit reticulocyte lysate assays. (Barthelemy, I. et al., *J. Biol. Chem.* 268:6541-6548 (1993).) Variants or saporin-6 is which an active site residue, Tyr72, Tyr120, Glu176, Arg 179 or Trp208 (amino acids 72, 120, 176, 179 or 208 of SEQ ID NO:65), was replaced with alanine had reduced cytotoxic activity in in vitro assays. (Bagga, S. et al., *J. Biol. Chem.* 278:4813-4820 (2003).) Accordingly, if preparing additional functional variants of saporin is desired, mutation, substitution, replacement, deletion or modification of the active site residues should be avoided. Preferably, a functional variant of saporin that contains fewer amino acids than naturally occurring mature polypeptide includes at least the active site. For example, a variant of saporin-6 that contains fewer amino acids than naturally occurring mature saporin-6 can include the active site residues of mature saporin-6 (Tyr72, Tyr120, Glu176, Arg 179 and Trp208 (amino acids 72, 120, 176, 179 and 208 of SEQ ID NO:65)), and be at least about 137 amino acids in length, at least about 150 amino acids in length, at least about 175 amino acids in length, at least about 200 amino acids in length, at least about 225 amino acids in length or at least about 250 amino acids in length.

A "functional variant" of saporin has ribosome-inactivating activity (e.g., rRNA N-Glycosidase activity) and/or cytotoxic activity. Such activity can readily be assessed using any suitable method, such as inhibition of protein synthesis using the well-known rabbit reticulocyte lysate assay or any of the well-known cytotoxicity assays that employ tumor cell lines. (See, e.g., Bagga, S. et al., *J. Biol. Chem.* 278:4813-4820 (2003) and Barthelemy, I. et al., *J. Biol. Chem.* 268:6541-6548 (1993).)

In some embodiments, a functional variant of saporin has at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% amino acid sequence identity with mature saporin-6 (SEQ ID NO:65).

The invention relates to drug compositions that comprise a drug and a polypeptide binding moiety that contains a binding site (e.g., an antigen-binding site) that has binding specificity for a polypeptide that enhances serum half-life in vivo. As described herein in detail with respect to drug compositions that comprise an antigen-binding fragment of an antibody that has binding specificity for serum albumin, the drug and the polypeptide binding moiety can be bonded to each other covalently or noncovalently. In some embodiments, the drug composition is a fusion protein that comprises a polypeptide drug and a polypeptide binding moiety that contains an antigen-binding site that has binding specificity for a polypeptide that enhances serum half-life in vivo. In other embodiments, the drug composition comprises a drug that is covalently or noncovalently bonded to a polypeptide binding moiety that contains an antigen-binding site that has binding specificity for a polypeptide that enhances serum half-life in vivo.

Typically, a polypeptide that enhances serum half-life in vivo is a polypeptide which occurs naturally in vivo and which resists degradation or removal by endogenous mechanisms which remove unwanted material from the organism (e.g., human). For example, a polypeptide that enhances serum half-life in vivo can be selected from proteins from the extracellular matrix, proteins found in blood, proteins found at the blood brain barrier or in neural tissue, proteins localized to the kidney, liver, lung, heart, skin or bone, stress proteins, disease-specific proteins, or proteins involved in Fc transport.

Suitable polypeptides that enhance serum half-life in vivo include, for example, transferrin receptor specific ligand-neuropharmaceutical agent fusion proteins (see U.S. Pat. No. 5,977,307, the teachings of which are incorporated herein by reference), brain capillary endothelial cell receptor, transferrin, transferrin receptor (e.g., soluble transferrin receptor), insulin, insulin-like growth factor 1 (IGF 1) receptor, insulin-like growth factor 2 (IGF 2) receptor, insulin receptor, blood coagulation factor X, α1-antitrypsin and HNF 1α. Suitable polypeptides that enhance serum half-life also include alpha-1 glycoprotein (orosomucoid; AAG), alpha-1 antichymotrypsin (ACT), alpha-1 microglobulin (protein HC; AIM), antithrombin III (AT III), apolipoprotein A-1 (Apo A-1), apolipoprotein B (Apo B), ceruloplasmin (Cp), complement component C3 (C3), complement component C4 (C4), C1 esterase inhibitor (C1 INH), C-reactive protein (CRP), ferritin (FER), hemopexin (HPX), lipoprotein(a) (Lp(a)), mannose-binding protein (MBP), myoglobin (Myo), prealbumin (transthyretin; PAL), retinol-binding protein (RBP), and rheumatoid factor (RF).

Suitable proteins from the extracellular matrix include, for example, collagens, laminins, integrins and fibronectin. Collagens are the major proteins of the extracellular matrix. About 15 types of collagen molecules are currently known, found in different parts of the body, e.g. type I collagen (accounting for 90% of body collagen) found in bone, skin, tendon, ligaments, cornea, internal organs or type II collagen found in cartilage, vertebral disc, notochord, and vitreous humor of the eye.

Suitable proteins from the blood include, for example, plasma proteins (e.g., fibrin, α-2 macroglobulin, serum albumin, fibrinogen (e.g., fibrinogen A, fibrinogen B), serum amyloid protein A, haptoglobin, profilin, ubiquitin, uteroglobulin and β-2-microglobulin), enzymes and enzyme inhibitors (e.g., plasminogen, lysozyme, cystatin C, alpha-1-antitrypsin and pancreatic trypsin inhibitor), proteins of the immune system, such as immunoglobulin proteins (e.g., IgA, IgD, IgE, IgG, IgM, immunoglobulin light chains (kappa/lambda)), transport proteins (e.g., retinol binding protein, α-1 microglobulin), defensins (e.g., beta-defensin 1, neutrophil defensin 1, neutrophil defensin 2 and neutrophil defensin 3) and the like.

Suitable proteins found at the blood brain barrier or in neural tissue include, for example, melanocortin receptor, myelin, ascorbate transporter and the like.

Suitable polypeptides that enhances serum half-life in vivo also include proteins localized to the kidney (e.g., polycystin, type IV collagen, organic anion transporter K1, Heymann's antigen), proteins localized to the liver (e.g., alcohol dehydrogenase, G250), proteins localized to the lung (e.g., secretory component, which binds IgA), proteins localized to the heart (e.g., HSP 27, which is associated with dilated cardiomyopathy), proteins localized to the skin (e.g., keratin), bone specific proteins such as morphogenic proteins (BMPs), which are a subset of the transforming growth factor β superfamily of proteins that demonstrate osteogenic activity (e.g., BMP-2, BMP-4, BMP-5, BMP-6, BMP-7, BMP-8), tumor specific proteins (e.g., trophoblast antigen, herceptin receptor, oestrogen receptor, cathepsins (e.g., cathepsin B, which can be found in liver and spleen)).

Suitable disease-specific proteins include, for example, antigens expressed only on activated T-cells, including LAG-3 (lymphocyte activation gene), osteoprotegerin ligand (OPGL; see *Nature* 402, 304-309 (1999)), OX40 (a member of the TNF receptor family, expressed on activated T cells and specifically up-regulated in human T cell leukemia virus type-I (HTLV-I)-producing cells; see *Immunol.* 165 (1):263-70 (2000)). Suitable disease-specific proteins also include, for example, metalloproteases (associated with arthritis/cancers) including CG6512 *Drosophila*, human paraplegin, human FtsH, human AFG3L2, murine ftsH; and angiogenic growth factors, including acidic fibroblast growth factor (FGF-1), basic fibroblast growth factor (FGF-2), vascular endothelial growth factor/vascular permeability factor (VEGF/VPF), transforming growth factor-α (TGF α), tumor necrosis factor-alpha (TNF-α), angiogenin, interleukin-3 (IL-3), interleukin-8 (IL-8), platelet-derived endothelial growth factor (PD-ECGF), placental growth factor (P1GF), midkine platelet-derived growth factor-BB (PDGF), and fractalkine.

Suitable polypeptides that enhance serum half-life in vivo also include stress proteins such as heat shock proteins (HSPs). HSPs are normally found intracellularly. When they are found extracellularly, it is an indicator that a cell has died and spilled out its contents. This unprogrammed cell death (necrosis) occurs when as a result of trauma, disease or injury, extracellular HSPs trigger a response from the immune system. Binding to extracellular HSP can result in localizing the compositions of the invention to a disease site.

Suitable proteins involved in Fc transport include, for example, Brambell receptor (also known as FcRB). This Fc receptor has two functions, both of which are potentially useful for delivery. The functions are (1) transport of IgG from mother to child across the placenta (2) protection of IgG from degradation thereby prolonging its serum half-life. It is thought that the receptor recycles IgG from endosomes. (See, Holliger et al, *Nat Biotechnol* 15(7):632-6 (1997).)

The drug compositions of the invention can comprise any polypeptide binding moiety that contains a binding site (e.g., an antigen-binding site) that has binding specificity for a polypeptide that enhances serum half-life in vivo. Preferably, the polypeptide binding moiety comprises at least 31, at least about 40, at least about 50, at least about 60, at least about 70, at least about 80 amino acids, at least about 90 amino acids, at least about 100 amino acids or at lease about 110 amino acids as a separate molecular entity. Preferably, the polypeptide binding moiety binds a polypeptide that enhances serum half-life in vivo with a KD of at least about 5 mM KD (KD=$K_{off}$ (kd)/$K_{on}$ (ka)). In some embodiments, the polypeptide binding moiety binds a polypeptide that enhances serum half-life in vivo with a KD of about 10 to about 100 nM, or about 100 nM to about 500 nM, or about 500 nM to about 5 mM, as determined by surface plasmon resonance (e.g., using a BIACORE instrument). In particular embodiments, the polypeptide binding moiety binds a polypeptide that enhances serum half-life in vivo with a KD of about 50 nM, or about 70 nM, or about 100 nM, or about 150 nM or about 200 nM.

Preferably, the polypeptide binding moiety that contains a binding site (e.g., an antigen-binding site) that has binding specificity for a polypeptide that enhances serum half-life in vivo is not a prokaryotic or bacterial polypeptide or peptide. Preferably, the polypeptide binding moiety is a eukaryotic, mammalian or human polypeptide or peptide.

In certain embodiments, the polypeptide binding moiety that contains a binding site (e.g., an antigen-binding site) that has binding specificity for a polypeptide that enhances serum half-life in vivo is a folded protein domain. In other embodiments, the polypeptide binding moiety has a molecular weight of at least about 4 KDa, at least about 4.5 KDa, at least about 5 KDa, at least about 5.5 KDa, at least about 6 KDa, at least about 6.5 KDa, at least about 7 KDa, at least about 7.5 KDa or at least about 8 KDa as a separate molecular entity.

Suitable polypeptide binding moieties that contain a binding site (e.g., an antigen-binding site) that has binding specificity for a polypeptide that enhances serum half-life in vivo can be identified using any suitable method, such as by screening naturally occurring or non-naturally occurring polypeptides in a suitable adhesion assay. As described herein, preferred polypeptide binding moieties that have an antigen-binding site for a polypeptide that enhances serum half-life in vivo are antigen-binding fragments of antibodies that have binding specificity for serum albumin. However, antigen-binding fragments of antibodies that have binding specificity for other polypeptides that enhance serum half-life in vivo can be used in the invention.

If desired, one or more of the complementarity determining regions (CDRs) of an antibody or antigen-binding fragment thereof that binds a polypeptide that enhances serum half-life in vivo can be formatted into a non-immunoglobulin structure that retains the antigen-binding specificity of the antibody or antigen-binding fragment. The drug compositions of the invention can comprise such a non-immunoglobulin binding moiety. Such non-immunoglobulin binding moieties can be prepared using any suitable method, for example natural bacterial receptors such as SpA have been used as scaffolds for the grafting of CDRs to generate polypeptide binding moieties which specifically bind an epitope. Details of this procedure are described in U.S. Pat. No. 5,831,012, the teachings of which are incorporated herein by reference. Other suitable scaffolds include those based on fibronectin and affibodies. Details of suitable procedures are described in WO 98/58965. Other suitable scaffolds include lipocallin and CTLA4, as described in van den Beuken et al., *J. Mol. Biol.* 310:591-601 (2001), and scaffolds such as those described in WO 00/69907 (Medical Research Council), which are based for example on the ring structure of bacterial GroEL or other chaperone polypeptides.

In some embodiments, the drug composition of the invention comprises a non-immunoglobulin binding moiety that has binding specificity for serum albumin, wherein the non-immunoglobulin binding moiety comprises one, two or three of the CDRs of a $V_H$, $V_K$ or $V_{HH}$ described herein and a suitable scaffold. In certain embodiments, the non-immunoglobulin binding moiety comprises CDR3 but not CDR1 or CDR2 of a $V_H$, $V_K$ or $V_{HH}$ described herein and a suitable scaffold. In other embodiments, the non-immunoglobulin binding moiety comprises CDR1 and CDR2, but not CDR3 of a $V_H$, $V_K$ or $V_{HH}$ described herein and a suitable scaffold. In other embodiments, the non-immunoglobulin binding moiety comprises CDR1, CDR2 and CDR3 of a $V_H$, $V_K$ or $V_{HH}$ described herein and a suitable scaffold. In other embodiments, the drug composition comprises only CDR3 of a $V_H$, $V_K$ or $V_{HH}$ described herein and a drug.

The drug compositions of the invention can be prepared using suitable methods, such as the methods described herein for preparation of drug fusions, drug conjugates and noncovalent drug conjugates. Additionally, the drug compositions of the invention have the advantages and the utilities that are described in detail herein with respect to drug fusions, drug conjugates and noncovalent drug conjugates.

The invention provides drug compositions (e.g., drug conjugates, noncovalent drug conjugates, drug fusions) that have improved pharmacokinetic properties (e.g., increase serum half-life) and other advantages in comparison to the drug alone (unconjugated drug, unfused drug). The drug conjugates, noncovalent drug conjugates and drug fusions comprise an antigen-binding fragment of an antibody that has binding specificity for serum albumin and one or more desired drugs.

As described herein, drug compositions (e.g., drug conjugates, noncovalent drug conjugates, drug fusions) of the invention can have dramatically prolonged in vivo serum half-life and/or increased AUC, as compared to drug alone. In addition, the activity of the drug is generally not substantially altered in the drug composition (e.g., drug conjugate, noncovalent drug conjugate, drug fusion). However, some change in the activity of a drug composition compared to drug alone is acceptable and is generally compensated for by the improved pharmacokinetic properties of the drug composition (e.g., drug conjugate, noncovalent drug conjugate, drug fusion). For example, drug compositions (e.g., drug conjugates, noncovalent drug conjugates, drug fusions) may bind the drug target with lower affinity than drug alone, but have about equivalent or superior efficacy in comparison to drug alone due to the improved pharmacokinetic properties (e.g., prolonged in vivo serum half-life, larger AUC) of the drug composition. In addition, lower amounts of drug compositions (e.g., drug conjugates, noncovalent drug conjugates and drug fusions) can be administered to achieve the desired therapeutic or diagnostic effect. Preferably the activity of the drug composition (e.g., drug conjugate, noncovalent drug conjugate, drug fusion) differs from that of the drug alone by a factor of no more than about 100, or no more than about 50, or no more than about 10, or no more than about 5, or no more than about 4, or no more than about 3, or no more than about 2. For example, a drug can have a KD, Ki or neutralizing dose 50 (ND50) of 1 nM, and a drug composition (e.g., drug conjugate, noncovalent drug conjugate, drug fusion) can have a KD, Ki or ND50 of about 2 nM, or about 3 nM, or about 4 nM, or about 5 nM, or about 10 nM.

Preferably, the activity of the drug composition (e.g., drug conjugate, noncovalent drug conjugate, drug fusion) is not substantially reduced as compared to the activity of the drug. In certain embodiments, the activity of the drug composition is reduced, relative to the activity of drug, by no more than about 10%, no more than about 9%, no more than about 8%, no more than about 7%, no more than about 6%, no more than about 5%, no more than about 4%, no more than about 3%, no more than about 2%, no more than about 1% or is substantially unchanged. Alternatively stated, the drug composition (e.g., drug conjugate, noncovalent drug conjugate, drug fusion) retains at least about 90%, at least about 91%, at least about 92%, at least about 93%, at least about 94%, at least about 95%, at least about 96%, at least about 97%, at least about 98%, at least about 99% of the activity of the drug, or substantially the same activity as the drug. Preferably, the activity of drug compositions (e.g., drug conjugate, noncovalent drug conjugate, drug fusion) and drugs are determined and/or compared on a "drug basis."

As described and shown herein, the drug compositions (e.g., drug conjugate, noncovalent drug conjugate, drug fusion) of the invention can have greater activity (e.g., in vivo activity) than drug alone. For example, as shown in Example 6, DOM7m-16/IL-1ra was more effective in treating arthritis in a mouse model than IL-1ra when these agents were administered at the same dose by weight (10 mg/Kg or 1 mg/Kg). DOM7m-16/IL-1ra was more effective even though its molecular weight is approximately twice the molecular weight of IL-1ra. Thus, mice that received DOM7m-16/IL-1ra received only about half of the IL-1ra (as a moiety in DOM7m-16/IL1-ra) as mice that received IL-1ra.

In certain embodiments, the drug composition (e.g., drug conjugate, noncovalent drug conjugate, drug fusion) has greater activity (e.g., in vivo activity) than drug, for example, the drug composition can have at least about 100%, at least about 150%, at least about 200%, at least about 250%, at least about 300%, at least about 350%, at least about 400%, at least about 450%, or at least about 500% of the activity of drug. Preferably, the activity of drug compositions (e.g., drug conjugate, noncovalent drug conjugate, drug fusion) and drugs are determined and/or compared on a "drug basis." The activity of drug compositions (e.g., drug conjugate, noncovalent drug conjugate, drug fusion) and drugs can be determined using a suitable in vitro or in vivo system. In certain embodiments, a drug composition (e.g., drug conjugate, noncovalent drug conjugate, drug fusion) has greater activity than the drug it comprises, as determined in vivo. In other embodiments, a drug composition (e.g., drug conjugate, noncovalent drug conjugate, drug fusion) has greater activity than the drug it comprises, as determined in vitro.

Drug compositions (e.g., drug conjugates, noncovalent drug conjugates, drug fusions) that comprise a domain antibody (dAb) that has binding specificity for serum albumin provide further advantages. Domain antibodies are very stable, are small relative to antibodies and other antigen-binding fragments of antibodies, can be produced in high yields by expression in *E. coli* or yeast (e.g., *Pichia pastoris*), and as described herein antigen-binding fragments of antibodies that bind serum albumin can be easily selected from libraries of human origin or from any desired species. Accordingly, drug compositions (e.g., drug conjugates, noncovalent drug conjugates, drug fusions) that comprise a dAb that binds serum albumin can be produced more easily than therapeutics that are generally produced in mammalian cells (e.g., human, humanized or chimeric antibodies) and dAbs that are not immunogenic can be used (e.g., a human dAb can be used for a drug fusion or drug conjugate for treating or diagnosing disease in humans).

The immunogenicity of a drug can be reduced when the drug is part of a drug composition (e.g., drug conjugate, noncovalent drug conjugate, drug fusion) that contains a polypeptide binding moiety that binds serum albumin (e.g., an antigen-binding fragment of an antibody that binds serum albumin) Accordingly, a drug can be less immunogenic (than drug alone) or be substantially non-immunogenic in the context of a drug composition that contains a polypeptide binding moiety that binds serum albumin (e.g., drug conjugate, noncovalent drug conjugate, drug fusion). Thus, such drug compositions (e.g., drug conjugates, noncovalent drug conjugates, drug fusions) can be administered to a subject repeatedly over time with minimal loss of efficacy due to the elaboration of anti-drug antibodies by the subject's immune system.

Additionally, the drug compositions (e.g., drug conjugates, noncovalent drug conjugates, drug fusions) described herein can have an enhanced safety profile and fewer side effects than drug alone. For example, as a result of the serum albumin-binding activity of the antigen-binding fragment of an antibody that has binding specificity for serum albumin, the drug fusions and conjugates (drug conjugate, noncovalent drug conjugate) have enhanced residence time in the vascular circulation. Additionally, the conjugates and drug fusions are substantially unable to cross the blood brain barrier and to accumulate in the central nervous system following systemic administration (e.g., intravascular administration). Accordingly, conjugates (drug conjugate, noncovalent drug conjugate) and drug fusions that contain a drug that has neurological toxicity or undesirable psychotropic effects can be administered with greater safety and reduced side effects in comparison to the drug alone. Similarly, the conjugates (drug conjugate, noncovalent drug conjugate) and drug fusions can have reduced toxicity toward particular organs (e.g., kidney or liver) than drug alone. The conjugates and drug fusions described herein can also be used to sequester a drug or a target that binds a drug (e.g, a toxin) in the vascular circulation, thereby decreasing the effects of the drug or target on tissues (e.g., inhibiting the effects of a toxin).

Suitable methods for pharmacokinetic analysis and determination of in vivo half-life are well known in the art. Such methods are described, for example, in Kenneth, A et al: Chemical Stability of Pharmaceuticals: A Handbook for Pharmacists, and in Peters et al, Pharmacokinetc analysis: A Practical Approach (1996). Reference is also made to "Pharmacokinetics", M Gibaldi & D Perron, published by Marcel Dekker, $2^{nd}$ Rev. edition (1982), which describes pharmacokinetic parameters such as t alpha and t beta half-lives (t½ alpha, t½ beta) and area under curve (AUC).

Half-lives (t½ alpha and t½ beta) and AUC can be determined from a curve of serum concentration of conjugate or fusion against time. The WinNonlin analysis package (available from Pharsight Corp., Mountain View, Calif. 94040, USA) can be used, for example, to model the curve. In a first phase (the alpha phase) the drug composition (e.g., drug conjugate, noncovalent drug conjugate, drug fusion) is undergoing mainly distribution in the patient, with some elimination. A second phase (beta phase) is the terminal phase when the drug composition (e.g., drug conjugate, noncovalent drug conjugate, drug fusion) has been distributed and the serum concentration is decreasing as the drug composition is cleared from the patient. The t alpha half-life is the half-life of the first phase and the t beta half-life is the half-life of the second phase. Thus, the present invention provides a drug composition (e.g., drug conjugate, noncovalent drug conjugate, drug fusion) or a composition comprising a drug composition (e.g., drug conjugate, noncovalent drug conjugate, drug fusion) according to the invention having a tα half-life in the range of 15 minutes or more. In one embodiment, the lower end of the range is 30 minutes, 45 minutes, 1 hour, 2 hours, 3 hours, 4 hours, 5 hours, 6 hours, 7 hours, 8 hours, 9 hours, 10 hours, 11 hours or 12 hours. In addition, or alternatively, a drug composition (e.g., drug conjugate, noncovalent drug conjugate, drug fusion) or composition according to the invention will have a tα half-life in the range of up to and including 12 hours. In one embodiment, the upper end of the range is 11, 10, 9, 8, 7, 6 or 5 hours. An example of a suitable range is 1 to 6 hours, 2 to 5 hours or 3 to 4 hours.

Advantageously, the present invention provides drug compositions (e.g., drug conjugates, noncovalent drug conjugates, drug fusions) having a tβ half-life in the range of 2.5 hours or more. In one embodiment, the lower end of the range is 3 hours, 4 hours, 5 hours, 6 hours, 7 hours, 8 hours, 9 hours, 10 hours, 11 hours, or 12 hours. In some embodiments, the drug compositions (e.g., drug conjugates, noncovalent drug conjugates, drug fusions) have a tβ half-life in the range of up to and including 21 days. In one embodiment, the upper end of the range is 12 hours, 24 hours, 2 days, 3 days, 5 days, 10 days, 15 days or 20 days. In particular embodiments, a drug composition (e.g., drug conjugate, noncovalent drug conjugate, drug fusion) according to the invention will have a tβ half-life in the range 12 to 60 hours. In a further embodiment, it will be in the range 12 to 48 hours. In a further embodiment still, it will be in the range 12 to 26 hours.

In addition, or alternatively to the above criteria, the present invention provides drug compositions (e.g., drug conjugates, noncovalent drug conjugates, drug fusions) having an AUC value (area under the curve) in the range of 0.01 mg·min/mL or more, or 1 mg·min/mL or more. In one embodiment, the lower end of the range is 0.01, 0.1, 1, 5, 10, 15, 20, 30, 100, 200 or 300 mg·min/mL. In particular embodiments, the drug composition (e.g., drug conjugate, noncovalent drug conjugate, drug fusion) has an AUC in the range of up to 600 mg·min/mL. In one embodiment, the upper end of the range is 500, 400, 300, 200, 150, 100, 75 or 50 mg·min/mL In other embodiments, the drug composition (e.g., drug conjugate, noncovalent drug conjugate, drug fusion) has an AUC in the range selected from the group consisting of the following: 15 to 150 mg·min/mL, 15 to 100 mg min/mL, 15 to 75 mg·min/mL, 15 to 50 mg·min/mL, 0.01 to 50 mg·min/mL, 0.1 to 50 mg·min/mL, 1 to 50 mg·min/mL, 5 to 50 mg·min/mL, and 10 to 50 mg·min/mL.

The invention relates to drug compositions (e.g., drug conjugates, noncovalent drug conjugates, drug fusions) that comprise a drug and a polypeptide binding moiety that contains a binding site (e.g., an antigen-binding site) that has binding specificity for a polypeptide that enhances serum half-life in vivo. In preferred embodiments of drug compositions, the polypeptide binding moiety that contains a binding site (e.g., an antigen-binding site) that has binding specificity for a polypeptide that enhances serum half-life in vivo, has binding specificity for serum albumin.

In some embodiments, the drug composition comprises a drug that is covalently bonded to a polypeptide binding moiety that contains a binding site (e.g., an antigen-binding site) that has binding specificity for a polypeptide that enhances serum half-life in vivo. In these embodiments, the drug can be covalently bonded to the polypeptide binding domain at any suitable position, such as the amino-terminus, the carboxyl-terminus or through suitable amino acid side chains (e.g., the ε amino group of lysine).

In other embodiments, the drug composition comprises a drug that is noncovalently bonded to a polypeptide binding moiety that contains a binding site (e.g., an antigen-binding site) that has binding specificity for a polypeptide that enhances serum half-life in vivo. In such embodiments, the drug can be noncovalently bonded to the antigen-binding fragment directly (e.g., through electrostatic interaction, hydrophobic interaction) or indirectly (e.g., through noncovalent binding of complementary binding partners (e.g., biotin and avidin), wherein one partner is covalently bonded to drug and the complementary binding partner is covalently bonded to the antigen-binding fragment). When complementary binding partners are employed, one of the binding partners can be covalently bonded to the drug directly or through a suitable linker moiety, and the complementary binding partner can be covalently bonded to the polypeptide binding domain directly or through a suitable linker moiety.

In other embodiments, the drug composition is a fusion protein that comprises a polypeptide binding moiety that contains a binding site (e.g., an antigen-binding site) that has binding specificity for a polypeptide that enhances serum half-life in vivo and a polypeptide drug. The fusion proteins comprise a continuous polypeptide chain, said chain comprising a polypeptide binding moiety that contains a binding site (e.g., an antigen-binding site) that has binding specificity for a polypeptide that enhances serum half-life in vivo as a first moiety, and a polypeptide drug as a second moiety, which are present as discrete parts (moieties) of the polypeptide chain. The first and second moieties can be directly bonded to each other through a peptide bond, or linked through a suitable amino acid, or peptide or polypeptide linker. Additional moieties (e.g., third, fourth) and/or linker sequences can be present as appropriate. The first moiety can be in an N-terminal location, C-terminal location or internal relative to the second moiety (i.e., the polypeptide drug). In certain embodiments, the fusion protein comprises one or more one or more polypeptide binding moieties that contain a binding site that has binding specificity for a polypeptide that enhances serum half-life in vivo and one or more polypeptide drug moieties. In these embodiments, the fusion protein can comprise one to about ten (e.g., 1, 2, 3, 4, 5, 6, 7, 8, 9 or 10) polypeptide drug moieties that can be the same or different, and one to about twenty (e.g., 1, 2, 3, 4, 5, 6, 7, 8, 9, 10, 11, 12, 13, 14, 15, 16, 17, 18 19 or 20) polypeptide binding moieties that contain a binding site that has binding specificity for a polypeptide that enhances serum half-life in vivo that can be the same or different.

The polypeptide binding moieties that contain a binding site that has binding specificity for a polypeptide that enhances serum half-life in vivo and polypeptide drug moieties can be present in any desired location. For example, proceeding from the amino terminus to the carboxyl terminus, the moieties can be present in the following order: one or more polypeptide binding moieties, one or more polypeptide drug moieties, one or more polypeptide binding moieties. In another example, proceeding from the amino terminus to the carboxyl terminus, the moieties can be present in the following order: one or more polypeptide binding moieties, one or more polypeptide drug moieties, one or more polypeptide binding moieties, one or more polypeptide drug moieties, one or more polypeptide binding moieties. As described herein, the polypeptide binding moieties and polypeptide drug moieties can be directly bonded to each other through a peptide bond, or linked through a suitable amino acid, or peptide or polypeptide linker.

In certain embodiments, the fusion protein is a continuous polypeptide chain that has the formula (amino-terminal to carboxy-terminal):

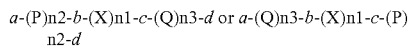

wherein X is a polypeptide drug;

P and Q are each independently a polypeptide binding moiety that contains a binding site that has binding specificity for a polypeptide that enhances serum half-life in vivo;

a, b, c and d are each independently absent or one to about 100 amino acid residues;

n1, n2 and n3 represent the number of X, P or Q moieties present, respectively;

n1 is one to about 10;
n2 is zero to about 10; and
n3 is zero to about 10, with the proviso that both n2 and n3 are not zero; and
with the proviso that when n1 and n2 are both one and n3 is zero, X does not comprise an antibody chain or a fragment of an antibody chain.

In some embodiments, n2 is one, two, three, four, five or six, and n3 is zero. In other embodiments, n3 is one, two, three, four, five or six, and n2 is zero. In other embodiments, n1, n2 and n3 are each one.

In certain embodiments, X does not comprises an antibody chain or a fragment of an antibody chain.

In preferred embodiments, P and Q are each independently a polypeptide binding moiety that has binding specificity for serum albumin.

In particularly preferred embodiments, the drug composition (e.g., drug conjugate, noncovalent drug conjugate, drug fusion) comprises a polypeptide binding moiety that contains a binding site (e.g., an antigen-binding site) that has binding specificity for a polypeptide that enhances serum half-life in vivo, wherein the polypeptide binding domain is an antigen-binding fragment of an antibody that has binding specificity for serum albumin.

The invention also relates to a method is for increasing the in vivo serum half-life of a drug, comprising bonding a drug to a polypeptide binding moiety having a binding site that has binding specificity for a polypeptide that enhances serum half-life in vivo, whereby a drug composition (e.g., drug conjugate, noncovalent drug conjugate, drug fusion) that has a longer in vivo serum half-life, relative to drug, is produced.

In some embodiments, the method is for increasing the in vivo serum half-life of a drug without substantially reducing the activity of the drug, comprising bonding a drug to a polypeptide binding moiety having a binding site that has binding specificity for a polypeptide that enhances serum half-life in vivo, whereby a drug composition (e.g., drug conjugate, noncovalent drug conjugate, drug fusion) that has a longer in vivo serum half-life relative to said drug, and has at least about 90% of the activity of said drug, is produced.

In other embodiments, the method is for increasing the in vivo serum half-life of a drug and reducing the immunogenicity of the drug, comprising bonding a drug to a polypeptide binding moiety having a binding site that has binding specificity for a polypeptide that enhances serum half-life in vivo, whereby a drug composition (e.g., drug conjugate, noncovalent drug conjugate, drug fusion) that has a longer in vivo serum half-life relative to drug, and is less immunogenic than said drug, is produced.

In other embodiments, the method is for decreasing the immunogenicity of a drug without substantially reducing the activity of the drug, comprising bonding a drug to a polypeptide binding moiety having a binding site that has binding specificity for a polypeptide that enhances serum half-life in vivo, whereby a drug composition (e.g., drug conjugate, noncovalent drug conjugate, drug fusion) that is less immunogenic than said drug, and has at least about 90% of the activity of said drug is produced.

In other embodiments, the method is for increasing the in vivo serum half-life of a drug, and reducing the immunogenicity of the drug without substantially reducing the activity of the drug, comprising bonding a drug to a polypeptide binding moiety having a binding site that has binding specificity for a polypeptide that enhances serum half-life in vivo, whereby a drug composition (e.g., drug conjugate, noncovalent drug conjugate, drug fusion) that has a longer in vivo serum half-life relative to said drug, is less immunogenic than said drug, and has at least about 90% of the activity of said drug is produced.

The drug and the polypeptide binding moiety having a binding site that has binding specificity for a polypeptide that enhances serum half-life in vivo can be bonded via a covalent bond (e.g., peptide bond) or noncovalent bond, with or without the use of linkers, as described herein. In some embodiments, the drug and the polypeptide binding moiety having a binding site that has binding specificity for a polypeptide that enhances serum half-life in vivo are bonded via a covalent bond. For example, the drug composition produced is a drug conjugate or drug fusion. In other embodiments, the drug and the polypeptide binding moiety having a binding site that has binding specificity for a polypeptide that enhances serum half-life in vivo are bonded via a noncovalent bond, and the drug composition is a noncovalent drug conjugate.

The drug composition produced using the method can have greater activity (e.g., in vivo activity) than the drug. In some embodiments, the method is for producing a drug composition that has greater activity (e.g., in vivo activity) than drug alone, comprising bonding a drug to a polypeptide binding moiety having a binding site that has binding specificity for a polypeptide that enhances serum half-life in vivo, whereby a drug composition (e.g., drug conjugate, noncovalent drug conjugate, drug fusion) that has greater activity, relative to drug, is produced. In such embodiments, preferably, the activity of the drug composition is greater than the activity of the drug as described herein.

In preferred embodiments, the polypeptide binding moiety has binding specificity for serum albumin. In particularly preferred embodiments, the polypeptide binding moiety is an antigen-binding fragment of an antibody that has binding specificity for serum albumin.

In certain embodiments, the method comprises selecting said polypeptide binding moiety from one or more polypeptides (e.g., antigen-binding fragments of an antibody that has binding specificity for serum albumin), wherein the selected polypeptide binding moiety binds a polypeptide that enhances serum half-life in vivo with a KD of at least about 5 mM.

The invention also relates to use of a polypeptide binding moiety having a binding site that has binding specificity for a polypeptide that enhances serum half-life in vivo for the manufacture of medicament, the medicament comprising a drug composition (e.g., drug conjugate, noncovalent drug conjugate, drug fusion) in which a drug is bonded to said polypeptide binding moiety, for increasing in vivo serum half-life of the drug.

In some embodiments, the use is for the manufacture of a medicament, the medicament comprising a drug composition (e.g., drug conjugate, noncovalent drug conjugate, drug fusion) in which a drug is bonded to said polypeptide binding moiety, for increasing in vivo serum half-life of the drug without reducing the activity of the drug by more than about 10%.

In other embodiments, the use is for the manufacture of a medicament, the medicament comprising a drug composition (e.g., drug conjugate, noncovalent drug conjugate, drug fusion) in which a drug is bonded to said polypeptide binding moiety, for increasing in vivo serum half-life of the drug and reducing the immunogenicity of the drug.

In other embodiments, the use is for the manufacture of a medicament, the medicament comprising a drug composition (e.g., drug conjugate, noncovalent drug conjugate, drug fusion) in which a drug is bonded to said polypeptide binding moiety, for decreasing the immunogenicity of a drug without reducing the activity of the drug by more than about 10%.

In other embodiments, the use is for the manufacture of a medicament, the medicament comprising a drug composition (e.g., drug conjugate, noncovalent drug conjugate, drug fusion) in which a drug is bonded to said polypeptide binding moiety, for increasing in vivo serum half-life of the drug, and reducing the immunogenicity of the drug without reducing the activity of the drug by more than about 10%.

The drug composition can comprise a drug and polypeptide binding moiety having a binding site that has binding specificity for a polypeptide that enhances serum half-life in vivo that are bonded via a covalent bond (e.g., peptide bond) or noncovalent bond, with or without the use of linkers, as described herein. In some embodiments, the drug and the polypeptide binding moiety having a binding site that has binding specificity for a polypeptide that enhances serum half-life in vivo are bonded via a covalent bond. For example, the drug composition can be a drug conjugate or drug fusion. In other embodiments, the drug and the polypeptide binding moiety having a binding site that has binding specificity for a polypeptide that enhances serum half-life in vivo are bonded via a noncovalent bond, and the drug composition is a noncovalent drug conjugate.

In certain embodiments, the use is for the manufacture of a medicament, the medicament comprising a drug composition (e.g., drug conjugate, noncovalent drug conjugate, drug fusion) in which a drug is bonded to said polypeptide binding moiety, for increasing the activity (e.g., in vivo activity) than said drug. In such embodiments, preferably, the activity of the drug composition is greater than the activity of the drug as described herein.

In preferred embodiments, the polypeptide binding moiety has binding specificity for serum albumin. In particularly preferred embodiments, the polypeptide binding moiety is an antigen-binding fragment of an antibody that has binding specificity for serum albumin.

Antigen-Binding Fragment of an Antibody that Binds Serum Albumin

The drug conjugates, noncovalent drug conjugates and drug fusions of the invention comprise an (i.e., one or more) antigen-binding fragment of an antibody that binds serum albumin. The antigen-binding fragment can have binding specificity for serum albumin of an animal to which the drug conjugate or drug fusion will be administered. Preferably, the antigen-binding fragment has binding specificity for human serum albumin. However, veterinary applications are contemplated and the antigen-binding fragment can have binding specificity for serum albumin from a desired animal, for example serum albumin from dog, cat, horse, cow, chicken, sheep, pig, goat, deer, mink, and the like. In some embodiments the antigen-binding fragment has binding specificity for serum albumin from more than one species. For example, as described herein, human dAbs that have binding specificity for rat serum albumin and mouse serum albumin, and a dAb that has binding specificity for rat, mouse and human serum albumin have been produced. (Table 1 and FIG. 7) Such dAbs provide the advantage of allowing preclinical and clinical studies using the same drug conjugate or drug fusion and obviate the need to conduct preclinical studies with a suitable surrogate drug fusion or drug conjugate.

Antigen-binding fragments suitable for use in the invention include, for example, Fab fragments, Fab' fragments, F(ab')$_2$ fragments, Fv fragments (including single chain Fv (scFv) and disulfide bonded Fv), a single variable domain, and dAbs ($V_H$, $V_L$). Such antigen-binding fragments can be produced using any suitable method, such as by proteolysis of an antibody using pepsin, papain or other protease having the requisite cleavage specificity, or using recombinant techniques. For example, Fv fragments can be prepared by digesting an antibody with a suitable protease or using recombinant DNA technology. For example, a nucleic acid can be prepared that encodes a light chain variable region and heavy chain variable region that are connected by a suitable peptide linker, such as a chain of two to about twenty Glycyl residues. The nucleic acid can be introduced into a suitable host (e.g., *E. coli*) using any suitable technique (e.g., transfection, transformation, infection), and the host can be maintained under conditions suitable for expression of a single chain Fv fragment. A variety of antigen-binding fragments of antibodies can be prepared using antibody genes in which one or more stop codons have been introduced upstream of the natural stop site. For example, an expression construct encoding a F(ab')$_2$ portion of an immunoglobulin heavy chain can be designed by introducing a translation stop codon at the 3' end of the sequence encoding the hinge region of the heavy chain. The drug conjugates, noncovalent drug conjugates and drug fusions of the invention can comprise the individual heavy and light chains of antibodies that bind serum albumin or portions of the individual chains that bind serum albumin (e.g., a single $V_H$, $V_\kappa$ or $V_\lambda$).

Antibodies and antigen-binding fragments thereof which bind a desired serum albumin (e.g., human serum albumin) can be selected from a suitable collection of natural or artificial antibodies or raised against an appropriate immunogen in a suitable host. For example, antibodies can be raised by immunizing a suitable host (e.g., mouse, human antibody-transgenic mouse, rat, rabbit, chicken, goat, non-human primate (e.g., monkey)) with serum albumin (e.g., isolated or purified human serum albumin) or a peptide of serum albumin (e.g., a peptide comprising at least about 8, 9, 10, 11, 12, 15, 20, 25, 30, 33, 35, 37, or 40 amino acid residues). Antibodies and antigen-binding fragments that bind serum albumin can also be selected from a library of recombinant antibodies or antigen-binding fragments, such as a phage display library. Such libraries can contain antibodies or antigen-binding fragments of antibodies that contain natural or artificial amino acid sequences. For example, the library can contain Fab fragments which contain artificial CDRs (e.g., random amino acid sequences) and human framework regions. (See, for example, U.S. Pat. No. 6,300,064 (Knappik, et al.).) In other examples, the library contains scFv fragments or dAbs (single $V_H$, single $V_\kappa$ or single $V_\lambda$) with sequence diversity in one or more CDRs. (See, e.g., WO 99/20749 (Tomlinson and Winter), WO 03/002609 A2 (Winter et al.), WO 2004/003019A2 (Winter et al.).)

Suitable antibodies and antigen-binding fragments thereof that bind serum albumin include, for example, human antibodies and antigen-binding fragments thereof, humanized antibodies and antigen-binding fragments thereof, chimeric antibodies and antigen-binding fragments thereof, rodent (e.g., mouse, rat) antibodies and antigen-binding fragments thereof, and Camelid antibodies and antigen-binding fragments thereof. In certain embodiments, the drug conjugates, noncovalent drug conjugates and drug fusions comprises a Camelid $V_{HH}$ that binds serum albumin. Camelid $V_{HH}$s are immunoglobulin single variable domain polypeptides which are derived from heavy chain antibodies that are naturally devoid of light chains. Such antibodies occur in Camelid species including camel, llama, alpaca, dromedary, and guanaco. $V_{HH}$ molecules are about ten times smaller than IgG molecules, and as single polypeptides, are very stable and resistant to extreme pH and temperature conditions. Suitable Camelid $V_{HH}$ that bind serum albumin include those disclosed in WO 2004/041862 (Ablynx N.V.) and herein (FIG. 15 and SEQ ID NOS:77-88). In certain embodiments, the Camelid $V_{HH}$ binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with SEQ ID NO: 72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, or SEQ ID NO:88. Amino acid sequence identity is preferably determined using a suitable sequence alignment algorithm and default parameters, such as BLAST P (Karlin and Altschul, *Proc. Natl. Acad. Sci. USA* 87(6):2264-2268 (1990)).

Preparation of the immunizing antigen, and polyclonal and monoclonal antibody production can be performed using any suitable technique. A variety of methods have been described. (See, e.g., Kohler et al., *Nature*, 256: 495-497 (1975) and *Eur. J. Immunol.* 6: 511-519 (1976); Milstein et al., *Nature* 266: 550-552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991).) Generally, where a monoclonal antibody is desired, a hybridoma is produced by fusing suitable cells from an immortal cell line (e.g., a myeloma cell line such as SP2/0, P3X63Ag8.653 or a heteromyeloma) with antibody-producing cells. Antibody-producing cells can be obtained from the peripheral blood or, preferably the spleen or lymph nodes, of humans, human-antibody transgenic animals or other suitable animals immunized with the antigen of interest. Cells that produce antibodies of human origin (e.g., a human antibody) can be produced using suitable methods, for example, fusion of a human antibody-producing cell and a heteromyeloma or trioma, or immortalization of an activated human B cell via infection with Epstein Barr virus. (See, e.g., U.S. Pat. No. 6,197,582 (Trakht); Niedbala et al., *Hybridoma*, 17:299-304 (1998); Zanella et al., *J Immunol Methods,* 156:205-215 (1992); Gustafsson et al., *Hum Antibodies Hybridomas*, 2:26-32 (1991).) The fused or immortalized antibody-producing cells (hybridomas) can be isolated using selective culture conditions, and cloned by limiting dilution. Cells which produce antibodies with the desired specificity can be identified using a suitable assay (e.g., ELISA).

Antibodies also can be prepared directly (e.g., synthesized or cloned) from an isolated antigen-specific antibody producing cell (e.g., a cell from the peripheral blood or, preferably the spleen or lymph nodes determined to produce an antibody with desired specificity), of humans, human-antibody transgenic animals or other suitable animals immunized with the antigen of interest (see, e.g., U.S. Pat. No. 5,627,052 (Schrader)).

When the drug conjugate, noncovalent drug conjugate or drug fusion is for administration to a human, the antibody or antigen-binding fragment thereof that binds serum albumin (e.g., human serum albumin) can be a human, humanized or chimeric antibody or an antigen-binding fragment of such an antibody. These types of antibodies and antigen-binding fragments are less immunogenic or non-immunogenic in humans and provide well-known advantages. For example, drug conjugates, noncovalent drug conjugates or drug fusions that contain an antigen-binding fragment of a human, humanized or chimeric antibody can be administered repeatedly to a human with less or no loss of efficacy (compared with other fully immunogenic antibodies) due to elaboration of human antibodies that bind to the drug conjugate or drug fusion. When the drug conjugate, noncovalent drug conjugate or drug fusion is intended for veterinary administration, analogous antibodies or antigen-binding fragments can be used. For example, CDRs from a murine or human antibody can be grafted onto framework regions from a desired animal, such as a horse or cow.

Human antibodies and nucleic acids encoding same can be obtained, for example, from a human or from human-antibody transgenic animals. Human-antibody transgenic animals (e.g., mice) are animals that are capable of producing a repertoire of human antibodies, such as XENOMOUSE (Abgenix, Fremont, Calif.), HUMAB-MOUSE, KIRIN TC MOUSE or KM-MOUSE (MEDAREX, Princeton, N.J.). Generally, the genome of human-antibody transgenic animals has been altered to include a transgene comprising DNA from a human immunoglobulin locus that can undergo functional rearrangement. An endogenous immunoglobulin locus in a human-antibody transgenic animal can be disrupted or deleted to eliminate the capacity of the animal to produce antibodies encoded by an endogenous gene. Suitable methods for producing human-antibody transgenic animals are well known in the art. (See, for example, U.S. Pat. Nos. 5,939,598 and 6,075,181 (Kucherlapati et al.), U.S. Pat. Nos. 5,569,825, 5,545,806, 5,625,126, 5,633,425, 5,661,016, and 5,789,650 (Lonberg et al.), Jakobovits et al., *Proc. Natl. Acad. Sci. USA,* 90: 2551-2555 (1993), Jakobovits et al., *Nature,* 362: 255-258 (1993), Jakobovits et al. WO 98/50433, Jakobovits et al. WO 98/24893, Lonberg et al. WO 98/24884, Lonberg et al. WO 97/13852, Lonberg et al. WO 94/25585, Lonberg et al. EP 0 814 259 A2, Lonberg et al. GB 2 272 440 A, Lonberg et al., *Nature* 368:856-859 (1994), Lonberg et al., *Int Rev Immunol* 13(1):65-93 (1995), Kucherlapati et al. WO 96/34096, Kucherlapati et al. EP 0 463 151 B1, Kucherlapati et al. EP 0 710 719 A1, Surani et al. U.S. Pat. No. 5,545,807, Bruggemann et al. WO 90/04036, Bruggemann et al. EP 0 438 474 B1, Taylor et al., *Int. Immunol.* 6(4)579-591 (1994), Taylor et al., *Nucleic Acids Research* 20(23):6287-6295 (1992), Green et al., *Nature Genetics* 7:13-21 (1994), Mendez et al., *Nature Genetics* 15:146-156 (1997), Tuaillon et al., *Proc Natl Acad Sci USA* 90(8):3720-3724 (1993) and Fishwild et al., *Nat Biotechnol* 14(7):845-851 (1996), the teachings of each of the foregoing are incorporated herein by reference in their entirety.)

Human-antibody transgenic animals can be immunized with a suitable antigen (e.g., human serum albumin), and antibody producing cells can be isolated and fused to form hybridomas using conventional methods. Hybridomas that produce human antibodies having the desired characteristics (e.g., specificity, affinity) can be identified using any suitable assay (e.g., ELISA) and, if desired, selected and subcloned using suitable culture techniques.

Humanized antibodies and other CDR-grafted antibodies can be prepared using any suitable method. The CDRs of a CDR-grafted antibody can be derived from a suitable antibody which binds a serum albumin (referred to as a donor antibody). Other sources of suitable CDRs include natural and artificial serum albumin-specific antibodies obtained from human or nonhuman sources, such as rodent (e.g., mouse, rat, rabbit), chicken, pig, goat, non-human primate (e.g., monkey) or a library.

The framework regions of a humanized antibody are preferably of human origin, and can be derived from any human antibody variable region having sequence similarity to the analogous or equivalent region (e.g., heavy chain variable region or light chain variable region) of the antigen-binding region of the donor antibody. Other sources of framework regions of human origin include human variable region consensus sequences. (See, e.g., Kettleborough, C. A. et al., *Protein Engineering* 4:773-783 (1991); Carter et al., WO 94/04679; Kabat, E. A., et al., *Sequences of Proteins of Immunological Interest,* Fifth Edition, U.S. Department of Health and Human Services, U.S. Government Printing Office (1991)). Other types of CDR grafted antibodies can contain framework regions of suitable origin, such as framework regions encoded by germline antibody gene segments from horse, cow, dog, cat and the like.

Framework regions of human origin can include amino acid substitutions or replacements, such as "back mutations" which replace an amino acid residue in the framework region of human or animal origin with a residue from the corresponding position of the donor antibody. One or more mutations in the framework region can be made, including deletions, insertions and substitutions of one or more amino acids. Variants can be produced by a variety of suitable methods, including mutagenesis of nonhuman donor or acceptor human chains. (See, e.g., U.S. Pat. No. 5,693,762 (Queen et al.) and U.S. Pat. No. 5,859,205 (Adair et al.), the entire teachings of which are incorporated herein by reference.)

Constant regions of antibodies, antibody chains (e.g., heavy chain, light chain) or fragments or portions thereof, if present, can be derived from any suitable source. For example, constant regions of human, humanized and certain chimeric antibodies, antibody chains (e.g., heavy chain, light chain) or fragments or portions thereof, if present can be of human origin and can be derived from any suitable human antibody or antibody chain. For example, a constant region of human origin or portion thereof can be derived from a human κ or λ light chain, and/or a human γ (e.g., γ1, γ2, γ3, γ4), μ, α (e.g., α1, α2), δ or ε heavy chain, including allelic variants. In certain embodiments, the antibody or antigen-binding fragment (e.g., antibody of human origin, human antibody) can include amino acid substitutions or replacements that alter or tailor function (e.g., effector function). For example, a constant region of human origin (e.g., γ1 constant region, γ2 constant region) can be designed to reduce complement activation and/or Fc receptor binding. (See, for example, U.S. Pat. No. 5,648,260 (Winter et al.), U.S. Pat. No. 5,624,821 (Winter et al.) and U.S. Pat. No. 5,834,597 (Tso et al.), the entire teachings of which are incorporated herein by reference.) Preferably, the amino acid sequence of a constant region of human origin that contains such amino acid substitutions or replacements is at least about 95% identical over the full length to the amino acid sequence of the unaltered constant region of human origin, more preferably at least about 99% identical over the full length to the amino acid sequence of the unaltered constant region of human origin.

Humanized antibodies, CDR grafted antibodies or antigen-binding fragments of a humanized or CDR grafted antibody can be prepared using any suitable method. Several such methods are well-known in the art. (See, e.g., U.S. Pat. No. 5,225,539 (Winter), U.S. Pat. No. 5,530,101 (Queen et al.).) The portions of a humanized or CDR grafted antibody (e.g., CDRs, framework, constant region) can be obtained or derived directly from suitable antibodies (e.g., by de novo synthesis of a portion), or nucleic acids encoding an antibody or chain thereof having the desired property (e.g., binds serum albumin) can be produced and expressed. To prepare a portion of a chain, one or more stop codons can be introduced at the desired position. For example, nucleic acid (e.g., DNA) sequences coding for humanized or CDR grafted variable regions can be constructed using PCR mutagenesis methods to alter existing DNA sequences. (See, e.g., Kamman, M., et al., *Nucl. Acids Res.* 17:5404 (1989).) PCR primers coding for the new CDRs can be hybridized to a DNA template of a previously humanized variable region which is based on the same, or a very similar, human variable region (Sato, K., et al., *Cancer Research* 53:851-856 (1993)). If a similar DNA sequence is not available for use as a template, a nucleic acid comprising a sequence encoding a variable region sequence can be constructed from synthetic oligonucleotides (see e.g., Kolbinger, F., *Protein Engineering* 8:971-980 (1993)). A sequence encoding a signal peptide can also be incorporated into the nucleic acid (e.g., on synthesis, upon insertion into a vector). The natural signal peptide sequence from the acceptor antibody, a signal peptide sequence from another antibody or other suitable sequence can be used (see, e.g., Kettleborough, C. A., *Protein Engineering* 4:773-783 (1991)). Using these methods or other suitable methods, variants can be readily produced. In one embodiment, cloned variable regions can be mutated, and sequences encoding variants with the desired specificity can be selected (e.g., from a phage library; see, e.g., U.S. Pat. No. 5,514,548 (Krebber et al.) and WO 93/06213 (Hoogenboom et al.)).

The antibody or antigen-binding fragment that binds serum albumin can be a chimeric antibody or an antigen-binding fragment of a chimeric antibody. The chimeric antibody or antigen-binding fragment thereof comprises a variable region from one species (e.g., mouse) and at least a portion of a constant region from another species (e.g., human). Chimeric antibodies and antigen-binding fragments of chimeric antibodies can be prepared using any suitable method. Several suitable methods are well-known in the art. (See, e.g., U.S. Pat. No. 4,816,567 (Cabilly et al.), U.S. Pat. No. 5,116,946 (Capon et al.))

A preferred method for obtaining antigen-binding fragments of antibodies that bind serum albumin comprises selecting an antigen-binding fragment (e.g., scFvs, dAbs) that has binding specificity for a desired serum albumin from a repertoire of antigen-binding fragments. For example, as described herein dAbs that bind serum albumin can be selected from a suitable phage display library. A number of suitable bacteriophage display libraries and selection methods (e.g., monovalent display and multivalent display systems) have been described. (See, e.g., Griffiths et al., U.S. Pat. No. 6,555,313 B1 (incorporated herein by reference); Johnson et al., U.S. Pat. No. 5,733,743 (incorporated herein by reference); McCafferty et al., U.S. Pat. No. 5,969,108 (incorporated herein by reference); Mulligan-Kehoe, U.S. Pat. No. 5,702,892 (incorporated herein by reference); Winter, G. et al., *Annu. Rev. Immunol.* 12:433-455 (1994); Soumillion, P. et al., *Appl. Biochem. Biotechnol.* 47(2-3):175-189 (1994); Castagnoli, L. et al., *Comb. Chem. High Throughput Screen*, 4(2):121-133 (2001); WO 99/20749 (Tomlinson and Winter); WO 03/002609 A2 (Winter et al.); WO 2004/003019A2 (Winter et al.).) The polypeptides displayed in a bacteriophage library can be displayed on any suitable bacteriophage, such as a filamentous phage (e.g., fd, M13, F1), a lytic phage (e.g., T4, T7, lambda), or an RNA phage (e.g., MS2), for example, and selected for binding to serum albumin (e.g., human serum albumin)

Generally, a library of phage that displays a repertoire of polypeptides as fusion proteins with a suitable phage coat protein is used. Such a library can be produced using any suitable methods, such as introducing a library of phage vectors or phagemid vectors encoding the displayed antibodies or antigen-binding fragments thereof into suitable host bacteria, and culturing the resulting bacteria to produce phage (e.g., using a suitable helper phage or complementing plasmid if desired). The library of phage can be recovered from such a culture using any suitable method, such as precipitation and centrifugation.

The library can comprise a repertoire of antibodies or antigen-binding fragments thereof that contains any desired amount of amino acid sequence diversity. For example, the repertoire can contain antibodies or antigen-binding fragments thereof that have amino acid sequences that correspond to naturally occurring antibodies from a desired organism, and/or can contain one or more regions of random or randomized amino acid sequences (e.g., CDR sequences). The antibodies or antigen-binding fragments thereof in such a repertoire or library can comprise defined regions of random or randomized amino acid sequence and regions of common amino acid sequence. In certain embodiments, all or substantially all polypeptides in a repertoire are a desired type of antigen-binding fragment of an antibody (e.g., human $V_H$ or human $V_L$). For example, each polypeptide in the repertoire can contain a $V_H$, a $V_L$ or an Fv (e.g., a single chain Fv).

Amino acid sequence diversity can be introduced into any desired region of antibodies or antigen-binding fragments thereof using any suitable method. For example, amino acid sequence diversity can be introduced into a target region, such as a complementarity determining region of an antibody variable domain, by preparing a library of nucleic acids that encode the diversified antibodies or antigen-binding fragments thereof using any suitable mutagenesis methods (e.g., low fidelity PCR, oligonucleotide-mediated or site directed mutagenesis, diversification using NNK codons) or any other suitable method. If desired, a region of the antibodies or antigen-binding fragments thereof to be diversified can be randomized.

A suitable phage display library can be used to selected antibodies or antigen-binding fragments of antibodies that bind serum albumin and have other beneficial properties. For example, antibodies or antigen-binding fragments that resist aggregation when unfolded can be selected. Aggregation is influenced by polypeptide concentration and is thought to arise in many cases from partially folded or unfolded intermediates. Factors and conditions that favor partially folded intermediates, such as elevated temperature and high polypeptide concentration, promote irreversible aggregation. (Fink, A. L., *Folding & Design* 3:R1-R23 (1998).) For example, storing purified polypeptides in concentrated form, such as a lyophilized preparation, frequently results in irreversible aggregation of at least a portion of the polypeptides. Also, production of a polypeptide by expression in biological systems, such as *E. coli*, often results in the formation of inclusion bodies which contain aggregated polypeptides. Recovering active polypeptides from inclusion bodies can be very difficult and require adding additional steps, such as a refolding step, to a biological production system.

Antibodies and antigen-binding fragments that resist aggregation and unfold reversibly when heated can be selected from a suitable phage display library. Generally, a phage display library comprising a repertoire of displayed antibodies or antigen-binding fragments thereof is heated to a temperature (Ts) at which at least a portion of the displayed antibodies or antigen-binding fragments thereof are unfolded, then cooled to a temperature (Tc) wherein Ts>Tc, whereby at least a portion of the antibodies or antigen-binding fragments thereof have refolded and a portion of the polypeptides have aggregated. Then, antibodies or antigen-binding fragments thereof that unfold reversibly and bind serum albumin are recovered at a temperature (Tr). The recovered antibody or antigen-binding fragment thereof that unfolds reversibly has a melting temperature (Tm), and preferably, the repertoire was heated to Ts, cooled to Tc and the antibody or antigen-binding fragment thereof that unfolds reversibly was isolated at Tr, such that Ts>Tm>Tc, and Ts>Tm>Tr. Generally, the phage display library is heated to about 80° C. and cooled to about room temperature or about 4° C. before selection. Antibodies or antigen-binding fragment thereof that unfold reversibly and resist aggregation can also be designed or engineered by replacing certain amino acid residue with residues that confer the ability to unfold reversibly. (See, WO 2004/101790 (Jespers et al.), and U.S. Provisional Patent Application Nos. 60/470,340 (filed on May 14, 2003) and 60/554,021 (filed on Mar. 17, 2004) for detailed discussion of methods for selecting and for designing or engineering antibodies or antigen-binding fragments thereof that unfold reversibly. The teachings of WO 2004/101790 and both of the foregoing U.S. Provisional Patent Applications are incorporated herein by reference).

Antibodies or antigen-binding fragments thereof that unfold reversibly and resist aggregation provide several advantages. For example, due to their resistance to aggregation, antibodies or antigen-binding fragments thereof that unfold reversibly can readily be produced in high yield as soluble proteins by expression using a suitable biological production system, such as E. coli. In addition, antibodies or antigen-binding fragments thereof that unfold reversibly can be formulated and/or stored at higher concentrations than conventional polypeptides, and with less aggregation and loss of activity. DOM7h-26 (SEQ ID NO:20) is a human $V_H$ that unfolds reversibly.

Preferably, the antibody or antigen-binding fragment thereof that binds serum albumin comprises a variable domain ($V_H$, $V_\kappa$, $V_\lambda$) in which one or more of the framework regions (FR) comprise (a) the amino acid sequence of a human framework region, (b) at least 8 contiguous amino acids of the amino acid sequence of a human framework region, or (c) an amino acid sequence encoded by a human germline antibody gene segment, wherein said framework regions are as defined by Kabat. In certain embodiments, the amino acid sequence of one or more of the framework regions is the same as the amino acid sequence of a corresponding framework region encoded by a human germline antibody gene segment, or the amino acid sequences of one or more of said framework regions collectively comprise up to 5 amino acid differences relative to the amino acid sequence of said corresponding framework region encoded by a human germline antibody gene segment.

In other embodiments, the amino acid sequences of FR1, FR2, FR3 and FR4 are the same as the amino acid sequences of corresponding framework regions encoded by a human germline antibody gene segment, or the amino acid sequences of FR1, FR2, FR3 and FR4 collectively contain up to 10 amino acid differences relative to the amino acid sequences of corresponding framework regions encoded by said human germline antibody gene segments. In other embodiments, the amino acid sequence of said FR1, FR2 and FR3 are the same as the amino acid sequences of corresponding framework regions encoded by said human germline antibody gene segment.

In particular embodiments, the antigen binding fragment of an antibody that binds serum albumin comprises an immunoglobulin variable domain (e.g., $V_H$, $V_L$) based on a human germline sequence, and if desired can have one or more diversified regions, such as the complementarity determining regions. Suitable human germline sequence for $V_H$ include, for example, sequences encoded by the $V_H$ gene segments DP4, DP7, DP8, DP9, DP10, DP31, DP33, DP45, DP46, DP47, DP49, DP50, DP51, DP53, DP54, DP65, DP66, DP67, DP68 and DP69, and the JH segments JH1, JH2, JH3, JH4, JH4b, JH5 and JH6. Suitable human germline sequence for $V_L$ include, for example, sequences encoded by the $V_\kappa$ gene segments DPK1, DPK2, DPK3, DPK4, DPK5, DPK6, DPK7, DPK8, DPK9, DPK10, DPK12, DPK13, DPK15, DPK16, DPK18, DPK19, DPK20, DPK21, DPK22, DPK23, DPK24, DPK25, DPK26 and DPK 28, and the Jκ segments Jκ 1, Jκ 2, Jκ 3, Jκ 4 and Jκ 5.

In certain embodiments, the drug conjugate, noncovalent drug conjugate or drug fusion does not contain a mouse, rat and/or rabbit antibody that binds serum albumin or antigen-binding fragment of such an antibody.

The antigen-binding fragment can bind serum albumin with any desired affinity, on rate and off rate. The affinity (KD), on rate ($K_{on}$ or $k_a$) and off rate ($K_{off}$ or $k_d$) can be selected to obtain a desired serum half-life for a particular drug. For example, it may be desirable to obtain a maximal serum half-life for a drug that neutralizes an inflammatory mediator of a chronic inflammatory disorder (e.g., a dAb that binds and neutralizes an inflammatory cytokine), while a shorter half-life may be desirable for a drug that has some toxicity (e.g., a chemotherapeutic agent). Generally, a fast on rate and a fast or moderate off rate for binding to serum albumin is preferred. Drug conjugates and drug fusions that comprise an antigen-binding fragment with these characteristics will quickly bind serum albumin after being administered, and will dissociate and rebind serum albumin rapidly. These characteristics will reduce rapid clearance of the drug (e.g., through the kidneys) but still provide efficient delivery and access to the drug target.

The antigen-binding fragment that binds serum albumin (e.g., dAb) generally binds with a KD of about 1 nM to about 500 µM. In some embodiments, the antigen-binding fragment binds serum albumin with a KD (KD=$K_{off}$(kd)/$K_{on}$(ka)) of about 10 to about 100 nM, or about 100 nM to about 500 nM, or about 500 nM to about 5 mM, as determined by surface plasmon resonance (e.g., using a BIACORE instrument). In particular embodiments, the drug conjugate, noncovalent drug conjugate or drug fusion comprises and antigen-binding fragment of an antibody (e.g., a dAb) that binds serum albumin (e.g., human serum albumin) with a KD of about 50 nM, or about 70 nM, or about 100 nM, or about 150 nM or about 200 nM. The improved pharmacokinetic properties (e.g., prolonged t½β, increased AUC) of drug conjugates, noncovalent drug conjugates and drug fusions described herein may correlate with the affinity of the antigen-binding fragment that binds serum albumin. Accordingly, drug conjugates, noncovalent drug conjugates and drug fusions that have improved pharmacokinetic properties can generally be prepared using an antigen-binding fragment that binds serum albumin (e.g., human serum albumin) with high affinity (e.g., KD of about 500 nM or less, about 250 nM or less, about 100 nM or less, about 50 nM or less, about 10 nM or less, or about 1 nM or less, or about 100 pM or less).

Preferably, the drug that is conjugated or fused to the antigen-binding fragment that binds serum albumin, binds to its target (the drug target) with an affinity (KD) that is stronger than the affinity of the antigen-binding fragment for serum albumin and/or a $K_{off}$ (kd) that is faster that the $K_{off}$ of the antigen binding fragment for serum albumin, as measured by surface plasmon resonance (e.g., using a BIACORE instrument). For example, the drug can bind its target with an affinity that is about 1 to about 100000, or about 100 to about 100000, or about 1000 to about 100000, or about 10000 to about 100000 times stronger than the affinity of antigen-binding fragment that binds SA for SA. For example, the antigen-binding fragment of the antibody that binds SA can bind with an affinity of about 10 µM, while the drug binds its target with an affinity of about 100 pM.

In particular embodiments, the antigen-binding fragment of an antibody that binds serum albumin is a dAb that binds human serum albumin. For example, a $V_\kappa$ dAb having an amino acid sequence selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25 and SEQ ID NO:26, or a $V_H$ dAb having an amino acid sequence selected from the group consisting of SEQ ID NO:16, SEQ ID NO:17, SEQ ID NO:18, SEQ ID NO:19, SEQ ID NO:20, SEQ ID NO:21, SEQ ID NO:22 and SEQ ID NO:23. In other embodiments, the antigen-binding fragment of an antibody that binds serum albumin is a dAb that binds human serum albumin and comprises the CDRs of any of the foregoing amino acid sequences. In other embodiments, the antigen-binding fragment of an antibody that binds serum albumin is a dAb that binds human serum albumin and comprises an amino acid sequence that has at least about 80%, or at least about 85%, or at least about 90%, or at least about 95%, or at least about 96%, or at least about 97%, or at least about 98%, or at least about 99% amino acid sequence identity with SEQ ID NO:10, SEQ ID NO:11, SEQ ID NO:12, SEQ ID NO:13, SEQ ID NO:14, SEQ ID NO:15, SEQ ID NO:24, SEQ ID NO:25, SEQ ID NO:26, SEQ ID NO:16, SEQ ID NO:17, SEQ ID NO:18, SEQ ID NO:19, SEQ ID NO:20, SEQ ID NO:21, SEQ ID NO:22 or SEQ ID NO:23. Amino acid sequence identity is preferably determined using a suitable sequence alignment algorithm and default parameters, such as BLAST P (Karlin and Altschul, *Proc. Natl. Acad. Sci. USA* 87(6):2264-2268 (1990)).

Drugs

Certain drug compositions of the invention (e.g., drug conjugates, noncovalent drug conjugates) can comprise any drug (e.g., small organic molecule, nucleic acid, polypeptide) that can be administered to an individual to produce a beneficial therapeutic or diagnostic effect, for example, through binding to and/or altering the function of a biological target molecule in the individual. Other drug compositions of the invention (e.g., drug fusions) can comprise a polypeptide or peptide drug. In preferred embodiments of drug fusions, the drug does not comprise an antibody chain or fragment of an antibody chain (e.g., $V_H$, $V_\kappa$, $V_\lambda$).

Suitable drugs for use in the invention include, for example, immunosuppressive agents (e.g., cyclosporin A, rapamycin, FK506, prednisone), antiviral agents (acyclovir, ganciclovir, indinavir), antibiotics (penicillin, mynocyclin, tetracycline), anti-inflammatory agents (aspirin, ibuprofen, prednisone), cytotoxins or cytotoxic agents (e.g., paclitaxel, cytochalasin B, gramicidin D, ethidium bromide, emetine, mitomycin C, etoposide, tenoposide, vincristine, vinblastine, colchicine, doxorubicin, daunorubicin, dihydroxy anthracindione, mitoxantrone, mithramycin, actinomycin D, 1-dihydrotestosterone, glucocorticoids, procaine, tetracaine, lidocaine, propranolol, puromycin, and analogs or homologs of any of the foregoing agents. Suitable drugs also include antimetabolites (e.g., methotrexate, 6-mercaptopurine, 6-thioguanine, cytarabine, 5-fluorouracil decarbazine), alkylating agents (e.g., mechlorethamine, thioepachlorambucil, CC-1065, melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), radionuclides (e.g., iodine-125, -126) yttrium (e.g., yttrium-90, -91) and praseodymium (e.g., praseodymium-144, -145), and protease inhibitors (e.g., inhibitors of matrix metalloproteinases). Other suitable drugs are nucleic acids such as antisense nucleic acids and RNAi. Calicheamicin is also suitable for use in the invention.

Suitable drugs also include analgesic agents, including narcotics (e.g., codeine, nalmefene, naloxone, fentanyl, meperidine, morphine, tramadol, propoxyphene, oxycodone, methadone, nalbuphine), nonsteroidal anti-inflammatory agents (e.g., indomethacin, ketorolac, arthrotec, ibuprofen, naproxen, salicylate, celecoxib, rofecoxib), acetaminophen, capsaicin, ziconotide and the like.

In certain embodiments, the drug is a polypeptide toxin, for example, a toxin such as abrin, ricin A, pseudomonas exotoxin, or diphtheria toxin. Other suitable polypeptide drugs include antibodies or antigen-binding fragments (e.g., dAbs) of antibodies, polypeptide agonists, activators, secretagogues, antagonists or inhibitors. For example, the polypeptide or peptide drug can bind and agonise or antagonize a cell surface protein, such as a CD antigen, cytokine receptor (e.g., interleukin receptor, chemokine receptor), adhesion molecule or costimulatory molecule. For example, the polypeptide drug can bind a cytokine, growth factors, cytokine receptor, growth factor receptor and other target ligand, which include but are not limited to: ApoE, Apo-SAA, BDNF, Cardiotrophin-1, CEA, CD40, CD40 Ligand, CD56, CD38, CD138, EGF, EGF receptor, ENA-78, Eotaxin, Eotaxin-2, Exodus-2, FAPα, FGF-acidic, FGF-basic, fibroblast growth factor-10, FLT3 ligand, Fractalkine (CX3C), GDNF, G-CSF, GM-CSF, GF-β1, human serum albumin, insulin, IFN-γ, IGF-I, IGF-II, IL-1α, IL-1β, IL-1 receptor, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumour necrosis factor (TNF), TNF-α, TNF-β, TNF receptor I, TNF receptor II, TNIL-1, TPO, VEGF, VEGF A, VEGF B, VEGF C, VEGF D, VEGF receptor 1, VEGF receptor 2, VEGF receptor 3, GCP-2, GRO/MGSA, GRO-β, GRO-γ, HCC1, 1-309, HER 1, HER 2, HER 3 and HER 4. It will be appreciated that this list is by no means exhaustive.

Suitable drugs also include hormones, including pituitary hormone (PTH), adrenocorticotropic hormone (ACTH), renin, luteinizing hormone-releasing hormone (LHRH), gonadotropin-releasing hormone (GnRH), luteinizing hormone (LH), follicle stimulating hormone (FSH), aldosterone, and the like. Suitable drugs also include keratinocyte growth factor, interferons (e.g., IFN-α, IFN-β, IFN-γ), erythropoietin (EPO), proteases, elastases, LHRH analogs, agonists and antagonists, opioid receptor agonists, such as kappa opioid receptor agonists (e.g., dynorphin A), calcitonin and calcitonin analogs, antidiuretic hormone (vasopressin), oxytocin antagonists, vasoactive intestinal peptide, thrombin inhibitors, von Willebrand factor, surfactants and snail venom (e.g., ziconotide).

Suitable drugs also include peptides and polypeptides that have anti-cancer activities (e.g., proliferation inhibiting, growth inhibiting, apoptosis inducing, metastasis inhibiting, adhesion inhibiting, neovascularization inhibiting). Several such peptides and polypeptides are known in the art. (See. e.g., Janin Y. L., *Amino Acids*, 25:1-40 (2003). The entire teaching of this reference, particularly the peptides and polypeptides disclosed therein, are incorporated herein by reference.) The amino acid sequences of several such peptides are presented in Table 8.

Other suitable drugs include peptides and polypeptides that have anti-viral activity. Several such peptides and polypeptides are known in the art, for example the peptides and polypeptides disclosed in Giannecchini, et al., *J Viro.*, 77(6): 3724-33 (2003); Wang, J., et al., *Clin Chem* (2003); Hilleman, M. R., *Vaccine*, 21(32):4626-49 (2003); Tziveleka, L. A., et al., *Curr Top Med Chem*, 3(13):1512-35 (2003); Poritz, M. A., et al., Virology, 313(1):170-83 (2003); Oevermann, A., et al., *Antiviral Res*, 59(1):23-33 (2003); Cole, A. M. et al., *Curr Pharm Des*, 9(18):1463-73 (2003); Pinon, J. D., et al., *Virol*, 77(5):3281-90 (2003); Sia, S. K., et al., *Proc Natl Acad Sci USA*, 99(23):14664-9 (2002); Bahbouhi, B., et al., *Biochem J*, 66(Pt 3):863-72 (2002); de Soultrait, V. R., et al, *J Mol Biol*, 18(1):45-58 (2002); Witherell, G., *Curr Opin Investig Drugs*, 2(3):340-7 (2001); Ruff, M. R., et al., *Antiviral Res*, 52(1): 63-75 (2001); Bultmann, H., et al., *J. Virol*, 75(6):2634-45 (2001); Egal, M., et al., *Int J Antimicrob AGents*, 13(1):57-60 (1999); and Robinson, W. E., Jr., *J Leukoc Biol*, 63(1):94-100 (1998). The entire teachings of these references, particularly the peptides and polypeptides disclosed therein, are incorporated herein by reference. These peptides and polypeptides are examples of drugs that can be used in the compositions, drug fusions, drug conjugates, noncovalent drug conjugates of the present invention.

The polypeptide drug can also be a cytokine or growth factor or soluble portion of a receptor (e.g., a cytokine receptor, growth factor receptor, hormone receptor) or other polypeptide such as the polypeptides listed above. For example, suitable polypeptide drugs also include receptor (e.g., growth factor receptor, cytokine receptor, hormone receptor) agonists and antagonists, such as interleukin 1 receptor antagonist (Eisenberg et al., *Nature* 343:341-346 (1990)), thrombopoietin receptor agonists (e.g., GW395058 (de Serres et al., Stem Cells 17:316-326 (1999)), melanocortin receptor antagonists (e.g., MCR-4 antagonists (Cepoi et al., *Brain Res.* 1000:64-71 (2004)), anginex, 6 DBF7 (Mayo et al., *J. Biol. Chem.* 278:45746-45752 (2003)), chemokine mimetics (e.g., RANTES mimetics (Nardese et al., *Nat. Struct. Biol.* 8:611-615 (2001)), growth hormone (e.g., human growth hormone), growth hormone analogs and growth hormone secretagogues (e.g., CP-424,391 (MacAndrew et al., *Eur. J. Pharmacol.* 432:195-202 (2001)), growth hormone releasing hormone mimetics (e.g., MK-677 (Chapman et al., *J. Clin. Endocrinol. Metab.* 82:3455-3463 (1997)), inhibitors of cellular adhesion molecule interactions (e.g., LFA-1/ICAM-1, VLA-1/VCAM-1 (Yusuf-Makagiansar et al., *Med. Res. Rev.* 22:146-167 (2002)), mimetics of interferon (e.g., SYR6 (Sato et al., *Biochem. J.* 371(Pt.2):603-608 (2003), mimetics of herceptin (*Nature Biotechnol.* 18:137 (2000)), inhibitors of antigen presentation (Bolin et al., *J. Med. Chem.* 43:2135-2148 (2000)), GPIIB/IIIA antagonists (e.g., FK633 (Aoki et al., *Thromb. Res.* 81:439-450 (1996)), alphavbeta3 antagonists (e.g., SC56631 (Engleman et al., *J. Clin. Invest.* 99:2284-2292 (1997)), erythropoietin mimetics (e.g., EMP1 (Johnson et al., *Biochemistry* 37:3699-3710 (1998)), opioid receptor antagonists (e.g., [(2S,3R)-TMT1] DPDPE (Liao et al., *J. Med. Chem.* 41:4767-4776 (1998)), hematopoietic factors (e.g., erythropoietin (EPO), granulocyte colony stimulating factor (GM-CSF)).

Additional suitable peptide and polypeptide drugs include peptide antagonists that bind human type 1 IL-1 receptor (e.g., AF 11377 (FEWTPGYWQPYALPL, SEQ ID NO:56), AF11869 (FEWTPGYWQJYALPL, SEQ ID NO:57 (J=1-azetidine-2-carboxylic acid), FEWTPGYWQJY (SEQ ID NO:58), FEWTPGWYQJY (SEQ ID NO:59), FEWTPGWYQJYALPL (SEQ ID NO:60), or any of the foregoing sequences optionally containing an acylated amino terminus and/or an aminated carboxyl terminus (Akeson et al., *J. Biol. Chem.* 271:30517-305123 (1996)), peptide antagonists of TNF-alpha-mediated cytotoxicity (e.g., those disclosed in Chirinos-Rojas et al, *J. Immunol.* 161:5621-5626 (1998)), peptide agonists of erythropoietin receptor (e.g., those disclosed in McConnel et al., *Biol. Chem.* 379:1279-1286 (1998) or Wrighton et al., *Science* 273:458-464 (1996)), glucagon-like peptide-1 (GLP-1, e.g., GLP-1(7-37), GLP-1(7-36) amide and analogs thereof (see, e.g., Ritzel U. et al., *J. Endocrinology* 159:93-102 (1998)), and interferons (e.g., INFα, INFβ, INFγ). Additional suitable polypeptide and peptide drugs include integrin inhibitors (e.g., RGD peptides, such as H-Glu[cyclo(Arg-Gly-Asp-D-Phe-Lys)]₂ (Janssen, M. L., et al., *Cancer Research* 62:6146-6151 (2002)), cyclo(Arg-Gly-Asp-D-Phe-Lys) (Kantlehner M., et al., *Agnew. Chem. Int. Ed.* 38:560 (1999)), cyclo(Arg-Gly-Asp-D-Tyr-Lys) (Haubner, R., et al., *J. Nucl. Med.* 42:326-336 (2001)), ribosome-inactivating proteins (RIPs) such as Saporin (e.g., SEQ ID NO:67), matrix metalloproteinase inhibitors (e.g., U.S. Pat. No. 5,616,605), and antiviral peptides and polypeptides, such as HIV fusion inhibitors (e.g., T-1249 and T-20 (FUZEON® (enfuvirtide); Trimeris Inc.), and soluble receptor antagonists such as immunoadhesins (e.g., LFA3-Ig, CTLA4-Ig).

Antimicrobial polypeptide and peptide drugs are also suitable for use in the invention. Examples of suitable antimicrobial polypeptide and peptide drugs include adenoregulin, dermcidin-1L, cathelicidins (e.g., cathelicidin-like peptide, human LL-37/hCAP-18), defensins, including α-defensins (e.g., human neutrophil peptide 1 (HNP-1), HNP-2, HNP-3, HNP-4, human defensin 5, human defensin 6), β-defensins (e.g., human β-defensin-1, human β-defensin-2), and θ-defensins (e.g., θ-defensin-1), histatins (e.g., histatin 1, histatin 3, histatin 5), lactoferricin-derived peptide and related peptides (see, Tomita M., et al., *Acta Paediatr. Jpn.* 36:585-591 (1994) and Strom, M. B., et al. *Biochem Cell Biol.* 80:65-74 (2002)).

Drug Fusions

The drug fusions of the invention are fusion proteins that comprise a continuous polypeptide chain, said chain comprising an antigen-binding fragment of an antibody that binds serum albumin as a first moiety, linked to a second moiety that is a polypeptide drug. The first and second moieties can be directly bonded to each other through a peptide bond, or linked through a suitable amino acid, or peptide or polypeptide linker. Additional moieties (e.g., third, fourth) and/or linker sequences can be present as appropriate. The first moiety can be in an N-terminal location, C-terminal location or internal relative to the second moiety (i.e., the polypeptide drug). In certain embodiments, each moiety can be present in more than one copy. For example, the drug fusion can comprise two or more first moieties each comprising an antigen-binding fragment of an antibody that binds serum albumin (e.g., a $V_H$ that binds human serum albumin and a $V_L$ that bind human serum albumin or two or more $V_H$s or $V_L$s that bind human serum albumin)

In some embodiments the drug fusion is a continuous polypeptide chain that has the formula:

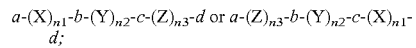

wherein X is a polypeptide drug that has binding specificity for a first target;

Y is a single chain antigen-binding fragment of an antibody that has binding specificity for serum albumin;

Z is a polypeptide drug that has binding specificity for a second target;

a, b, c and d are each independently absent or one to about 100 amino acid residues;

n1 is one to about 10;

n2 is one to about 10; and n3 is zero to about 10, with the proviso that when n1 and n2 are both one and n3 is zero, X does not comprise an antibody chain or a fragment of an antibody chain.

In one embodiment, neither X nor Z comprises an antibody chain or a fragment of an antibody chain. In one embodiment, n1 is one, n3 is one and n2 is two, three, four, five, six, seven, eight or nine. Preferably, Y is an immunoglobulin heavy chain variable domain ($V_H$) that has binding specificity for serum albumin, or an immunoglobulin light chain variable domain ($V_L$) that has binding specificity for serum albumin. More preferably, Y is a dAb (e.g., a $V_H$, $V_\kappa$ or $V_\lambda$) that binds human serum albumin. In a particular embodiment, X or Z is human IL-1ra or a functional variant of human IL-1ra.

In certain embodiments, Y comprises an amino acid sequence selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25 and SEQ ID NO:26. In other embodiments, Y comprises an amino acid sequence selected from the group consisting of SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

In other embodiments, the drug fusion comprises moieties X' and Y', wherein X' is a polypeptide drug, with the proviso that X' does not comprise an antibody chain or a fragment of an antibody chain; and Y' is a single chain antigen-binding fragment of an antibody that has binding specificity for serum albumin. Preferably, Y' is an immunoglobulin heavy chain variable domain ($V_H$) that has binding specificity for serum albumin, or an immunoglobulin light chain variable domain ($V_L$) that has binding specificity for serum albumin. More preferably, Y' is a dAb (e.g., a $V_H$, $V_\kappa$ or $V_\lambda$) that binds human serum albumin. X' can be located amino terminally to Y', or Y' can be located amino terminally to X'. In some embodiments, X' and Y' are separated by an amino acid, or by a peptide or polypeptide linker that comprises from two to about 100 amino acids. In a particular embodiment, X' is human IL-1ra or a functional variant of human IL-1ra.

In certain embodiments, Y' comprises an amino acid sequence selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25 and SEQ ID NO:26. In other embodiments, Y' comprises an amino acid sequence selected from the group consisting of SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

In particular embodiments the drug fusion comprises a dAb that binds serum albumin and human IL-1ra (e.g., SEQ ID NO: 28). Preferably, the dAb binds human serum albumin and comprises human framework regions.

In other embodiments, the drug fusion or drug conjugate comprises a functional variant of human IL-1ra that has at least about 80%, or at least about 85%, or at least about 90%, or at least about 95%, or at least about 96%, or at least about 97%, or at least about 98%, or at least about 99% amino acid sequence identity with the mature 152 amino acid form of human IL-1ra and antagonizes human Interleukin-1 type 1 receptor. (See, Eisenberg et al., Nature 343:341-346 (1990).) The variant can comprise one or more additional amino acids (e.g., comprise 153 or 154 or more amino acids). The drug fusions of the invention can be produced using any suitable method. For example, some embodiments can be produced by the insertion of a nucleic acid encoding the drug fusion into a suitable expression vector. The resulting construct is then introduced into a suitable host cell for expression. Upon expression, fusion protein can be isolated or purified from a cell lysate or preferably from the culture media or periplasm using any suitable method. (See e.g., *Current Protocols in Molecular Biology* (Ausubel, F. M. et al., eds., Vol. 2, Suppl. 26, pp. 16.4.1-16.7.8 (1991)).

Suitable expression vectors can contain a number of components, for example, an origin of replication, a selectable marker gene, one or more expression control elements, such as a transcription control element (e.g., promoter, enhancer, terminator) and/or one or more translation signals, a signal sequence or leader sequence, and the like. Expression control elements and a signal sequence, if present, can be provided by the vector or other source. For example, the transcriptional and/or translational control sequences of a cloned nucleic acid encoding an antibody chain can be used to direct expression.

A promoter can be provided for expression in a desired host cell. Promoters can be constitutive or inducible. For example, a promoter can be operably linked to a nucleic acid encoding an antibody, antibody chain or portion thereof, such that it directs transcription of the nucleic acid. A variety of suitable promoters for procaryotic (e.g., lac, tac, T3, T7 promoters for *E. coli*) and eucaryotic (e.g., simian virus 40 early or late promoter, Rous sarcoma virus long terminal repeat promoter, cytomegalovirus promoter, adenovirus late promoter) hosts are available.

In addition, expression vectors typically comprise a selectable marker for selection of host cells carrying the vector, and, in the case of a replicable expression vector, an origin or replication. Genes encoding products which confer antibiotic or drug resistance are common selectable markers and may be used in procaryotic (e.g., lactamase gene (ampicillin resistance), Tet gene for tetracycline resistance) and eucaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated. Suitable expression vectors for expression in mammalian cells and prokaryotic cells (*E. coli*), insect cells (Drosophila Schnieder S2 cells, Sf9) and yeast (*P. methanolica, P. pastoris, S. cerevisiae*) are well-known in the art.

Recombinant host cells that express a drug fusion and a method of preparing a drug fusion as described herein are provided. The recombinant host cell comprises a recombinant nucleic acid encoding a drug fusion. Drug fusions can be produced by the expression of a recombinant nucleic acid encoding the protein in a suitable host cell, or using other suitable methods. For example, the expression constructs described herein can be introduced into a suitable host cell, and the resulting cell can be maintained (e.g., in culture, in an animal) under conditions suitable for expression of the constructs. Suitable host cells can be prokaryotic, including bacterial cells such as *E. coli, B. subtilis* and or other suitable bacteria, eucaryotic, such as fungal or yeast cells (e.g., *Pichia*

*pastoris, Aspergillus species, Saccharomyces cerevisiae, Schizosaccharomyces pombe, Neurospora crassa*), or other lower eucaryotic cells, and cells of higher eucaryotes such as those from insects (e.g., Sf9 insect cells (WO 94/26087 (O'Connor)) or mammals (e.g., COS cells, such as COS-1 (ATCC Accession No. CRL-1650) and COS-7 (ATCC Accession No. CRL-1651), CHO (e.g., ATCC Accession No. CRL-9096), 293 (ATCC Accession No. CRL-1573), HeLa (ATCC Accession No. CCL-2), CV1 (ATCC Accession No. CCL-70), WOP (Dailey et al., *J. Virol.* 54:739-749 (1985)), 3T3, 293T (Pear et al., *Proc. Natl. Acad. Sci. U.S.A.*, 90:8392-8396 (1993)), NSO cells, SP2/0, HuT 78 cells, and the like (see, e.g., Ausubel, F. M. et al., eds. *Current Protocols in Molecular Biology*, Greene Publishing Associates and John Wiley & Sons Inc., (1993)).

The invention also includes a method of producing a drug fusion, comprising maintaining a recombinant host cell of the invention under conditions appropriate for expression of a drug fusion. The method can further comprise the step of isolating or recovering the drug fusion, if desired. In another embodiment, the components of the drug fusion (e.g., dAb that binds human serum albumin and IL-1ra) are chemically assembled to created a continuous polypeptide chain.

Conjugates

In another aspect, the invention provides conjugates comprising an antigen-binding fragment of an antibody that binds serum albumin that is bonded to a drug. Such conjugates include "drug conjugates," which comprise an antigen-binding fragment of an antibody that binds serum albumin to which a drug is covalently bonded, and "noncovlaent drug conjugates," which comprise an antigen-binding fragment of an antibody that binds serum albumin to which a drug is noncovalently bonded. Preferably, the conjugates are sufficiently stable so that the antigen-binding fragment of an antibody that binds serum albumin and drug remain substantially bonded (either covalently or noncovalently) to each other under in vivo conditions (e.g., when administered to a human). Preferably, no more than about 20%, no more than about 15%, no more than about 10%, no more than about 9%, no more than about 8%, no more than about 7%, no more than about 6%, no more than about 5%, no more than about 4%, no more than about 3%, no more than about 2%, no more than about 1% or substantially none of the conjugates dissociate or break down to release drug and antigen-binding fragment under in vivo conditions. For example, stability under "in vivo" conditions can be conveniently assessed by incubating drug conjugate or noncovalent drug conjugate for 24 hours in serum (e.g., human serum) at 37° C. In one example of such a method, equal amounts of a drug conjugate and the unconjugated drug are diluted into two different vials of serum. Half of the contents of each vial is immediately frozen at −20° C., and the other half incubated for 24 hours at 37° C. All four samples can then be analyzed using any suitable method, such as SDS-PAGE and/or Western blotting. Western blots can be probed using an antibody that binds the drug. All drug in the drug conjugate lanes will run at the size of the drug conjugate if there was no dissociation. Many other suitable methods can be used to assess stability under "in vivo" conditions, for example, by analyzing samples prepared as described above using suitable analytic methods, such as chromatography (e.g., gel filtration, ion exchange, reversed phase), ELISA, mass spectroscopy and the like.

Drug Conjugates

In another aspect, the invention provides a drug conjugate comprising an antigen-binding fragment of an antibody that has binding specificity for serum albumin, and a drug that is covalently bonded to said antigen-binding fragment, with the proviso that the drug conjugate is not a single continuous polypeptide chain.

In some embodiments, the drug conjugate comprises an immunoglobulin heavy chain variable domain ($V_H$) that has binding specificity for serum albumin, or an immunoglobulin light chain variable domain ($V_L$) that has binding specificity for serum albumin, and a drug that is covalently bonded to said $V_H$ or $V_L$, with the proviso that the drug conjugate is not a single continuous polypeptide chain. Preferably the drug conjugate comprises a single $V_H$ that binds serum albumin or a single $V_L$ that binds serum albumin. In certain embodiments, the drug conjugate comprises a $V_k$ dAb that binds human serum albumin and comprises an amino acid sequence selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25 and SEQ ID NO:26. In other embodiments, the drug conjugate comprises a $V_H$ dAb that binds human serum albumin and comprises an amino acid sequence selected from the group consisting of SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

The drug conjugates can comprise any desired drug and can be prepared using any suitable methods. For example, the drug can be bonded to the antigen-binding fragment of an antibody that binds serum albumin directly or indirectly through a suitable linker moiety at one or more positions, such as the amino-terminus, the carboxyl-terminus or through amino acid side chains. In one embodiment, the drug conjugate comprises a dAb that binds human serum albumin and a polypeptide drug (e.g., human IL-1ra or a functional variant of human IL-1ra), and the amino-terminus of the polypeptide drug (e.g., human IL-1ra or a functional variant of human IL-1ra) is bonded to the carboxyl-terminus of the dAb directly or through a suitable linker moiety. In other embodiments, the drug conjugate comprises a dAb that binds human serum albumin and two or more different drugs that are covalently bonded to the dAb. For example, a first drug can be covalently bonded (directly or indirectly) to the carboxyl terminus of the dAb and a second drug can be covalently bonded (directly or indirectly) to the amino-terminus or through a side chain amino group (e.g., ε amino group of lysine). Such drug conjugates can be prepared using well-known methods of selective coupling. (See, e.g., Hermanson, G. T., *Bioconjugate Techniques*, Academic Press: San Diego, Calif. (1996).)

A variety of methods for conjugating drugs to an antigen-binding fragment of an antibody that has binding specificity for serum albumin can be used. The particular method selected will depend on the drug to be conjugated. If desired, linkers that contain terminal functional groups can be used to link the antigen-binding fragment and the drug. Generally, conjugation is accomplished by reacting a drug that contains a reactive functional group (or is modified to contain a reactive functional group) with a linker or directly with an antigen-binding fragment of an antibody that binds serum albumin. Covalent bonds form by reacting a drug that contains (or is modified to contain) a chemical moiety or functional group that can, under appropriate conditions, react with a second chemical group thereby forming a covalent bond. If desired, a suitable reactive chemical group can be added to the antigen-binding fragment or to a linker using any suitable method. (See, e.g., Hermanson, G. T., *Bioconjugate Techniques*, Academic Press: San Diego, Calif. (1996).) Many suitable reactive chemical group combinations are known in the art, for example an amine group can react with an electrophilic group such as tosylate, mesylate, halo (chloro, bromo, fluoro, iodo), N-hydroxysuccinimidyl ester (NHS), and the like. Thiols can react with maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996)).

In some embodiments, the antigen-binding fragment of an antibody that has binding specificity for serum albumin is bonded to a drug by reaction of two thiols to form a disulfide bond. In other embodiments, the antigen-binding fragment of an antibody that has binding specificity for serum albumin is bonded to a drug by reaction of an isothiocyanate group and a primary amine to produce an isothiourea bond.

Suitable linker moieties can be linear or branched and include, for example, tetraethylene glycol, $C_2$-$C_{12}$ alkylene, —NH—$(CH_2)_p$—NH— or —$(CH_2)_p$—NH— (wherein p is one to twelve), —$CH_2$—O—$CH_2$—$CH_2$—O—$CH_2$—$CH_2$—O—CH—NH—, a polypeptide chain comprising one to about 100 (preferably one to about 12) amino acids and the like.

Noncovalent Drug Conjugates

Some noncovalent bonds (e.g, hydrogen bonds, van der Waals interactions) can produce stable, highly specific intermolecular connections. For example, molecular recognition interactions achieved through multiple noncovalent bonds between complementary binding partners underlie many important biological interactions, such as the binding of enzymes to their substrates, the recognition of antigens by antibodies, the binding of ligands to their receptors, and stabilization of the three dimensional structure of proteins and peptide. Accordingly, such weak noncovalent interactions (e.g., hydrogen bonding, van Der Waals interactions, electrostatic interactions, hydrophobic interactions and the like) can be utilized to bind a drug to the antigen-binding fragment of an antibody that has binding specificity for serum albumin.

Preferably, the noncovalent bond linking the antigen-binding fragment and drug be of sufficient strength that the antigen-binding fragment and drug remain substantially bonded to each under in vivo conditions (e.g., when administered to a human). Generally, the noncovalent bond linking the antigen-binding fragment and drug has a strength of at least about $10^{10} M^{-1}$. In preferred embodiments, the strength of the noncovalent bond is at least about $10^{11} M^{-1}$, at least about $10^{12} M^{-1}$, at least about $10^{13} M^{-1}$, at least about $10^{14} M^{-1}$ or at least about $10^{15} M^{-1}$. The interactions between biotin and avidin and between biotin and streptavidin are known to be very efficient and stable under many conditions, and as described herein noncovalent bonds between biotin and avidin or between biotin and streptavidin can be used to prepare a noncovalent drug conjugate of the invention.

The noncovalent bond can be formed directly between the antigen-binding fragment of an antibody that has a specificity for serum albumin and drug, or can be formed between suitable complementary binding partners (e.g., biotin and avidin or streptavidin) wherein one partner is covalently bonded to drug and the complementary binding partner is covalently bonded to the antigen-binding fragment. When complementary binding partners are employed, one of the binding partners can be covalently bonded to the drug directly or through a suitable linker moiety, and the complementary binding partner can be covalently bonded to the antigen-binding fragment of an antibody that binds serum albumin directly or through a suitable linker moiety.

Complementary binding partners are pairs of molecules that selectively bind to each other. Many complementary binding partners are known in the art, for example, antibody (or an antigen-binding fragment thereof) and its cognate antigen or epitope, enzymes and their substrates, and receptors and their ligands. Preferred complementary binding partners are biotin and avidin, and biotin and streptavidin.

Direct or indirect covalent bonding of a member of a complementary binding pair to an antigen-binding fragment that has binding specificity for serum albumin or a drug can be accomplished as described above, for example, by reacting a complementary binding partner that contains a reactive functional group (or is modified to contain a reactive functional group) with an antigen-binding fragment of an antibody that binds serum albumin, with or without the use of a linker. The particular method selected will depend on the compounds (e.g., drug, complementary binding partner, antigen-binding fragment of an antibody that binds serum albumin) to be conjugated. If desired, linkers (e.g., homobifunctional linkers, heterobifunctional linkers) that contain terminal reactive functional groups can be used to link the antigen-binding fragment and/or the drug to a complementary binding partner. In one embodiment, a heterobifunctional linker that contains two distinct reactive moieties can be used. The heterobifunctional linker can be selected so that one of the reactive moieties will react with the antigen-binding fragment of an antibody that has binding specificity for serum albumin or the drug, and the other reactive moiety will react with the complementary binding partner. Any suitable linker (e.g., heterobifunctional linker) can be used and many such linkers are known in the art and available for commercial sources (e.g., Pierce Biotechnology, Inc., IL).

Compositions and Therapeutic and Diagnostic Methods

Compositions comprising drug compositions of the invention (e.g., drug conjugates, noncovalent drug conjugates, drug fusions), including pharmaceutical or physiological compositions (e.g., for human and/or veterinary administration) are provided. Pharmaceutical or physiological compositions comprise one or more drug compositions (e.g., drug conjugate, noncovalent drug conjugate, drug fusion), and a pharmaceutically or physiologically acceptable carrier. Typically, these carriers include aqueous or alcoholic/aqueous solutions, emulsions or suspensions, including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates. Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) *Remington's Pharmaceutical Sciences*, 16th Edition).

The compositions can comprise a desired amount of drug composition (e.g., drug conjugate, noncovalent drug conjugate, drug fusion). For example the compositions can comprise about 5% to about 99% drug conjugate, noncovalent drug conjugate or drug fusion by weight. In particular embodiments, the composition can comprise about 10% to about 99%, or about 20% to about 99%, or about 30% to about 99% or about 40% to about 99%, or about 50% to about 99%, or about 60% to about 99%, or about 70% to about 99%, or about 80% to about 99%, or about 90% to about 99%, or about 95% to about 99% drug composition (e.g., drug conjugate, noncovalent drug conjugate, drug fusion), by weight. In one example, the composition is freeze dried (lyophilized).

The drug compositions (e.g., drug conjugates, noncovalent drug conjugates, drug fusions), described herein will typically find use in preventing, suppressing or treating inflammatory states (e.g., acute and/or chronic inflammatory diseases), such as chronic obstructive pulmonary disease (e.g., chronic bronchitis, chronic obstructive bronchitis, emphysema), allergic hypersensitivity, cancer, bacterial or viral infection, pneumonia, such as bacterial pneumonia (e.g., Staphylococcal pneumonia)), autoimmune disorders (which include, but are not limited to, Type I diabetes, multiple sclerosis, arthritis (e.g., osteoarthritis, rheumatoid arthritis, juvenile rheumatoid arthritis, psoriatic arthritis, lupus arthritis, spondylarthropathy (e.g., ankylosing spondylitis)), systemic lupus erythematosus, inflammatory bowel disease (e.g., Crohn's disease, ulcerative colitis), Behcet's syndrome and myasthenia gravis), endometriosis, psoriasis, abdominal adhesions (e.g., post abdominal surgery), asthma, and septic shock. The drug compositions (e.g., drug conjugates, noncovalent drug conjugates, drug fusions), described herein can be used for preventing, suppressing or treating pain, such as chronic or acute traumatic pain, chronic or acute neuropathic pain, acute or chronic musculoskeletal pain, chronic or acute cancer pain and the like. The drug compositions (e.g., drug conjugates, noncovalent drug conjugates, drug fusions), described herein can also be administered for diagnostic purposes.

Cancers that can be prevented, suppressed or treated using the drug compositions (e.g., drug conjugates, noncovalent drug conjugates, drug fusions), described herein include lymphomas (e.g., B cell lymphoma, acute myeloid lymphoma, Hodgkin's lymphoma, non-Hodgkin's lymphoma), myelomas (e.g., multiple myeloma), lung cancer (e.g., small cell lung carcinoma, non-small cell lung carcinoma), colorectal cancer, head and neck cancer, pancreatic cancer, liver cancer, stomach cancer, breast cancer, ovarian cancer, bladder cancer, leukemias (e.g., acute myelogenous leukemia, chronic myelogenous leukemia, acute lymphocytic leukemia, chronic lymphocytic leukemia), adenocarcinomas, renal cancer, haematopoetic cancers (e.g., myelodysplastic syndrome, myeloproliferative disorder (e.g., polycythemia vera, essential (or primary) thrombocythemia, idiopathic myelofibrosis), and the like.

The drug compositions (e.g., drug conjugates, noncovalent drug conjugates, drug fusions) described herein are also suitable for use in preventing, suppressing or treating endometriosis, fibrosis, infertility, premature labour, erectile dysfunction, osteoporosis, diabetes (e.g., type II diabetes), growth disorder, HIV infection, respiratory distress syndrome, tumors and bedwetting.

In the instant application, the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of drug compositions (e.g., drug conjugates, noncovalent drug conjugates, drug fusions) in protecting against or treating the disease are available. Methods for the testing of systemic lupus erythematosus (SLE) in susceptible mice are known in the art (Knight et al. (1978) *J. Exp. Med.,* 147: 1653; Reinersten et al. (1978) *New Eng. J. Med.,* 299: 515). Myasthenia Gravis (MG) is tested in SJL/J female mice by inducing the disease with soluble AchR protein from another species (Lindstrom et al. (1988) *Adv. Immunol.,* 42: 233). Arthritis is induced in a susceptible strain of mice by injection of Type II collagen (Stuart et al. (1984) *Ann. Rev. Immunol.,* 42: 233). A model by which adjuvant arthritis is induced in susceptible rats by injection of mycobacterial heat shock protein has been described (Van Eden et al. (1988) *Nature,* 331: 171). Effectiveness for treating osteoarthritis can be assessed in a murine model in which arthritis is induced by intra-articular injection of collagenase (Blom, A. B. et al., *Osteoarthritis Cartilage* 12:627-635 (2004). Thyroiditis is induced in mice by administration of thyroglobulin as described (Maron et al. (1980) *J. Exp. Med.,* 152: 1115). Insulin dependent diabetes mellitus (IDDM) occurs naturally or can be induced in certain strains of mice such as those described by Kanasawa et al. (1984) *Diabetologia,* 27: 113. EAE in mouse and rat serves as a model for MS in human. In this model, the demyelinating disease is induced by administration of myelin basic protein (see Paterson (1986) *Textbook of Immunopathology,* Mischer et al., eds., Grune and Stratton, N.Y., pp. 179-213; McFarlin et al. (1973) *Science,* 179: 478: and Satoh et al. (1987) *J. Immunol.,* 138: 179).

The drug compositions (e.g., drug conjugates, noncovalent drug conjugates, drug fusions) of the present invention may be used as separately administered compositions or in conjunction with other agents. These can include various immunotherapeutic drugs, such as cylcosporine, methotrexate, adriamycin or cisplatinum, immunotoxins and the like. Pharmaceutical compositions can include "cocktails" of various cytotoxic or other agents in conjunction with the drug composition (e.g., drug conjugate, noncovalent drug conjugate, drug fusion) of the present invention, or combinations of drug compositions (e.g., drug conjugates, noncovalent drug conjugates, drug fusions) according to the present invention comprising different drugs.

The drug compositions (e.g., drug conjugates, noncovalent drug conjugates, drug fusions) can be administered to any individual or subject in accordance with any suitable techniques. A variety of routes of administration are possible including, for example, oral, dietary, topical, transdermal, rectal, parenteral (e.g., intravenous, intraarterial, intramuscular, subcutaneous, intradermal, intraperitoneal, intrathecal, intraarticular injection), and inhalation (e.g., intrabronchial, intranasal or oral inhalation, intranasal drops) routes of administration, depending on the drug composition and disease or condition to be treated. Administration can be local or systemic as indicated. The preferred mode of administration can vary depending upon the drug composition (e.g., drug conjugate, noncovalent drug conjugate, drug fusion) chosen, and the condition (e.g., disease) being treated. The dosage and frequency of administration will depend on the age, sex and condition of the patient, concurrent administration of other drugs, counterindications and other parameters to be taken into account by the clinician. A therapeutically effective amount of a drug composition (e.g., drug conjugate, noncovalent drug conjugate, drug fusion) is administered. A therapeutically effective amount is an amount sufficient to achieve the desired therapeutic effect, under the conditions of administration.

The term "subject" or "individual" is defined herein to include animals such as mammals, including, but not limited to, primates (e.g., humans), cows, sheep, goats, horses, dogs, cats, rabbits, guinea pigs, rats, mice or other bovine, ovine, equine, canine, feline, rodent or murine species.

The drug composition (e.g., drug conjugate, noncovalent drug conjugate, drug fusion) can be administered as a neutral compound or as a salt. Salts of compounds (e.g., drug compositions, drug conjugates, noncovalent drug conjugates, drug fusions) containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium and the like.

The invention also provides a kit for use in administering a drug composition (e.g., drug conjugate, noncovalent drug conjugate, drug fusion) to a subject (e.g., patient), comprising a drug composition (e.g., drug conjugate, noncovalent drug conjugate, drug fusion), a drug delivery device and, optionally, instructions for use. The drug composition (e.g., drug conjugate, noncovalent drug conjugate, drug fusion) can be provided as a formulation, such as a freeze dried formulation. In certain embodiments, the drug delivery device is selected from the group consisting of a syringe, an inhaler, an intranasal or ocular administration device (e.g., a mister, eye or nose dropper), and a needleless injection device.

The drug composition (e.g., drug conjugate, noncovalent drug conjugate, drug fusion) of this invention can be lyophilized for storage and reconstituted in a suitable carrier prior to use. Any suitable lyophilization method (e.g., spray drying, cake drying) and/or reconstitution techniques can be employed. It will be appreciated by those skilled in the art that lyophilisation and reconstitution can lead to varying degrees of antibody activity loss (e.g., with conventional immunoglobulins, IgM antibodies tend to have greater activity loss than IgG antibodies) and that use levels may have to be adjusted to compensate. In a particular embodiment, the invention provides a composition comprising a lyophilized (freeze dried) drug composition (e.g., drug conjugate, noncovalent drug conjugate, drug fusion) as described herein. Preferably, the lyophilized (freeze dried) drug composition (e.g., drug conjugate, noncovalent drug conjugate, drug fusion) loses no more than about 20%, or no more than about 25%, or no more than about 30%, or no more than about 35%, or no more than about 40%, or no more than about 45%, or no more than about 50% of its activity (e.g., binding activity for serum albumin) when rehydrated. Activity is the amount of drug composition (e.g., drug conjugate, noncovalent drug conjugate, drug fusion) required to produce the effect of the drug composition before it was lyophilized. For example, the amount of drug conjugate or drug fusion needed to achieve and maintain a desired serum concentration for a desired period of time. The activity of the drug composition (e.g., drug conjugate, noncovalent drug conjugate, drug fusion) can be determined using any suitable method before lyophilization, and the activity can be determined using the same method after rehydration to determine amount of lost activity.

Compositions containing the drug composition (e.g., drug conjugate, noncovalent drug conjugate, drug fusion) or a cocktail thereof can be administered for prophylactic and/or therapeutic treatments. In certain therapeutic applications, an amount sufficient to achieve the desired therapeutic or prophylactic effect, under the conditions of administration, such as at least partial inhibition, suppression, modulation, killing, or some other measurable parameter, of a population of selected cells is defined as a "therapeutically-effective amount or dose." Amounts needed to achieve this dosage will depend upon the severity of the disease and the general state of the patient's own immune system and general health, but generally range from about 10 µg/kg to about 80 mg/kg, or about 0.005 to 5.0 mg of drug conjugate or drug fusion per kilogram of body weight, with doses of 0.05 to 2.0 mg/kg/dose being more commonly used. For example, a drug composition (e.g., drug fusion, drug conjugate, noncovalent drug conjugate) of the invention can be administered daily (e.g., up to four administrations per day), every two days, every three days, twice weekly, once weekly, once every two weeks, once a month, or once every two months, at a dose of, for example, about 10 µg/kg to about 80 mg/kg, about 100 µg/kg to about 80 mg/kg, about 1 mg/kg to about 80 mg/kg, about 1 mg/kg to about 70 mg/kg, about 1 mg/kg to about 60 mg/kg, about 1 mg/kg to about 50 mg/kg, about 1 mg/kg to about 40 mg/kg, about 1 mg/kg to about 30 mg/kg, about 1 mg/kg to about 20 mg/kg, about 1 mg/kg to about 10 mg/kg, about 10 µg/kg to about 10 mg/kg, about 10 µg/kg to about 5 mg/kg, about 10 µg/kg to about 2.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg or about 10 mg/kg.

For prophylactic applications, compositions containing the drug composition (e.g., drug conjugate, noncovalent drug conjugate, drug fusion) or cocktails thereof may also be administered in similar or slightly lower dosages. A composition containing a drug composition (e.g., drug conjugate, noncovalent drug conjugate, drug fusion) according to the present invention may be utilised in prophylactic and therapeutic settings to aid in the alteration, inactivation, killing or removal of a select target cell population in a mammal

EXAMPLES

Interleukin 1 receptor antagonist (IL1-ra) is an antagonist that blocks the biologic activity of IL-1 by competitively inhibiting IL-1 binding to the interleukin-1 type 1 receptor (IL-1R1). IL-1 production is induced in response to inflammatory stimuli and mediates various physiologic responses including inflammatory and immunological responses. IL-1 has a range of activities including cartilage degredation and stimulation of bone resorption. In rheumatoid arthritis patients, the amount of locally produced IL-1 is elevated and the levels of naturally occurring IL1-ra are insufficient to compete with these abnormally increased amounts. There are several treatments available for RA including disease modifying antirheumatic drugs (DMARDS) such as methotrexate, and biologics such as KINERET® (anakinra, Amgen Inc).

KINERET® (anakinra, Amgen Inc) is a recombinant, non-glycosylated form of the human interleukin-1 receptor antagonist which consists of 153 amino acids and has a molecular weight of 17.3 kilodaltons. (The amino acid sequence of KINERET® (anakinra, Amgen Inc) corresponds to the 152 amino acids in naturally occurring IL-1ra and an additional N-terminal methionine.) KINERET® (anakinra, Amgen Inc) is indicated for the reduction in signs and symptoms of moderate to severe rheumatoid arthritis in patients 18 years of age or older who have failed one or more DMARDs. Dosage is a single use daily subcutaneous injection of 100 mgs of drug. The $T_{\beta^{1/2}}$ is 4-6 hours and 71% of patients develop injection site reactions in 14-28 days.

Here we demonstrate that linking a therapeutic polypeptide to a serum-albumin binding dAb results in a compound which (i) has activity similar to the therapeutic polypeptide alone and (ii) also binds serum albumin. Furthermore, the present invention provides a method to create a long serum half-life version of the therapeutic polypeptide. For example, we have linked a serum albumin binding dAb to IL1-ra which results in a compound of longer serum half-life than IL1-ra alone.

Example 1

Selection of Domain Antibodies that Bind Mouse, Rat and Human Serum Albumin

This example explains a method for making a single domain antibody (dAb) directed against serum albumin. Selection of dAbs against mouse serum albumin (MSA), human serum albumin (HSA) and rat serum albumin (RSA) is described.

The dAbs against mouse serum albumin were selected as described in WO 2004/003019 A2. Three human phage display antibody libraries were used. Each library was based on a single human framework for $V_H$ (V3-23/DP47 and $J_H$4b) or $V_\kappa$ (o12%2/DPK9 and $J_\kappa$1) with side chain diversity encoded by NNK codons incorporated in complementarity determining regions (CDR1, CDR2 and CDR3).
Library 1 ($V_H$):
Diversity at positions: H30, H31, H33, H35, H50, H52, H52a, H53, H55, H56, H58, H95, H97, H98.
Library size: $6.2 \times 10^9$
Library 2 ($V_H$):
Diversity at positions: H30, H31, H33, H35, H50, H52, H52a, H53, H55, H56, H58, H95, H97, H98, H99, H100, H100A, H100B.
Library size: $4.3 \times 10^9$
Library 3 ($V_\kappa$):
Diversity at positions: L30, L31, L32, L34, L50, L53, L91, L92, L93, L94, L96
Library size: $2 \times 10^9$ The $V_H$ and $V_\kappa$ libraries had been preselected for binding to generic ligands protein A and protein L respectively so that the majority of clones in the selected libraries were functional. The sizes of the libraries shown above correspond to the sizes after preselection.

Two rounds of selection were performed on serum albumin using each of the libraries separately. For each selection, antigen was coated on immunotube (nunc) in 4 mL of PBS at a concentration of 100 µg/ml. In the first round of selection, each of the three libraries was panned separately against HSA (Sigma) or MSA (Sigma). In the second round of selection, phage from each of the six first round selections was panned against (i) the same antigen again (eg 1$^{st}$ round MSA, 2nd round MSA) and (ii) against the reciprocal antigen (eg 1$^{st}$ round MSA, 2nd round HSA) resulting in a total of twelve 2nd round selections. In each case, after the second round of selection 48 clones were tested for binding to HSA and MSA. Soluble dAb fragments were produced as described for scFv fragments by Harrison et al, *Methods Enzymol.* 1996; 267: 83-109 and standard ELISA protocol was followed (Hoogenboom et al. (1991) *Nucleic Acids Res.,* 19: 4133) except that 2% tween PBS was used as a blocking buffer and bound dAbs were detected with either protein L-HRP (Sigma) (for the VκS) and protein A-HRP (Amersham Pharmacia Biotech) (for the $V_H$s).

dAbs that gave a signal above background indicating binding to MSA, HSA or both were tested in ELISA insoluble form for binding to plastic alone but all were specific for serum albumin. Clones were then sequenced (see Table 1) revealing that 21 unique dAb sequences had been identified. The minimum similarity (at the amino acid level) between the $V_\kappa$ dAb clones selected was 86.25% ((69/80) X100; the result when all the diversified residues are different, e.g., clones 24 and 34). The minimum similarity between the $V_H$ dAb clones selected was 94% ((127/136) X100).

Next, the serum albumin binding dAbs were tested for their ability to capture biotinylated antigen from solution. ELISA protocol (as above) was followed except that ELISA plate was coated with 1 µg/ml protein L (for the $V_\kappa$ clones) and 1 µg/ml protein A (for the $V_H$ clones). Soluble dAb was captured from solution as in the protocol and detection was with biotinylated MSA or HSA and streptavidin HRP. The biotinylated MSA and HSA had been prepared according to the manufacturer's instructions, with the aim of achieving an average of 2 biotins per serum albumin molecule. Twenty four clones were identified that captured biotinylated MSA from solution in the ELISA. Two of these (clones 2 and 38 below) also captured biotinylated HSA. Next, the dAbs were tested for their ability to bind MSA coated on a CM5 biacore chip. Eight clones were found that bound MSA on the biacore.

dAbs against human serum albumin and rat serum albumin were selected as previously described for the anti-MSA dAbs except for the following modifications to the protocol: The phage library of synthetic $V_H$ domains was the library 4G, which is based on a human $V_H$3 comprising the DP47 germline gene and the $J_H$4 segment. The diversity at the following specific positions was introduced by mutagenesis (using NNK codons; numbering according to Kabat) in CDR1: 30, 31, 33, 35; in CDR2: 50, 52, 52a, 53, 55, 56; and in CDR3: 4-12 diversified residues: e.g. H95, H96, H97, and H98 in 4G H11 and H95, H96, H97, H98, H99, H100, H100a, H100b, H100c, H100d, H100e and H100f in 4G H19. The last three CDR3 residues are FDY so CDR3 lengths vary from 7-15 residues. The library comprises $>1 \times 10^{10}$ individual clones.

A subset of the $V_H$ and $V_\kappa$ libraries had been preselected for binding to generic ligands protein A and protein L respectively so that the majority of clones in the unselected libraries were functional. The sizes of the libraries shown above correspond to the sizes after preselection.

Two rounds of selection were performed on rat and human serum albumin using subsets of the $V_H$ and $V_\kappa$ libraries separately. For each selection, antigen was either (i) coated on immunotube (nunc) in 4 ml of PBS at a concentration of 100 µg/ml or (ii) biotinylated and then used for soluble selection followed by capture on streptavidin beads (in the 1$^{st}$ round) and neutravidin beads (in the 2$^{nd}$ round). (See Table 1 for details of the selection strategy used to isolate each clone.) In each case, after the second round of selection 24 phage clones were tested for binding to HSA or RSA.

If a significant proportion of the clones in one of the selections were positive in the phage ELISA, then DNA from this selection was cloned into an expression vector for production of soluble dAb, and individual colonies were picked. Soluble dAb fragments were produced as described for scFv fragments by Harrison et al (Methods Enzymol. 1996; 267:83-109) and standard ELISA protocol was followed (Hoogenboom et al. (1991) Nucleic Acids Res., 19: 4133) except that 2% TWEEN PBS was used as a blocking buffer and bound dAbs were detected with anti-myc-HRP. Clones that were positive in ELISA were then screened for binding to MSA, RSA or HSA using a BIACORE surface plasmon resonance instrument (Biacore AB). dAbs which bound to MSA, RSA or HSA were further analysed. Clones were then sequenced and unique dAb sequences identified.

TABLE 1

Selection protocols for dAbs that bind serum albumin

| dAb | Library | R1 selection | R2 selection | Biacore binding |
|---|---|---|---|---|
| DOM7r-1 | 4G Vκ | 10 µg/ml tube RSA | 10 µg/ml tube RSA | RSA |
| DOM7r-3 | 4G Vκ | 10 µg/ml tube RSA | 10 µg/ml tube RSA | RSA |
| DOM7r-4 | 4G Vκ | 10 µg/ml tube RSA | 10 µg/ml tube RSA | RSA, MSA |
| DOM7r-5 | 4G Vκ | 10 µg/ml tube RSA | 10 µg/ml tube RSA | RSA |
| DOM7r-7 | 4G Vκ | 10 µg/ml tube RSA | 10 µg/ml tube RSA | RSA, MSA |
| DOM7r-8 | 4G Vκ | 10 µg/ml tube RSA | 10 µg/ml tube RSA | RSA, MSA |
| DOM7h-1 | 4G Vκ | 10 µg/ml tube HSA | 10 µg/ml tube HSA | HSA |
| DOM7h-2 | 4G Vκ | Soluble 100 nM HSA | Soluble 50 nM HSA | HSA |
| DOM7h-3 | 4G Vκ | 10 µg/ml tube HSA | 10 µg/ml tube HSA | — |
| DOM7h-4 | 4G Vκ | 10 µg/ml tube HSA | 10 µg/ml tube HSA | — |
| DOM7h-6 | 4G Vκ | | | |
| DOM7h-7 | 4G Vκ | | | |
| DOM7h-8 | 4G Vκ | Soluble 200 nM HAS | Soluble 50 nM RSA | HSA, RSA, MSA |
| DOM7r-13 | 4G Vκ | Soluble 200 nM HAS | Soluble 50 nM RSA | RSA, MSA |
| DOM7r-14 | 4G Vκ | Soluble 200 nM HAS | Soluble 50 nM RSA | RSA, MSA |
| DOM7h-21 | 4G VH | 100 µg/ml HSA tube | 100 µg/ml HSA tube | HSA |
| DOM7h-22 | 4G VH | 100 µg/ml HSA tube | 100 µg/ml HSA tube | HSA |
| DOM7h-23 | 4G VH | 100 µg/ml HSA tube | 100 µg/ml HSA tube | HSA |
| DOM7h-24 | 4G VH | 100 µg/ml HSA tube | 100 µg/ml HSA tube | HSA |
| DOM7h-25 | 4G VH | 100 µg/ml HSA tube | 100 µg/ml HSA tube | HSA |
| DOM7h-26 | 4G VH | 100 µg/ml HSA tube | 100 µg/ml HSA tube | HSA |
| DOM7h-27 | 4G VH | 100 µg/ml HSA tube | 100 µg/ml HSA tube | HSA | dAbs that bound serum albumin on a BIACORE chip (Biacore AB) were then further analysed to obtain information on affinity. The analysis was performed using a CM5 chip (carboxymethylated dextran matrix) that was coated with serum albumin. Flow cell 1 was an uncoated, blocked negative control, flow cell 2 was coated with HSA, flow cell 3 was coated with RSA and flow cell 4 was coated with MSA. The serum albumins were immobilised in acetate buffer pH 5.5 using the BIACORE coating wizard which was programmed to aim for 500 resonance units (RUs) of coated material. Each dAb of interest was expressed in the periplasm of E. coli on a 200 mL-500 mL scale and purified from the supernatant using batch absorbtion to protein A-streamline affinity resin (Amersham, UK) for the $V_H$s and to protein L-agarose affinity resin (Affitech, Norway) for the $V_κ$s followed by elution with glycine at pH 2.2 and buffer exchange to PBS. A range of concentrations of dAb were prepared (in the range 5 nM to 5 µM) by dilution into BIACORE HBS-EP buffer and flowed across the BIACORE chip.

Figure 6A:
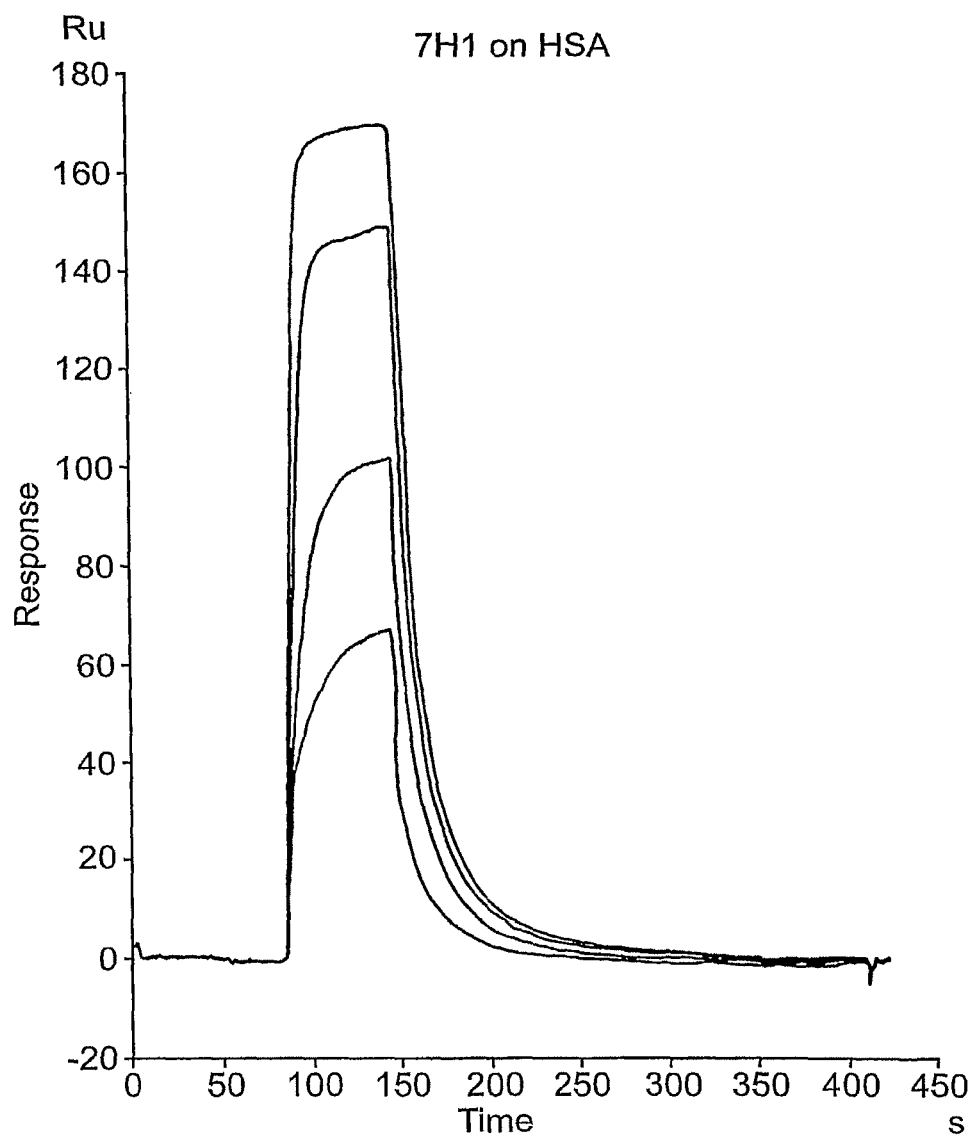
FIGS. 6A-6C are sensograms and tables showing BIA-CORE affinity data for clone DOM7h-1 binding to human serum albumin (HSA) (6A), DOM7h-7 binding to HSA (6B) and DOM7r-1 binding to rat serum albumin (RSA) (6C).
Figure 6B:
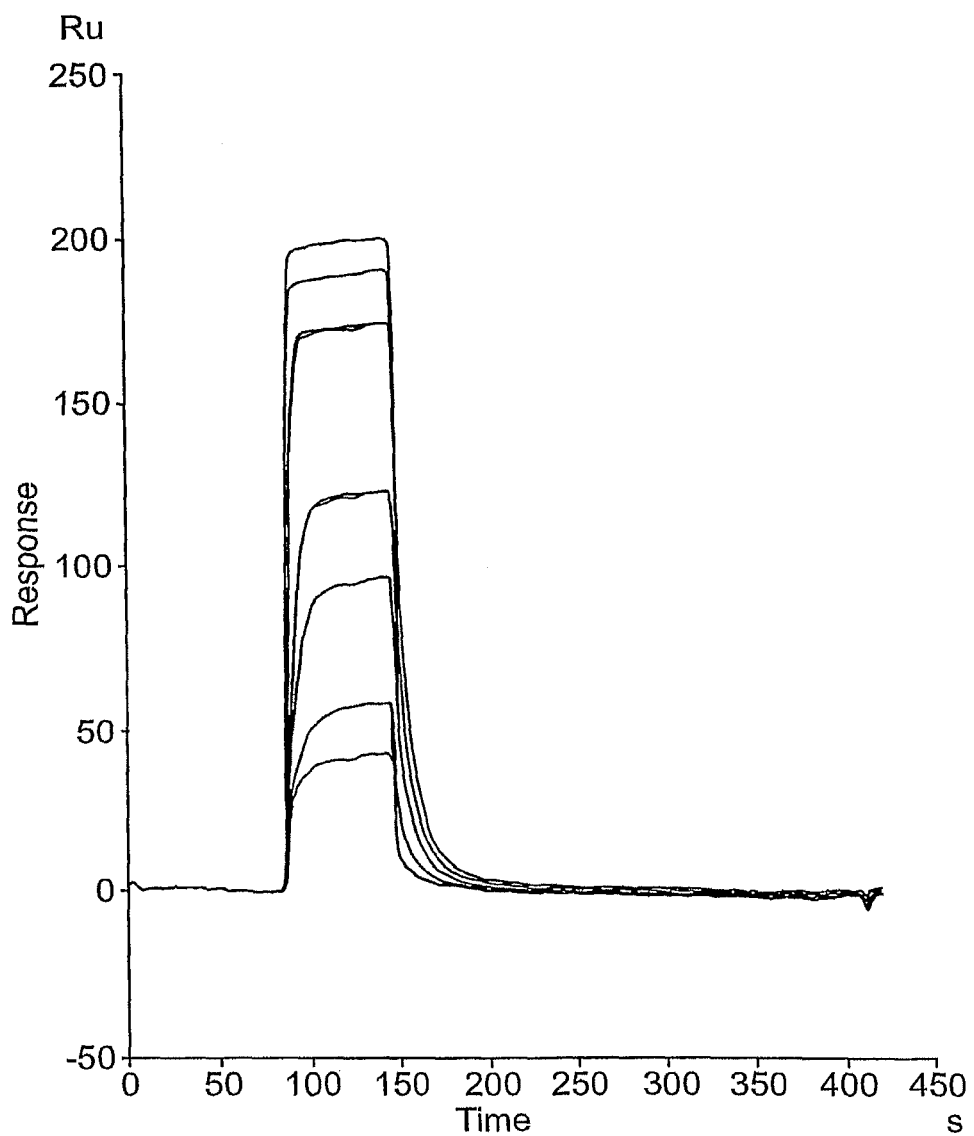
Figure 6C:
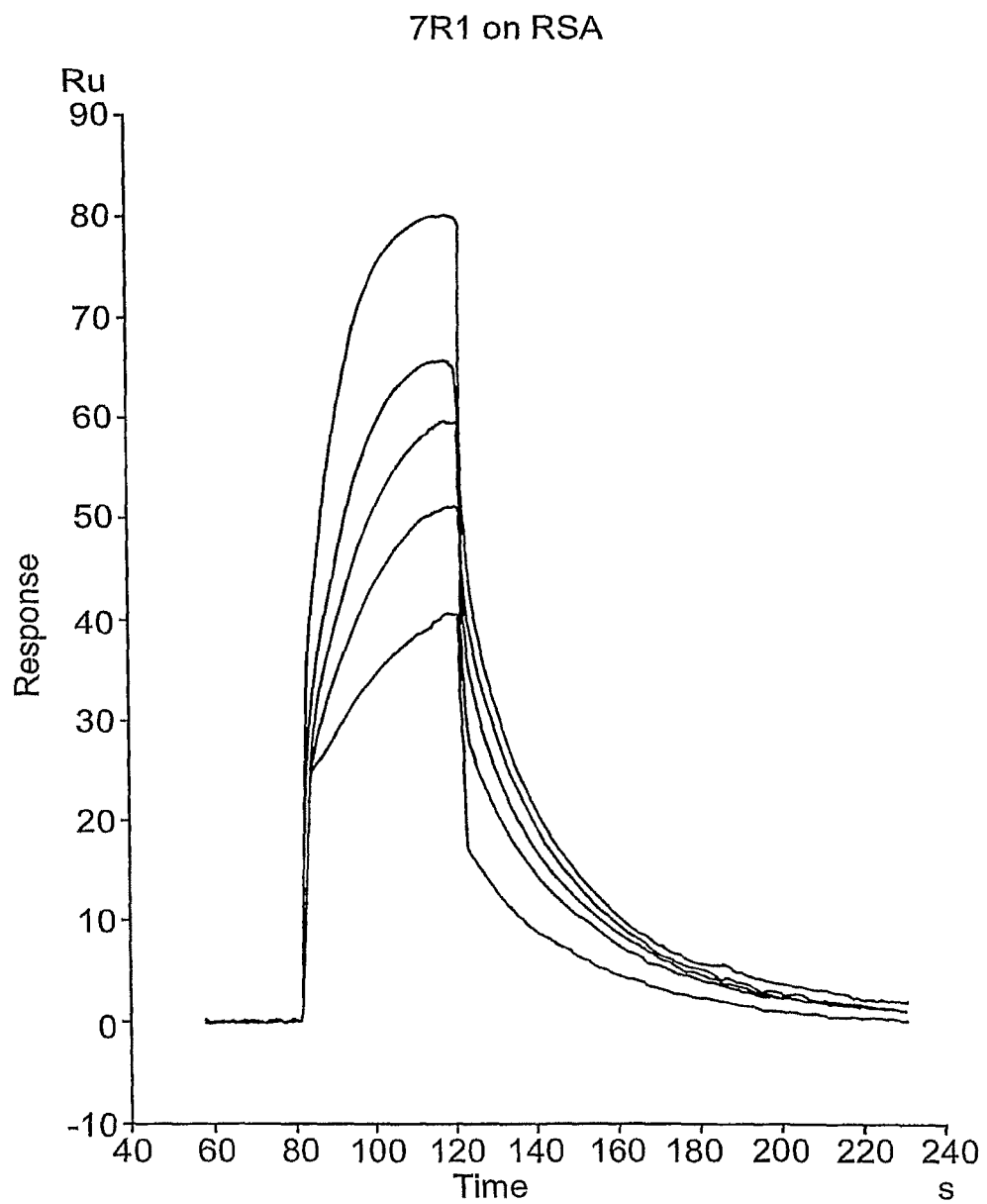

Affinity (KD) was calculated from the BIACORE traces by fitting onrate and offrate curves to traces generated by concentrations of dAb in the region of the KD. dAbs with a range of different affinities to serum albumin were identified. Included in the range 10-100 nM, were the affinities of DOM7h-8 for HSA, DOM7h-2 for HSA and DOM7r-1 for RSA. Included in the range 100 nM to 500 nM were the affinities of DOM7h-7 for HSA, DOM7h-8 for RSA and DOM7h-26 for HSA. Included in the range 500 nM to 5 µM were the affinities of DOM7h-23 for HSA and DOM7h-1 for HSA. Example traces are included in FIGS. 6A-6C.

Example 2

Formatting Anti-Serum Albumin Antibodies as a Fusion with IL-1 Receptor Antagonist (IL-1ra)

Figure 2A:
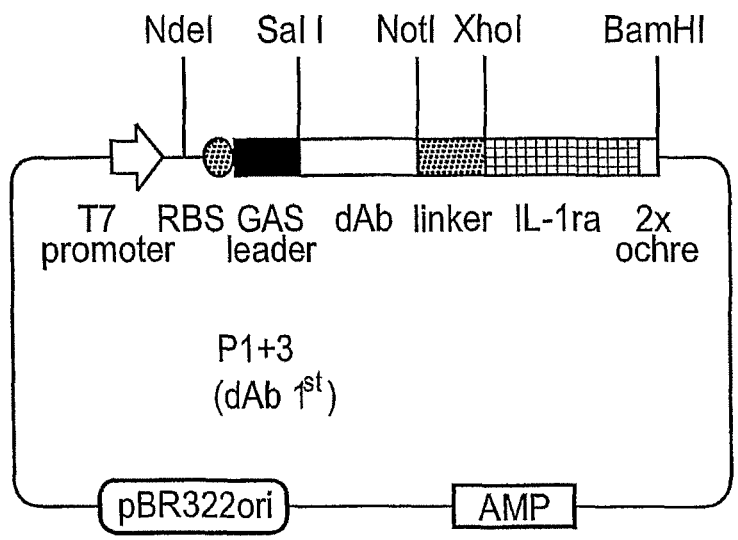
FIGS. 2A and 2B are schematics maps of the vectors used to express the MSA16IL-1ra (also referred to as DOM7m-16/IL-1ra) and IL-1raMSA16 (also referred to as IL-1ra/DOM7m-16) fusions, respectively.
Figure 2B:
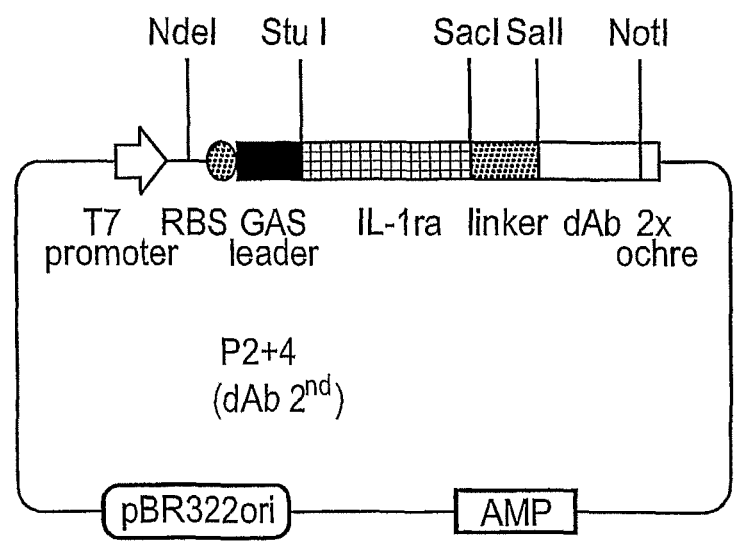
Figure 3A:
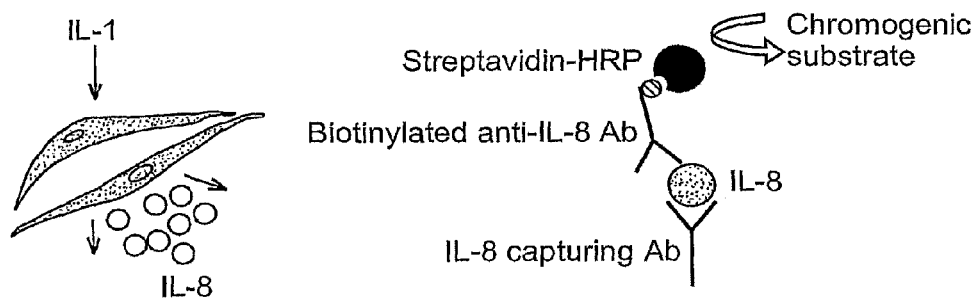
FIG. 3A is an illustration showing that IL-1 induces the production of IL-8 by HeLa cells, and showing the mechanism by which IL-8 is detected in an ELISA assay.
Figure 3B:
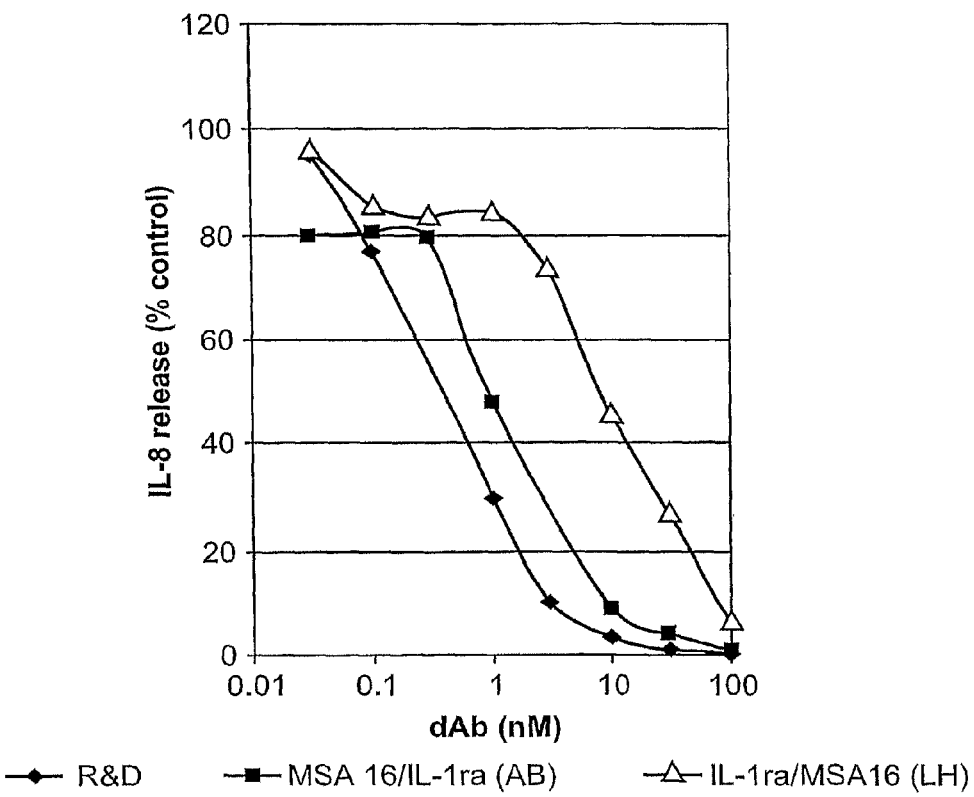
FIG. 3B is a graph showing that IL-1ra (♦, labeled "R&D"), MSA16IL-1ra (■) and IL-1raMSA16 (▲) each inhibited IL-1-induced secretion of IL-8 by cultured MRC-5 cells. The observed inhibition was dose dependent for IL-1ra, MSA16IL-1ra and IL-1raMSA16.
Figure 4A:
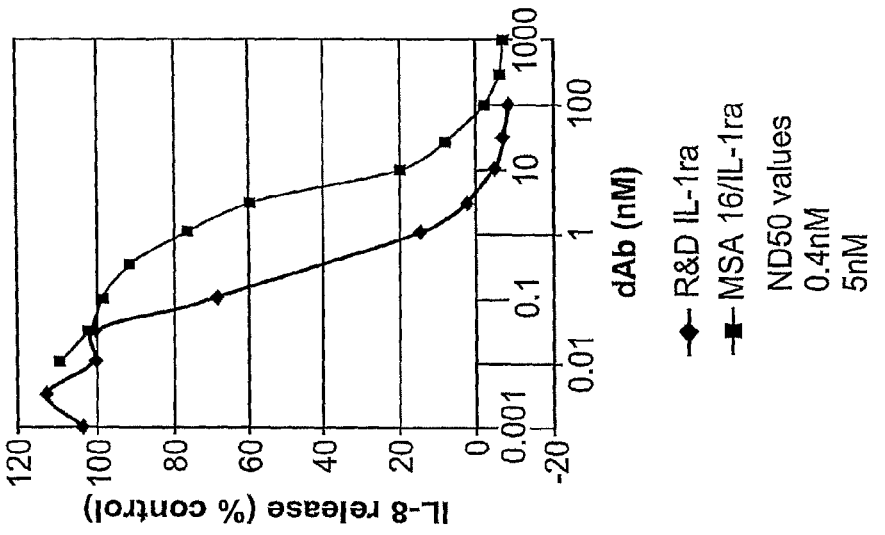
FIGS. 4A-4C are graphs showing that IL-1ra (♦) and MSA16IL-1ra (■) both inhibited IL-1-induced secretion of IL-8 by cultured MRC-5 cells in assays that included no mouse serum albumin (4A), 5% mouse serum albumin (4B) or 10% mouse serum albumin (4C). The observed inhibition was dose dependent for IL-1ra and MSA16IL-1ra under all conditions tested.
Figure 4B:
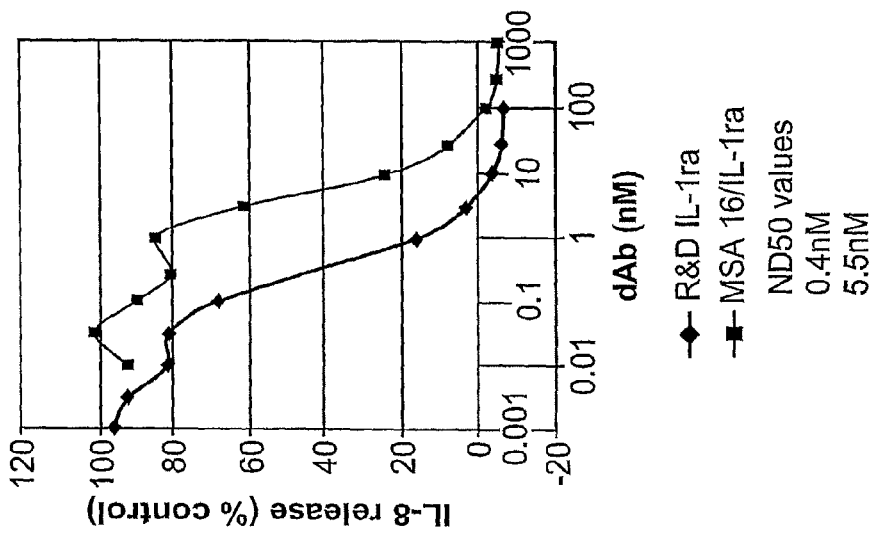
Figure 4C:
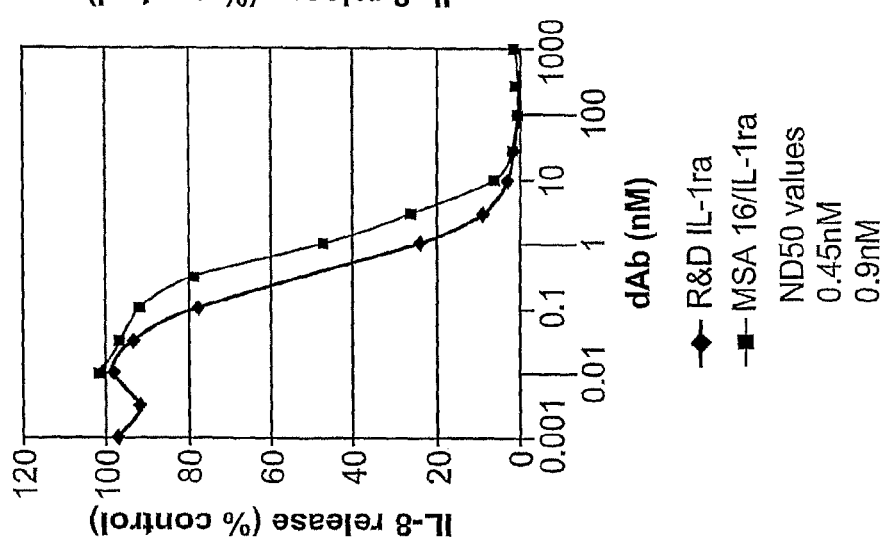
Figure 5:
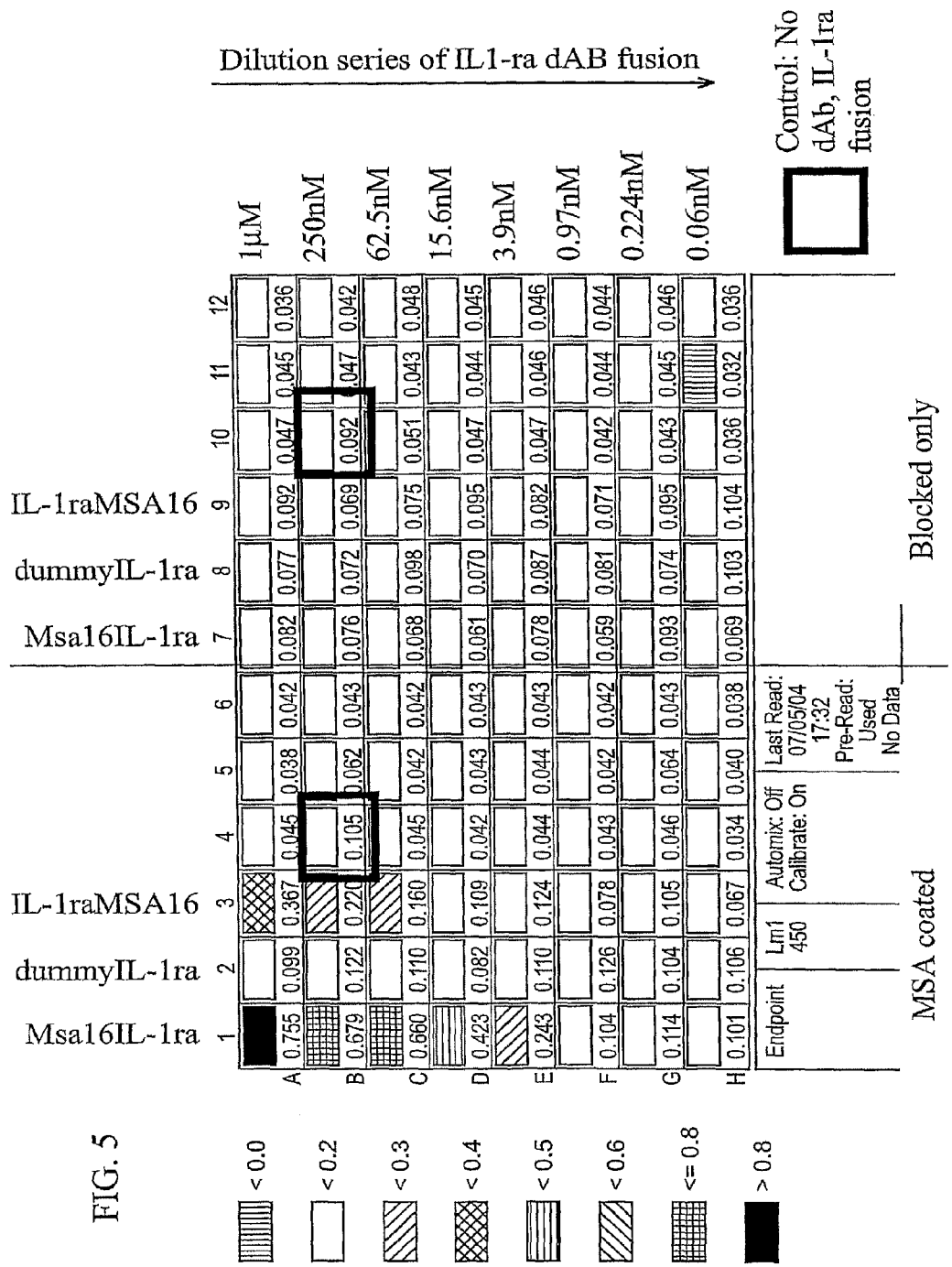
FIG. 5 is a schematic presentation of the results of an ELISA demonstrating that the MSA16IL1-ra fusion and the IL-1raMSA16 fusion both bound serum albumin, but the dummyIL1-ra fusion did not.

This example describes a method for making a fusion protein comprising IL-1ra and a dAb that binds to serum albumin. Two fusions were made, one with the dAb N-terminal of the IL-1ra (MSA16IL1-ra) and one with the dAb C-terminal of the IL-1ra (IL1-raMSA 16). The sequences of the fusions and the vector are shown in FIGS. 2C and 2D. A control fusion that did not bind MSA was also produced, and its sequence is shown in FIG. 2E.

KINERET (anakinra, Amgen Inc) has a short half-life of 4-6 hours, and the recommended dosing regime calls for daily injections. This regime lead to injection site reaction in 14-28 days in 71% of cases. Therefore a form of human IL-1ra that has a longer serum half-life would be beneficially and could increase efficacy and reduce dosing frequency. These are both desirable properties for a pharmaceutical.

Cloning

Briefly, two multiple cloning sites (MCSs) were designed as detailed below and inserted into an expression vector with a T7 promotor. The restriction sites were designed for the insertion of IL1-ra, dAb, GAS leader and linker. One (MCS 1+3) encodes a protein with the dAb N terminal of the IL-1ra and the other (MCS 2+4) encode a protein with the dAb C terminal of the IL-1ra.

Cloning site 1+3 for dAbIL1-ra fusion
NdeI, stuffer, SalI, NotI, stuffer, XhoI, BamHI (SEQ ID NO: 35)
gcgcatatgttagtgcgtcgacgtcaaaaggccatagcgggcggccgctg caggtctcgagtgcgatggatcc Cloning site 2+4 for IL1-radAb fusion
NdeI, stuffer, StUI, SacI, stuffer, SalI, NotI, TAA TAA BamHI (SEQ ID NO: 36)
gcgcatatgttaagcgaggccttctggagagagctcaggagtgtcgacgg acatccagatgacccaggcggccgctaataaggatccaatgc The GAS leader was then inserted into each vector by digesting the MCS using the appropriate restriction enzymes and ligating annealed primers coding for the leader. Next, linker DNA coding for the linker was inserted in a similar manner. DNA coding for IL-1ra was obtained by PCR (using primers designed to add the required restriction sites) from a cDNA clone and inserted into a TOPO cloning vector. After confirming the correct sequence by nucleic acid sequencing, DNA coding for IL-1ra was excised from the TOPO vector and ligated into the vectors containing leader and linker. Lastly, DNA coding for the dAb was excised from the dAb expression vector and inserted into the vectors by SalI/NotI digest of insert (purified by gel purification) and vector.

Expression and Purification

MSA16IL1-ra, IL1-raMSA16 and dummyIL-1ra were expressed in the periplasm of E. coli and purified from the supernatant using batch absorbtion to protein L-agarose affinity resin (Affitech, Norway) followed by elution with glycine at pH 2.2. The purified dAbs were then analysed by SDS-PAGE gel electrophoresis followed by coomassie staining. For one of the proteins (IL-1raMSA 16), >90% of the protein was of the expected size and therefore was analysed for activity without further purification. The other proteins (MSA16IL1-ra and dummy IL-1ra) were contaminated by a smaller band and were therefore further purified by FPLC ion exchange chromatography on the RESOURSEQ ion exchange column at pH 9. Protein was eluted using a linear salt gradient form 0-500 mM NaCl. After analysis by SDS-PAGE gel electrophoresis, fractions containing a protein of the expected size were combined yielding a combined fraction of >90% purity. This protein was used for further analysis Example 3

Determination of Activity of dAb IL1-ra Fusion In Vitro MRC-5 IL-8 Assay

MSA16IL-1ra fusions were tested for the ability to neutralise the induction of IL-8 secretion by IL-1 in MRC-5 cells (ATCC Accession No. CCL-171; American Type Culture Collection, Manassas, Va.). The method is adapted from Akeson, L. et al (1996) Journal of Biological Chemistry 271, 30517-30523, which describes the induction of IL-8 by IL-1 in HUVEC, MRC-5 cells were used instead of the HUVEC cell line. Briefly, MRC-5 cells plated in microtitre plates were incubated overnight with dAbIL-1ra fusion proteins or IL-1ra control, and IL-1 (100 pg/mL). Post incubation the supernatant was aspirated off the cells and IL-8 concentration measured via a sandwich ELISA (R&D Systems).

The activity of IL-1ra in the fusion proteins led to a reduction in IL-8 secretion. The reduction of IL-8 secretion resulting from activity of the MSA16IL1-ra fusion and from activity of the IL-1raMSA16 fusion was compared to the reduction seen with the IL-1ra control (recombinant human IL-1ra, R&D systems). The neutralizing dose 50 ($ND_{50}$) of each of the tested proteins was determined and is presented in Table 2.

TABLE 2

| Protein | $ND_{50}$ |
|---|---|
| IL-1ra | 0.5 nM |
| MSA16IL-1ra | 2 nM |
| IL-1raMSA16 | 8 nM |

The results demonstrate that IL-1ra remained active as part of a fusion construct with an anti-serum albumin dAb. The MSA16IL-1ra protein was further studied to assess its pharmacokinetics (PK study).

Serum Albumin, Anti IL-1ra Sandwich ELISA

Three dAb/IL-1ra fusions were tested for the ability to bind serum albumin and simultaneously be detected by a monoclonal anti-IL1ra antibody. The fusions tested were MSA16IL-1ra, IL-1raMSA16 and dummyIL-1ra. Briefly, ELISA plate was coated overnight with mouse serum albumin at 10 µg/ml, washed 5× with 0.05% Tween PBS and then blocked for 1 hour with 4% Marvel PBS. After blocking, the plate was washed 5× with 0.05% Tween PBS and then incubated for 1 hour with each dAb, Il-1ra fusion diluted in 4% MPBS. Each fusion was incubated at 1 µM concentration and at 7 sequential 4-fold dilutions (ie down to 60 µM). After the incubation, plates were washed 5× with 0.05% Tween PBS and then incubated for 1 hour with the manufacturers recommended dilution of a rabbit polyclonal antibody (ab-2573) to human IL-1 receptor antagonist (Abcam, UK) diluted in 4% MPBS. After this incubation, plates were washed 5× with 0.05% Tween PBS and then incubated for 1 h with a 1/2000 dilution of secondary antibody (anti-rabbit IgG-HRP) diluted in 4% MPBS. Following incubation with the secondary antibody, plates were washed 3× with 0.05% Tween PBS and 2× with PBS and then developed with 50 µl per well of TMB microwell peroxidase substrate (KPL, MA) and the reaction stopped with 50 µl per well of HCL. Absorbtion was read at 450 nM.

Both the MSA16IL-1ra and IL-1raMSA16 proteins were detected at more than 2× background level at 1 µM concentration in the sandwich ELISA. The MSA16IL-1ra protein was detected at 2× background or higher at dilutions down to 3.9 nM, whereas the IL-1raMSA16 protein was detected at 2× background only down to 500 nM. Binding of the MSA16IL-1ra fusion to serum albumin was shown to be specific for serum albumin as the control construct (dummyIL-1ra) did not bind serum albumin.

Example 4

Determination of Serum Half-Life of Drug Fusions in Mouse PK Studies

A. Determination of the Serum Half-Life in Mouse of a MSA Binding dAb/HA Epitope Tag Fusion Protein The MSA binding dAb/HA epitope tag fusion protein was expressed in the periplasm of *E. coli* and purified using batch absorbtion to protein L-agarose affinity resin (Affitech, Norway) followed by elution with glycine at pH 2.2. Serum half-life of the fusion protein was determined in mouse following a single intravenous (i.v.) injection at approx 1.5 mg/kg into CD1 strain male animals. Analysis of serum levels was by ELISA using goat anti-HA (Abcam, UK) capture and protein L-HRP (Invitrogen, USA) detection which was blocked with 4% Marvel. Washing was with 0.05% Tween-20, PBS. Standard curves of known concentrations of MSA binding dAb/HA fusion were set up in the presence of 1× mouse serum to ensure comparability with the test samples. Modelling with a 1 compartment model (WinNonlin Software, Pharsight Corp., USA) showed the MSA binding dAb/HA epitope tag fusion protein had a terminal phase t½ of 29.1 hours and an area under the curve of 559 hr·µg/ml. This demonstrates a large improvement over the predicted half-life for a HA epitope tag peptide alone which could be a short as only several minutes.

The results of this study using the HA epitope tag as a drug model, demonstrate that the in vivo serum half-life of a drug can be extended when the drug is prepared as a drug fusion or drug conjugate with an antigen-binding fragment of (e.g., dAb) of an antibody that binds serum albumin.

The in vivo half-life in mice of the anti-MSA dAbs DOM7m-16 and DOM7m-26, and a control dAb that does not bind MSA were also assessed. Again, DOM7m-16, DOM7m-26 and the control dAb contained an HA epitope tag, which serves as a model for a drug (e.g., a protein, polypeptide or peptide drug). In this study, the control dAb, that does not bind MSA, had an in vivo half-life of 20 minutes, whereas the in vivo half-lives of DOM7m-16 and DOM7m-26 were significantly extended. (FIG. 12) DOM7m-16 was found to have an in vivo half-life in mice of 29.5 hours in further studies.

In another study, the in vivo half-life (t½β) of DOM7h-8 which contained an HA epitope tag was evaluated in mice.

Modelling with a 2 compartment model (WinNonlin Software, Pharsight Corp., USA) showed that DOM7h-8 had a t½β of 29.1 hours.

The results of each of these study using the HA epitope tag as a model for a drug (e.g., a protein, polypeptide or peptide drug), demonstrate that the in vivo serum half-life of a drug can be dramatically extended when the drug is prepared as a drug fusion or drug conjugate with an antigen-binding fragment of (e.g., dAb) of an antibody that binds serum albumin.

B. Determination of the Serum Half-Life in Mouse of MSA Binding dAb/IL-1ra Fusion Protein The MSA binding dAb/IL-1ra fusion protein (MSA16IL-1ra) was expressed in the periplasm of *E. coli* and purified using batch absorbtion to protein L-agarose affinity resin (Affitech, Norway) followed by elution with glycine at pH 2.2. Serum half-life of the MSA16IL-1ra (DOM7m-16/IL-1ra), an IL-1ra fusion with a dAb that does not bind MSA (Dummy dAb/IL-1ra), and an anti-MSA dAb fused to the HA epitope tag (DOM7m-16 HA tag) was determined in mice following a single i.v. injection at approximately 1.5 mg/kg into CD1 strain male animals.

Analysis of serum levels was by Il-1ra sandwich ELISA (R&D Systems, USA). Standard curves of known concentrations of dAb/IL-1ra fusion were set up in the presence of 1× mouse serum to ensure comparability with the test samples. Modelling was performed using the WinNonlin pharmacokinetics software (Pharsight Corp., USA).

It was expected that the IL-1ra fusion with the anti-MSA dAb would increase the serum half-life considerably when compared with the control which was a fusion of a non-MSA binding dAb with IL-1ra. The control non-MSA binding dAb/IL-1ra fusion was predicted to have a short serum half-life.

The results of the study are presented in Table 3, and show that the IL-1ra fusion with anti-MSA dAb (DOM7m-16/IL-1ra had a serum half-life that was about 10 times longer than the IL-1ra fusion with a dAb that does not bind MSA (Dummy dAb/IL-1ra). The results also revealed that there was a >200 fold improvement (increase) in the area under the concentration time curve for DOM7m-16/IL-1ra (AUC: 267 hr·μg/ml) as compared to dummy/IL-1ra (AUC: 1.5 hr·μg/ml)

TABLE 3

| Agent | Serum Half-life |
|---|---|
| DOM7m-16/IL-1ra | 4.3 hours |
| dummy/IL-1ra | 0.4 hours |
| DOM7m-16 HA tag | 29 hours |

The results of these studies demonstrate that the in vivo serum half-life and AUC of a drug can be significantly extended when the drug is prepared as a drug fusion or drug conjugate with an antigen-binding fragment of (e.g., dAb) of an antibody that binds serum albumin.

Example 5

Determination of the Serum Half-Life in Rats of RSA Binding dAb/HA Epitope Tag Fusion Proteins Anti-rat serum albumin dAbs were expressed with C-terminal HA tags in the periplasm of *E. coli* and purified using batch absorbtion to protein L-agarose affinity resin (Affitech, Norway) for Vk dAbs and batch absorbtion to protein A affinity resin for VH dAbs, followed by elution with glycine at pH 2.2. In order to determine serum half-life, groups of 4 rats were given a single i.v. injection at 1.5 mg/Kg of DOM7r-27, DOM7r-31, DOM7r-16, DOM7r-3, DOM7h-8 or a control dAb (HEL4) that binds an irrelevant antigen. Serum samples were obtained by serial bleeds from a tail vein over a 7 day period and analyzed by sandwich ELISA using goat anti-HA (Abeam, cambridge UK) coated on an ELISA plate, followed by detection with protein A-HRP (for the $V_H$ dAbs) or protein L-HRP (for $V_k$ dAbs). Standard curves of known concentrations of dAb were set up in the presence of 1× rat serum to ensure comparability with the test samples. Modelling with a 2 compartment model (using WinNonlin pharmacokinetics software (Pharsight Corp., USA)) was used to calculate t½β and area under the curve (AUC) (Table 4). The t½β for HEL4 control in rats is up to 30 minutes, and based on the data obtain the AUC for DOM7h-8 is expected to be between about 150 hr·μg/mL and about 2500 hr·μg/mL.

TABLE 4

| Agent | Scaffold | Affinity (KD) for rat serum albumin | t½β | AUC (hr · μg/mL) |
|---|---|---|---|---|
| DOM7r-3 | $V_k$ | 12 nM | 13.7 hours | 224 |
| DOM7r-16 | $V_k$ | 1 μM | 34.4 hours | 170 |
| DOM7r-27 | $V_H$ | 250 nM | 14.8 hours | 78.9 |
| DOM7r-31 | $V_H$ | 5 μM | 5.96 hours | 71.2 |

The results of this rat study using the HA epitope tag as a model for a drug (e.g., a protein, polypeptide or peptide drug), demonstrate that the in vivo serum half-life of a drug can be dramatically extended when the drug is prepared as a drug fusion or drug conjugate with an antigen-binding fragment of (e.g., dAb) of an antibody that binds serum albumin.

Prediction of Half-Life in Humans.

The in vivo half-life of a dAb, drug fusion or drug conjugate in humans can be estimated from half-life data obtained in animals using allometric scaling. The log of the in vivo half-lives determined in 3 animals is plotted against the log of the weight of the animal. A line is drawn through the plotted points and the slope and y-intercept of the line are used to calculate the in vivo half-life in humas using the formula log Y=log(a)+b log(W), in which Y is the in vivo half-life in humans, log(a) is the y-intercept, b is the slope, and W is the weight of a human. The line can be produced using in vivo half-life data obtain in animals that weigh about 35 grams (e.g., mice), about 260 grams (e.g., rats) and about 2,710 grams. For this calculation, the weight of a human can be considered to be 70,000 grams. Based on half-life values obtained in mice and rats, dAbs that bind human serum albumin, such as DOM7h-8, are expected to have t½β of about 5.5 hours to about 40 hours and AUC of about 150 hr·μg/mL to about 2500 hr·μg/mL, in humans.

Example 6

Efficacy of Anti-SA dAb/IL-1ra Drug Fusion in Mouse Collagen Induced Arthritis Model of Rheumatoid Arthritis Efficacy of the fusion DOM7m-16/IL-1ra and efficacy of IL-1ra in a recognized mouse model of rheumatoid arthritis (type II collagen induced arthritis (CIA) in DBA/1 mice) was assessed. Throughout the study, mice were maintained in a test facility in standard type 2 cages that were housed in a HEPA-filtered Scantainer at 20-24° C. with a 12-hours light, 12-hours dark cycle. Food (Harlan-Teklad universal diet 2016) and UV sterilized water were provided ad libitum. The mice were imported to the test facility at least 7 days before the start of the study to assure proper acclimatization.

DBA/1 mice at 7-8 weeks of age (obtained from Taconic M and B, Domholtveg, Denmark) were injected once with an emulsion of Arthrogen-CIA adjuvant and Arthrogen-CIA collagen (both MD biosciences) emulsified at a 1:1 ratio until the emulsion was stable. The emulsion was considered to be stable when a drop of the emulsion added to a beaker of water formed a solid clump. The mice were then injected with the emulsion.

Twenty-one days after the emulsion was injected, the 20 animals with the most advanced arthritic disease were eliminated from the study, and the remaining mice were divided into groups of 10 animals (each group contained 5 males and 5 females). The mice were treated as shown in Table 5, and all treatments were delivered at a concentration calculated so that 10 ml/Kg were administered.

TABLE 5

| Group | Treatment |
|---|---|
| 1 | IL-1ra, 1 mg/Kg (intrapertoneal (ip.) bolus) |
| 2 | IL-1ra, 10 mg/Kg (ip. bolus) |
| 3 | DOM7m-16/IL-1ra, 1 mg/Kg (ip. bolus) |
| 4 | DOM7m-16/IL-1ra, 10 mg/Kg (ip. bolus) |
| 5 | ENBREL ® (entarecept; Immunex Corporation), 5 mg/Kg (ip. bolus) |
| 6 | saline (negative control), 10 ml/Kg (ip. bolus) |
| 7 | Dexamethasone (positive control), 0.4 mg/Kg (subcutaneous injection) |

Clinical scores for the severity of arthritis were recorded 3 times a week from day 21 to day 49. Mice were euthanized at day 49. Individual mice were euthanized earlier if they presented an arthritic score of 12 or more, or had serious problems moving.

For clinical scoring, each limb was scored according to the criteria below and the scores for all four limbs were added to produce the total score for the mouse. This method resulted is a score of 0 to 16 for each mouse. Scoring criteria were: 0=normal; 1=mild but definite redness and swelling of the ankle or wrist, or apparent redness and swelling limited to individual digits, regardless of the number of affected digits; 2=moderate redness and swelling of ankle and wrist; 3=severe redness and swelling of the entire paw including digits; 4=maximally inflamed limb with involvement of multiple joints.

Group average arthritic scores were calculated for each treatment group on every treatment day using clinical scores from individual mice. Any animals that had been removed from the study for ethical reasons were allocated the maximum score of 16. The group average arthritic scores were plotted against time (FIG. 13).

Statistical analysis of the group average arthritic scores on day 49 were performed using the Wilcoxon test. This statistical analysis revealed that the two groups treated with DOM7m-16/IL-1ra (at 1 mg/Kg or 10 mg/Kg (Groups 3 and 4)) had significantly improved arthritic scores at day 49 (at the $P<1\%$ and $P<0.05\%$ significance levels respectively) when compared to the saline control group (Group 6). In contrast, treatment with IL-1ra at 1 mg/Kg (Group 1) did not result in statistically significant improvement in the arthritic score at day 49, while treatment with IL-1ra at 10 mg/Kg (Group 2) resulted in a significant improvement at the $P<5\%$ significance level. Treatment with ENBREL® (entarecept; Immunex Corporation) (Group 5) resulted in significant improvement in the arthritic score at day 49 at the $P<10\%$ significance level.

Treatment with DOM7m-16/IL-1ra at the 10 mg/Kg dose (Group 4), was effective at improving the arthritic score at day 49 (significant at the $P<0.5\%$ level) when compared to standard treatment with ENBREL® (entarecept; Immunex Corporation) at 5 mg/Kg (Group 5). In addition, treatment with DOM7m-16/IL-1ra at the lower 1 mg/Kg dose (Group 3), was more efficacious at improving the arthritic score at day 49 than treatment with IL-1ra alone at the same dosage (Group 1) (significant at the $P<10\%$ level).

The results of the study show that at certain doses DOM7m-16/IL-1ra was more effective than IL-1ra or ENBREL® (entarecept; Immunex Corporation) in this study. The response to IL-1ra was dose dependent, as expected, and the response to DOM7m-16/IL-1ra was also dose dependent. The average scores for treatment with DOM7m-16/IL-1ra at 1 mg/Kg were consistently lower than the average scores obtained by treatment with IL-1ra at 10 mg/kg. These plotted results (FIG. 13) indicate that treatment with DOM7m-16/IL-1ra was about 10 times more effective than IL-1ra in this study.

This superior efficacy of DOM7m-16/IL-1ra was observed even though the DOM7-16/IL-1ra fusion protein contains about half the number of IL-1 receptor binding epitopes as IL-1ra on a weight basis (e.g., 1 mg of DOM7m-16/IL-1ra (MW .31.2 kD) contains about half the number of IL-1 receptor binding epitopes as 1 mg of IL-1ra (MW .17.1 kD).

The results of this study demonstrate that a dAb that binds serum albumin can be linked to IL-1ra (a clinically proven therapy for RA) and that the resulting drug fusion has both long serum half-life properties (conferred by the dAb) and IL-1 receptor binding properties (conferred by the IL-1ra). Due to the serum residence time of the drug fusion, the dose of DOM7-16/IL-1ra that was effective for treating CIA was dramatically reduced relative to IL-1ra.

The results of this study demonstrate that in addition to the benefits of extended half-life and increased AUC, drugs prepared as drug fusions or drug conjugates with an antigen-binding fragment of (e.g., dAb) of an antibody that binds serum albumin are highly effective therapeutic agents that provide advantages over drug alone. For example, as demonstrated in the mouse CIA model, a lower dose of drug fusion was effective and inhibited the joint inflammation and joint damage caused by IL-1 over a longer period of time in comparison to IL-1ra alone, and provided greater protection against disease progression.

Example 7

Anti-SA dAb/Saporin Noncovalent Drug Conjugate

The ribosome-inactivating protein Saporin (an anti-cancer drug) is highly stable to denaturants and proteases and has been used as a targeted toxin to T lymphocytes. A non-covalent drug conjugate was prepared by coupling Saporin to DOM7h-8 via a biotin-streptavidin link. Results obtained with this non-covalent drug conjugate demonstrates that the DOM7h-8 retains its serum albumin binding characteristics when coupled to a drug.

A variant DOM7h-8 referred to as DOM7h-8cys, in which the C-terminal arginine at position 108 (amino acid 108 of SEQ ID NO:24) was replaced with a cysteine residue was prepared by expression of a recombinant nucleic acid in HB2151 cells. The cells were grown and induced at 30° C. in overnight expression autoinduction TB readymix (Merck KGa, Germany) for 72 hours before recovery of the supernatant by centrifugation. DOM7h-8cys was purified from the supernatant using affinity capture on protein L-agarose. The resin was then washed with 10 column volumes of 2×PBS and DOM7h-8cys was eluted with 0.1 M glycine pH2. Eluted DOM7h-8cys was neutralized with 0.2× volume of Tris pH8 and concentrated to 1 mg/ml (using a CENTRICON 20 ml concentrator (Millipore Corp., MA).

Concentrated DOM7h-8cys was buffer exchanged to PBS using a NAPS desalting column (GE Healthcare/Amersham Biosciences, NJ) and concentration determined. The dAb was then biotinylated (via primary amines) using EZ-LINK sulfo-NHS-LC-biotin (Pierce Biotechnology Inc., IL). The biotinylated dAb was mixed with streptavidin-saporin (Advanced Targeting Systems, San Deigo) in a 1:1 molar ratio.

In order to confirm that the dAb/saporin complex was formed, a sandwich ELISA was used to detect intact complexes. Human serum albumin (HSA) was coated onto half of the wells of an ELISA plate (Nunc, N.Y.) overnight at 10 mg/ml in a volume of 100 μl per well. After overnight incubation, the plate was washed 3 times with PBS, 0.05% Tween and then the whole plate was blocked for 2 hours with 2% PBS. After blocking, the plate was washed 3 times with PBS, 0.05% Tween and then incubated for 1 hour with DOM7h-8/saporin non-covalent conjugate diluted to 0.5 μM in 2% Tween PBS. As controls on the same ELISA plate, uncoupled saporin at 0.5 μM and uncoupled DOM7h8 at 0.5 μM were incubated in 2% Tween PBS. Additional controls were the same three diluted proteins incubated on wells of the ELISA plate not coated with HAS and blocked with 2% Tween. After the incubation, the plate was washed 3 times with PBS, 0.05% Tween and then incubated for 1 hour with 1/2000 dilution of goat anti-saporin polyclonal antibody (Advanced Therapeutic Systems) diluted in 2% Tween PBS. After the incubation, the plate was washed 3 times with PBS, 0.05% Tween and then incubated for 1 hour with the secondary detection antibody (of 1/2000 anti-goat Ig HRP conjugate). After the incubation, the plate was washed 3 times with PBS, 0.05% Tween and once with PBS and tapped dry on paper. The ELISA was developed with 100 μl 3,3',5,5'-tetramethylbenzidine as substrate and the reaction stopped with 50 μl 1M hydrochloric acid. The presence of non-covalent conjugates of DOM7h-8 and saporin was confirmed by comparing the OD600 of the conjugate with that of either of the unconjugated parts.

TABLE 6

|  | DOM7h-8/Saporin | DOM7h-8 alone | Saporin alone |
|---|---|---|---|
| OD600 (plate coated with HAS) | 0.311 | 0.060 | 0.079 |
| OD600 (plate blocked with 2% Tween PBS) | 0.078 | 0.068 | 0.075 |

The results of this study demonstrate that a drug can be conjugated to an antigen-binding fragment of an antibody that binds serum albumin, and that the conjugated antigen-binding fragment retains serum albumin-binding activity. In addition, due to the stability and strength of the biotin-streptavidin interaction, the results show that covalently bonded and noncovalently bonded conjugates can be prepared that retain the serum albumin-binding activity of the antigen-binding fragment of an antibody that binds serum albumin.

Example 8

Anti-SA dAb/Fluorescein Conjugate

Fluorescein isothiocyanate (FITC) can be cross linked with amino, sulfhydryl, imidazoyl, tyrosyl or carbonyl groups on a protein. It has a molecular weight of 389 Da which is comparable in size to many small molecule drugs. Results obtained with this conjugate demonstrate that the anti-SA dAb maintains its serum albumin binding characteristics when coupled to a small chemical entity, and indicate that small molecule drugs can be conjugated to anti-SA dAbs.

Concentrated DOM7h-8cys was prepared as described in Example 7. The concentrated dAb was buffer exchanged to 50 mM Borate pH 8 (coupling buffer) using a NAPS desalting column (GE Healthcare/Amersham Biosciences, NJ) and then concentrated to 2.3 mg/ml using a 2 ml CENTRICON concentrator (Millipore Corp., MA). The FITC (Pierce Biotechnology Inc.) was diluted to 10 mg/ml in dimethyl formamide (DMF) according to the manufacturer's instructions and then mixed with the dAb in coupling buffer at a molar ratio of 24:1 FITC:dAb. The reaction was allowed to proceed for 30 minutes. At this point, excess unreacted FITC was removed from the reaction using a PD 10 desalting column (GE Healthcare/Amersham Biosciences, NJ) that was pre-equilibrated with PBS, and the DOM7h-8cys/FITC conjugate was eluted with PBS.

In order to confirm that the FITC/dAb coupling reaction was successful, a sandwich ELISA was used to detect coupled dAb. Human serum albumin (HSA) was coated onto half of the wells of an ELISA plate (Nunc, N.Y.) overnight at 10 μg/ml in a volume of 100 μl per well. After overnight incubation, the whole plate was washed 3 times with PBS, 0.05% Tween and then all the wells were blocked for 2 hours with 2% Tween PBS. After blocking, the plate was washed 3 times with PBS, 0.05% Tween and then incubated for 1 hour with DOM7h-8cys/FITC diluted to 1 μM in 2% Tween PBS. As controls on the same ELISA plate, a control FITC coupled antibody at 1 μM and uncoupled DOM7h-8 at 1 μM were incubated in 2% Tween PBS. Additional controls were the same three diluted proteins incubated on wells of the ELISA plate not coated with HSA and blocked with 2% Tween. After the incubation, the plate was washed 3 times with PBS, 0.05% Tween and then incubated for 1 hour with 1/500 dilution of rat anti FITC antibody (Serotec) diluted in 2% Tween PBS. After the incubation, the plate was washed 3 times with PBS, 0.05% Tween, and then incubated for 1 hour with the secondary detection antibody diluted in 2% Tween PBS (1/5000 anti-rat Ig HRP conjugate). After the incubation, the plate was washed 3 times with PBS, 0.05% Tween and once with PBS and tapped dry on paper. The ELISA was developed with 100 μl per well 3,3',5,5'-tetramethylbenzidine as substrate and the reaction stopped with 50 μl per well 1M hydrochloric acid. The presence of conjugates of DOM7h-8 and FITC was confirmed by comparing the OD600 of the conjugate with that of either of the unconjugated parts.

TABLE 7

|  | DOM7h-8/FITC | DOM7h-8 alone | FITC coupled antibody (negative control) |
|---|---|---|---|
| OD600 (plate coated with HSA) | 0.380 | 0.042 | 0.049 |
| OD600 (plate blocked with 2% Tween PBS) | 0.041 | 0.041 | 0.045 |

Example 9

Anti-SA dAb/Peptide Conjugates

Many peptides have therapeutic effects. Model peptides with an N- or C-terminal cysteine can be coupled to an anti-serum albumin dAb.

In this case, four different peptides will be used: peptide 1 YPYDVPDYAKKKKKKC (SEQ ID NO:68); peptide 2 CKKKKKKYPYDVPDYA (SEQ ID NO:69); peptide 3 HHHHHHKKKKKKC (SEQ ID NO:70) and peptide 4: CKKKKKKHHHHHH (SEQ ID NO:71). Peptides 1 and 2 include the sequence of the hemagglutinin tag (HA tag) and peptides 3 and 4 include the sequence of the His tag. Concentrated DOM7h-8cys will be prepared as described in Example 7.

The concentrated dAb will be reduced with 5 mM dithiothreitol and then buffer exchanged to coupling buffer (20 mM BisTris pH 6.5, 5 mM EDTA, 10% glycerol) using a NAPS desalting column (GE Healthcare/Amersham Biosciences, NJ). Cysteines will be blocked (to prevent the dAb dimerizing with itself) using a final concentration of 5 mM dithiodipyridine which will be added to the dAb solution form a stock of 100 mM dithiodipyridine in DMSO. The dAb and dithiodipyrdine will be left to couple for 20-30 minutes. Unreacted dithiodipyridine will then be removed using a PD10 desalting column and the dAb will be eluted in coupling buffer (20 mM BisTris pH 6.5, 5 mM EDTA, 10% glycerol). The resulting protein will then be frozen until required.

Peptides 1-4 will be individually dissolved in water at a concentration of 200 µM, will be reduced using 5 mM DTT and then will be desalted using a NAPS desalting column (GE Healthcare/Amersham Biosciences, NJ). Each peptide will then be added to a solution of reduced and blocked dAb at a 20:1 ratio, for the peptide-dAb coupling to occur. In order to confirm success of the peptide, dAb coupling reactions, a sandwich ELISA will be used to detect anti-SA dAb/peptide conjugates.

Human serum albumin will be coated onto an ELISA plate (Nunc, N.Y.) overnight at 10 µg/ml in a volume of 100 µl per well. After overnight incubation, the plate will be washed 3 times with PBS, 0.05% Tween and then will be blocked for 2 hours with 4% Marvel PBS. After blocking, the plate will be washed 3 times with PBS, 0.05% Tween and then will be incubated for 1 hour with DOM7h-8/peptide conjugates diluted to 1 µM in 4% Marvel PBS. As controls on the same ELISA plate, uncoupled peptide at 20 µM and uncoupled DOM7h-8 at 1 µM will be incubated in 4% MPBS. After the incubation, the plate will be washed 3 times with PBS, 0.05% Tween and then will be incubated for 1 hour with 1/2000 dilution of goat anti-HA antibody (Abcam) for peptides 1 and 2, and a 1/2000 dilution of Ni NTA-HRP (for peptides 3 and 4) diluted in 4% Marvel PBS. After incubation, the plate will be washed 3 times with PBS, 0.05% Tween and the wells with the goat anti HA antibody will be incubated for 1 h with secondary anti-goat HRP antibody diluted 1/2000 in 4% MPBS (other wells were blocked for 1 h). After the incubation, the plate will be washed 3 times with PBS, 0.05% Tween and once with PBS and will then be tapped dry on paper. The ELISA will be developed with 3,3',5,5'-tetramethylbenzidine as substrate and the reaction will be stopped with 1M hydrochloric acid. The presence of conjugates of DOM7h-8/peptide conjugate will be confirmed by comparing the OD600 of the conjugate with that of either of the unconjugated parts.

TABLE 8

Anticancer Peptides

| Peptide Category | Peptide Sequence | Action/Application |
| --- | --- | --- |
| LH-RH Agonists and Antagonists | p-Glu-His-Trp-Ser-Tyr-Gly-Leu-Arg-Pro-Gly-NH2<br>SEQ ID NO: 89 | Treatment of sex hormone dependent malignant diseases |
| Gastrin Releasing Peptide | p-Glu-Gln-Arg-Leu-Gly-Asn-Gln-Trp-Ala-Val-Gly-His-Leu-Met-NH2<br>SEQ ID NO: 90 | Small Cell Lung Carcinoma |
| Somatostatin | p-Ala-Gly-Cys-Lys-Asn-Phe-Trp-Lys-Thr-Phe-Thr-Ser-Cys<br>SEQ ID NO: 91 | Tumors (general) |
| GH-RH | Gln-Trp-Ala-Val-Gly-His-Leu-psi(CH2-NH)-Leu-NH2 (RC-3094)<br>SEQ ID NO: 92 | Glioblastoma Tumor, Prostate Tumor |
| VEGF | Arg-Arg-Lys-Arg-Arg-Arg<br>SEQ ID NO: 93 | Human Colon Carcinoma |
| | Ala-Thr-Trp-Leu-Pro-Pro-Arg<br>SEQ ID NO: 94 | Tumor Cell Proliferation |
| | Arg-Thr-Glu-Leu-Asn-Val-Gly-Ile-Asp-Phe-Asn-Trp-Glu-Tyr-Pro-Ala-Ser-Lys<br>SEQ ID NO: 95 | Tumor Cell Proliferation and Migration |
| | His-His-Glu-Val-Val-Lys-Phe-Mel-Asp-Val-Tyr-Gln<br>SEQ ID NO: 96 | Inhibits endothelial cell responses |
| | Asn-Ile-Thr-Val-Thr-Leu-Lys-Lys-Phe-Pro-Leu<br>SEQ ID NO: 97 | Angiogenesis Inhibitor |
| EGF | Cys-His-Ser-Gly-Tyr-Val-Gly-Val-Arg-Cys<br>SEQ ID NO: 98 | Inhibits EGF based cell proliferation |

TABLE 8-continued

Anticancer Peptides

| Peptide Category | Peptide Sequence | Action/Application |
|---|---|---|
| | Tyr-Cys-Asp-Gly-Phe-Tyr-Ala-Cys-Tyr-Met-Asp-Val-Nh2<br>SEQ ID NO: 99 | Binds to HER2 |
| IL-6 | Gly-Gly-Cys-Lys-Leu-Trp-Thr-Ile-Pro-Glu-Cys-Gly-Gly<br>SEQ ID NO: 100 | Inhibits cellular growth |
| IL-8 | Ala-Val-Leu-Pro-Arg<br>SEQ ID NO: 101 | Apoptosis induction and antitumor effect in vivo |
| PDGF | Tyr-Gly-Arg-Pro-Arg-Glu-Ser-Gly-Lys-Lys-Arg-Lys-Arg-Lys-Arg-Leu-Lys-Pro-Thr<br>SEQ ID NO: 102 | Inhibits growth of malignant glioma |
| TNF | AcCys-Pro-Ser-Glu-Gly-Leu-Cys-NH2<br>SEQ ID NO: 103 | Inhibits Tumor Growth |
| | Ac-Cys-Pro-Ser-Glu-Gly-Thr-Pro-Ser-Thr-His-Val-Leu-Cys-NH2<br>SEQ ID NO: 104 | |
| | Ac-Leu-Ala-Asn-Gly-Val-Glu<br>SEQ ID NO: 105 | |
| | Pro-Gln-Ala-Glu-Gly-Gln-Leu-NH2<br>SEQ ID NO: 106 | |
| | Val-Ala-Asn-Pro-Gln-Ala-Glu-Gly-Gln-Leu<br>SEQ ID NO: 107 | |
| | Cyclic Lys-Gly-Asp-Gln-Leu-Ser<br>SEQ ID NO: 108 | |
| | Cyclic Tyr-Ser-Cln-Val-Leu-Phe-Lys-Gly<br>SEQ ID NO: 109 | |
| Alpha-feto Protein | Glu-Met-Thr-Pro-Val-Asn-Pro-Gly<br>SEQ ID NO: 110 | Inhibits Estrogen Dependent Breast Cancer Cells |
| Sialyl-Lewis mimics | Ile-Glu-Leu-Leu-Gln-Ala-Arg<br>SEQ ID NO: 111 | Inhibits lung colonization of tumor cells |
| Urokinase-type Plasminogen activator | Cys-Val-Ser-Asn-Lys-Tyr-Phe-Ser-Asn-Ile-His-Trp-Cys<br>SEQ ID NO: 112 | Antagonist for uPA/uPAR |
| | Phe-X-X-Tyr-Lys-Trp<br>SEQ ID NO: 113 | Antagonist for uPA/uPAR |
| | Lys-Trp-X-X-Ar<br>SEQ ID NO: 114 | Antagonist for uPA/uPAR |
| | Leu-Asn-Phe-Ser-Gln-Tyr-Leu-Trp-Tyr-Thr-NH2<br>SEQ ID NO: 115 | Antagonist for uPA/uPAR |
| | Ac-Lys-Pro-Ser-Ser-Pro-Pro-Glu-Glu-NH2<br>SEQ ID NO: 116 | Inhibits tumor progression and angiogenesis |
| p53 | Ac-Met-Pro-Arg-Phe-Met-Asp-Tyr-Trp-Glu-Gly-Leu-Asn-NH2<br>SEQ ID NO: 117 | Inhibits Hdm2 and p53 binding |
| | Met-Val-Arg-Arg-Phe-Leu-Val-Thr-Leu-Arg-Ile-Arg-Arg-Ala-Cys-Gly-Pro-Pro-Arg-Val<br>SEQ ID NO: 118 | Prevents p53 ubiquitination |

TABLE 8-continued

Anticancer Peptides

| Peptide Category | Peptide Sequence | Action/Application |
|---|---|---|
| | Gly-Ser-Arg-Ala-His-Ser-Ser-His-Leu-Lys-Ser-Lys-Gly-Gln-Ser-Thr-Ser-Arg-His-Lys-Lys-Leu<br>SEQ ID NO: 119 | Activates p53 |
| p34cdc2 | Cys-Ala-Phe-Tyr-Ile<br>SEQ ID NO: 120 | Inhibits interaction between p34/p33 and pRb2 and p107 |
| | Leu-Cys-Ala-Phe-Tyr-Ile-Met-Ala-Lys<br>SEQ ID NO: 121 | |
| | Met-Cys-Ser-Met-Tyr-Gly-Ile-Cys-Lys<br>SEQ ID NO: 122 | |
| Cdk2 | Tyr-Ser-Phe-Val-His-Gly-Phe-Phe-Asn-Phe-Arg-Val-Ser-Trp-Arg-Glu-Met-Leu-Ala<br>SEQ ID NO: 123 | Inhibits interaction between Cdk2 and histone H1 |
| p21WAF1 | Lys-Arg-Arg-Gln-Thr-Ser-Met-Thr-Ala-Phe-Tyr-His-Ser-Lys-Arg-Arg-Leu-Ile-Phe-Ser<br>SEQ ID NO: 124 | Induces G1/S growth arrest |
| | Lys-Arg-Arg-Leu-Ile-Phe-Ser-Lys<br>SEQ ID NO: 125 | |
| | Phe-Leu-Asp-Thr-Leu-Val-Val-Leu-His-Arg<br>SEQ ID NO: 126 | |
| E2F/DP transcription | Arg-Cys-Val-Arg-Cys-Arg-Phe-Val-Val-Trp-Ile-Gly-Leu-Arg-Val-Arg-Cys-Leu-Val<br>SEQ ID NO: 127 | Inhibits E2F function in vitro |
| | Leu-Asn-Trp-Ala-Trp-Ala-Ala-Glu-Val-Leu-Lys-Val-Gln-Lys-Arg-Arg-Ile-Tyr-Asp-Ile-Thr-Asn-Val<br>SEQ ID NO: 128 | |
| | Leu-Glu-Gly-Ile-Gln-Leu-Ile-Ala-NH2<br>SEQ ID NO: 129 | |
| | Phe-Trp-Leu-Arg-Phe-Thr<br>SEQ ID NO: 130 | |
| | Trp-Val-Arg-Trp-His-Phe<br>SEQ ID NO: 131 | |
| | Trp-Val-Arg-Trp-His<br>SEQ ID NO: 132 | |
| | Trp-His-Phe-Ile-Phe-Trp<br>SEQ ID NO: 133 | |
| | Ile-Trp-Leu-Ser-Gly-Leu-Ser-Arg-Gly-Val-Trp-Val-Ser-Phe-Pro<br>SEQ ID NO: 134 | |
| | Gly-Ser-Arg-Ile-Leu-Thr-Phe-Arg-Ser-Gly-Ser-Trp-Tyr-Ala-Ser<br>SEQ ID NO: 135 | |
| | Asp-Glu-Leu-Lys-Arg-Ala-Phe-Ala-Ala-Leu-Arg-Asp-Gln-Ile<br>SEQ ID NO: 136 | |
| Bcl2 | Lys-Lys-Leu-Ser-Glu-Cys-Leu-Lys-Lys-Arg-Ile-Gly-Asp-Glu-Leu-Asp-Ser<br>SEQ ID NO: 137 | Triggers apoptosis in a cell free system |
| | Gly-Gln-Val-Gly-Arg-Gln-Leu-Ala-Ile- | |

TABLE 8-continued

Anticancer Peptides

| Peptide Category | Peptide Sequence | Action/Application |
|---|---|---|
| | Ile-Gly-Asp-Asp-Ile-Asn-Arg<br>SEQ ID NO: 138 | |
| | Arg-Asn-Ile-Ala-Arg-His-Leu-Ala-Gln-<br>Val-Gly-Asp-Ser-Met-Asp-Arg<br>SEQ ID NO: 139 | |
| Integrins | Tyr-Ile-Gly-Ser-Arg-NH2<br>SEQ ID NO: 140 | Inhibits tumor cell binding to ECMs |
| | Ac-Tyr-Ile-Gly-Ser-Arg-NH2<br>SEQ ID NO: 141 | |
| | Ac-Tyr-Ile-Gly-Ser-Arg-NHCH3<br>SEQ ID NO: 142 | |
| | Ac-Tyr-Ile-Gly-Ser-Arg-N(CH3)2<br>SEQ ID NO: 143 | |
| | Phe(pNH2)-Ile-Gly-Ser-Arg-NH2<br>SEQ ID NO: 144 | |
| | Ac-Tyr-Ile-Gly-Ser-Arg-NHCH(CH3)2<br>SEQ ID NO: 145 | |
| | CO(Asp-Tyr-Ile-Gly-Ser-Arg-NHPr)2<br>SEQ ID NO: 146 | |
| | Arg-Gly-Asp<br>SEQ ID NO: 147 | |
| | Tyr-Ile-Gly-Ser-Arg<br>SEQ ID NO: 148 | |
| | Ile-Pro-Cys-Asn-Asn-Lys-Gly-Ala-His-<br>Ser-Val-Gly-Leu-Met-Trp-Trp-Met-Leu-<br>Ala-Arg<br>SEQ ID NO: 149 | |
| Angiostatin Analogues | Ser-Pro-His-Arg-Pro-Arg-Phe-Ser-Pro-<br>Ala<br>SEQ ID NO: 150 | |
| | Ser-Pro-His-Ala-His-Gly-Tyr-Ile-Pro-<br>Ser<br>SEQ ID NO: 151 | |
| | Thr-Pro-His-Thr-His-Asn-Arg-Thr-Pro-<br>Glu<br>SEQ ID NO: 152 | |
| | Thr-Pro-His-Arg-His-Gln-Lys-Thr-Pro-<br>Glu<br>SEQ ID NO: 153 | |
| | Glu-Pro-His-Arg-His-Ser-Ile-Phe-Thr-<br>Pro-Glu<br>SEQ ID NO: 154 | |
| Cadherins | Ac-Cys-His-Ala-Val-Cys-NH2<br>SEQ ID NO: 155 | Inhibits Angiogenesis |
| Histone Deacetylase | Cys-Glu-Lys-His-Ile-Met-Glu-Lys-Ile-<br>Gln-Gly-Arg-Gly-Asp-Asp-Asp-Asp<br>SEQ ID NO: 156 | Leukemia Inhibition |
| MMP2 | Cys-Thr-Thr-His-Trp-Gly-Phe-Thr-Leu-<br>Cys<br>SEQ ID NO: 156 | Tumor Metastasis |

While this invention has been particularly shown and described with references to preferred embodiments thereof, it will be understood by those skilled in the art that various changes in form and details may be made therein without departing from the scope of the invention encompassed by the appended claims.

What is claimed is:

1. A drug fusion comprising moieties X' and Y', wherein
X' is a polypeptide drug, with the proviso that X' does not comprise an antibody chain or a fragment of an antibody chain; and
Y' is an immunoglobulin single variable domain that has binding specificity for serum albumin, wherein Y' is an amino acid sequence selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25, SEQ ID NO:26, SEQ ID NO:16, SEQ ID NO:17, SEQ ID NO:18, SEQ ID NO:19, SEQ ID NO:20, SEQ ID NO:21, SEQ ID NO:22 and SEQ ID NO:23; and
wherein said drug fusion has a longer in vivo serum half-life relative to said polypeptide drug.

2. The drug fusion of claim 1, wherein X' is located amino terminally to Y'.

3. The drug fusion of claim 1, wherein Y' is located amino terminally to X'.

4. A drug fusion comprising moieties X' and Y', wherein
X' is a polypeptide drug, with the proviso that X' does not comprise an antibody chain or a fragment of an antibody chain; and
Y' is an immunoglobulin light chain single variable domain that has binding specificity for serum albumin; and
wherein Y' comprises the amino acid sequence selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25 and SEQ ID NO:26.

5. A drug fusion comprising moieties X' and Y', wherein
X' is a polypeptide drug, with the proviso that X' does not comprise an antibody chain or a fragment of an antibody chain; and
Y' is an immunoglobulin heavy chain single variable domain that has binding specificity for serum albumin; and
wherein Y' comprises the amino acid sequence from the group consisting of SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

6. A drug conjugate comprising an immunoglobulin heavy chain single variable domain that has binding specificity for serum albumin, or an immunoglobulin light chain single variable domain that has binding specificity for serum albumin, and a drug that is covalently bonded to said immunoglobulin heavy chain single variable domain or said immunoglobulin light chain single variable domain, with the proviso that said drug does not comprise an antibody chain or a fragment of an antibody chain,
wherein said immunoglobulin heavy chain single variable domain that has binding specificity for serum albumin, or said immunoglobulin light chain single variable domain that has binding specificity for serum albumin comprises an amino acid sequence selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25, SEQ ID NO:26, SEQ ID NO:16, SEQ ID NO:17, SEQ ID NO:18, SEQ ID NO:19, SEQ ID NO:20, SEQ ID NO:21, SEQ ID NO:22 and SEQ ID NO:23, and
wherein said drug conjugate has a longer in vivo serum half-life relative to said drug.

7. The drug conjugate of claim 6, wherein the drug conjugate comprises a immunoglobulin heavy chain single variable domain.

8. The drug conjugate of claim 6, wherein the drug conjugate comprises a immunoglobulin light chain single variable domain.

9. The drug conjugate of claim 6, wherein said drug is covalently bonded to said immunoglobulin heavy chain single variable domain or said immunoglobulin light chain single variable domain through a linker moiety.

10. The drug conjugate of claim 6, wherein two or more different drugs are covalently bonded to said immunoglobulin heavy chain single variable domain or said immunoglobulin light chain single variable domain.

11. The drug conjugate of claim 6, wherein the drug is a polypeptide.

12. The drug conjugate of claim 11, wherein said polypeptide is IL-1ra or a functional variant of IL-1ra.

13. The drug conjugate of claim 6, wherein the drug is an analgesic agent, an anti-cancer agent, a hormone or an antimicrobial polypeptide or peptide.

14. A drug conjugate comprising an immunoglobulin heavy chain single variable domain that has binding specificity for serum albumin, or an immunoglobulin light chain single variable domain that has binding specificity for serum albumin, and a drug that is covalently bonded to said immunoglobulin heavy chain single variable domain or said immunoglobulin light chain single variable domain, with the proviso that said drug does not comprise an antibody chain or a fragment of an antibody chain;
wherein said immunoglobulin heavy chain single variable domain that has binding specificity for serum albumin, or said immunoglobulin light chain single variable domain that has binding specificity for serum albumin comprises an amino acid sequence selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25, SEQ ID NO:26, SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

15. A pharmaceutical composition comprising the drug fusion of claim 1 and a physiologically acceptable carrier.

16. A pharmaceutical composition comprising the drug conjugate of claim 6 and a physiologically acceptable carrier.

17. A noncovalent drug conjugate comprising an immunoglobulin single variable domain that has binding specificity for serum albumin, and a drug that is noncovalently bonded to said immunoglobulin single variable domain, wherein said immunoglobulin single variable domain is selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25, SEQ ID NO:26, SEQ ID NO:16, SEQ ID NO:17, SEQ ID NO:18, SEQ ID NO:19, SEQ ID NO:20, SEQ ID NO:21, SEQ ID NO:22 and SEQ ID NO:23,
with the proviso that said drug does not comprise an antibody chain or a fragment of an antibody chain, and wherein said noncovalent drug conjugate has a longer in vivo serum half-life relative to said drug.

18. The noncovalent drug conjugate of claim 17, wherein said immunoglobulin heavy chain single variable domain or said immunoglobulin light chain single variable domain and said drug are noncovalently bonded through complementary binding partners.

19. The noncovalent drug conjugate of claim 18, wherein said complementary binding partners are biotin and avidin, or biotin and streptavidin.

20. A method for increasing the in vivo serum half-life of a drug without substantially reducing the activity of the drug, comprising binding a drug to a polypeptide binding moiety selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25, SEQ ID NO:26, SEQ ID NO:16, SEQ ID NO:17, SEQ ID NO:18, SEQ ID NO:19, SEQ ID NO:20, SEQ ID NO:21, SEQ ID NO:22 and SEQ ID NO:23, whereby a drug composition is produced,
wherein said drug composition has a longer in vivo serum half-life relative to said drug.

21. A method for increasing the in vivo serum half-life of a drug and reducing the immunogenicity of the drug, comprising binding a drug to a polypeptide binding moiety selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25, SEQ ID NO:26, SEQ ID NO:16, SEQ ID NO:17, SEQ ID NO:18, SEQ ID NO:19, SEQ ID NO:20, SEQ ID NO:21, SEQ ID NO:22 and SEQ ID NO:23, whereby a drug composition is produced,
wherein said drug composition has a longer in vivo serum half-life relative to said drug, and is less immunogenic than said drug.

22. A method for decreasing the immunogenicity of a drug without substantially reducing the activity of the drug, comprising binding a drug to a polypeptide binding moiety selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25, SEQ ID NO:26, SEQ ID NO:16, SEQ ID NO:17, SEQ ID NO:18, SEQ ID NO:19, SEQ ID NO:20, SEQ ID NO:21, SEQ ID NO:22 and SEQ ID NO:23, whereby a drug composition is produced,
wherein said drug composition is less immunogenic than said drug.

23. A method for increasing the in vivo serum half-life of a drug and reducing the immunogenicity of the drug without substantially reducing the activity of the drug, comprising binding a drug to a polypeptide binding moiety selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25, SEQ ID NO:26, SEQ ID NO:16, SEQ ID NO:17, SEQ ID NO:18, SEQ ID NO:19, SEQ ID NO:20, SEQ ID NO:21, SEQ ID NO:22 and SEQ ID NO:23, whereby a drug composition is produced,
   wherein said drug and composition has a longer in vivo serum half-life relative to said drug, is less immunogenic than said drug.

24. The method of any one of claims 20-23, comprising covalently binding said drug to said polypeptide binding moiety.

25. The method of claim 24, wherein the drug composition is a drug fusion or drug conjugate.

26. The method of any one of claims 20-23, comprising noncovalently binding said drug to said polypeptide binding moiety.

27. The method of claim 26, wherein the drug composition is a noncovalent drug conjugate.

28. The method of any one of claims 20-23, wherein the method further comprises selecting said polypeptide binding moiety from one or more polypeptides, wherein the selected polypeptide binding moiety binds a polypeptide that enhances serum half-life in vivo with a KD of at least about 5 mM.

29. The method of any one of claims 20-23, wherein the drug composition has greater activity than said drug.

30. A drug composition comprising a drug that is bound to a polypeptide binding moiety selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25, SEQ ID NO:26, SEQ ID NO:16, SEQ ID NO:17, SEQ ID NO:18, SEQ ID NO:19, SEQ ID NO:20, SEQ ID NO:21, SEQ ID NO:22 and SEQ ID NO:23,
   wherein said drug composition has a longer in vivo serum half-life relative to drug.

31. A drug composition comprising a drug that is bound to a polypeptide binding moiety selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25, SEQ ID NO:26, SEQ ID NO:16, SEQ ID NO:17, SEQ ID NO:18, SEQ ID NO:19, SEQ ID NO:20, SEQ ID NO:21, SEQ ID NO:22 and SEQ ID NO:23,
   wherein said drug composition has a longer in vivo serum half-life relative to said drug, and is less immunogenic than said drug.

32. A drug composition comprising a drug that is bound to a polypeptide binding moiety selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25, SEQ ID NO:26, SEQ ID NO:16, SEQ ID NO:17, SEQ ID NO:18, SEQ ID NO:19, SEQ ID NO:20, SEQ ID NO:21, SEQ ID NO:22 and SEQ ID NO:23,
   wherein said drug composition is less immunogenic than said drug.

33. A drug composition comprising a drug that is bound to a polypeptide binding moiety selected from the group consisting of SEQ ID NO:10, SEQ ID NO:11, SEQ ID NO:12, SEQ ID NO:13, SEQ ID NO:14, SEQ ID NO:15, SEQ ID NO:24, SEQ ID NO:25, SEQ ID NO:26, SEQ ID NO:16, SEQ ID NO:17, SEQ ID NO:18, SEQ ID NO:19, SEQ ID NO:20, SEQ ID NO:21, SEQ ID NO:22 and SEQ ID NO:23,
   wherein said drug composition has a longer in vivo serum half-life relative to said drug, is less immunogenic than said drug.

34. The drug composition of any one of claims 30-33, wherein the drug is noncovalently bound to said polypeptide binding moiety.

35. The drug composition of claim 34, wherein said drug composition is a noncovalent drug conjugate.

36. The drug composition of any one of claims 30-33, wherein the drug composition has greater activity than said drug.

37. The drug fusion of claim 1, wherein X' is selected from the group consisting of an immunosuppressive agent, an antiviral agent, an antibiotic, an anti-inflammatory agent, a cytotoxin, a cytotoxic agent, an antimetabolite, a protease inhibitor, an analgesic agent, a polypeptide toxin, a polypeptide agonists, an activator, a secretagogue, an antagonist, an inhibitor, a hormone, a keratinocyte growth factor, interferon, erythropoietin, protease, elastase, LHRH analog, LHRH agonist, LHRH antagonist, an opiod receptor antagonist, calcitonin, a calcitonin analog, an antidiuretic hormone, an oxytocin antagonist, a vasoactive intestinal peptide, a thrombin inhibitor, von Villebrand factor, a surfactant, snail venom, a cytokine, a growth factor, a soluble portion of a cytokine receptor, a soluble portion of a growth factor receptor, a soluble portion of a hormone receptor, peptides and polypeptides that have anti-cancer activities, peptides and polypeptides that have anti-viral activity, an antimicrobial a receptor antagonist, a chemokine mimetic, an inhibitor of cellular adhesion molecule interactions, an integrin inhibitor, a ribosome-inactivating protein, a matrix metalloproteinase inhibitor, and an antiviral peptide or polypeptide.

38. The drug conjugate of claim 6 or claim 17, wherein said drug binds a CD antigen, a cytokine, a cytokine receptor, an adhesion molecule, a costimulatory molecule, a growth factor or a growth factor receptor.

\* \* \* \* \*

```
                            SEQUENCE LISTING

<160> NUMBER OF SEQ ID NOS: 158

<210> SEQ ID NO 1
<211> LENGTH: 108
<212> TYPE: PRT
<213> ORGANISM: Homo sapiens

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ile Lys His
            20                  25                  30

Leu Lys Trp Tyr Gln Gln Lys Pro Gly Lys Ala Pro Lys Leu Leu Ile
        35                  40                  45

Tyr Gly Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Arg Trp Pro Gln
                85                  90                  95

Thr Phe Gly Gln Gly Thr Lys Val Glu Ile Lys Arg
            100                 105

<210> SEQ ID NO 2
<211> LENGTH: 108
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Phe Arg His
            20                  25                  30

Leu Lys Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Ala Leu Tyr Pro Lys
                85                  90                  95

Thr Phe Gly Gln Gly Thr Lys Val Glu Ile Lys Arg
            100                 105

<210> SEQ ID NO 3
<211> LENGTH: 108
<212> TYPE: PRT
<213> ORGANISM: Homo sapiens

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Tyr His
            20                  25                  30
```

```
Leu Lys Trp Tyr Gln Gln Lys Pro Gly Lys Ala Pro Lys Leu Leu Ile
         35                  40                  45

Tyr Lys Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Arg Lys Val Pro Arg
                 85                  90                  95

Thr Phe Gly Gln Gly Thr Lys Val Glu Ile Lys Arg
            100                 105
```

<210> SEQ ID NO 4
<211> LENGTH: 108
<212> TYPE: PRT
<213> ORGANISM: Homo sapiens

<400> SEQUENCE: 4

```
Asp Ile Gln Thr Thr Gln Ser Pro Ser Ser Leu Ser Ala Ser Val Gly
 1                5                  10                  15

Asp Arg Val Thr Ile Thr Cys Arg Ala Ser Gln Tyr Ile Gly Arg Tyr
             20                  25                  30

Leu Arg Trp Tyr Gln Gln Lys Pro Gly Lys Ala Pro Lys Leu Leu Ile
         35                  40                  45

Tyr Asp Ser Ser Val Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Arg Tyr Arg Met Pro Tyr
                 85                  90                  95

Thr Phe Gly Gln Gly Thr Arg Val Glu Ile Lys Arg
            100                 105
```

<210> SEQ ID NO 5
<211> LENGTH: 108
<212> TYPE: PRT
<213> ORGANISM: Homo sapiens

<400> SEQUENCE: 5

```
Asp Ile Gln Met Thr Gln Ser Pro Ser Ser Leu Ser Ala Ser Val Gly
 1                5                  10                  15

Asp Arg Val Thr Ile Thr Cys Arg Ala Ser Gln Tyr Ile Gly Arg Tyr
             20                  25                  30

Leu Arg Trp Tyr Gln Gln Lys Pro Gly Lys Ala Pro Lys Leu Leu Ile
         35                  40                  45

Tyr Asp Ser Ser Val Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Arg Tyr Met Gln Pro Phe
                 85                  90                  95

Thr Phe Gly Gln Gly Thr Lys Val Glu Ile Lys Arg
            100                 105
```

<210> SEQ ID NO 6
<211> LENGTH: 108
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Arg Tyr
            20                  25                  30

Leu Arg Trp Tyr Gln Gln Lys Pro Gly Lys Ala Pro Lys Leu Leu Ile
        35                  40                  45

Tyr Asn Gly Ser Gln Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Leu Gln Pro Tyr
                85                  90                  95

Thr Phe Gly Gln Gly Thr Lys Val Glu Ile Lys Arg
            100                 105

<210> SEQ ID NO 7
<211> LENGTH: 108
<212> TYPE: PRT
<213> ORGANISM: Homo sapiens

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Ser Arg Gln
            20                  25                  30

Leu Arg Trp Tyr Gln Gln Lys Pro Gly Lys Ala Pro Arg Leu Leu Ile
        35                  40                  45

Tyr Gly Ala Ser Val Leu Gln Ser Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Ile Thr Pro Tyr
                85                  90                  95

Thr Phe Gly Gln Gly Thr Lys Val Glu Val Lys Arg
            100                 105

<210> SEQ ID NO 8
<211> LENGTH: 108
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Gly Arg Tyr
            20                  25                  30

Leu Arg Trp Tyr Gln Gln Lys Pro Gly Lys Ala Pro Lys Leu Leu Ile
        35                  40                  45

Tyr Asp Ser Ser Val Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Ser Ser Pro Tyr
                85                  90                  95

Thr Phe Gly Gln Gly Thr Lys Val Glu Ile Lys Arg

<210> SEQ ID NO 9
<211> LENGTH: 108
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile His Arg Gln
            20                  25                  30

Leu Lys Trp Tyr Gln Gln Lys Pro Gly Lys Ala Pro Lys Leu Leu Ile
        35                  40                  45

Tyr Tyr Ala Ser Ile Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Phe Ser Lys Pro Ser
                85                  90                  95

Thr Phe Gly Gln Gly Thr Lys Val Glu Ile Lys Arg
            100                 105

<210> SEQ ID NO 10
<211> LENGTH: 108
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Ala Thr Tyr
            20                  25                  30

Leu Asn Trp Tyr Gln Gln Lys Pro Gly Lys Ala Pro Lys Leu Leu Ile
        35                  40                  45

Tyr Arg Ser Ser Leu Gln Ser Ala Val Pro Ser Arg Phe Ser Gly
50                  55                  60

Ser Gly Ser Gly Thr Val Phe Thr Leu Thr Ile Ser Ser Leu Gln Pro
65                  70                  75                  80

Glu Asp Phe Ala Thr Tyr Tyr Cys Gln Gln Thr Tyr Ala Val Pro Pro
                85                  90                  95

Thr Phe Gly Gln Gly Thr Lys Val Glu Ile Lys Arg
            100                 105

<210> SEQ ID NO 11
<211> LENGTH: 108
<212> TYPE: PRT
<213> ORGANISM: Homo sapiens

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Asp Thr Gly
            20                  25                  30

Leu Ala Trp Tyr Gln Gln Lys Pro Gly Lys Ala Pro Arg Leu Leu Ile
        35                  40                  45

Tyr Asn Val Ser Arg Leu Gln Ser Gly Val Pro Ser Arg Phe Ser Gly
50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Trp Gly Ser Pro Thr
                 85                  90                  95

Thr Phe Gly Gln Gly Thr Lys Val Glu Ile Lys Arg
            100                 105
```

```
<210> SEQ ID NO 12
<211> LENGTH: 108
<212> TYPE: PRT
<213> ORGANISM: Homo sapiens

<400> SEQUENCE: 12
```

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Glu Ile Tyr Ser Trp
                 20                  25                  30

Leu Ala Trp Tyr Gln Gln Arg Pro Gly Lys Ala Pro Lys Leu Leu Ile
             35                  40                  45

Tyr Asn Ala Ser His Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Ile Gly Asp Pro Val
                 85                  90                  95

Thr Phe Gly Gln Gly Thr Lys Val Glu Ile Lys Arg
            100                 105
```

```
<210> SEQ ID NO 13
<211> LENGTH: 108
<212> TYPE: PRT
<213> ORGANISM: Homo sapiens

<400> SEQUENCE: 13
```

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Thr Leu Leu Ile
             35                  40                  45

Tyr Arg Leu Ser Val Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Tyr Asn Val Pro Pro
                 85                  90                  95

Thr Phe Gly Gln Gly Thr Lys Val Glu Ile Lys Arg
            100                 105
```

```
<210> SEQ ID NO 14
<211> LENGTH: 108
<212> TYPE: PRT
<213> ORGANISM: Homo sapiens

<400> SEQUENCE: 14
```

```
Asp Ile Gln Met Thr Gln Ser Pro Ser Ser Leu Ser Ala Ser Val Gly
  1               5                  10                  15
```

-continued

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Asn Ser Phe Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Thr Val Pro Pro
                85                  90                  95

Thr Phe Gly Gln Gly Thr Lys Val Glu Ile Lys Gln
            100                 105

<210> SEQ ID NO 15
<211> LENGTH: 108
<212> TYPE: PRT
<213> ORGANISM: Homo sapiens

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Asn Ser Gln Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Phe Ala Val Pro Pro
                85                  90                  95

Thr Phe Gly Gln Gly Thr Lys Val Glu Ile Lys Arg
            100                 105

<210> SEQ ID NO 16
<211> LENGTH: 123
<212> TYPE: PRT
<213> ORGANISM: Homo sapiens

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Trp Met Ser Trp Val Arg Gln Ala Pro Gly Lys Gly Leu Glu Trp Val
        35                  40                  45

Ser Ser Ile Asp Phe Met Gly Pro His Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Thr Ser Met Leu Pro Met Lys Gly Lys Phe Asp Tyr
            100                 105                 110

Trp Gly Gln Gly Thr Leu Val Thr Val Ser Ser
        115                 120

<210> SEQ ID NO 17
<211> LENGTH: 118
<212> TYPE: PRT
<213> ORGANISM: Homo sapiens

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Tyr Asp Tyr
            20                  25                  30

Asn Met Ser Trp Val Arg Gln Ala Pro Gly Lys Gly Leu Glu Trp Val
        35                  40                  45

Ser Thr Ile Thr His Thr Gly Gly Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Asn Pro Ser Tyr Gln Phe Asp Tyr Trp Gly Gln Gly Thr
            100                 105                 110

Leu Val Thr Val Ser Ser
        115

<210> SEQ ID NO 18
<211> LENGTH: 118
<212> TYPE: PRT
<213> ORGANISM: Homo sapiens

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Arg Tyr
            20                  25                  30

Ser Met Ser Trp Val Arg Gln Ala Pro Gly Lys Gly Leu Glu Trp Val
        35                  40                  45

Ser Thr Ile Leu Pro Gly Gly Asp Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Thr Pro Asp Tyr Met Phe Asp Tyr Trp Gly Gln Gly Thr
            100                 105                 110

Leu Val Thr Val Ser Ser
        115

<210> SEQ ID NO 19
<211> LENGTH: 117
<212> TYPE: PRT
<213> ORGANISM: Homo sapiens

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Lys Tyr
            20                  25                  30

Asn Met Ala Trp Val Arg Gln Ala Pro Gly Lys Gly Leu Glu Trp Val

```
            35                  40                  45
Ser Thr Ile Leu Gly Glu Gly Asn Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Thr Met Asp Tyr Lys Phe Asp Tyr Trp Gly Gln Gly Thr Leu
            100                 105                 110

Val Thr Val Ser Ser
            115

<210> SEQ ID NO 20
<211> LENGTH: 118
<212> TYPE: PRT
<213> ORGANISM: Homo sapiens

<400> SEQUENCE: 20

Glu Val Gln Leu Leu Glu Ser Gly Gly Gly Leu Val Gln Pro Gly Gly
 1               5                  10                  15

Ser Leu Arg Leu Ser Cys Thr Ala Ser Gly Phe Thr Phe Asp Glu Tyr
                20                  25                  30

Asn Met Ser Trp Val Arg Gln Ala Pro Gly Lys Gly Leu Glu Trp Val
            35                  40                  45

Ser Thr Ile Leu Pro His Gly Asp Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gln Asp Pro Leu Tyr Arg Phe Asp Tyr Trp Gly Gln Gly Thr
            100                 105                 110

Leu Val Thr Val Ser Ser
            115

<210> SEQ ID NO 21
<211> LENGTH: 120
<212> TYPE: PRT
<213> ORGANISM: Homo sapiens

<400> SEQUENCE: 21

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Leu Tyr
                20                  25                  30

Asp Met Ser Trp Val Arg Gln Ala Pro Gly Lys Gly Leu Glu Trp Val
            35                  40                  45

Ser Ser Ile Val Asn Ser Gly Val Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Asn Gln Ser Tyr His Trp Asp Phe Asp Tyr Trp Gly Gln
            100                 105                 110

Gly Thr Leu Val Thr Val Ser Ser
```

```
              115                 120
```

<210> SEQ ID NO 22
<211> LENGTH: 118
<212> TYPE: PRT
<213> ORGANISM: Homo sapiens

<400> SEQUENCE: 22

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Arg Met Ser Trp Val Arg Gln Ala Pro Gly Lys Gly Leu Glu Trp Val
        35                  40                  45

Ser Thr Ile Ile Ser Asn Gly Lys Phe Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Asp Trp Met Tyr Met Phe Asp Tyr Trp Gly Gln Gly Thr
            100                 105                 110

Leu Val Thr Val Ser Ser
            115
```

<210> SEQ ID NO 23
<211> LENGTH: 35
<212> TYPE: PRT
<213> ORGANISM: Artificial Sequence
<220> FEATURE:
<223> OTHER INFORMATION: Consensus sequence
<220> FEATURE:
<221> NAME/KEY: SITE
<222> LOCATION: (30)...(31)
<223> OTHER INFORMATION: Xaa = any amino acid

<400> SEQUENCE: 23

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Xaa Xaa Tyr
            20                  25                  30

Asn Met Ser
        35
```

<210> SEQ ID NO 24
<211> LENGTH: 108
<212> TYPE: PRT
<213> ORGANISM: Homo sapiens

<400> SEQUENCE: 24

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Asn Ser Pro Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Thr Tyr Arg Val Pro Pro
                85                  90                  95

Thr Phe Gly Gln Gly Thr Lys Val Glu Ile Lys Arg
            100                 105
```

<210> SEQ ID NO 25
<211> LENGTH: 108
<212> TYPE: PRT
<213> ORGANISM: Homo sapiens

<400> SEQUENCE: 25

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln His Ile His Arg Glu
                20                  25                  30

Leu Arg Trp Tyr Gln Gln Lys Pro Gly Lys Ala Pro Lys Leu Leu Ile
            35                  40                  45

Tyr Gln Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Tyr Leu Pro Pro Tyr
                85                  90                  95

Thr Phe Gly Gln Gly Thr Lys Val Glu Ile Lys Arg
            100                 105
```

<210> SEQ ID NO 26
<211> LENGTH: 108
<212> TYPE: PRT
<213> ORGANISM: Homo sapiens

<400> SEQUENCE: 26

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln His Ile His Arg Glu
                20                  25                  30

Leu Arg Trp Tyr Gln Gln Lys Pro Gly Lys Ala Pro Lys Leu Leu Ile
            35                  40                  45

Tyr Gln Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Arg Val Pro Tyr
                85                  90                  95

Thr Phe Gly Gln Gly Thr Lys Val Glu Ile Lys Arg
            100                 105
```

<210> SEQ ID NO 27
<211> LENGTH: 879
<212> TYPE: DNA
<213> ORGANISM: Artificial Sequence
<220> FEATURE:
<223> OTHER INFORMATION: Encodes fusion protein

<400> SEQUENCE: 27

```
aggccttctg ggagaaaatc cagcaagatg caagccttca gaatctggga tgttaaccag      60
aagaccttct atctgaggaa caaccaacta gttgccggat acttgcaagg accaaatgtc     120
```

```
aatttagaag aaaagataga tgtggtaccc attgagcctc atgctctgtt cttgggaatc    180
catggaggga gatgtgcct  gtcctgtgtc aagtctggtg atgagaccag actccagctg    240
gaggcagtta acatcactga cctgagcgag aacagaaagc aggacaagcg cttcgccttc    300
atccgctcag acagtgggcc caccaccagt tttgagtctg ccgcctgccc cggttggttc    360
ctctgcacag cgatggaagc tgaccagccc gtcagcctca ccaatatgcc tgacgaaggc    420
gtcatggtca ccaaattcta cttccaggag gacgagagct caggtggagg cggttcaggc    480
ggaggtggca gcggcggtgg cgggtcaggt ggtggcggaa gcggcggtgg cgggtcgacg    540
gacatccaga tgacccagtc tccatcctcc ctgtctgcat ctgtaggaga ccgtgtcacc    600
atcacttgcc gggcaagtca gagcattatt aagcatttaa agtggtacca gcagaaacca    660
gggaaagccc ctaagctcct gatctatggt gcatcccggt tgcaaagtgg ggtcccatca    720
cgtttcagtg gcagtggatc tgggacagat ttcactctca ccatcagcag tctgcaacct    780
gaagattttg ctacgtacta ctgtcaacag ggggctcggt ggcctcagac gttcggccaa    840
gggaccaagg tggaaatcaa acgggcggcc gcataataa                           879
```

<210> SEQ ID NO 28
<211> LENGTH: 291
<212> TYPE: PRT
<213> ORGANISM: Artificial Sequence
<220> FEATURE:
<223> OTHER INFORMATION: Fusion protein

<400> SEQUENCE: 28

```
Arg Pro Ser Gly Arg Lys Ser Ser Lys Met Gln Ala Phe Arg Ile Trp
 1               5                  10                  15

Asp Val Asn Gln Lys Thr Phe Tyr Leu Arg Asn Asn Gln Leu Val Ala
            20                  25                  30

Gly Tyr Leu Gln Gly Pro Asn Val Asn Leu Glu Glu Lys Ile Asp Val
        35                  40                  45

Val Pro Ile Glu Pro His Ala Leu Phe Leu Gly Ile His Gly Gly Lys
    50                  55                  60

Met Cys Leu Ser Cys Val Lys Ser Gly Asp Glu Thr Arg Leu Gln Leu
65                  70                  75                  80

Glu Ala Val Asn Ile Thr Asp Leu Ser Glu Asn Arg Lys Gln Asp Lys
                85                  90                  95

Arg Phe Ala Phe Ile Arg Ser Asp Ser Gly Pro Thr Thr Ser Phe Glu
            100                 105                 110

Ser Ala Ala Cys Pro Gly Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Tyr Phe Gln Glu Asp Glu Ser Ser Gly Gly Gly Gly Ser Gly
145                 150                 155                 160

Gly Gly Gly Ser Gly Gly Gly Ser Gly Gly Gly Ser Gly
            165                 170                 175

Gly Gly Ser Thr Asp Ile Gln Met Thr Gln Ser Pro Ser Ser Leu Ser
        180                 185                 190

Ala Ser Val Gly Asp Arg Val Thr Ile Thr Cys Arg Ala Ser Gln Ser
    195                 200                 205

Ile Ile Lys His Leu Lys Trp Tyr Gln Gln Lys Pro Gly Lys Ala Pro
210                 215                 220

Lys Leu Leu Ile Tyr Gly Ala Ser Arg Leu Gln Ser Gly Val Pro Ser
```

```
                225                 230                 235                 240
Arg Phe Ser Gly Ser Gly Ser Gly Thr Asp Phe Thr Leu Thr Ile Ser
                    245                 250                 255

Ser Leu Gln Pro Glu Asp Phe Ala Thr Tyr Tyr Cys Gln Gln Gly Ala
                260                 265                 270

Arg Trp Pro Gln Thr Phe Gly Gln Gly Thr Lys Val Glu Ile Lys Arg
            275                 280                 285

Ala Ala Ala
    290

<210> SEQ ID NO 29
<211> LENGTH: 879
<212> TYPE: DNA
<213> ORGANISM: Artificial Sequence
<220> FEATURE:
<223> OTHER INFORMATION: Encodes fusion protein

<400> SEQUENCE: 29
tcgacggaca tccagatgac ccagtctcca tcctccctgt ctgcatctgt aggagaccgt    60
gtcaccatca cttgccgggc aagtcagagc attattaagc atttaaagtg gtaccagcag   120
aaaccaggga aagcccctaa gctcctgatc tatggtgcat cccggttgca agtgggggtc   180
ccatcacgtt tcagtggcag tggatctggg acagatttca ctctcaccat cagcagtctg   240
caacctgaag attttgctac gtactactgt caacaggggg ctcggtggcc tcagacgttc   300
ggccaaggga ccaaggtgga aatcaaacgg gcggccgcaa gcggtggagg cggttcaggc   360
ggaggtggca gcggcggtgg cgggtcaggt ggtggcggaa gcggcggtgg cggctcgagg   420
ccctctggga gaaaatccag caagatgcaa gccttcagaa tctgggatgt aaccagaag    480 accttctatc tgaggaacaa ccaactagtt gccggatact tgcaaggacc aaatgtcaat   540
ttagaagaaa agatagatgt ggtacccatt gagcctcatg ctctgttctt gggaatccat   600
ggagggaaga tgtgcctgtc ctgtgtcaag tctggtgatg agaccagact ccagctggag   660
gcagttaaca tcactgacct gagcgagaac agaaagcagg acaagcgctt cgccttcatc   720
cgctcagaca gtgggcccac caccagtttt gagtctgccg cctgccccgg ttggttcctc   780
tgcacagcga tggaagctga ccagcccgtc agcctcacca atatgcctga cgaaggcgtc   840
atggtcacca aattctactt ccaggaggac gagtaataa                          879

<210> SEQ ID NO 30
<211> LENGTH: 291
<212> TYPE: PRT
<213> ORGANISM: Artificial Sequence
<220> FEATURE:
<223> OTHER INFORMATION: Fusion protein

<400> SEQUENCE: 30

Ser Thr Asp Ile Gln Met Thr Gln Ser Pro Ser Ser Leu Ser Ala Ser
  1               5                  10                  15

Val Gly Asp Arg Val Thr Ile Thr Cys Arg Ala Ser Gln Ser Ile Ile
             20                  25                  30

Lys His Leu Lys Trp Tyr Gln Gln Lys Pro Gly Lys Ala Pro Lys Leu
         35                  40                  45

Leu Ile Tyr Gly Ala Ser Arg Leu Gln Ser Gly Val Pro Ser Arg Phe
     50                  55                  60

Ser Gly Ser Gly Ser Gly Thr Asp Phe Thr Leu Thr Ile Ser Ser Leu
 65                  70                  75                  80
```

```
Gln Pro Glu Asp Phe Ala Thr Tyr Tyr Cys Gln Gln Gly Ala Arg Trp
                 85                  90                  95
Pro Gln Thr Phe Gly Gln Gly Thr Lys Val Glu Ile Lys Arg Ala Ala
            100                 105                 110
Ala Ser Gly Gly Gly Gly Ser Gly Gly Gly Gly Ser Gly Gly Gly Gly
        115                 120                 125
Ser Gly Gly Gly Gly Ser Gly Gly Gly Ser Arg Pro Ser Gly Arg
    130                 135                 140
Lys Ser Ser Lys Met Gln Ala Phe Arg Ile Trp Asp Val Asn Gln Lys
145                 150                 155                 160
Thr Phe Tyr Leu Arg Asn Asn Gln Leu Val Ala Gly Tyr Leu Gln Gly
                165                 170                 175
Pro Asn Val Asn Leu Glu Glu Lys Ile Asp Val Val Pro Ile Glu Pro
            180                 185                 190
His Ala Leu Phe Leu Gly Ile His Gly Gly Lys Met Cys Leu Ser Cys
        195                 200                 205
Val Lys Ser Gly Asp Glu Thr Arg Leu Gln Leu Glu Ala Val Asn Ile
    210                 215                 220
Thr Asp Leu Ser Glu Asn Arg Lys Gln Asp Lys Arg Phe Ala Phe Ile
225                 230                 235                 240
Arg Ser Asp Ser Gly Pro Thr Thr Ser Phe Glu Ser Ala Ala Cys Pro
                245                 250                 255
Gly Trp Phe Leu Cys Thr Ala Met Glu Ala Asp Gln Pro Val Ser Leu
            260                 265                 270
Thr Asn Met Pro Asp Glu Gly Val Met Val Thr Lys Phe Tyr Phe Gln
        275                 280                 285
Glu Asp Glu
    290

<210> SEQ ID NO 31
<211> LENGTH: 879
<212> TYPE: DNA
<213> ORGANISM: Artificial Sequence
<220> FEATURE:
<223> OTHER INFORMATION: Encodes fusion protein

<400> SEQUENCE: 31
tcgacggaca tccagatgac ccagtctcca tcctccctgt ctgcatctgt aggagaccgt    60
gtcaccatca cttgccgggc aagtcagagc attagcagct atttaaattg gtaccagcag   120
aaaccaggga aagcccctaa gctcctgatc tatgctgcat ccagtttgca aagtggggtc   180
ccatcacgtt tcagtggcag tggatctggg acagatttca ctctcaccat cagcagtctg   240
caacctgaag attttgctac gtactactgt caacagagtt acagtacccc taatacgttc   300
ggccaaggga ccaaggtgga aatcaaacgg gcggccgcaa gcggtggagg cggttcaggc   360
ggaggtggca gcggcggtgg cgggtcaggt ggtggcggaa gcggcggtgg cggctcgagg   420
ccctctggga gaaaatccag caagatgcaa gccttcagaa tctgggatgt aaccagaag   480 accttctatc tgaggaacaa ccaactagtt gccggatact gcaaggacc aaatgtcaat   540 ttagaagaaa agatagatgt ggtacccatt gagcctcatg ctctgttctt gggaatccat   600
ggagggaaga tgtgcctgtc ctgtgtcaag tctggtgatg agaccagact ccagctggag   660
gcagttaaca tcactgacct gagcgagaac agaaagcagg acaagcgctt cgccttcatc   720
cgctcagaca gtgccccac caccagtttt gagtctgccg cctgcccgg ttggttcctc   780 tgcacagcga tggaagctga ccagcccgtc agcctcacca atatgcctga cgaaggcgtc   840
```

```
atggtcacca aattctactt ccaggaggac gagtaataa                              879
```

<210> SEQ ID NO 32
<211> LENGTH: 290
<212> TYPE: PRT
<213> ORGANISM: Artificial Sequence
<220> FEATURE:
<223> OTHER INFORMATION: Fusion protein

<400> SEQUENCE: 32

```
Ser Thr Asp Ile Gln Met Thr Gln Ser Pro Ser Ser Leu Ser Ala Ser
  1               5                  10                  15

Val Gly Asp Arg Val Thr Ile Thr Cys Arg Ala Ser Gln Ser Ile Ser
             20                  25                  30

Ser Tyr Leu Asn Trp Tyr Gln Gln Lys Pro Gly Lys Ala Pro Lys Leu
         35                  40                  45

Leu Ile Tyr Ala Ala Ser Ser Leu Gln Ser Gly Val Pro Ser Arg Phe
     50                  55                  60

Ser Gly Ser Gly Ser Gly Thr Asp Phe Thr Leu Thr Ile Ser Ser Leu
 65                  70                  75                  80

Gln Pro Glu Asp Phe Ala Thr Tyr Tyr Cys Gln Gln Ser Tyr Ser Thr
                 85                  90                  95

Pro Asn Thr Gly Gln Gly Thr Lys Val Glu Ile Lys Arg Ala Ala Ala
            100                 105                 110

Ser Gly Gly Gly Gly Ser Gly Gly Gly Ser Gly Gly Gly Gly Ser
            115                 120                 125

Gly Gly Gly Gly Ser Gly Gly Gly Ser Arg Pro Ser Gly Arg Lys
            130                 135                 140

Ser Ser Lys Met Gln Ala Phe Arg Ile Trp Asp Val Asn Gln Lys Thr
145                 150                 155                 160

Phe Tyr Leu Arg Asn Asn Gln Leu Val Ala Gly Tyr Leu Gln Gly Pro
                165                 170                 175

Asn Val Asn Leu Glu Glu Lys Ile Asp Val Val Pro Ile Glu Pro His
            180                 185                 190

Ala Leu Phe Leu Gly Ile His Gly Gly Lys Met Cys Leu Ser Cys Val
            195                 200                 205

Lys Ser Gly Asp Glu Thr Arg Leu Gln Leu Glu Ala Val Asn Ile Thr
210                 215                 220

Asp Leu Ser Glu Asn Arg Lys Gln Asp Lys Arg Phe Ala Phe Ile Arg
225                 230                 235                 240

Ser Asp Ser Gly Pro Thr Thr Ser Phe Glu Ser Ala Ala Cys Pro Gly
                245                 250                 255

Trp Phe Leu Cys Thr Ala Met Glu Ala Asp Gln Pro Val Ser Leu Thr
            260                 265                 270

Asn Met Pro Asp Glu Gly Val Met Val Thr Lys Phe Tyr Phe Gln Glu
        275                 280                 285

Asp Glu
    290
```

<210> SEQ ID NO 33
<211> LENGTH: 1760
<212> TYPE: DNA
<213> ORGANISM: Homo sapiens

<400> SEQUENCE: 33

```
atttctttat aaaccacaac tctgggcccg caatggcagt ccactgcctt gctgcagtca    60
```

```
cagaatggaa atctgcagag gcctccgcag tcacctaatc actctcctcc tcttcctgtt    120
ccattcagag acgatctgcc gaccctctgg gagaaaatcc agcaagatgc aagccttcag    180
aatctgggat gttaaccaga agaccttcta tctgaggaac aaccaactag ttgctggata    240
cttgcaagga ccaaatgtca atttagaaga aagatagat gtggtaccca ttgagcctca    300
tgctctgttc ttgggaatcc atggagggaa gatgtgcctg tcctgtgtca agtctggtga    360
tgagaccaga ctccagctgg aggcagttaa catcactgac ctgagcgaga acagaaagca    420
ggacaagcgc ttcgccttca tccgctcaga cagcggcccc accaccagtt ttgagtctgc    480
cgcctgcccc ggttggttcc tctgcacagc gatggaagct gaccagcccg tcagcctcac    540
caatatgcct gacgaaggcg tcatggtcac caaattctac ttccaggagg acgagtagta    600
ctgcccaggc ctgcctgttc ccattcttgc atggcaagga ctgcagggac tgccagtccc    660
cctgccccag ggctcccggc tatggggca ctgaggacca gccattgagg ggtggaccct    720
cagaaggcgt cacaagaacc tggtcacagg actctgcctc ctcttcaact gaccagcctc    780
catgctgcct ccagaatggt cttttctaatg tgtgaatcag agcacagcag ccctgcaca    840
aagcccttcc atgtcgcctc tgcattcagg atcaaacccc gaccacctgc ccaacctgct    900
ctcctcttgc cactgcctct cctccctca ttccaccttc ccatgccctg gatccatcag    960
gccacttgat gaccccccaac caagtggctc ccacaccctg ttttacaaaa aagaaaagac   1020
cagtccatga gggaggtttt taagggtttg tggaaaatga aaattaggat ttcatgattt   1080
tttttttttca gtccccgtga aggagagccc ttcatttgga gattatgttc tttcggggag   1140
aggctgagga cttaaaatat tcctgcattt gtgaaatgat ggtgaaagta agtggtagct   1200
tttcccttct ttttcttctt tttttgtgat gtcccaactt gtaaaaatta aaagttatgg   1260
tactatgtta gccccataat ttttttttttc cttttaaaac acttccataa tctggactcc   1320
tctgtccagg cactgctgcc cagcctccaa gctccatctc cactccagat tttttacagc   1380
tgcctgcagt actttacctc ctatcagaag tttctcagct cccaaggctc tgagcaaatg   1440
tggctcctgg gggttctttc ttcctctgct gaaggaataa attgctcctt gacattgtag   1500
agcttctggc acttggagac ttgtatgaaa gatggctgtg cctctgcctg tctccccac   1560
cgggctggga gctctgcaga gcaggaaaca tgactcgtat atgtctcagg tccctgcagg   1620
gccaagcacc tagcctcgct cttggcaggt actcagcgaa tgaatgctgt atatgttggg   1680
tgcaaagttc cctacttcct gtgacttcag ctctgtttta caataaaatc ttgaaaatgc   1740
ctaaaaaaaa aaaaaaaaaa                                               1760
```

<210> SEQ ID NO 34
<211> LENGTH: 177
<212> TYPE: PRT
<213> ORGANISM: Homo sapiens

<400> SEQUENCE: 34

Met Glu Ile Cys Arg Gly Leu Arg Ser His Leu Ile Thr Leu Leu Leu
 1               5                  10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

```
Val Asn Leu Glu Glu Lys Ile Asp Val Val Pro Ile Glu Pro His Ala
 65                  70                  75                  80

Leu Phe Leu Gly Ile His Gly Gly Lys Met Cys Leu Ser Cys Val Lys
                 85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu
```

<210> SEQ ID NO 35
<211> LENGTH: 73
<212> TYPE: DNA
<213> ORGANISM: Artificial Sequence
<220> FEATURE:
<223> OTHER INFORMATION: Multiple cloning site

<400> SEQUENCE: 35
gcgcatatgt tagtgcgtcg acgtcaaaag gccatagcgg gcggccgctg caggtctcga    60
gtgcgatgga tcc    73

<210> SEQ ID NO 36
<211> LENGTH: 92
<212> TYPE: DNA
<213> ORGANISM: Artificial Sequence
<220> FEATURE:
<223> OTHER INFORMATION: Multiple cloning site

<400> SEQUENCE: 36
gcgcatatgt taagcgaggc cttctggaga gagctcagga gtgtcgacgg acatccagat    60
gacccaggcg gccgctaata aggatccaat gc    92

<210> SEQ ID NO 37
<211> LENGTH: 108
<212> TYPE: PRT
<213> ORGANISM: Homo sapiens

<400> SEQUENCE: 37

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Gly Arg Arg
             20                  25                  30

Leu Lys Trp Tyr Gln Gln Lys Pro Gly Ala Ala Pro Arg Leu Leu Ile
         35                  40                  45

Tyr Arg Thr Ser Trp Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Ser Gln Trp Pro His
                 85                  90                  95

Thr Phe Gly Gln Gly Thr Lys Val Glu Ile Lys Arg
                100                 105
```

```
<210> SEQ ID NO 38
<211> LENGTH: 108
<212> TYPE: PRT
<213> ORGANISM: Homo sapiens

<400> SEQUENCE: 38
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Tyr Lys Asn
            20                  25                  30

Leu Arg Trp Tyr Gln Gln Lys Pro Gly Lys Ala Pro Lys Leu Leu Ile
        35                  40                  45

Tyr Asn Ser Ser Ile Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Leu Ser Pro Tyr
                85                  90                  95

Thr Phe Gly Gln Gly Thr Lys Val Glu Ile Lys Arg
            100                 105

```
<210> SEQ ID NO 39
<211> LENGTH: 108
<212> TYPE: PRT
<213> ORGANISM: Homo sapiens

<400> SEQUENCE: 39
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Tyr Asn Asn
            20                  25                  30

Leu Arg Trp Tyr Gln Gln Lys Pro Gly Lys Ala Pro Lys Leu Leu Ile
        35                  40                  45

Tyr Asn Thr Ser Ile Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Trp Arg Ala Pro Tyr
                85                  90                  95

Thr Phe Gly Gln Gly Thr Lys Val Glu Ile Lys Arg
            100                 105

```
<210> SEQ ID NO 40
<211> LENGTH: 108
<212> TYPE: PRT
<213> ORGANISM: Homo sapiens

<400> SEQUENCE: 40
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Tyr Lys Ser
            20                  25                  30

Leu Gly Trp Tyr Gln Gln Lys Pro Gly Lys Ala Pro Lys Leu Leu Ile
        35                  40                  45

Tyr Gln Ser Ser Leu Leu Gln Ser Gly Val Pro Ser Arg Phe Ser Gly
50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr His Gln Met Pro Arg
                 85                  90                  95

Thr Phe Gly Gln Gly Thr Lys Val Glu Ile Lys Arg
                100                 105

<210> SEQ ID NO 41
<211> LENGTH: 108
<212> TYPE: PRT
<213> ORGANISM: Homo sapiens

<400> SEQUENCE: 41

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Tyr Arg His
                 20                  25                  30

Leu Arg Trp Tyr Gln Gln Lys Pro Gly Lys Ala Pro Lys Leu Leu Ile
                 35                  40                  45

Tyr Asp Ala Ser Arg Leu Gln Ser Gly Val Pro Thr Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr His Asn Pro Pro Lys
                 85                  90                  95

Thr Phe Gly Gln Gly Thr Lys Val Glu Ile Lys Arg
                100                 105

<210> SEQ ID NO 42
<211> LENGTH: 116
<212> TYPE: PRT
<213> ORGANISM: Homo sapiens

<400> SEQUENCE: 42

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Trp Pro Tyr
                 20                  25                  30

Thr Met Ser Trp Val Arg Gln Ala Pro Gly Lys Gly Leu Glu Trp Val
                 35                  40                  45

Ser Thr Ile Ser Pro Phe Gly Ser Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Gly Lys Asp Phe Asp Tyr Trp Gly Gln Gly Thr Leu Val
                100                 105                 110

Thr Val Ser Ser
        115

<210> SEQ ID NO 43
<211> LENGTH: 117
<212> TYPE: PRT
<213> ORGANISM: Homo sapiens

<400> SEQUENCE: 43

Glu Val Gln Leu Leu Glu Ser Gly Gly Gly Leu Val Gln Pro Gly Gly
  1               5                  10                  15
```

```
                1               5                  10                 15
            Ser Leu Arg Leu Ser Cys Ala Ala Ser Gly Phe Thr Phe Trp Pro Tyr
                           20                  25                 30

Thr Met Ser Trp Val Arg Gln Ala Pro Gly Lys Gly Leu Glu Trp Val
                           35                  40                 45

Ser Thr Ile Ser Pro Phe Gly Ser Thr Thr Tyr Tyr Ala Asp Ser Val
                           50                  55                 60

Lys Gly Arg Phe Thr Ile Ser Arg Asp Asn Ser Lys Asn Thr Leu Tyr
             65                 70                  75                 80

Leu Gln Met Asn Ser Leu Arg Ala Glu Asp Thr Ala Val Tyr Tyr Cys
                           85                  90                 95

Ala Lys Gly Asn Leu Glu Pro Phe Asp Tyr Trp Gly Gln Gly Thr Leu
                           100                 105                110

Val Thr Val Ser Ser
                           115

<210> SEQ ID NO 44
<211> LENGTH: 117
<212> TYPE: PRT
<213> ORGANISM: Homo sapiens

<400> SEQUENCE: 44

Glu Val Gln Leu Leu Glu Ser Gly Gly Gly Leu Val Gln Pro Gly Gly
             1               5                  10                 15

Ser Leu Arg Leu Ser Cys Ala Ala Ser Gly Phe Thr Phe Trp Pro Tyr
                           20                  25                 30

Thr Met Ser Trp Val Arg Gln Ala Pro Gly Lys Gly Leu Glu Trp Val
                           35                  40                 45

Ser Thr Ile Ser Pro Phe Gly Ser Thr Thr Tyr Tyr Ala Asp Ser Val
                           50                  55                 60

Lys Gly Arg Phe Thr Ile Ser Arg Asp Asn Ser Lys Asn Thr Leu Tyr
             65                 70                  75                 80

Leu Gln Met Asn Ser Leu Arg Ala Glu Asp Thr Ala Val Tyr Tyr Cys
                           85                  90                 95

Ala Lys Lys Leu Ser Asn Gly Phe Asp Tyr Trp Gly Gln Gly Thr Leu
                           100                 105                110

Val Thr Val Ser Ser
                           115

<210> SEQ ID NO 45
<211> LENGTH: 118
<212> TYPE: PRT
<213> ORGANISM: Homo sapiens

<400> SEQUENCE: 45

Glu Val Gln Leu Leu Glu Ser Gly Gly Gly Leu Val Gln Pro Gly Gly
             1               5                  10                 15

Ser Leu Arg Leu Ser Cys Ala Ala Ser Gly Phe Thr Phe Trp Pro Tyr
                           20                  25                 30

Thr Met Ser Trp Val Arg Gln Ala Pro Gly Lys Gly Leu Glu Trp Val
                           35                  40                 45

Ser Thr Ile Ser Pro Phe Gly Ser Thr Thr Tyr Tyr Ala Asp Ser Val
                           50                  55                 60

Lys Gly Arg Phe Thr Ile Ser Arg Asp Asn Ser Lys Asn Thr Leu Tyr
             65                 70                  75                 80

Leu Gln Met Asn Ser Leu Arg Ala Glu Asp Thr Ala Val Tyr Tyr Cys
```

-continued

```
                    85                  90                  95

Ala Lys Val Val Lys Asp Asn Thr Phe Asp Tyr Trp Gly Gln Gly Thr
            100                 105                 110

Leu Val Thr Val Ser Ser
            115

<210> SEQ ID NO 46
<211> LENGTH: 118
<212> TYPE: PRT
<213> ORGANISM: Homo sapiens

<400> SEQUENCE: 46

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Trp Pro Tyr
             20                  25                  30

Thr Met Ser Trp Val Arg Gln Ala Pro Gly Lys Gly Leu Glu Trp Val
         35                  40                  45

Ser Thr Ile Ser Pro Phe Gly Ser Thr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asn Thr Gly Gly Lys Gln Phe Asp Tyr Trp Gly Gln Gly Thr
            100                 105                 110

Leu Val Thr Val Ser Ser
            115

<210> SEQ ID NO 47
<211> LENGTH: 118
<212> TYPE: PRT
<213> ORGANISM: Homo sapiens

<400> SEQUENCE: 47

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Trp Pro Tyr
             20                  25                  30

Thr Met Ser Trp Val Arg Gln Ala Pro Gly Lys Gly Leu Glu Trp Val
         35                  40                  45

Ser Thr Ile Ser Pro Phe Gly Ser Thr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Lys Thr Gly Pro Ser Ser Phe Asp Tyr Trp Gly Gln Gly Thr
            100                 105                 110

Leu Val Thr Val Ser Ser
            115

<210> SEQ ID NO 48
<211> LENGTH: 120
<212> TYPE: PRT
<213> ORGANISM: Homo sapiens

<400> SEQUENCE: 48
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Pro Tyr
            20                  25                  30

Thr Met Ser Trp Val Arg Gln Ala Pro Gly Lys Gly Leu Glu Trp Val
        35                  40                  45

Ser Thr Ile Ser Pro Phe Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Thr Glu Asn Arg Gly Val Ser Phe Asp Tyr Trp Gly Gln
            100                 105                 110

Gly Thr Leu Val Thr Val Ser Ser
        115                 120

<210> SEQ ID NO 49
<211> LENGTH: 122
<212> TYPE: PRT
<213> ORGANISM: Homo sapiens

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Pro Tyr
            20                  25                  30

Thr Met Ser Trp Val Arg Gln Ala Pro Gly Lys Gly Leu Glu Trp Val
        35                  40                  45

Ser Thr Ile Ser Pro Phe Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Asp Val Leu Lys Thr Gly Leu Asp Gly Phe Asp Tyr Trp
            100                 105                 110

Gly Gln Gly Thr Leu Val Thr Val Ser Ser
        115                 120

<210> SEQ ID NO 50
<211> LENGTH: 120
<212> TYPE: PRT
<213> ORGANISM: Homo sapiens

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Met Ala Tyr
            20                  25                  30

Gln Met Ala Trp Val Arg Gln Ala Pro Gly Lys Gly Leu Glu Trp Val
        35                  40                  45

Ser Thr Ile His Gln Thr Gly Phe Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

-continued

Leu Gln Met Asn Ser Leu Arg Ala Glu Asp Thr Ala Val Tyr Tyr Cys
                    85                  90                  95

Ala Lys Val Arg Ser Met Arg Pro Tyr Lys Phe Asp Tyr Trp Gly Gln
                100                 105                 110

Gly Thr Leu Val Thr Val Ser Ser
            115                 120

<210> SEQ ID NO 51
<211> LENGTH: 120
<212> TYPE: PRT
<213> ORGANISM: Homo sapiens

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Asp Tyr
                20                  25                  30

Asp Met Thr Trp Val Arg Gln Ala Pro Gly Lys Gly Leu Glu Trp Val
            35                  40                  45

Ser Met Ile Ser Ser Ser Gly Leu Trp Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Lys Gly Phe Arg Leu Phe Pro Arg Thr Phe Asp Tyr Trp Gly Gln
                100                 105                 110

Gly Thr Leu Val Thr Val Ser Ser
            115                 120

<210> SEQ ID NO 52
<211> LENGTH: 121
<212> TYPE: PRT
<213> ORGANISM: Homo sapiens

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Asp Tyr
                20                  25                  30

Val Met Gly Trp Ala Arg Gln Ala Pro Gly Lys Gly Leu Glu Trp Val
            35                  40                  45

Ser Leu Ile Lys Pro Asn Gly Ser Pro Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Lys Gly Arg Gly Arg Phe Asn Val Leu Gln Phe Asp Tyr Trp Gly
                100                 105                 110

Gln Gly Thr Leu Val Thr Val Ser Ser
            115                 120

<210> SEQ ID NO 53
<211> LENGTH: 118
<212> TYPE: PRT
<213> ORGANISM: Homo sapiens

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Arg His Tyr
            20                  25                  30

Arg Met Gly Trp Val Arg Gln Ala Pro Gly Lys Gly Leu Glu Trp Val
        35                  40                  45

Ser Trp Ile Arg Pro Asp Gly Thr Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Met Gly Asp Arg Phe Asp Tyr Trp Gly Gln Gly Thr
            100                 105                 110

Leu Val Thr Val Ser Ser
            115

<210> SEQ ID NO 54
<211> LENGTH: 116
<212> TYPE: PRT
<213> ORGANISM: Homo sapiens

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Met Trp Asp
            20                  25                  30

Lys Met Gly Trp Val Arg Gln Ala Pro Gly Lys Gly Leu Glu Trp Val
        35                  40                  45

Ser Phe Ile Gly Arg Glu Gly Tyr Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Val Ala Ser Phe Asp Tyr Trp Gly Gln Gly Thr Leu Val
            100                 105                 110

Thr Val Ser Ser
        115

<210> SEQ ID NO 55
<211> LENGTH: 117
<212> TYPE: PRT
<213> ORGANISM: Homo sapiens

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Ala Tyr
            20                  25                  30

Pro Met Ser Trp Val Arg Gln Ala Pro Gly Lys Gly Leu Glu Trp Val
        35                  40                  45

Ser Ser Ile Ser Ser Trp Gly Thr Gly Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Gly Gln Gly Ser Phe Asp Tyr Trp Gly Gln Gly Thr Leu
            100                 105                 110

Val Thr Val Ser Ser
        115

<210> SEQ ID NO 56
<211> LENGTH: 15
<212> TYPE: PRT
<213> ORGANISM: Unknown
<220> FEATURE:
<223> OTHER INFORMATION: Binds human type 1 IL-1 receptor

<400> SEQUENCE: 56

Phe Glu Trp Thr Pro Gly Tyr Trp Gln Pro Tyr Ala Leu Pro Leu
 1               5                  10                  15

<210> SEQ ID NO 57
<211> LENGTH: 15
<212> TYPE: PRT
<213> ORGANISM: Unknown
<220> FEATURE:
<223> OTHER INFORMATION: Binds human type 1 IL-1 receptor
<220> FEATURE:
<221> NAME/KEY: SITE
<222> LOCATION: 10
<223> OTHER INFORMATION: Xaa = 1-azetidine-2-carboxylic acid

<400> SEQUENCE: 57

Phe Glu Trp Thr Pro Gly Tyr Trp Gln Xaa Tyr Ala Leu Pro Leu
 1               5                  10                  15

<210> SEQ ID NO 58
<211> LENGTH: 11
<212> TYPE: PRT
<213> ORGANISM: Unknown
<220> FEATURE:
<223> OTHER INFORMATION: Binds human type 1 IL-1 receptor
<220> FEATURE:
<221> NAME/KEY: SITE
<222> LOCATION: 10
<223> OTHER INFORMATION: Xaa = 1-azetidine-2-carboxylic acid

<400> SEQUENCE: 58

Phe Glu Trp Thr Pro Gly Tyr Trp Gln Xaa Tyr
 1               5                  10

<210> SEQ ID NO 59
<211> LENGTH: 11
<212> TYPE: PRT
<213> ORGANISM: Unknown
<220> FEATURE:
<223> OTHER INFORMATION: Binds human type 1 IL-1 receptor
<220> FEATURE:
<221> NAME/KEY: SITE
<222> LOCATION: 10
<223> OTHER INFORMATION: Xaa = 1-azetidine-2-carboxylic acid

<400> SEQUENCE: 59

Phe Glu Trp Thr Pro Gly Trp Tyr Gln Xaa Tyr
 1               5                  10

<210> SEQ ID NO 60
<211> LENGTH: 292
```

<212> TYPE: PRT
<213> ORGANISM: Saponaria officinalis

<400> SEQUENCE: 60

Met Lys Ile Tyr Val Ala Thr Ile Ala Trp Ile Leu Leu Gln Phe
1               5                   10                  15

Ser Ala Trp Thr Thr Thr Asp Ala Val Thr Ser Ile Thr Leu Asp Leu
            20                  25                  30

Val Asn Pro Thr Ala Gly Gln Tyr Ser Ser Phe Val Asp Lys Ile Arg
            35                  40                  45

Asn Asn Val Lys Asp Pro Asn Leu Lys Tyr Gly Gly Thr Asp Ile Ala
50                  55                  60

Val Ile Gly Pro Pro Ser Lys Asp Lys Phe Leu Arg Ile Asn Phe Gln
65                  70                  75                  80

Ser Ser Arg Gly Thr Val Ser Leu Gly Leu Lys Arg Asp Asn Leu Tyr
                85                  90                  95

Val Val Ala Tyr Leu Ala Met Asp Asn Thr Asn Val Asn Arg Ala Tyr
                100                 105                 110

Tyr Phe Lys Ser Glu Ile Thr Ser Ala Glu Leu Thr Ala Leu Phe Pro
            115                 120                 125

Glu Ala Thr Thr Ala Asn Gln Lys Ala Leu Glu Tyr Thr Glu Asp Tyr
130                 135                 140

Gln Ser Ile Glu Lys Asn Ala Gln Ile Thr Gln Gly Asp Lys Ser Arg
145                 150                 155                 160

Lys Glu Leu Gly Leu Gly Ile Asp Leu Leu Leu Thr Phe Met Glu Ala
                165                 170                 175

Val Asn Lys Lys Ala Arg Val Val Lys Asn Glu Ala Arg Phe Leu Leu
                180                 185                 190

Ile Ala Ile Gln Met Thr Ala Glu Val Ala Arg Phe Arg Tyr Ile Gln
            195                 200                 205

Asn Leu Val Thr Lys Asn Phe Pro Asn Lys Phe Asp Ser Asp Asn Lys
        210                 215                 220

Val Ile Gln Phe Glu Val Ser Trp Arg Lys Ile Ser Thr Ala Ile Tyr
225                 230                 235                 240

Gly Asp Ala Lys Asn Gly Val Phe Asn Lys Asp Tyr Asp Phe Gly Phe
                245                 250                 255

Gly Lys Val Arg Gln Val Lys Asp Leu Gln Met Gly Leu Leu Met Tyr
                260                 265                 270

Leu Gly Lys Pro Lys Ser Ser Asn Glu Ala Asn Ser Thr Ala Tyr Ala
            275                 280                 285

Thr Thr Val Leu
    290

<210> SEQ ID NO 61
<211> LENGTH: 236
<212> TYPE: PRT
<213> ORGANISM: Saponaria officinalis

<400> SEQUENCE: 61

Asp Pro Asn Leu Lys Tyr Gly Gly Thr Asp Ile Ala Val Ile Gly Pro
1               5                   10                  15

Pro Ser Arg Asp Lys Phe Leu Arg Leu Asn Phe Gln Ser Ser Arg Gly
            20                  25                  30

Thr Val Ser Leu Gly Leu Lys Arg Glu Asn Leu Tyr Val Val Ala Tyr
            35                  40                  45

```
Leu Ala Met Asp Asn Ala Asn Val Asn Arg Ala Tyr Tyr Phe Gly Thr
 50                  55                  60

Glu Ile Thr Ser Ala Glu Leu Thr Thr Leu Leu Pro Glu Ala Thr Val
 65                  70                  75                  80

Ala Asn Gln Lys Ala Leu Glu Tyr Thr Glu Asp Tyr Gln Ser Ile Glu
                 85                  90                  95

Lys Asn Ala Lys Ile Thr Glu Gly Asp Lys Thr Arg Lys Glu Leu Gly
                100                 105                 110

Leu Gly Ile Asn Leu Leu Ser Thr Leu Met Asp Ala Val Asn Lys Lys
            115                 120                 125

Ala Arg Val Val Lys Asn Glu Ala Arg Phe Leu Leu Ile Ala Ile Gln
130                 135                 140

Met Thr Ala Glu Ala Ala Arg Phe Arg Tyr Ile Gln Asn Leu Val Thr
145                 150                 155                 160

Lys Asn Phe Pro Asn Lys Phe Asn Ser Glu Asp Lys Val Ile Gln Phe
                165                 170                 175

Gln Val Asn Trp Ser Lys Ile Ser Lys Ala Ile Tyr Gly Asp Ala Lys
            180                 185                 190

Asn Gly Val Phe Asn Lys Asp Tyr Asp Phe Gly Phe Gly Lys Val Arg
                195                 200                 205

Gln Val Lys Asp Leu Gln Met Gly Leu Leu Met Tyr Leu Gly Thr Thr
        210                 215                 220

Pro Asn Asn Ala Ala Asp Arg Tyr Arg Ala Glu Leu
225                 230                 235

<210> SEQ ID NO 62
<211> LENGTH: 157
<212> TYPE: PRT
<213> ORGANISM: Saponaria officinalis

<400> SEQUENCE: 62

Met Lys Ile Tyr Val Val Ala Thr Ile Ala Trp Ile Leu Leu Gln Phe
  1               5                  10                  15

Ser Ala Trp Thr Thr Thr Asp Ala Val Thr Ser Ile Thr Leu Asp Leu
                 20                  25                  30

Val Asn Pro Thr Ala Gly Gln Tyr Ser Ser Phe Val Asp Lys Ile Arg
             35                  40                  45

Asn Asn Val Lys Asp Pro Asn Leu Lys Tyr Gly Gly Thr Asp Ile Ala
 50                  55                  60

Val Ile Gly Pro Pro Ser Lys Gly Lys Phe Leu Arg Ile Asn Phe Gln
 65                  70                  75                  80

Ser Ser Arg Gly Thr Val Ser Leu Gly Leu Lys Arg Asp Asn Leu Tyr
                 85                  90                  95

Val Val Ala Tyr Leu Ala Met Asp Asn Thr Asn Val Asn Arg Ala Tyr
            100                 105                 110

Tyr Phe Arg Ser Glu Ile Thr Ser Ala Glu Leu Thr Ala Leu Phe Pro
        115                 120                 125

Glu Ala Thr Thr Ala Asn Gln Lys Ala Leu Glu Tyr Thr Glu Asp Tyr
130                 135                 140

Gln Ser Ile Glu Lys Asn Ala Gln Ile Thr Gln Glu Asp
145                 150                 155

<210> SEQ ID NO 63
<211> LENGTH: 253
<212> TYPE: PRT
<213> ORGANISM: Saponaria officinalis
```

-continued

<400> SEQUENCE: 63

```
Val Thr Ser Ile Thr Leu Asp Leu Val Asn Pro Thr Ala Gly Gln Tyr
  1               5                  10                  15

Ser Ser Phe Val Asp Lys Ile Arg Asn Val Lys Asp Pro Asn Leu
             20                  25                  30

Lys Tyr Gly Gly Thr Asp Ile Ala Val Ile Gly Pro Pro Ser Lys Glu
         35                  40                  45

Lys Phe Leu Arg Ile Asn Phe Gln Ser Ser Arg Gly Thr Val Ser Leu
 50                  55                  60

Gly Leu Lys Arg Asp Asn Leu Tyr Val Val Ala Tyr Leu Ala Met Asp
 65                  70                  75                  80

Asn Thr Asn Val Asn Arg Ala Tyr Tyr Phe Arg Ser Glu Ile Thr Ser
                 85                  90                  95

Ala Glu Leu Thr Ala Leu Phe Pro Glu Ala Thr Ala Asn Gln Lys
            100                 105                 110

Ala Leu Glu Tyr Thr Glu Asp Tyr Gln Ser Ile Glu Lys Asn Ala Gln
        115                 120                 125

Ile Thr Gln Gly Asp Lys Ser Arg Lys Glu Leu Gly Leu Gly Ile Asp
130                 135                 140

Leu Leu Leu Thr Ser Met Glu Ala Val Asn Lys Lys Ala Arg Val Val
145                 150                 155                 160

Lys Asn Glu Ala Arg Phe Leu Leu Ile Ala Ile Gln Met Thr Ala Glu
                165                 170                 175

Val Ala Arg Phe Arg Tyr Ile Gln Asn Leu Val Thr Lys Asn Phe Pro
            180                 185                 190

Asn Lys Phe Asp Ser Asp Asn Lys Val Ile Gln Phe Glu Val Ser Trp
        195                 200                 205

Arg Lys Ile Ser Thr Ala Ile Tyr Gly Asp Ala Lys Asn Gly Val Phe
210                 215                 220

Asn Lys Asp Tyr Asp Phe Gly Phe Gly Lys Val Arg Gln Val Lys Asp
225                 230                 235                 240

Leu Gln Met Gly Leu Leu Met Tyr Leu Gly Lys Pro Lys
                245                 250
```

<210> SEQ ID NO 64
<211> LENGTH: 299
<212> TYPE: PRT
<213> ORGANISM: Saponaria officinalis

<400> SEQUENCE: 64

```
Met Lys Ile Tyr Val Val Ala Thr Ile Ala Trp Ile Leu Leu Gln Phe
  1               5                  10                  15

Ser Ala Trp Thr Thr Thr Asp Ala Val Thr Ser Ile Thr Leu Asp Leu
             20                  25                  30

Val Asn Pro Thr Ala Gly Gln Tyr Ser Ser Phe Val Asp Lys Ile Arg
         35                  40                  45

Asn Asn Val Lys Asp Pro Asn Leu Lys Tyr Gly Gly Thr Asp Ile Ala
 50                  55                  60

Val Ile Gly Pro Pro Ser Lys Glu Lys Phe Leu Arg Ile Asn Phe Gln
 65                  70                  75                  80

Ser Ser Arg Gly Thr Val Ser Leu Gly Leu Lys Arg Asp Asn Leu Tyr
                 85                  90                  95

Val Val Ala Tyr Leu Ala Met Asp Asn Thr Asn Val Asn Arg Ala Tyr
            100                 105                 110
```

```
Tyr Phe Arg Ser Glu Ile Thr Ser Ala Glu Ser Thr Ala Leu Phe Pro
            115                 120                 125
Glu Ala Thr Thr Ala Asn Gln Lys Ala Leu Glu Tyr Thr Glu Asp Tyr
130                 135                 140
Gln Ser Ile Glu Lys Asn Ala Gln Ile Thr Gln Gly Asp Gln Ser Arg
145                 150                 155                 160
Lys Glu Leu Gly Leu Gly Ile Asp Leu Leu Ser Thr Ser Met Glu Ala
                165                 170                 175
Val Asn Lys Lys Ala Arg Val Val Lys Asp Glu Ala Arg Phe Leu Leu
            180                 185                 190
Ile Ala Ile Gln Met Thr Ala Glu Ala Ala Arg Phe Arg Tyr Ile Gln
            195                 200                 205
Asn Leu Val Ile Lys Asn Phe Pro Asn Lys Phe Asn Ser Glu Asn Lys
        210                 215                 220
Val Ile Gln Phe Glu Val Asn Trp Lys Ile Ser Thr Ala Ile Tyr
225                 230                 235                 240
Gly Asp Ala Lys Asn Gly Val Phe Asn Lys Asp Tyr Asp Phe Gly Phe
                245                 250                 255
Gly Lys Val Arg Gln Val Lys Asp Leu Gln Met Gly Leu Leu Met Tyr
            260                 265                 270
Leu Gly Lys Pro Lys Ser Ser Asn Glu Ala Asn Ser Thr Val Arg His
        275                 280                 285
Tyr Gly Pro Leu Lys Pro Thr Leu Leu Ile Thr
290                 295

<210> SEQ ID NO 65
<211> LENGTH: 254
<212> TYPE: PRT
<213> ORGANISM: Saponaria officinalis

<400> SEQUENCE: 65

Ala Val Thr Ser Ile Thr Leu Asp Leu Val Asn Pro Thr Ala Gly Gln
1               5                   10                  15
Tyr Ser Ser Phe Val Asp Lys Ile Arg Asn Asn Val Lys Asp Pro Asn
            20                  25                  30
Leu Lys Tyr Gly Gly Thr Asp Ile Ala Val Ile Gly Pro Pro Ser Lys
        35                  40                  45
Glu Lys Phe Leu Arg Ile Asn Phe Gln Ser Ser Arg Gly Thr Val Ser
    50                  55                  60
Leu Gly Leu Lys Arg Asp Asn Leu Tyr Val Val Ala Tyr Leu Ala Met
65                  70                  75                  80
Asp Asn Thr Asn Val Asn Arg Ala Tyr Tyr Phe Arg Ser Glu Ile Thr
                85                  90                  95
Ser Ala Glu Ser Thr Ala Leu Phe Pro Glu Ala Thr Thr Ala Asn Gln
            100                 105                 110
Lys Ala Leu Glu Tyr Thr Glu Asp Tyr Gln Ser Ile Glu Lys Asn Ala
        115                 120                 125
Gln Ile Thr Gln Gly Asp Gln Ser Arg Lys Glu Leu Gly Leu Gly Ile
    130                 135                 140
Asp Leu Leu Ser Thr Ser Met Glu Ala Val Asn Lys Lys Ala Arg Val
145                 150                 155                 160
Val Lys Asp Glu Ala Arg Phe Leu Leu Ile Ala Ile Gln Met Thr Ala
                165                 170                 175
Glu Ala Ala Arg Phe Arg Tyr Ile Gln Asn Leu Val Ile Lys Asn Phe
```

```
                    180                 185                 190
Pro Asn Lys Phe Asn Ser Glu Asn Lys Val Ile Gln Phe Glu Val Asn
        195                 200                 205

Trp Lys Lys Ile Ser Thr Ala Ile Tyr Gly Asp Ala Lys Asn Gly Val
210                 215                 220

Phe Asn Lys Asp Tyr Asp Phe Gly Phe Gly Lys Val Arg Gln Val Lys
225                 230                 235                 240

Asp Leu Gln Met Gly Leu Leu Met Tyr Leu Gly Lys Pro Lys
                245                 250

<210> SEQ ID NO 66
<211> LENGTH: 253
<212> TYPE: PRT
<213> ORGANISM: Saponaria officinalis

<400> SEQUENCE: 66

Val Thr Ser Ile Thr Leu Asp Leu Val Asn Pro Thr Ala Gly Gln Tyr
1               5                   10                  15

Ser Ser Phe Val Asp Lys Ile Arg Asn Asn Val Lys Asp Pro Asn Leu
                20                  25                  30

Lys Tyr Gly Gly Thr Asp Ile Ala Val Ile Gly Pro Pro Ser Lys Glu
            35                  40                  45

Lys Phe Leu Arg Ile Asn Phe Gln Ser Ser Arg Gly Thr Val Ser Leu
        50                  55                  60

Gly Leu Lys Arg Asp Asn Leu Tyr Val Val Ala Tyr Leu Ala Met Asp
65                  70                  75                  80

Asn Thr Asn Val Asn Arg Ala Tyr Tyr Phe Arg Ser Glu Ile Thr Ser
                85                  90                  95

Ala Glu Leu Thr Ala Leu Phe Pro Glu Ala Thr Thr Ala Asn Gln Lys
            100                 105                 110

Ala Leu Glu Tyr Thr Glu Asp Tyr Gln Ser Ile Glu Lys Asn Ala Gln
        115                 120                 125

Ile Thr Gln Gly Asp Lys Ser Arg Lys Glu Leu Gly Leu Gly Ile Asp
130                 135                 140

Leu Leu Leu Thr Ser Met Glu Ala Val Asn Lys Lys Ala Arg Val Val
145                 150                 155                 160

Lys Asn Glu Ala Arg Phe Leu Leu Ile Ala Ile Gln Met Thr Ala Glu
                165                 170                 175

Ala Ala Arg Phe Arg Tyr Ile Gln Asn Leu Val Ile Lys Asn Phe Pro
            180                 185                 190

Asn Lys Phe Asn Ser Glu Asn Lys Val Ile Gln Phe Glu Val Asn Trp
        195                 200                 205

Lys Lys Ile Ser Thr Ala Ile Tyr Gly Asp Ala Lys Asn Gly Val Phe
210                 215                 220

Asn Lys Asp Tyr Asp Phe Gly Phe Gly Lys Val Arg Gln Val Lys Asp
225                 230                 235                 240

Leu Gln Met Gly Leu Leu Met Tyr Leu Gly Lys Pro Lys
                245                 250

<210> SEQ ID NO 67
<211> LENGTH: 275
<212> TYPE: PRT
<213> ORGANISM: Saponaria officinalis
<220> FEATURE:
<221> NAME/KEY: SITE
<222> LOCATION: (48)...(48)
<223> OTHER INFORMATION: Xaa = Glu or Asp
```

```
<220> FEATURE:
<221> NAME/KEY: SITE
<222> LOCATION: (91)...(91)
<223> OTHER INFORMATION: Xaa = Arg or Lys
<220> FEATURE:
<221> NAME/KEY: SITE
<222> LOCATION: (99)...(99)
<223> OTHER INFORMATION: Xaa = Ser or Leu
<220> FEATURE:
<221> NAME/KEY: SITE
<222> LOCATION: (134)...(134)
<223> OTHER INFORMATION: Xaa = Gln or Lys
<220> FEATURE:
<221> NAME/KEY: SITE
<222> LOCATION: (147)...(147)
<223> OTHER INFORMATION: Xaa = Ser or Leu
<220> FEATURE:
<221> NAME/KEY: SITE
<222> LOCATION: (149)...(149)
<223> OTHER INFORMATION: Xaa = Ser or Phe
<220> FEATURE:
<221> NAME/KEY: SITE
<222> LOCATION: (162)...(162)
<223> OTHER INFORMATION: Xaa = Asp or Asn
<220> FEATURE:
<221> NAME/KEY: SITE
<222> LOCATION: (177)...(177)
<223> OTHER INFORMATION: Xaa = Ala or Val
<220> FEATURE:
<221> NAME/KEY: SITE
<222> LOCATION: (188)...(188)
<223> OTHER INFORMATION: Xaa = Ile or Thr
<220> FEATURE:
<221> NAME/KEY: SITE
<222> LOCATION: (196)...(196)
<223> OTHER INFORMATION: Xaa = Asn or Asp
<220> FEATURE:
<221> NAME/KEY: SITE
<222> LOCATION: (198)...(198)
<223> OTHER INFORMATION: Xaa = Glu or Asp
<220> FEATURE:
<221> NAME/KEY: SITE
<222> LOCATION: (207)...(207)
<223> OTHER INFORMATION: Xaa = Asn or Ser
<220> FEATURE:
<221> NAME/KEY: SITE
<222> LOCATION: (209)...(209)
<223> OTHER INFORMATION: Xaa = Lys or Arg

<400> SEQUENCE: 67

Val Thr Ser Ile Thr Leu Asp Leu Val Asn Pro Thr Ala Gly Gln Tyr
 1               5                  10                  15

Ser Ser Phe Val Asp Lys Ile Arg Asn Val Lys Asp Pro Asn Leu
            20                  25                  30

Lys Tyr Gly Gly Thr Asp Ile Ala Val Ile Gly Pro Pro Ser Lys Xaa
         35                  40                  45

Lys Phe Leu Arg Ile Asn Phe Gln Ser Ser Arg Gly Thr Val Ser Leu
     50                  55                  60

Gly Leu Lys Arg Asp Asn Leu Tyr Val Val Ala Tyr Leu Ala Met Asp
65                  70                  75                  80

Asn Thr Asn Val Asn Arg Ala Tyr Tyr Phe Xaa Ser Glu Ile Thr Ser
                 85                  90                  95

Ala Glu Xaa Thr Ala Leu Phe Pro Glu Ala Thr Thr Ala Asn Gln Lys
            100                 105                 110

Ala Leu Glu Tyr Thr Glu Asp Tyr Gln Ser Ile Glu Lys Asn Ala Gln
        115                 120                 125

Ile Thr Gln Gly Asp Xaa Ser Arg Lys Glu Leu Gly Leu Gly Ile Asp
    130                 135                 140

Leu Leu Xaa Thr Xaa Met Glu Ala Val Asn Lys Lys Ala Arg Val Val
```

```
              145                 150                 155                 160
Lys Xaa Glu Ala Arg Phe Leu Leu Ile Ala Ile Gln Met Thr Ala Glu
                165                 170                 175

Xaa Ala Arg Phe Arg Tyr Ile Gln Asn Leu Val Xaa Lys Asn Phe Pro
            180                 185                 190

Asn Lys Phe Xaa Ser Xaa Asn Lys Val Ile Gln Phe Glu Val Xaa Trp
        195                 200                 205

Xaa Lys Ile Ser Thr Ala Ile Tyr Gly Asp Ala Lys Asn Gly Val Phe
    210                 215                 220

Asn Lys Asp Tyr Asp Phe Gly Phe Gly Lys Val Arg Gln Val Lys Asp
225                 230                 235                 240

Leu Gln Met Gly Leu Leu Met Tyr Leu Gly Lys Pro Lys Ser Ser Asn
                245                 250                 255

Glu Ala Asn Ser Thr Val Arg His Tyr Gly Pro Leu Pro Thr Leu
                260                 265                 270

Leu Ile Thr
        275
```

<210> SEQ ID NO 68
<211> LENGTH: 16
<212> TYPE: PRT
<213> ORGANISM: Unknown
<220> FEATURE:
<223> OTHER INFORMATION: Hemagglutinin tag peptide

<400> SEQUENCE: 68

```
Tyr Pro Tyr Asp Val Pro Asp Tyr Ala Lys Lys Lys Lys Lys Lys Cys
1               5                   10                  15
```

<210> SEQ ID NO 69
<211> LENGTH: 16
<212> TYPE: PRT
<213> ORGANISM: Unknown
<220> FEATURE:
<223> OTHER INFORMATION: Hemagglutinin tag peptide

<400> SEQUENCE: 69

```
Cys Lys Lys Lys Lys Lys Lys Tyr Pro Tyr Asp Val Pro Asp Tyr Ala
1               5                   10                  15
```

<210> SEQ ID NO 70
<211> LENGTH: 13
<212> TYPE: PRT
<213> ORGANISM: Artificial Sequence
<220> FEATURE:
<223> OTHER INFORMATION: His tag peptide

<400> SEQUENCE: 70

```
His His His His His His Lys Lys Lys Lys Lys Lys Cys
1               5                   10
```

<210> SEQ ID NO 71
<211> LENGTH: 13
<212> TYPE: PRT
<213> ORGANISM: Artificial Sequence
<220> FEATURE:
<223> OTHER INFORMATION: His tag peptide

<400> SEQUENCE: 71

```
Cys Lys Lys Lys Lys Lys Lys His His His His His His
1               5                   10
```

```
<210> SEQ ID NO 72
<211> LENGTH: 115
<212> TYPE: PRT
<213> ORGANISM: Unknown
<220> FEATURE:
<223> OTHER INFORMATION: Camelid

<400> SEQUENCE: 72

Gln Val Gln Leu Gln Glu Ser Gly Gly Gly Leu Val Gln Pro Gly Gly
 1               5                  10                  15

Ser Leu Arg Leu Ser Cys Glu Ala Ser Gly Phe Thr Phe Ser Arg Phe
            20                  25                  30

Gly Met Thr Trp Val Arg Gln Ala Pro Gly Lys Gly Val Glu Trp Val
        35                  40                  45

Ser Gly Ile Ser Ser Leu Gly Asp Ser Thr Leu Tyr Ala Asp Ser Val
    50                  55                  60

Lys Gly Arg Phe Thr Ile Ser Arg Asp Asn Ala Lys Asn Thr Leu Tyr
 65                 70                  75                  80

Leu Gln Met Asn Ser Leu Lys Pro Glu Asp Thr Ala Val Tyr Tyr Cys
                85                  90                  95

Thr Ile Gly Gly Ser Leu Asn Pro Gly Gly Gln Gly Thr Gln Val Thr
            100                 105                 110

Val Ser Ser
        115

<210> SEQ ID NO 73
<211> LENGTH: 115
<212> TYPE: PRT
<213> ORGANISM: Unknown
<220> FEATURE:
<223> OTHER INFORMATION: Camelid

<400> SEQUENCE: 73

Gln Val Gln Leu Gln Glu Ser Gly Gly Gly Leu Val Gln Pro Gly Asn
 1               5                  10                  15

Ser Leu Arg Leu Ser Cys Ala Ala Ser Gly Phe Thr Phe Arg Asn Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asn Thr Ile Tyr Ala Asp Ser Val
    50                  55                  60

Lys Asp Arg Phe Thr Ile Ser Arg Asp Asn Ala Lys Ser Thr Leu Tyr
 65                 70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 74
<211> LENGTH: 114
<212> TYPE: PRT
<213> ORGANISM: Unknown
<220> FEATURE:
<223> OTHER INFORMATION: Camelid

<400> SEQUENCE: 74

Gln Val Gln Leu Gln Glu Ser Gly Gly Gly Leu Val Gln Pro Gly Gly
 1               5                  10                  15
```

```
Ser Leu Arg Leu Thr Cys Thr Ala Ser Gly Phe Thr Phe Ser Ser Phe
             20                  25                  30

Gly Met Ser Trp Val Arg Gln Ala Pro Gly Lys Gly Leu Glu Trp Val
         35                  40                  45

Ser Ala Ile Ser Ser Asp Ser Gly Thr Lys Asn Tyr Ala Asp Ser Val
     50                  55                  60

Lys Gly Arg Phe Thr Ile Ser Arg Asp Asn Ala Lys Lys Met Leu Phe
 65                  70                  75                  80

Leu Gln Met Asn Ser Leu Arg Pro Glu Asp Thr Ala Val Tyr Tyr Cys
                 85                  90                  95

Val Ile Gly Arg Gly Ser Pro Ser Gln Gly Thr Gln Val Thr Val
             100                 105                 110

Ser Ser
```

```
<210> SEQ ID NO 75
<211> LENGTH: 114
<212> TYPE: PRT
<213> ORGANISM: Unknown
<220> FEATURE:
<223> OTHER INFORMATION: Camelid

<400> SEQUENCE: 75

Gln Val Gln Leu Gln Glu Ser Gly Gly Gly Leu Val Gln Pro Gly Gly
 1               5                  10                  15

Ser Leu Arg Leu Thr Cys Thr Ala Ser Gly Phe Thr Phe Arg Ser Phe
             20                  25                  30

Gly Met Ser Trp Val Arg Gln Ala Pro Gly Lys Gly Leu Glu Trp Val
         35                  40                  45

Ser Ala Ile Ser Ala Asp Gly Ser Asp Lys Arg Tyr Ala Asp Ser Val
     50                  55                  60

Lys Gly Arg Phe Thr Ile Ser Arg Asp Asn Gly Lys Lys Met Leu Thr
 65                  70                  75                  80

Leu Asp Met Asn Ser Leu Lys Pro Glu Asp Thr Ala Val Tyr Tyr Cys
                 85                  90                  95

Val Ile Gly Arg Gly Ser Pro Ala Ser Gln Gly Thr Gln Val Thr Val
             100                 105                 110

Ser Ser
```

```
<210> SEQ ID NO 76
<211> LENGTH: 128
<212> TYPE: PRT
<213> ORGANISM: Unknown
<220> FEATURE:
<223> OTHER INFORMATION: Camelid

<400> SEQUENCE: 76

Ala Val Gln Leu Val Glu Ser Gly Gly Gly Leu Val Gln Ala Gly Asp
 1               5                  10                  15

Ser Leu Arg Leu Ser Cys Val Val Ser Gly Thr Thr Phe Ser Ser Ala
             20                  25                  30

Ala Met Gly Trp Phe Arg Gln Ala Pro Gly Lys Glu Arg Glu Phe Val
         35                  40                  45

Gly Ala Ile Lys Trp Ser Gly Thr Ser Thr Tyr Tyr Thr Asp Ser Val
     50                  55                  60

Lys Gly Arg Phe Thr Ile Ser Arg Asp Asn Val Lys Asn Thr Val Tyr
 65                  70                  75                  80
```

```
Leu Gln Met Asn Asn Leu Lys Pro Glu Asp Thr Gly Val Tyr Thr Cys
                85                  90                  95

Ala Ala Asp Arg Asp Arg Tyr Arg Asp Arg Met Gly Pro Met Thr Thr
            100                 105                 110

Thr Asp Phe Arg Phe Trp Gly Gln Gly Thr Gln Val Thr Val Ser Ser
        115                 120                 125

<210> SEQ ID NO 77
<211> LENGTH: 123
<212> TYPE: PRT
<213> ORGANISM: Unknown
<220> FEATURE:
<223> OTHER INFORMATION: Camelid

<400> SEQUENCE: 77

Gln Val Lys Leu Glu Glu Ser Gly Gly Gly Leu Val Gln Thr Gly Gly
 1               5                  10                  15

Ser Leu Arg Leu Ser Cys Ala Ala Ser Gly Arg Thr Phe Ser Ser Phe
            20                  25                  30

Ala Met Gly Trp Phe Arg Gln Ala Pro Gly Arg Glu Arg Glu Phe Val
        35                  40                  45

Ala Ser Ile Gly Ser Ser Gly Ile Thr Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Leu Cys Tyr Cys
                85                  90                  95

Ala Val Asn Arg Tyr Gly Ile Pro Tyr Arg Ser Gly Thr Gln Tyr Gln
            100                 105                 110

Asn Trp Gly Gln Gly Thr Gln Val Thr Ser Ser
        115                 120

<210> SEQ ID NO 78
<211> LENGTH: 120
<212> TYPE: PRT
<213> ORGANISM: Unknown
<220> FEATURE:
<223> OTHER INFORMATION: Camelid

<400> SEQUENCE: 78

Glu Val Gln Leu Glu Glu Ser Gly Gly Gly Leu Val Gln Pro Gly Gly
 1               5                  10                  15

Ser Leu Arg Leu Ser Cys Ala Ala Ser Gly Leu Thr Phe Asn Asp Tyr
            20                  25                  30

Ala Met Gly Trp Tyr Arg Gln Ala Pro Gly Lys Glu Arg Asp Met Val
        35                  40                  45

Ala Thr Ile Ser Ile Gly Gly Arg Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Ile Tyr Tyr Cys Val
                85                  90                  95

Ala His Arg Gln Thr Val Val Arg Gly Pro Tyr Leu Leu Trp Gly Gln
            100                 105                 110

Gly Thr Gln Val Thr Val Ser Ser
        115                 120

<210> SEQ ID NO 79
```

```
<211> LENGTH: 123
<212> TYPE: PRT
<213> ORGANISM: Unknown
<220> FEATURE:
<223> OTHER INFORMATION: Camelid

<400> SEQUENCE: 79

Gln Val Gln Leu Val Glu Ser Gly Gly Lys Leu Val Gln Ala Gly Gly
 1               5                  10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Phe Val
        35                  40                  45

Ala Gly Ser Gly Arg Ser Asn Ser Tyr Asn Tyr Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Thr Asn Leu Trp Pro Arg Asp Arg Asn Leu Tyr Ala Tyr
            100                 105                 110

Trp Gly Gln Gly Thr Gln Val Thr Val Ser Ser
            115                 120

<210> SEQ ID NO 80
<211> LENGTH: 125
<212> TYPE: PRT
<213> ORGANISM: Unknown
<220> FEATURE:
<223> OTHER INFORMATION: Camelid

<400> SEQUENCE: 80

Glu Val Gln Leu Val Glu Ser Gly Gly Gly Leu Val Gln Ala Gly Asp
 1               5                  10                  15

Ser Leu Arg Leu Ser Cys Ala Ala Ser Gly Arg Ser Leu Gly Ile Tyr
            20                  25                  30

Arg Met Gly Trp Phe Arg Gln Val Pro Gly Lys Glu Arg Glu Phe Val
        35                  40                  45

Ala Ala Ile Ser Trp Ser Gly Gly Thr Thr Arg Tyr Leu Asp Ser Val
    50                  55                  60

Lys Gly Arg Phe Thr Ile Ser Arg Asp Ser Thr Lys Asn Ala Val Tyr
65                  70                  75                  80

Leu Gln Met Asn Ser Leu Lys Pro Glu Asp Thr Ala Val Tyr Tyr Cys
                85                  90                  95

Ala Val Asp Ser Ser Gly Arg Leu Tyr Trp Thr Leu Ser Thr Ser Tyr
            100                 105                 110

Asp Tyr Trp Gly Gln Gly Thr Gln Val Thr Val Ser Ser
            115                 120                 125

<210> SEQ ID NO 81
<211> LENGTH: 125
<212> TYPE: PRT
<213> ORGANISM: Unknown
<220> FEATURE:
<223> OTHER INFORMATION: Camelid

<400> SEQUENCE: 81

Gln Val Gln Leu Val Glu Phe Gly Gly Gly Leu Val Gln Ala Gly Asp
 1               5                  10                  15
```

Ser Leu Arg Leu Ser Cys Ala Ala Ser Gly Arg Ser Leu Gly Ile Tyr
            20                  25                  30

Lys Met Ala Trp Phe Arg Gln Val Pro Gly Lys Glu Arg Glu Phe Val
            35                  40                  45

Ala Ala Ile Ser Trp Ser Gly Gly Thr Thr Arg Tyr Ile Asp Ser Val
 50                  55                  60

Lys Gly Arg Phe Thr Leu Ser Arg Asp Asn Lys Asn Met Val Tyr
 65                  70                  75                  80

Leu Gln Met Asn Ser Leu Lys Pro Asp Asp Thr Ala Val Tyr Tyr Cys
                85                  90                  95

Ala Val Asp Ser Ser Gly Arg Leu Tyr Trp Thr Leu Ser Thr Ser Tyr
            100                 105                 110

Asp Tyr Trp Gly Gln Gly Thr Gln Val Thr Val Ser Ser
            115                 120                 125

<210> SEQ ID NO 82
<211> LENGTH: 124
<212> TYPE: PRT
<213> ORGANISM: Unknown
<220> FEATURE:
<223> OTHER INFORMATION: Camelid

<400> SEQUENCE: 82

Glu Val Gln Leu Val Glu Ser Gly Gly Gly Leu Val Gln Ala Gly Gly
 1                5                  10                  15

Ser Leu Ser Leu Ser Cys Ala Ala Ser Gly Arg Thr Phe Ser Pro Tyr
            20                  25                  30

Thr Met Gly Trp Phe Arg Gln Ala Pro Gly Lys Glu Arg Glu Phe Leu
            35                  40                  45

Ala Gly Val Thr Trp Ser Gly Ser Ser Thr Phe Tyr Gly Asp Ser Val
 50                  55                  60

Lys Gly Arg Phe Thr Ala Ser Arg Asp Ser Ala Lys Asn Thr Val Thr
 65                  70                  75                  80

Leu Glu Met Asn Ser Leu Asn Pro Glu Asp Thr Ala Val Tyr Tyr Cys
                85                  90                  95

Ala Ala Ala Tyr Gly Gly Gly Leu Tyr Arg Asp Pro Arg Ser Tyr Asp
            100                 105                 110

Tyr Trp Gly Arg Gly Thr Gln Val Thr Val Ser Ser
            115                 120

<210> SEQ ID NO 83
<211> LENGTH: 131
<212> TYPE: PRT
<213> ORGANISM: Unknown
<220> FEATURE:
<223> OTHER INFORMATION: Camelid

<400> SEQUENCE: 83

Ala Val Gln Leu Val Glu Ser Gly Gly Gly Leu Val Gln Ala Gly Gly
 1                5                  10                  15

Ser Leu Arg Leu Ser Cys Ala Ala Ser Gly Phe Thr Leu Asp Ala Trp
            20                  25                  30

Pro Ile Ala Trp Phe Arg Gln Ala Pro Gly Lys Glu Arg Glu Gly Val
            35                  40                  45

Ser Cys Ile Arg Asp Gly Thr Thr Tyr Tyr Ala Asp Ser Val Lys Gly
 50                  55                  60

Arg Phe Thr Ile Ser Ser Asp Asn Ala Asn Asn Thr Val Tyr Leu Gln
 65                  70                  75                  80

```
Thr Asn Ser Leu Lys Pro Glu Asp Thr Ala Val Tyr Tyr Cys Ala Ala
                85                  90                  95

Pro Ser Gly Pro Ala Thr Gly Ser Ser His Thr Phe Gly Ile Tyr Trp
            100                 105                 110

Asn Leu Arg Asp Asp Tyr Asp Asn Trp Gly Gln Gly Thr Gln Val Thr
        115                 120                 125

Val Ser Ser
    130

<210> SEQ ID NO 84
<211> LENGTH: 126
<212> TYPE: PRT
<213> ORGANISM: Unknown
<220> FEATURE:
<223> OTHER INFORMATION: Camelid

<400> SEQUENCE: 84

Glu Val Gln Leu Val Glu Ser Gly Gly Leu Val Gln Ala Gly Gly
  1               5                  10                  15

Ser Leu Arg Leu Ser Cys Ala Ala Ser Gly Phe Thr Phe Asp His Tyr
             20                  25                  30

Thr Ile Gly Trp Phe Arg Gln Val Pro Gly Lys Glu Arg Glu Gly Val
         35                  40                  45

Ser Cys Ile Ser Ser Ser Asp Gly Ser Thr Tyr Tyr Ala Asp Ser Val
 50                  55                  60

Lys Gly Arg Phe Thr Ile Ser Ser Asp Asn Ala Lys Asn Thr Val Tyr
 65                  70                  75                  80

Leu Gln Met Asn Thr Leu Glu Pro Asp Asp Thr Ala Val Tyr Tyr Cys
                 85                  90                  95

Ala Ala Gly Gly Leu Leu Leu Arg Val Glu Glu Leu Gln Ala Ser Asp
             100                 105                 110

Tyr Asp Tyr Trp Gly Gln Gly Ile Gln Val Thr Val Ser Ser
         115                 120                 125

<210> SEQ ID NO 85
<211> LENGTH: 128
<212> TYPE: PRT
<213> ORGANISM: Unknown
<220> FEATURE:
<223> OTHER INFORMATION: Camelid

<400> SEQUENCE: 85

Ala Val Gln Leu Val Asp Ser Gly Gly Gly Leu Val Gln Pro Gly Gly
  1               5                  10                  15

Ser Leu Arg Leu Ser Cys Thr Ala Ser Gly Phe Thr Leu Asp Tyr Tyr
             20                  25                  30

Ala Ile Gly Trp Phe Arg Gln Ala Pro Gly Lys Glu Arg Glu Gly Val
         35                  40                  45

Ala Cys Ile Ser Asn Ser Asp Gly Ser Thr Tyr Tyr Gly Asp Ser Val
 50                  55                  60

Lys Gly Arg Phe Thr Ile Ser Arg Asp Asn Ala Lys Thr Thr Val Tyr
 65                  70                  75                  80

Leu Gln Met Asn Ser Leu Lys Pro Glu Asp Thr Ala Val Tyr Tyr Cys
                 85                  90                  95

Ala Thr Ala Asp Arg His Tyr Ser Ala Ser His His Pro Phe Ala Asp
             100                 105                 110

Phe Ala Phe Asn Ser Trp Gly Gln Gly Thr Gln Val Thr Val Ser Ser
```

```
<210> SEQ ID NO 86
<211> LENGTH: 120
<212> TYPE: PRT
<213> ORGANISM: Unknown
<220> FEATURE:
<223> OTHER INFORMATION: Camelid

<400> SEQUENCE: 86

Glu Val Gln Leu Val Glu Ser Gly Gly Gly Leu Val Gln Ala Gly Gly
 1               5                  10                  15

Ser Leu Arg Leu Ser Cys Ala Ala Tyr Gly Leu Thr Phe Trp Arg Ala
            20                  25                  30

Ala Met Ala Trp Phe Arg Arg Ala Pro Gly Lys Glu Arg Glu Leu Val
        35                  40                  45

Val Ala Arg Asn Trp Gly Asp Gly Ser Thr Arg Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Val Arg Thr Tyr Gly Ser Ala Thr Tyr Asp Ile Trp Gly Gln
            100                 105                 110

Gly Thr Gln Val Thr Val Ser Ser
        115                 120

<210> SEQ ID NO 87
<211> LENGTH: 123
<212> TYPE: PRT
<213> ORGANISM: Unknown
<220> FEATURE:
<223> OTHER INFORMATION: Camelid

<400> SEQUENCE: 87

Glu Val Gln Leu Val Glu Ser Gly Gly Gly Leu Val Gln Asp Gly Gly
 1               5                  10                  15

Ser Leu Arg Leu Ser Cys Ile Phe Ser Gly Arg Thr Phe Ala Asn Tyr
            20                  25                  30

Ala Met Gly Trp Phe Arg Gln Ala Pro Gly Lys Glu Arg Glu Phe Val
        35                  40                  45

Ala Ala Ile Asn Arg Asn Gly Gly Thr Thr Tyr Ala Asp Ala Leu
    50                  55                  60

Lys Gly Arg Phe Thr Ile Ser Arg Asp Asn Lys Asn Thr Ala Phe
65                  70                  75                  80

Leu Gln Met Asn Ser Leu Lys Pro Asp Asp Thr Ala Val Tyr Tyr Cys
                85                  90                  95

Ala Ala Arg Glu Trp Pro Phe Ser Thr Ile Pro Ser Gly Trp Arg Tyr
            100                 105                 110

Trp Gly Gln Gly Thr Gln Val Thr Val Ser Ser
        115                 120

<210> SEQ ID NO 88
<211> LENGTH: 125
<212> TYPE: PRT
<213> ORGANISM: Unknown
<220> FEATURE:
<223> OTHER INFORMATION: Camelid

<400> SEQUENCE: 88
```

-continued

```
Asp Val Gln Leu Val Glu Ser Gly Gly Gly Trp Val Gln Pro Gly Gly
1               5                   10                  15

Ser Leu Arg Leu Ser Cys Ala Ala Ser Gly Pro Thr Ala Ser Ser His
            20                  25                  30

Ala Ile Gly Trp Phe Arg Gln Ala Pro Gly Lys Glu Arg Glu Phe Val
        35                  40                  45

Val Gly Ile Asn Arg Gly Gly Val Thr Arg Asp Tyr Ala Asp Ser Val
    50                  55                  60

Lys Gly Arg Phe Ala Val Ser Arg Asp Asn Val Lys Asn Thr Val Tyr
65                  70                  75                  80

Leu Gln Met Asn Arg Leu Lys Pro Glu Asp Ser Ala Ile Tyr Ile Cys
                85                  90                  95

Ala Ala Arg Pro Glu Tyr Ser Phe Thr Ala Met Ser Lys Gly Asp Met
            100                 105                 110

Asp Tyr Trp Gly Lys Gly Thr Leu Val Thr Val Ser Ser
        115                 120                 125
```

<210> SEQ ID NO 89
<211> LENGTH: 10
<212> TYPE: PRT
<213> ORGANISM: Unknown
<220> FEATURE:
<223> OTHER INFORMATION: Anticancer peptide

<400> SEQUENCE: 89

```
Glu His Trp Ser Tyr Gly Leu Arg Pro Gly
1               5                   10
```

<210> SEQ ID NO 90
<211> LENGTH: 14
<212> TYPE: PRT
<213> ORGANISM: Unknown
<220> FEATURE:
<223> OTHER INFORMATION: Anticancer peptide

<400> SEQUENCE: 90

```
Glu Gln Arg Leu Gly Asn Gln Trp Ala Val Gly His Leu Met
1               5                   10
```

<210> SEQ ID NO 91
<211> LENGTH: 13
<212> TYPE: PRT
<213> ORGANISM: Unknown
<220> FEATURE:
<223> OTHER INFORMATION: Anticancer Peptide

<400> SEQUENCE: 91

```
Ala Gly Cys Lys Asn Phe Trp Lys Thr Phe Thr Ser Cys
1               5                   10
```

<210> SEQ ID NO 92
<211> LENGTH: 9
<212> TYPE: PRT
<213> ORGANISM: Unknown
<220> FEATURE:
<223> OTHER INFORMATION: Anticancer peptide
<220> FEATURE:
<221> NAME/KEY: SITE
<222> LOCATION: 8
<223> OTHER INFORMATION: Xaa = psi(CH2-NH)

<400> SEQUENCE: 92

```
Gln Trp Ala Val Gly His Leu Xaa Leu
```

```
1               5
```

<210> SEQ ID NO 93
<211> LENGTH: 6
<212> TYPE: PRT
<213> ORGANISM: Unknown
<220> FEATURE:
<223> OTHER INFORMATION: Anticancer peptide

<400> SEQUENCE: 93

```
Arg Arg Lys Arg Arg Arg
1               5
```

<210> SEQ ID NO 94
<211> LENGTH: 7
<212> TYPE: PRT
<213> ORGANISM: Unknown
<220> FEATURE:
<223> OTHER INFORMATION: Anticancer peptide

<400> SEQUENCE: 94

```
Ala Thr Trp Leu Pro Pro Arg
1               5
```

<210> SEQ ID NO 95
<211> LENGTH: 18
<212> TYPE: PRT
<213> ORGANISM: Unknown
<220> FEATURE:
<223> OTHER INFORMATION: Anticancer peptide

<400> SEQUENCE: 95

```
Arg Thr Glu Leu Asn Val Gly Ile Asp Phe Asn Trp Glu Tyr Pro Ala
1               5                   10                  15

Ser Lys
```

<210> SEQ ID NO 96
<211> LENGTH: 12
<212> TYPE: PRT
<213> ORGANISM: Unknown
<220> FEATURE:
<223> OTHER INFORMATION: Anticancer peptide

<400> SEQUENCE: 96

```
His His Glu Val Val Lys Phe Met Asp Val Tyr Gln
1               5                   10
```

<210> SEQ ID NO 97
<211> LENGTH: 11
<212> TYPE: PRT
<213> ORGANISM: Unknown
<220> FEATURE:
<223> OTHER INFORMATION: Anticancer peptide

<400> SEQUENCE: 97

```
Asn Ile Thr Val Thr Leu Lys Lys Phe Pro Leu
1               5                   10
```

<210> SEQ ID NO 98
<211> LENGTH: 10
<212> TYPE: PRT
<213> ORGANISM: Unknown
<220> FEATURE:
<223> OTHER INFORMATION: Anticancer peptide

<400> SEQUENCE: 98

```
Cys His Ser Gly Tyr Val Gly Val Arg Cys
 1               5                  10
```

<210> SEQ ID NO 99
<211> LENGTH: 12
<212> TYPE: PRT
<213> ORGANISM: Unknown
<220> FEATURE:
<223> OTHER INFORMATION: Anticancer peptide

<400> SEQUENCE: 99

```
Tyr Cys Asp Gly Phe Tyr Ala Cys Tyr Met Asp Val
 1               5                  10
```

<210> SEQ ID NO 100
<211> LENGTH: 13
<212> TYPE: PRT
<213> ORGANISM: Unknown
<220> FEATURE:
<223> OTHER INFORMATION: Anticancer peptide

<400> SEQUENCE: 100

```
Gly Gly Cys Lys Leu Trp Thr Ile Pro Glu Cys Gly Gly
 1               5                  10
```

<210> SEQ ID NO 101
<211> LENGTH: 5
<212> TYPE: PRT
<213> ORGANISM: Unknown
<220> FEATURE:
<223> OTHER INFORMATION: Anticancer peptide

<400> SEQUENCE: 101

```
Ala Val Leu Pro Arg
 1               5
```

<210> SEQ ID NO 102
<211> LENGTH: 19
<212> TYPE: PRT
<213> ORGANISM: Unknown
<220> FEATURE:
<223> OTHER INFORMATION: Anticancer peptide

<400> SEQUENCE: 102

```
Tyr Gly Arg Pro Arg Glu Ser Gly Lys Lys Arg Lys Arg Lys Arg Leu
 1               5                  10                  15

Lys Pro Thr
```

<210> SEQ ID NO 103
<211> LENGTH: 7
<212> TYPE: PRT
<213> ORGANISM: Unknown
<220> FEATURE:
<223> OTHER INFORMATION: Anticancer peptide

<400> SEQUENCE: 103

```
Cys Pro Ser Glu Gly Leu Cys
 1               5
```

<210> SEQ ID NO 104
<211> LENGTH: 13
<212> TYPE: PRT
<213> ORGANISM: Unknown
<220> FEATURE:
<223> OTHER INFORMATION: Anticancer peptide

<400> SEQUENCE: 104

```
Cys Pro Ser Glu Gly Thr Pro Ser Thr His Val Leu Cys
 1               5                  10
```

<210> SEQ ID NO 105
<211> LENGTH: 6
<212> TYPE: PRT
<213> ORGANISM: Unknown
<220> FEATURE:
<223> OTHER INFORMATION: Anticancer peptide

<400> SEQUENCE: 105

```
Leu Ala Asn Gly Val Glu
 1               5
```

<210> SEQ ID NO 106
<211> LENGTH: 7
<212> TYPE: PRT
<213> ORGANISM: Unknown
<220> FEATURE:
<223> OTHER INFORMATION: Anticancer peptide

<400> SEQUENCE: 106

```
Pro Gln Ala Glu Gly Gln Leu
 1               5
```

<210> SEQ ID NO 107
<211> LENGTH: 10
<212> TYPE: PRT
<213> ORGANISM: Unknown
<220> FEATURE:
<223> OTHER INFORMATION: Anticancer peptide

<400> SEQUENCE: 107

```
Val Ala Asn Pro Gln Ala Glu Gly Gln Leu
 1               5                  10
```

<210> SEQ ID NO 108
<211> LENGTH: 6
<212> TYPE: PRT
<213> ORGANISM: Unknown
<220> FEATURE:
<223> OTHER INFORMATION: Anticancer peptide
<220> FEATURE:
<221> NAME/KEY: SITE
<222> LOCATION: (1)...(6)
<223> OTHER INFORMATION: Cyclic peptide

<400> SEQUENCE: 108

```
Lys Gly Asp Gln Leu Ser
 1               5
```

<210> SEQ ID NO 109
<211> LENGTH: 8
<212> TYPE: PRT
<213> ORGANISM: Unknown
<220> FEATURE:
<223> OTHER INFORMATION: Anticancer peptide
<220> FEATURE:
<221> NAME/KEY: SITE
<222> LOCATION: (1)...(8)
<223> OTHER INFORMATION: Cyclic peptide
<220> FEATURE:
<221> NAME/KEY: SITE
<222> LOCATION: 3
<223> OTHER INFORMATION: Xaa = Cln

<400> SEQUENCE: 109

Tyr Ser Xaa Val Leu Phe Lys Gly

```
                                 1               5

<210> SEQ ID NO 110
<211> LENGTH: 8
<212> TYPE: PRT
<213> ORGANISM: Unknown
<220> FEATURE:
<223> OTHER INFORMATION: Anticancer peptide

<400> SEQUENCE: 110

Glu Met Thr Pro Val Asn Pro Gly
 1               5

<210> SEQ ID NO 111
<211> LENGTH: 7
<212> TYPE: PRT
<213> ORGANISM: Unknown
<220> FEATURE:
<223> OTHER INFORMATION: Anticancer peptide

<400> SEQUENCE: 111

Ile Glu Leu Leu Gln Ala Arg
 1               5

<210> SEQ ID NO 112
<211> LENGTH: 13
<212> TYPE: PRT
<213> ORGANISM: Unknown
<220> FEATURE:
<223> OTHER INFORMATION: Anticancer peptide

<400> SEQUENCE: 112

Cys Val Ser Asn Lys Tyr Phe Ser Asn Ile His Trp Cys
 1               5                  10

<210> SEQ ID NO 113
<211> LENGTH: 6
<212> TYPE: PRT
<213> ORGANISM: Unknown
<220> FEATURE:
<223> OTHER INFORMATION: Anticancer peptide
<220> FEATURE:
<221> NAME/KEY: SITE
<222> LOCATION: (2)...(3)
<223> OTHER INFORMATION: Xaa = any amino acid

<400> SEQUENCE: 113

Phe Xaa Xaa Tyr Lys Trp
 1               5

<210> SEQ ID NO 114
<211> LENGTH: 5
<212> TYPE: PRT
<213> ORGANISM: Unknown
<220> FEATURE:
<223> OTHER INFORMATION: Anticancer peptide
<220> FEATURE:
<221> NAME/KEY: SITE
<222> LOCATION: (3)...(4)
<223> OTHER INFORMATION: Xaa = any amino acid
<220> FEATURE:
<221> NAME/KEY: SITE
<222> LOCATION: (5)...(5)
<223> OTHER INFORMATION: Xaa = Ar

<400> SEQUENCE: 114

Lys Trp Xaa Xaa Xaa
 1               5
```

```
<210> SEQ ID NO 115
<211> LENGTH: 10
<212> TYPE: PRT
<213> ORGANISM: Unknown
<220> FEATURE:
<223> OTHER INFORMATION: Anticancer peptide

<400> SEQUENCE: 115

Leu Asn Phe Ser Gln Tyr Leu Trp Tyr Thr
 1               5                  10

<210> SEQ ID NO 116
<211> LENGTH: 8
<212> TYPE: PRT
<213> ORGANISM: Unknown
<220> FEATURE:
<223> OTHER INFORMATION: Anticancer peptide

<400> SEQUENCE: 116

Lys Pro Ser Ser Pro Pro Glu Glu
 1               5

<210> SEQ ID NO 117
<211> LENGTH: 12
<212> TYPE: PRT
<213> ORGANISM: Unknown
<220> FEATURE:
<223> OTHER INFORMATION: Anticancer peptide

<400> SEQUENCE: 117

Met Pro Arg Phe Met Asp Tyr Trp Glu Gly Leu Asn
 1               5                  10

<210> SEQ ID NO 118
<211> LENGTH: 20
<212> TYPE: PRT
<213> ORGANISM: Unknown
<220> FEATURE:
<223> OTHER INFORMATION: Anticancer peptide

<400> SEQUENCE: 118

Met Val Arg Arg Phe Leu Val Thr Leu Arg Ile Arg Arg Ala Cys Gly
 1               5                  10                  15

Pro Pro Arg Val
            20

<210> SEQ ID NO 119
<211> LENGTH: 22
<212> TYPE: PRT
<213> ORGANISM: Unknown
<220> FEATURE:
<223> OTHER INFORMATION: Anticancer peptide

<400> SEQUENCE: 119

Gly Ser Arg Ala His Ser Ser His Leu Lys Ser Lys Gly Gln Ser Thr
 1               5                  10                  15

Ser Arg His Lys Lys Leu
            20

<210> SEQ ID NO 120
<211> LENGTH: 5
<212> TYPE: PRT
<213> ORGANISM: Unknown
<220> FEATURE:
<223> OTHER INFORMATION: Anticancer peptide
```

```
<400> SEQUENCE: 120

Cys Ala Phe Tyr Ile
1               5

<210> SEQ ID NO 121
<211> LENGTH: 9
<212> TYPE: PRT
<213> ORGANISM: Unknown
<220> FEATURE:
<223> OTHER INFORMATION: Anticancer peptide

<400> SEQUENCE: 121

Leu Cys Ala Phe Tyr Ile Met Ala Lys
1               5

<210> SEQ ID NO 122
<211> LENGTH: 9
<212> TYPE: PRT
<213> ORGANISM: Unknown
<220> FEATURE:
<223> OTHER INFORMATION: Anticancer peptide

<400> SEQUENCE: 122

Met Cys Ser Met Tyr Gly Ile Cys Lys
1               5

<210> SEQ ID NO 123
<211> LENGTH: 19
<212> TYPE: PRT
<213> ORGANISM: Unknown
<220> FEATURE:
<223> OTHER INFORMATION: Anticancer peptide

<400> SEQUENCE: 123

Tyr Ser Phe Val His Gly Phe Phe Asn Phe Arg Val Ser Trp Arg Glu
1               5                   10                  15

Met Leu Ala

<210> SEQ ID NO 124
<211> LENGTH: 20
<212> TYPE: PRT
<213> ORGANISM: Unknown
<220> FEATURE:
<223> OTHER INFORMATION: Anticancer peptide

<400> SEQUENCE: 124

Lys Arg Arg Gln Thr Ser Met Thr Ala Phe Tyr His Ser Lys Arg Arg
1               5                   10                  15

Leu Ile Phe Ser
            20

<210> SEQ ID NO 125
<211> LENGTH: 8
<212> TYPE: PRT
<213> ORGANISM: Unknown
<220> FEATURE:
<223> OTHER INFORMATION: Anticancer peptide

<400> SEQUENCE: 125

Lys Arg Arg Leu Ile Phe Ser Lys
1               5

<210> SEQ ID NO 126
<211> LENGTH: 10
<212> TYPE: PRT
```

```
<213> ORGANISM: Unknown
<220> FEATURE:
<223> OTHER INFORMATION: Anticancer peptide

<400> SEQUENCE: 126

Phe Leu Asp Thr Leu Val Val Leu His Arg
1               5                   10

<210> SEQ ID NO 127
<211> LENGTH: 19
<212> TYPE: PRT
<213> ORGANISM: Unknown
<220> FEATURE:
<223> OTHER INFORMATION: Anticancer peptide

<400> SEQUENCE: 127

Arg Cys Val Arg Cys Arg Phe Val Val Trp Ile Gly Leu Arg Val Arg
1               5                   10                  15

Cys Leu Val

<210> SEQ ID NO 128
<211> LENGTH: 23
<212> TYPE: PRT
<213> ORGANISM: Unknown
<220> FEATURE:
<223> OTHER INFORMATION: Anticancer peptide

<400> SEQUENCE: 128

Leu Asn Trp Ala Trp Ala Ala Glu Val Leu Lys Val Gln Lys Arg Arg
1               5                   10                  15

Ile Tyr Asp Ile Thr Asn Val
            20

<210> SEQ ID NO 129
<211> LENGTH: 8
<212> TYPE: PRT
<213> ORGANISM: Unknown
<220> FEATURE:
<223> OTHER INFORMATION: Anticancer peptide

<400> SEQUENCE: 129

Leu Glu Gly Ile Gln Leu Ile Ala
1               5

<210> SEQ ID NO 130
<211> LENGTH: 6
<212> TYPE: PRT
<213> ORGANISM: Unknown
<220> FEATURE:
<223> OTHER INFORMATION: Anticancer peptide

<400> SEQUENCE: 130

Phe Trp Leu Arg Phe Thr
1               5

<210> SEQ ID NO 131
<211> LENGTH: 6
<212> TYPE: PRT
<213> ORGANISM: Unknown
<220> FEATURE:
<223> OTHER INFORMATION: Anticancer peptide

<400> SEQUENCE: 131

Trp Val Arg Trp His Phe
1               5
```

```
<210> SEQ ID NO 132
<211> LENGTH: 5
<212> TYPE: PRT
<213> ORGANISM: Unknown
<220> FEATURE:
<223> OTHER INFORMATION: Anticancer peptide

<400> SEQUENCE: 132

Trp Val Arg Trp His
1               5

<210> SEQ ID NO 133
<211> LENGTH: 6
<212> TYPE: PRT
<213> ORGANISM: Unknown
<220> FEATURE:
<223> OTHER INFORMATION: Anticancer peptide

<400> SEQUENCE: 133

Trp His Phe Ile Phe Trp
1               5

<210> SEQ ID NO 134
<211> LENGTH: 15
<212> TYPE: PRT
<213> ORGANISM: Unknown
<220> FEATURE:
<223> OTHER INFORMATION: Anticancer peptide

<400> SEQUENCE: 134

Ile Trp Leu Ser Gly Leu Ser Arg Gly Val Trp Val Ser Phe Pro
1               5                   10                  15

<210> SEQ ID NO 135
<211> LENGTH: 15
<212> TYPE: PRT
<213> ORGANISM: Unknown
<220> FEATURE:
<223> OTHER INFORMATION: Anticancer peptide

<400> SEQUENCE: 135

Gly Ser Arg Ile Leu Thr Phe Arg Ser Gly Ser Trp Tyr Ala Ser
1               5                   10                  15

<210> SEQ ID NO 136
<211> LENGTH: 14
<212> TYPE: PRT
<213> ORGANISM: Unknown
<220> FEATURE:
<223> OTHER INFORMATION: Anticancer peptide

<400> SEQUENCE: 136

Asp Glu Leu Lys Arg Ala Phe Ala Ala Leu Arg Asp Gln Ile
1               5                   10

<210> SEQ ID NO 137
<211> LENGTH: 17
<212> TYPE: PRT
<213> ORGANISM: Unknown
<220> FEATURE:
<223> OTHER INFORMATION: Anticancer peptide

<400> SEQUENCE: 137

Lys Lys Leu Ser Glu Cys Leu Lys Lys Arg Ile Gly Asp Glu Leu Asp
1               5                   10                  15

Ser
```

<210> SEQ ID NO 138
<211> LENGTH: 16
<212> TYPE: PRT
<213> ORGANISM: Unknown
<220> FEATURE:
<223> OTHER INFORMATION: Anticancer peptide

<400> SEQUENCE: 138

Gly Gln Val Gly Arg Gln Leu Ala Ile Ile Gly Asp Asp Ile Asn Arg
1               5                   10                  15

<210> SEQ ID NO 139
<211> LENGTH: 16
<212> TYPE: PRT
<213> ORGANISM: Unknown
<220> FEATURE:
<223> OTHER INFORMATION: Anticancer peptide

<400> SEQUENCE: 139

Arg Asn Ile Ala Arg His Leu Ala Gln Val Gly Asp Ser Met Asp Arg
1               5                   10                  15

<210> SEQ ID NO 140
<211> LENGTH: 5
<212> TYPE: PRT
<213> ORGANISM: Unknown
<220> FEATURE:
<223> OTHER INFORMATION: Anticancer peptide

<400> SEQUENCE: 140

Tyr Ile Gly Ser Arg
1               5

<210> SEQ ID NO 141
<211> LENGTH: 5
<212> TYPE: PRT
<213> ORGANISM: Unknown
<220> FEATURE:
<223> OTHER INFORMATION: Anticancer peptide

<400> SEQUENCE: 141

Tyr Ile Gly Ser Arg
1               5

<210> SEQ ID NO 142
<211> LENGTH: 5
<212> TYPE: PRT
<213> ORGANISM: Unknown
<220> FEATURE:
<223> OTHER INFORMATION: Anticancer peptide

<400> SEQUENCE: 142

Tyr Ile Gly Ser Arg
1               5

<210> SEQ ID NO 143
<211> LENGTH: 5
<212> TYPE: PRT
<213> ORGANISM: Unknown
<220> FEATURE:
<223> OTHER INFORMATION: Anticancer peptide

<400> SEQUENCE: 143

Tyr Ile Gly Ser Arg
1               5

<210> SEQ ID NO 144
<211> LENGTH: 5
<212> TYPE: PRT
<213> ORGANISM: Unknown
<220> FEATURE:
<223> OTHER INFORMATION: Anticancer peptide
<220> FEATURE:
<221> NAME/KEY: SITE
<222> LOCATION: 1
<223> OTHER INFORMATION: Xaa = para-aminoPhe

<400> SEQUENCE: 144

Xaa Ile Gly Ser Arg
 1               5

<210> SEQ ID NO 145
<211> LENGTH: 5
<212> TYPE: PRT
<213> ORGANISM: Unknown
<220> FEATURE:
<223> OTHER INFORMATION: Anticancer peptide

<400> SEQUENCE: 145

Tyr Ile Gly Ser Arg
 1               5

<210> SEQ ID NO 146
<211> LENGTH: 13
<212> TYPE: PRT
<213> ORGANISM: unknown
<220> FEATURE:
<223> OTHER INFORMATION: Anticancer peptide
<220> FEATURE:
<221> NAME/KEY: SITE
<222> LOCATION: 7
<223> OTHER INFORMATION: Xaa = C(O)

<400> SEQUENCE: 146

Arg Ser Gly Ile Tyr Asp Xaa Asp Tyr Ile Gly Ser Arg
 1               5                  10

<210> SEQ ID NO 147
<211> LENGTH: 3
<212> TYPE: PRT
<213> ORGANISM: Unknown
<220> FEATURE:
<223> OTHER INFORMATION: Anticancer peptide

<400> SEQUENCE: 147

Arg Gly Asp
 1

<210> SEQ ID NO 148
<211> LENGTH: 5
<212> TYPE: PRT
<213> ORGANISM: Unknown
<220> FEATURE:
<223> OTHER INFORMATION: Anticancer peptide

<400> SEQUENCE: 148

Tyr Ile Gly Ser Arg
 1               5

<210> SEQ ID NO 149
<211> LENGTH: 20
<212> TYPE: PRT
<213> ORGANISM: Unknown
<220> FEATURE:

<223> OTHER INFORMATION: Anticancer peptide

<400> SEQUENCE: 149

Ile Pro Cys Asn Asn Lys Gly Ala His Ser Val Gly Leu Met Trp Trp
1               5                   10                  15

Met Leu Ala Arg
            20

<210> SEQ ID NO 150
<211> LENGTH: 10
<212> TYPE: PRT
<213> ORGANISM: Unknown
<220> FEATURE:
<223> OTHER INFORMATION: Anticancer peptide

<400> SEQUENCE: 150

Ser Pro His Arg Pro Arg Phe Ser Pro Ala
1               5                   10

<210> SEQ ID NO 151
<211> LENGTH: 10
<212> TYPE: PRT
<213> ORGANISM: Unknown
<220> FEATURE:
<223> OTHER INFORMATION: Anticancer peptide

<400> SEQUENCE: 151

Ser Pro His Ala His Gly Tyr Ile Pro Ser
1               5                   10

<210> SEQ ID NO 152
<211> LENGTH: 10
<212> TYPE: PRT
<213> ORGANISM: Unknown
<220> FEATURE:
<223> OTHER INFORMATION: Anticancer peptide

<400> SEQUENCE: 152

Thr Pro His Thr His Asn Arg Thr Pro Glu
1               5                   10

<210> SEQ ID NO 153
<211> LENGTH: 10
<212> TYPE: PRT
<213> ORGANISM: Unknown
<220> FEATURE:
<223> OTHER INFORMATION: Anticancer peptide

<400> SEQUENCE: 153

Thr Pro His Arg His Gln Lys Thr Pro Glu
1               5                   10

<210> SEQ ID NO 154
<211> LENGTH: 11
<212> TYPE: PRT
<213> ORGANISM: Unknown
<220> FEATURE:
<223> OTHER INFORMATION: Anticancer peptide

<400> SEQUENCE: 154

Glu Pro His Arg His Ser Ile Phe Thr Pro Glu
1               5                   10

<210> SEQ ID NO 155
<211> LENGTH: 5
<212> TYPE: PRT

```
<213> ORGANISM: Unknown
<220> FEATURE:
<223> OTHER INFORMATION: Anticancer peptide

<400> SEQUENCE: 155

Cys His Ala Val Cys
1               5

<210> SEQ ID NO 156
<211> LENGTH: 17
<212> TYPE: PRT
<213> ORGANISM: Unknown
<220> FEATURE:
<223> OTHER INFORMATION: Anticancer peptide

<400> SEQUENCE: 156

Cys Glu Lys His Ile Met Glu Lys Ile Gln Gly Arg Gly Asp Asp Asp
1               5                   10                  15

Asp

<210> SEQ ID NO 157
<211> LENGTH: 10
<212> TYPE: PRT
<213> ORGANISM: Unknown
<220> FEATURE:
<223> OTHER INFORMATION: Anticancer peptide

<400> SEQUENCE: 157

Cys Thr Thr His Trp Gly Phe Thr Leu Cys
1               5                   10

<210> SEQ ID NO 158
<211> LENGTH: 15
<212> TYPE: PRT
<213> ORGANISM: Unknown
<220> FEATURE:
<223> OTHER INFORMATION: Binds human type 1 IL-1 receptor
<220> FEATURE:
<221> NAME/KEY: SITE
<222> LOCATION: 10
<223> OTHER INFORMATION: Xaa = 1-azetidine-2-carboxylic acid

<400> SEQUENCE: 158

Phe Glu Trp Thr Pro Gly Trp Tyr Gln Xaa Tyr Ala Leu Pro Leu
1               5                   10                  15
```